(12) United States Patent
Bhatia et al.

(10) Patent No.: US 9,994,809 B2
(45) Date of Patent: Jun. 12, 2018

(54) PROGRAMMABLE DRUG DELIVERY PROFILES OF TUMOR-TARGETED BACTERIA

(71) Applicant: Massachusetts Institute of Technology, Cambridge, MA (US)

(72) Inventors: Sangeeta N. Bhatia, Lexington, MA (US); Tal Danino, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days. days.

(21) Appl. No.: 14/428,341

(22) PCT Filed: Sep. 13, 2013

(86) PCT No.: PCT/US2013/059832
§ 371 (c)(1),
(2) Date: Mar. 13, 2015

(87) PCT Pub. No.: WO2014/043593
PCT Pub. Date: Mar. 20, 2014

(65) Prior Publication Data
US 2015/0225692 A1    Aug. 13, 2015

Related U.S. Application Data

(60) Provisional application No. 61/700,663, filed on Sep. 13, 2012.

(51) Int. Cl.
| | |
|---|---|
| *C12N 15/74* | (2006.01) |
| *C12N 1/20* | (2006.01) |
| *A61K 38/02* | (2006.01) |
| *A61K 49/00* | (2006.01) |
| *A61K 35/74* | (2015.01) |
| *A23L 1/30* | (2006.01) |
| *A61K 45/08* | (2006.01) |
| *A61K 45/06* | (2006.01) |
| *A23L 33/135* | (2016.01) |
| *A61K 38/00* | (2006.01) |

(52) U.S. Cl.
CPC .............. *C12N 1/20* (2013.01); *A23L 33/135* (2016.08); *A61K 35/74* (2013.01); *A61K 38/02* (2013.01); *A61K 45/06* (2013.01); *A61K 49/0017* (2013.01); *C12N 15/74* (2013.01); *A23V 2002/00* (2013.01); *A23Y 2220/00* (2013.01); *A23Y 2300/00* (2013.01); *A61K 38/00* (2013.01); *C07K 2319/55* (2013.01)

(58) Field of Classification Search
CPC .. A61K 2300/00; A61K 31/365; A61K 35/74; A61K 33/24; A61K 33/26; A61K 45/06; A61K 2039/5254; A61K 2039/5256; A61K 2039/70; A61K 31/00; A61K 39/12; A61K 39/155; A61K 2123/00; A61K 31/34; A61K 31/38
See application file for complete search history.

(56) References Cited

U.S. PATENT DOCUMENTS

| | | | |
|---|---|---|---|
| 5,633,274 | A | 5/1997 | Halperin et al. |
| 6,428,968 | B1 | 8/2002 | Molnar-Kimber et al. |
| 6,693,112 | B2 | 2/2004 | Smith |
| 6,849,272 | B1 | 2/2005 | Langer et al. |
| 7,655,444 | B2 | 2/2010 | Herman et al. |
| 8,257,714 | B2 | 9/2012 | Aylsworth et al. |
| 8,343,498 | B2 | 1/2013 | Alexis et al. |
| 8,466,110 | B2 | 6/2013 | Dewhirst et al. |
| 2011/0195847 | A1 | 8/2011 | Arrach et al. |
| 2011/0293567 | A1 | 12/2011 | Eils et al. |

FOREIGN PATENT DOCUMENTS

WO        2011/066541 A2    6/2011

OTHER PUBLICATIONS

Zhang et al (Acta Pharmaceutica Sinica B vol. 2, Issue 6 pp. 569-574).*
Li tet al 2012 Acta Pharmaceutica Sinica B vol. 2, Issue 6 pp. 562-568.*
Wall et al Oncotarget. Dec. 2010; 1(8): 721-728.*
Ryan et al ; Bioessays. Jan. 2006;28(1):84-94.*
Patyar et al 2010 (J Biomed Sci. 17(1): 21).*
Dai Yet al Biotechnol Bioeng. 2013;110:1769-81.*
Nguyen et al; Cancer Res. Jan. 1, 2010; 70(1):18-23. Epub Dec. 22, 2009*.*
Cagno et al Proteomics 2010, 10, 2175-2190.*
Anderson, J. C., et al., "Environmentally Controlled Invasion of Cancer Cells by Engineered Bacteria", Journal of Molecular Biology, 2006, vol. 355, No. 4, pp. 619-627.
Bermudez-Humaran, L. G., et al., "Lactococci and Lactobacilli as Mucosal Delivery Vectors for Therapeutic Proteins and DNA", Microbial Cell Factories, 2011, vol. 10, (Suppl 1):54 , pp. 1-10.
Chen, R., et al., "Application of Proapoptotic Peptide to Intratumorally Spreading Cancer Therapy", Cancer Research, Feb. 15, 2013, vol. 73, No. 4, pp. 1352-1361.
Cronin, M., et al., "High Resolution In Vivo Bioluminescent Imaging for the Study of Bacterial Tumour Targeting", PLoS ONE, Jan. 2012, vol. 7, Issue 1, pp. 1-11.
Dang, L. H., et al., "Combination Bacteriolytic Therapy for the Treatment of Experimental Tumors", PNAS, Dec. 18, 2001, vol. 98, No. 26, pp. 15155-15160.

(Continued)

*Primary Examiner* — Padmavathi Baskar
(74) *Attorney, Agent, or Firm* — McCarter & English, LLP

(57) ABSTRACT

The present invention relates to composition comprising at least one non-pathogenic bacterial cell, wherein the non-pathogenic bacterial cell comprises at least a first and a second nucleic acid sequence, the first nucleic acid sequence comprising at least one non-constitutive promoter operably linked to the second nucleic acid sequence that encodes therapeutic agent, wherein the non-constitutive promoter is an inducible promoter responsive to at least one stimuli and the at least one stimuli comprises the presence of a certain density or a certain number of bacterial cells comprising the first and second nucleic acid sequences.

14 Claims, 30 Drawing Sheets

(56) References Cited

OTHER PUBLICATIONS

Danino, T., et al., "A Synchronized Quorum of Genetic Clocks", Nature, Jan. 21, 2010, vol. 463 (7279), pp. 326-330.
Danino, T., et al., "In Vivo Gene Expression Dynamics of Tumor-Targeted Bacteria", ACS Synthetic Biology, 2012, vol. 1, pp. 465-470.
Egland, K. A., et al., "Quorum Sensing in Vibrio fischeri: Elements of the luxI Promoter", Molecular Microbiology, 1999, vol. 31, No. 4, pp. 1197-1204.
Forbes, N. S., "Engineering the Perfect (Bacterial) Cancer Therapy", Nature Reviews Cancer, Nov. 2010, vol. 10, No. 11, pp. 785-794.
Guo, H., et al., "Targeting Tumor Gene by shRNA-expressing *Salmonella*-mediated RNAi", Gene Therapy, 2011, vol. 18, pp. 95-105.
Hasty, J., et al., "Engineered Gene Circuits", Nature, Nov. 14, 2002, vol. 420, pp. 224-230.
Heimann, D. M., et al., "Continuous Intravenous Administration of Live Genetically Modified *Salmonella* Typhimurium in Patients with Metastic Melanoma", Journal of Immunotherapy, 2003, vol. 26, No. 2, pp. 179-180.
Hoffman, R. M., "Tumor-Seeking Salmonella Amino Acid Auxotrophs", Current Opinion in Biotechnology, 2011, vol. 22, pp. 917-923.
Hohmann, E. L., et al., "Evaluation of a phoPlphoQ-deleted, aroA-deleted live oral *Salmonella* typhi Vaccine Strain in Human Volunteers", Vaccine, 1996, vol. 14, No. 1, pp. 19-24.
Huang, X., et al., "On the Importance and Mechanisms of Burst Release in Matrix-Controlled Drug Delivery Systems", Journal of Controlled Release, 2001, vol. 73, pp. 121-136.
Leschner, S., et al., "Tumor Invasion of *Salmonella enterica* Serovar Typhimurium is Accompanied by Strong Hemorrhage Promoted by TNF-alpha", PLoS ONE, Aug. 2009, vol. 4, Issue 8, pp. 1-11.
Mangwani, N., et al., "Bacterial Quorum Sensing: Functional Features and Potential Applications in Biotechnology", Journal of Molecular Microbiology and Biotechnology, Sep. 4, 2012, vol. 22, pp. 215-227.
Nguyen, V. H., "Genetically Engineered *Salmonella* typhimurium as an Imageable Therapeutic Probe for Cancer", Cancer Research, Jan. 1, 2010, vol. 70, No. 1, pp. 18-23.
O'Brien, E. L., "Modeling Synthetic Gene Oscillators", Mathematical Biosciences, 2012, vol. 236, No. 1, pp. 1-15.
Paton, A. W., "Bioengineered Microbes in Disease Therapy", Trends in Molecular Medicine, Jul. 2012, vol. 18, No. 7, pp. 417-425.
Pawelek, J. M., et al., "Tumor-Targeted *Salmonella* as a Novel Anticancer Vector", Cancer Research, Oct. 15, 1997, vol. 57, pp. 4537-4544.
Pecota, D. C., et al., "Combining the hok/sok, par DE, and pnd Postsegregational Killer Loci to Enhance Plasmid Stability", Applied and Environmental Microbiology, May 1997, vol. 63, No. 5, pp. 1917-1924.
Prindle, A., et al., "Genetic Circuits in *Salmonella* typhimurium", ACS Synthetic Biology, 2012, vol. 1, pp. 458-464.
Prindle, A., et al., "Sensing Array of Radically Coupled Genetic Biopixels", Nature, 2011, vol. 481, pp. 39-44.
Shrivastava, S., et al., "Identification and Functional Characterization of Gene Components of Type VI Secretion System in Bacterial Genomes", PLos ONE, Aug. 2008, vol. 3, Issue 8, pp. 1-11.
Stewart, F. M., et al., "The Population Biology of Bacterial Plasmids: A PRIORI Conditions for the Existence of Conjugationally Transmitted Factors", Genetics, Oct. 1977, vol. 87, pp. 209-228.
Toso, J. F., et al., "Phase I Study of the Intravenous Administration of Attenuated *Salmonella* typhimurium to Patients with Metastic Melanoma", Journal of Clinical Oncology, Jan. 1, 2002, vol. 20, No. 1, pp. 142-152.
Wu, H.-C., "Incorporation of Bacterial Quorum Sensing in Synthetic Biology",Thesis, 2012, http://drum.lib.umd.edu/bitstream/1903/12779/Wu_umd_0117E_13096.pdf, pp. 1-90.
Yang, et al., "Designer Biosystem with Regulated Insulin Expression and Glucose Auto-Sensing for Diabetes", International Journal of Systems and Synthetic Biology, Jun. 2010, vol. 1, pp. 135-145.
Yu, Y. A., et al., "Visualization of Tumors and Metastases in Live Animals with Bacteria and Vaccinia Virus Encoding Light-Emitting Proteins", Nature Biotechnology, Mar. 2004, vol. 22, No. 3, pp. 313-320.
Zhao, M., et al., "Targeted Therapy with a *Salmonella* Typhimurium Leucine-Arginine Auxotroph Cures Orthotopic Human Breast Tumors in Nude Mice", Cancer Research, Aug. 1, 2006, vol. 66, No. 15, pp. 7647-7652.
Zhao, M., et al., "Tumor-Targeting Bacterial Therapy with amino acid auxotrophs of GFP-expressing *Salmonella* typhimurium", PNAS, Jan. 18, 2005, vol. 102, No. 3, pp. 755-760.
Zhou, S., et al., "Tumor-Targeted Delivery of TAT-Apoptin Fusion Gene Using *Escherichia coli* Nissle 1917 to Colorectal Cancer", Medical Hypotheses, 2011, vol. 76, No. 4, pp. 533-534.

\* cited by examiner

Quorum sensing    Constitutive

Correlations between in vivo and ex vivo imaging of tumors. High correlations are observed for each step of the process.

SEQUENCE LISTING

<160> NUMBER OF SEQ ID NOS: 7

<210> SEQ ID NO 1
<211> LENGTH: 12077
<212> TYPE: DNA
<213> ORGANISM: Artificial Sequence
<220> FEATURE:
<223> OTHER INFORMATION: plasmid 1

<400> SEQUENCE: 1

```
ctcgagttaa tttttaaagt atgggcaatc aattgctcct gttaaaattg ctttagaaat      60
actttggcag cggtttgttg tattgagttt catttgcgca ttggttaaat ggaaagtgac     120
agtacgctca ctgcagccta atattttga aatatcccaa gagcttttc cttcgcatgc      180 ccacgctaaa cattcttttt ctcttttggt taaatcgttg tttgatttat tatttgctat     240
atttattttt cgataattat caactagaga aggaacaatt aatggtatgt tcatacacgc     300
atgtaaaaat aaactatcta tatagttgtc tttttctgaa tgtgcaaaac taagcattcc     360
gaagccattg ttagccgtat gaatagggaa actaaaccca gtgataagac ctgatgtttt     420
cgcttcttta attacatttg gagatttttt atttacagca ttgttttcaa atatattcca     480
attaattggt gaatgattgg agttagaata atctactata ggatcatatt ttattaaatt     540
```

```
agcgtcatca taatattgcc tccatttttt agggtaatta tctagaattg aaatatcaga    600
tttaaccata gaatgaggat aaatgatcgc gagtaaataa tattcacaat gtaccatttt    660
agtcatatca gataagcatt gattaatatc attattgctt ctacaagctt taattttatt    720
aattattctg tatgtgtcgt cggcatttat gttttttcata cccatctctt tatccttacc   780
tattgtttgt cgcaagtttt gcgtgttata tatcattaaa acggtaatgg attgacattt    840
gattctaata aattggattt ttgtcacact attgtatcgc tgggaataca attacttaac    900
ataagcacct gtaggatcgt acaggtttac gcaagaaaat ggtttgttat agtcgaatga    960
attcattaaa gaggagaaag gtaccatgac tataatgata aaaaaatcgg attttttggc   1020
aattccatcg gaggagtata aaggtattct aagtcttcgt tatcaagtgt ttaagcaaag   1080
acttgagtgg gacttagttg tagaaaataa ccttgaatca gatgagtatg ataactcaaa   1140
tgcagaatat atttatgctt gtgatgatac tgaaaatgta agtggatgct ggcgtttatt   1200
acctacaaca ggtgattata tgctgaaaag tgttttttcct gaattgcttg gtcaacagag   1260
tgctcccaaa gatcctaata tagtcgaatt aagtcgtttt gctgtaggta aaaatagctc   1320
aaagataaat aactctgcta gtgaaattac aatgaaacta tttgaagcta tatataaaca   1380
cgctgttagt caaggtatta cagaatatgt aacagtaaca tcaacagcaa tagagcgatt   1440
tttaaagcgt attaaagttc cttgtcatcg tattggagac aaagaaattc atgtattagg   1500
tgatactaaa tcggttgtat tgtctatgcc tattaatgaa cagtttaaaa aagcagtctt   1560
aaatgcagcg aacgacgaaa attacgccct tgcagcgtaa acgcgtgcta gaggcatcaa   1620
ataaaacgaa aggctcagtc gaaagactgg gcctttcgtt ttatctgttg tttgtcggtg   1680
aacgctctcc tgagtaggac aaatccgccg ccctagacct agcattttta agtatgggc    1740 aatcaattgc tcctgttaaa attgctttag aaatactttg gcagcggttt gttgtattga   1800
gtttcatttg cgcattggtt aaatggaaag tgacagtacg ctcactgcag cctaatatt    1860 ttgaaatatc ccaagagctt ttccttcgc atgcccacgc taaacattct ttttctcttt    1920
tggttaaatc gttgtttgat ttattatttg ctatatttat ttttcgataa ttatcaacta   1980
gagaaggaac aattaatggt atgttcatac acgcatgtaa aaataaacta tctatatagt   2040
tgtctttttc tgaatgtgca aaactaagca ttccgaagcc attgttagcc gtatgaatag   2100
ggaaactaaa cccagtgata agacctgatg ttttcgcttc tttaattaca tttggagatt   2160
ttttatttac agcattgttt tcaaatatat tccaattaat tggtgaatga ttggagttag   2220
aataatctac tataggatca tatttttatta aattagcgtc atcataatat tgcctccatt   2280
ttttagggta attatctaga attgaaatat cagatttaac catagaatga ggataaatga   2340
tcgcgagtaa ataatattca caatgtacca ttttagtcat atcagataag cattgattaa   2400
tatcattatt gcttctacaa gctttaattt tattaattat tctgtatgtg tcgtcggcat   2460
ttatgttttt cataccccatc tctttatcct tacctattgt ttgtcgcaag ttttgcgtgt   2520
tatatatcat taaaacggta atggattgac atttgattct aataaattgg atttttgtca   2580
cactattgta tcgctgggaa tacaattact taacataagc acctgtagga tcgtacaggt   2640
ttacgcaaga aaatggtttg ttatagtcga atgaattcat taaagaggag aaaggtacca   2700
tgactaaaaa aatttcattc attattaacg gccaggttga aatctttccc gaaagtgatg   2760
atttagtgca atccattaat tttggtgata atagtgttta cctgccaata ttgaatgact   2820
ctcatgtaaa aaacattatt gattgtaatg gaaataacga attacggttg cataacattg   2880
tcaattttct ctatacggta gggcaaagat ggaaaaatga agaatactca agacgcagga   2940
```

```
catacattcg tgacttaaaa aaatatatgg gatattcaga agaaatggct aagctagagg    3000
ccaattggat atctatgatt ttatgttcta aaggcggcct ttatgatgtt gtagaaaatg    3060
aacttggttc tcgccatatc atggatgaat ggctacctca ggatgaaagt tatgttcggg    3120
cttttccgaa aggtaaatct gtacatcgt tggcaggtaa tgttccatta tctgggatca    3180
tgtctatatt acgcgcaatt ttaactaaga atcagtgtat tataaaaaca tcgtcaaccg    3240
atccttttac cgctaatgca ttagcgttaa gttttattga tgtagaccct aatcatccga    3300
taacgcgctc tttatctgtt atatattggc cccaccaagg tgatacatca ctcgcaaaag    3360
aaattatgcg acatgcggat gttattgtcg cttgggagg gccagatgcg attaattggg    3420
cggtagagca tgcgccatct tatgctgatg tgattaaatt tggttctaaa aagagtcttt    3480
gcattatcga taatcctgtt gatttgacgt ccgcagcgac aggtgcggct catgatgttt    3540 gttttttacga tcagcgagct tgttttttctg cccaaaacat atattacatg gaaatcatt    3600 atgaggaatt taagttagcg ttgatagaaa aacttaatct atatgcgcat atattaccga    3660
atgccaaaaa agattttgat gaaaaggcgg cctattcttt agttcaaaaa gaaagcttgt    3720
ttgctggatt aaaagtagag gtggatattc atcaacgttg gatgattatt gagtcaaatg    3780
caggtgtgga attaatcaa ccacttggca gatgtgtgta ccttcatcac gtcgataata    3840
ttgagcaaat attgccttat gttcaaaaaa ataagacgca aaccatatct attttttcctt    3900 gggagtcatc atttaaatat cgagatgcgt tagcattaaa aggtgcggaa aggattgtag    3960
aagcaggaat gaataacata tttcgagttg gtggatctca tgacggaatg agaccgttgc    4020
aacgattagt gacatatatt tctcatgaaa ggccatctaa ctatacggct aaggatgttg    4080
cggttgaaat agaacagact cgattcctgg aagaagataa gttccttgta tttgtcccat    4140
aataggtaaa agtatggaaa atgaatcaaa atataaaacc atcgaccacg ttatttgtgt    4200
tgaaggaaat aaaaaaattc atgtttggga aacgctgcca gaagaaaaca gcccaaagag    4260
aaagaatgcc attattattg cgtctggttt tgcccgcagg atggatcatt ttgctggtct    4320
ggcggaatat ttatcgcgga atggatttca tgtgatccgc tatgattcgc ttcaccacgt    4380
tggattgagt tcagggacaa ttgatgaatt tacaatgtct ataggaaagc agagcttgtt    4440
agcagtggtt gattggttaa ctacacgaaa aataaataac ttcggtatgt tggcttcaag    4500
cttatctgcg cggatagctt atgcaagcct atctgaaatc aatgcttcgt ttttaatcac    4560
cgcagtcggt gttgttaact aagatattc tcttgaaaga gctttagggt ttgattatct    4620
cagtctaccc attaatgaat tgccggataa tctagatttt gaaggccata aattgggtgc    4680
tgaagtcttt gcgagagatt gtcttgattt tggttgggaa gatttagctt ctacaattaa    4740
taacatgatg tatcttgata taccgtttat tgctttact gcaaataacg ataattgggt    4800
caagcaagat gaagttatca cattgttatc aaatattcgt agtaatcgat gcaagatata    4860
ttctttgtta ggaagttcgc atgacttgag tgaaaattta gtggtcctgc gcaatttta    4920 tcaatcggtt acgaaagccg ctatcgcgat ggataatgat catctggata ttgatgttga    4980
tattactgaa ccgtcatttg aacatttaac tattgcgaca gtcaatgaac gccgaatgag    5040
aattgagatt gaaaatcaag caatttctct gtcttaaaat ctattgagat attctatcac    5100
tcaaatagca ataaaggac tctctatgaa atttggaaac ttttttgctta cataccaacc    5160 tccccaattt tctcaaacag aggtaatgaa acgtttggtt aaattaggtc gcatctctga    5220
ggagtgtggt tttgataccg tatggttact ggagcatcat ttcacggagt ttggttttgct    5280
```

```
tggtaaccct tatgtcgctg ctgcatattt acttggcgcg actaaaaaat tgaatgtagg    5340
aactgccgct attgttcttc ccacagccca tccagtacgc caacttgaag atgtgaattt    5400
attggatcaa atgtcaaaag gacgatttcg gtttggtatt tgccgagggc tttacaacaa    5460
ggactttcgc gtattcggca cagatatgaa taacagtcgc gccttagcgg aatgctggta    5520
cgggctgata aagaatggca tgacagaggg atatatggaa gctgataatg aacatatcaa    5580
gttccataag gtaaaagtaa accccgcggc gtatagcaga ggtggcgcac cggtttatgt    5640
ggtggctgaa tcagcttcga cgactgagtg ggctgctcaa tttggcctac cgatgatatt    5700
aagttggatt ataaatacta acgaaaagaa agcacaactt gagctttata atgaagtggc    5760
tcaagaatat gggcacgata ttcataatat cgaccattgc ttatcatata aacatctgt    5820
agatcatgac tcaattaaag cgaaagagat ttgccggaaa tttctggggc attggtatga    5880
ttcttatgtg aatgctacga ctattttga tgattcagac caaacaagag gttatgattt    5940
caataaaggg cagtggcgtg actttgtatt aaaaggacat aaagatacta atcgccgtat    6000
tgattacagt tacgaaatca atcccgtggg aacgccgcag gaatgtattg acataattca    6060
aaaagacatt gatgctacag gaatatcaaa tatttgttgt ggatttgaag ctaatggaac    6120
agtagacgaa attattgctt ccatgaagct cttccagtct gatgtcatgc catttcttaa    6180
agaaaaacaa cgttcgctat tatattagct aaggagaaag aaatgaaatt tggattgttc    6240
ttccttaact tcatcaattc aacaactgtt caagaacaaa gtatagttcg catgcaggaa    6300
ataacggagt atgttgataa gttgaatttt gaacagattt tagtgtatga aaatcatttt    6360
tcagataatg gtgttgtcgg cgctcctctg actgtttctg gttttctgct cggtttaaca    6420
gagaaaatta aaattggttc attaaatcac atcattacaa ctcatcatcc tgtcgccata    6480
gcggaggaag cttgcttatt ggatcagtta agtgaaggga gatttatttt agggtttagt    6540
gattgcgaaa aaaagatga aatgcatttt tttaatcgcc cggttgaata tcaacagcaa    6600
ctatttgaag agtgttatga aatcattaac gatgctttaa caacaggcta ttgtaatcca    6660
gataacgatt tttatagctt ccctaaaata tctgtaaatc cccatgctta tacgccaggc    6720
ggacctcgga aatatgtaac agcaaccagt catcatattg ttgagtgggc ggccaaaaaa    6780
ggtattcctc tcatctttaa gtgggatgat tctaatgatg ttagatatga atatgctgaa    6840
agatataaag ccgttgcgga taaatatgac gttgacctat cagagataga ccatcagtta    6900
atgatattag ttaactataa cgaagatagt aataaagcta acaagagac gcgtgcattt    6960
attagtgatt atgttcttga aatgcaccct aatgaaaatt tcgaaaataa acttgaagaa    7020
ataattgcag aaaacgctgt cggaaattat acggagtgta aactgcggc taagttggca    7080
attgaaaagt gtggtgcgaa aagtgtattg ctgtcctttg aaccaatgaa tgatttgatg    7140
agccaaaaaa atgtaatcaa tattgttgat gataatatta agaagtacca catggaatat    7200
acctaataga tttcgagttg cagcgaggcg gcaagtgaac gaatcccag gagcatagat    7260
aactatgtga ctgggtgag tgaaagcagc caacaaagca gcagcttgaa agatgaaggg    7320
tataaaagag tatgacagca gtgctgccat actttctaat attatcttga ggagtaaaac    7380
aggtatgact tcatatgttg ataaacaaga aattacagca agctcagaaa ttgatgattt    7440
gattttttcg agcgatccat tagtgtggtc ttacgacgag caggaaaaaa tcagaaagaa    7500
acttgtgctt gatgcatttc gtaatcatta taaacattgt cgagaatatc gtcactactg    7560
tcaggcacac aaagtagatg acaatattac ggaaattgat gacatacctg tattcccaac    7620
atcggttttt aagtttactc gcttattaac ttctcaggaa aacgagattg aaagttggtt    7680
```

```
taccagtagc ggcacgaatg gtttaaaaag tcaggtggcg cgtgacagat taagtattga    7740
gagactctta ggctctgtga gttatggcat gaaatatgtt ggtagttggt ttgatcatca    7800
aatagaatta gtcaatttgg gaccagatag atttaatgct cataatattt ggtttaaata    7860
tgttatgagt ttggtggaat tgttatatcc tacgacattt accgtaacag aagaacgaat    7920
agattttgtt aaaacattga atagtcttga acgaataaaa aatcaaggga aagatctttg    7980
tcttattggt tcgccatact ttattttattt actctgccat tatatgaaag ataaaaaaat    8040
ctcattttct ggagataaaa gcctttatat cataaccgga ggcggctgga aaagttacga    8100
aaaagaatct ctgaaacgtg atgatttcaa tcatctttta tttgatactt tcaatctcag    8160
tgatattagt cagatccgag atatatttaa tcaagttgaa ctcaacactt gtttctttga    8220
ggatgaaatg cagcgtaaac atgttccgcc gtgggtatat gcgcgagcgc ttgatcctga    8280
aacgttgaaa cctgtacctg atggaacgcc ggggttgatg agttatatgg atgcgtcagc    8340
aaccagttat ccagcattta tgttaccga tgatgtcggg ataattagca gagaatatgg    8400
taagtatccc ggcgtgctcg ttgaaatttt acgtcgcgtc aatacgagga cgcagaaagg    8460
gtgtgcttta agcttaaccg aagcgtttga tagttgataa acgcgtgcta gaggcatcaa    8520
ataaaacgaa aggctcagtc gaaagactgg gcctttcgtt ttatctgttg tttgtcggtg    8580
aacgctctcc tgagtaggac aaatccgccg cctagctaat tttaaagta tgggcaatca    8640 attgctcctg ttaaaattgc tttagaaata ctttggcagc ggtttgttgt attgagtttc    8700
atttgcgcat tggttaaatg gaaagtgaca gtacgctcac tgcagcctaa tatttttgaa    8760
atatcccaag agcttttttcc ttcgcatgcc cacgctaaac attcttttttc tcttttggtt    8820 aaatcgttgt ttgatttatt atttgctata tttattttttc gataattatc aactagagaa    8880
ggaacaatta atggtatgtt catacacgca tgtaaaaata aactatctat atagttgtct    8940
ttttctgaat gtgcaaaact aagcattccg aagccattgt tagccgtatg aatagggaaa    9000
ctaaacccag tgataagacc tgatgttttc gcttctttaa ttacatttgg agattttta    9060 tttacagcat tgttttcaaa tatattccaa ttaattggtg aatgattgga gttagaataa    9120
tctactatag gatcatattt tattaaatta gcgtcatcat aatattgcct ccatttttta    9180
gggtaattat ctagaattga aatatcagat ttaaccatag aatgaggata aatgatcgcg    9240
agtaaataat attcacaatg taccatttta gtcatatcag ataagcattg attaatatca    9300
ttattgcttc tacaagcttt aatttttatta attattctgt atgtgtcgtc ggcatttatg    9360
tttttcatac ccatctcttt atccttacct attgtttgtc gcaagttttg cgtgttatat    9420
atcattaaaa cggtaatgga ttgacatttg attctaataa attggatttt tgtcacacta    9480
ttgtatcgct gggaatacaa ttacttaaca taagcacctg taggatcgta caggtttacg    9540
caagaaaatg gtttgttata gtcgaatgaa ttcattaaag aggagaaagg taccatgccc    9600
tccaaatcct tggttatgga atatttggct catcccagta cactcggctt ggctgttgga    9660
gttgcttgtg gcatgtgcct gggctggagc cttcgagtat gctttgggat gctccccaaa    9720
agcaagacga gcaagacaca cacagatact gaaagtgaag caagcatctt gggagacagc    9780
tctcgaggta ccggcggcgg cagcctgggc gatccgaaca gcggctgccg cggcgataaa    9840
ggcccggatt gctaaaagct taattagctg atctagacgc gtgctagagg catcaaataa    9900
aacgaaaggc tcagtcgaaa gactgggcct ttcgttttat ctgttgtttg tcggtgaacg    9960
ctctcctgag taggacaaat ccgccgccct agacctaggg gatatattcc gcttcctcgc    10020
```

| | | | | |
|---|---|---|---|---|
| tcactgactc | gctacgctcg | gtcgttcgac | tgcggcgagc | ggaaatggct | tacgaacggg | 10080 |
| gcggagattt | cctggaagat | gccaggaaga | tacttaacag | ggaagtgaga | gggccgcggc | 10140 |
| aaagccgttt | ttccataggc | tccgcccccc | tgacaagcat | cacgaaatct | gacgctcaaa | 10200 |
| tcagtggtgg | cgaaacccga | caggactata | aagataccag | gcgttccccc | ctggcggctc | 10260 |
| cctcgtgcgc | tctcctgttc | ctgcctttcg | gtttaccggt | gtcattccgc | tgttatggcc | 10320 |
| gcgtttgtct | cattccacgc | ctgacactca | gttccgggta | ggcagttcgc | tccaagctgg | 10380 |
| actgtatgca | cgaaccccccc | gttcagtccg | accgctgcgc | cttatccggt | aactatcgtc | 10440 |
| ttgagtccaa | cccggaaaga | catgcaaaag | caccactggc | agcagccact | ggtaattgat | 10500 |
| ttagaggagt | tagtcttgaa | gtcatgcgcc | ggttaaggct | aaactgaaag | gacaagtttt | 10560 |
| ggtgactgcg | ctcctccaag | ccagttacct | cggttcaaag | agttggtagc | tcagagaacc | 10620 |
| ttcgaaaaac | cgccctgcaa | ggcggttttt | tcgttttcag | agcaagagat | tacgcgcaga | 10680 |
| ccaaaacgat | ctcaagaaga | tcatcttatt | aatcagataa | aatatttcta | gatttcagtg | 10740 |
| caatttatct | cttcaaatgt | agcacctgaa | gtcagcccca | tacgatataa | gttgttacta | 10800 |
| gtgcttggat | tctcaccaat | aaaaaacgcc | cggcggcaac | cgagcgttct | gaacaaatcc | 10860 |
| agatggagtt | ctgaggtcat | tactggatct | atcaacagga | gtccaagcac | tcacgttaag | 10920 |
| ggattttggt | catgactagt | gcttggattc | tcaccaataa | aaaacgcccg | gcggcaaccg | 10980 |
| agcgttctga | acaaatccag | atggagtcct | gaggtcatta | ctggatctat | caacaggagt | 11040 |
| ccaagcgagc | tctcgaaccc | cagagtcccg | ctcagaagaa | ctcgtcaaga | aggcgataga | 11100 |
| aggcgatgcg | ctgcgaatcg | ggagcggcga | taccgtaaag | cacgaggaag | cggtcagccc | 11160 |
| attcgccgcc | aagctcttca | gcaatatcac | gggtagccaa | cgctatgtcc | tgatagcggt | 11220 |
| ccgccacacc | cagccggcca | cagtcgatga | atccagaaaa | gcggccattt | tccaccatga | 11280 |
| tattcggcaa | gcaggcatcg | ccatgggtca | cgacgagatc | ctcgccgtcg | ggcatgcgcg | 11340 |
| ccttgagcct | ggcgaacagt | tcggctggcg | cgagcccctg | atgctcttcg | tccagatcat | 11400 |
| cctgatcgac | aagaccggct | tccatccgag | tacgtgctcg | ctcgatgcga | tgtttcgctt | 11460 |
| ggtggtcgaa | tgggcaggta | gccggatcaa | gcgtatgcag | ccgccgcatt | gcatcagcca | 11520 |
| tgatggatac | tttctcggca | ggagcaaggt | gagatgacag | gagatcctgc | cccggcactt | 11580 |
| cgcccaatag | cagccagtcc | cttcccgctt | cagtgacaac | gtcgagcaca | gctgcgcaag | 11640 |
| gaacgcccgt | cgtggccagc | cacgatagcc | gcgctgcctc | gtcctgcagt | tcattcaggg | 11700 |
| caccggacag | gtcggtcttg | acaaaaagaa | ccgggcgccc | ctgcgctgac | agccggaaca | 11760 |
| cggcggcatc | agagcagccg | attgtctgtt | gtgcccagtc | atagccgaat | agcctctcca | 11820 |
| cccaagcggc | cggagaacct | gcgtgcaatc | catcttgttc | aatcatgcga | aacgatcctc | 11880 |
| atcctgtctc | ttgatcagat | cttgatcccc | tgcgccatca | gatccttggc | ggcaagaaag | 11940 |
| ccatccagtt | tactttgcag | ggcttcccaa | ccttaccaga | gggcgcccca | gctggcaatt | 12000 |
| ccgacgtcta | agaaaccatt | attatcatga | cattaaccta | taaaaatagg | cgtatcacga | 12060 |
| ggccctttcg | tcttcac | | | | | 12077 |

<210> SEQ ID NO 2
<211> LENGTH: 858
<212> TYPE: DNA
<213> ORGANISM: Vibrio fischeri

<400> SEQUENCE: 2

| | | | | | | |
|---|---|---|---|---|---|---|
| attttttaaag | tatgggcaat | caattgctcc | tgttaaaatt | gctttagaaa | tactttggca | 60 |

```
gcggtttgtt gtattgagtt tcatttgcgc attggttaaa tggaaagtga cagtacgctc      120
actgcagcct aatatttttg aaatatccca agagcttttt ccttcgcatg cccacgctaa      180
acattctttt tctcttttgg ttaaatcgtt gtttgattta ttatttgcta tatttatttt      240
tcgataatta tcaactagag aaggaacaat taatggtatg ttcatacacg catgtaaaaa      300
taaactatct atatagttgt cttttctga atgtgcaaaa ctaagcattc cgaagccatt       360
gttagccgta tgaataggga aactaaaccc agtgataaga cctgatgttt tcgcttcttt      420
aattacattt ggagattttt tatttacagc attgttttca aatatattcc aattaattgg     480
tgaatgattg gagttagaat aatctactat aggatcatat tttattaaat tagcgtcatc      540
ataatattgc ctccattttt tagggtaatt atctagaatt gaaatatcag atttaaccat      600
agaatgagga taaatgatcg cgagtaaata atattcacaa tgtaccattt tagtcatatc      660
agataagcat tgattaatat cattattgct tctacaagct ttaattttat taattattct      720
gtatgtgtcg tcggcattta tgtttttcat acccatctct ttatccttac ctattgtttg      780
tcgcaagttt tgcgtgttat atatcattaa aacggtaatg gattgacatt tgattctaat     840
aaattggatt tttgtcac                                                    858

<210> SEQ ID NO 3
<211> LENGTH: 612
<212> TYPE: DNA
<213> ORGANISM: Vibrio fischeri

<400> SEQUENCE: 3
atgactataa tgataaaaaa atcggatttt ttggcaattc catcggagga gtataaaggt       60
attctaagtc ttcgttatca agtgtttaag caaagacttg agtgggactt agttgtagaa      120
aataaccttg aatcagatga gtatgataac tcaaatgcag aatatattta tgcttgtgat      180
gatactgaaa atgtaagtgg atgctggcgt ttattaccta caacaggtga ttatatgctg      240
aaaagtgttt ttcctgaatt gcttggtcaa cagagtgctc ccaaagatcc taatatagtc      300
gaattaagtc gttttgctgt aggtaaaaat agctcaaaga taaataactc tgctagtgaa      360
attacaatga aactatttga agctatatat aaacacgctg ttagtcaagg tattacagaa      420
tatgtaacag taacatcaac agcaatagag cgattttttaa agcgtattaa agttccttgt     480
catcgtattg gagacaaaga aattcatgta ttaggtgata ctaaatcggt tgtattgtct      540
atgcctatta tgaacagtt taaaaaagca gtcttaaatg cagcgaacga cgaaaattac      600
gcccttgcag cg                                                          612

<210> SEQ ID NO 4
<211> LENGTH: 31
<212> TYPE: PRT
<213> ORGANISM: Artificial Sequence
<220> FEATURE:
<223> OTHER INFORMATION: Linker

<400> SEQUENCE: 4

Gly Gly Gly Gly Ser Gly Gly Gly Ser Gly Gly Gly Gly Ser Leu
1               5                   10                  15

Gly Asp Pro Asn Ser Gly Cys Arg Gly Asp Lys Gly Pro Asp Cys
            20                  25                  30

<210> SEQ ID NO 5
<211> LENGTH: 96
<212> TYPE: DNA
```

```
<213> ORGANISM: Artificial Sequence
<220> FEATURE:
<223> OTHER INFORMATION: iRGD

<400> SEQUENCE: 5
ggcggcggcg gcagcggcgg cggcggcagc ggcggcggcg gcagcctggg cgatccgaac     60
agcggctgcc gcggcgataa aggcccggat tgctaa                              96

<210> SEQ ID NO 6
<211> LENGTH: 186
<212> TYPE: DNA
<213> ORGANISM: Homo sapiens

<400> SEQUENCE: 6
atgccctcca atccttggt tatggaatat ttggctcatc ccagtacact cggcttggct     60
gttggagttg cttgtggcat gtgcctgggc tggagccttc gagtatgctt tgggatgctc   120
cccaaaagca agacgagcaa gacacacaca gatactgaaa gtgaagcaag catcttggga   180
gacagc                                                              186

<210> SEQ ID NO 7
<211> LENGTH: 5984
<212> TYPE: DNA
<213> ORGANISM: Artificial Sequence
<220> FEATURE:
<223> OTHER INFORMATION: pB33eCPX-NC-IRGD

<400> SEQUENCE: 7
gcaaactatt aactggcgaa ctacttactc tagcttcccg gcaacaatta atagactgga     60
tggaggcgga taaagttgca ggaccacttc tgcgctcggc ccttccggct ggctggttta   120
ttgctgataa atctggagcc ggtgagcgtg gtctcgcgg tatcattgca gcactggggc    180
cagatggtaa gccctcccgt atcgtagtta tctacacgac ggggagtcag gcaactatgg   240
atgaacgaaa tagacagatc gctgagatag gtgcctcact gattaagcat tggtaactgt   300
cagaccaagt ttactcatat atactttaga ttgatttacg cgccctgtag cggcgcatta   360
agcgcggcgg gtgtggtggt tacgcgcagc gtgaccgcta cacttgccag cgccctagcg   420
cccgctcctt tcgctttctt cccttccttt ctcgccacgt tcgccggctt tccccgtcaa   480
gctctaaatc gggggctccc tttagggttc cgatttagtg ctttacggca cctcgacccc   540
aaaaaacttg atttgggtga tggttcacgt agtgggccat cgccctgata acggttttt    600 cgccctttga cgttggagtc cacgttcttt aatagtggac tcttgttcca aacttgaaca   660
acactcaacc ctatctcggg ctattctttt gatttataag ggattttgcc gatttcggcc   720
tattggttaa aaaatgagct gatttaacaa aaatttaacg cgaattttaa caaaatatta   780
acgtttacaa tttaaaagga tctaggtgaa gatccttttt gataatctca tgaccaaaat   840
cccttaacgt gagttttcgt tccactgagc gtcagacccc gtagaaaaga tcaaaggatc   900
ttcttgagat cctttttttc tgcgcgtaat ctgctgcttg caaacaaaaa aaccaccgct   960
accagcggtg gtttgtttgc cggatcaaga gctaccaact cttttttccga aggtaactgg  1020 cttcagcaga gcgcagatac caaatactgt ccttctagtg tagccgtagt taggccacca  1080
cttcaagaac tctgtagcac cgcctacata cctcgctctg ctaatcctgt taccagtcag  1140
gcatttgaga agcacacggt cacactgctt ccggtagtca ataaccggt aaaccagcaa   1200 tagacataag cggctatttta acgaccctgc cctgaaccga cgaccgggtc gaatttgctt  1260
tcgaatttct gccattcatc cgcttattat cacttattca ggcgtagcac caggcgttta  1320
```

```
agggcaccaa taactgcctt aaaaaaatta cgccccgccc tgccactcat cgcagtactg    1380
ttgtaattca ttaagcattc tgccgacatg gaagccatca cagacggcat gatgaacctg    1440
aatcgccagc ggcatcagca ccttgtcgcc ttgcgtataa tatttgccca tggtgaaaac    1500
gggggcgaag aagttgtcca tattggccac gtttaaatca aaactggtga aactcaccca    1560
gggattggct gagacgaaaa acatattctc aataaaccct ttagggaaat aggccaggtt    1620
ttcaccgtaa cacgccacat cttgcgaata tatgtgtaga aactgccgga atcgtcgtg     1680 gtattcactc cagagcgatg aaaacgtttc agtttgctca tggaaaacgg tgtaacaagg    1740
gtgaacacta tcccatatca ccagctcacc gtctttcatt gccatacgga attccggatg    1800
agcattcatc aggcgggcaa gaatgtgaat aaaggccgga taaaacttgt gcttattttt    1860
ctttacggtc tttaaaaagg ccgtaatatc cagctgaacg gtctggttat aggtacattg    1920
agcaactgac tgaaatgcct caaaatgttc tttacgatgc cattgggata tatcaacggt    1980
ggtatatcca gtgattttttt tctccatttt agcttcctta gctcctgaaa atctcgataa    2040
ctcaaaaaat acgcccggta gtgatcttat ttcattatgg tgaaagttgg aacctcttac    2100
gtgccgatca acgtctcatt ttcgccaaaa gttggcccag gcttcccgg tatcaacagg     2160 gacaccagga tttatttatt ctgcgaagtg atcttccgtc acaggtattt attcggcgca    2220
aagtgcgtcg ggtgatgctg ccaacttact gatttagtgt atgatggtgt ttttgaggtg    2280
ctccagtggc ttctgtttct atcagctgtc cctcctgttc agctactgac ggggtggtgc    2340
gtaacggcaa aagcaccgcc ggacatcagc gctagcggag tgtatactgg cttactatgt    2400
tggcactgat gagggtgtca gtgaagtgct tcatgtggca ggagaaaaaa ggctgcaccg    2460
gtgcgtcagc agaatatgtg atacaggata tattccgctt cctcgctcac tgactcgcta    2520
cgctcggtcg ttcgactgcg gcgagcggaa atggcttacg aacggggcgg agatttcctg    2580
gaagatgcca ggaagatact aacaggaa gtgagagggc cgcggcaaag ccgttttttcc     2640 ataggctccg cccccctgac aagcatcacg aaatctgacg ctcaaatcag tggtggcgaa    2700
acccgacagg actataaaga taccaggcgt ttccccctgg cggctccctc gtgcgctctc    2760
ctgttcctgc ctttcggttt accggtgtca ttccgctgtt atggccgcgt ttgtctcatt    2820
ccacgcctga cactcagttc cgggtaggca gttcgctcca agctggactg tatgcacgaa    2880
ccccccgttc agtccgaccg ctgcgcctta tccggtaact atcgtcttga gtccaacccg    2940
gaaagacatg caaaagcacc actggcagca gccactggta attgatttag aggagttagt    3000
cttgaagtca tgcgccggtt aaggctaaac tgaaaggaca gttttggtg actgcgctcc     3060 tccaagccag ttacctcggt tcaaagagtt ggtagctcag agaaccttcg aaaaaccgcc    3120
ctgcaaggcg gttttttcgt tttcagcaag agagattacg cgcagaccaa aacgatctca    3180
agaagatcat cttattaatc agataaaata tttgctcatg agcccgaagt ggcgagcccg    3240
atcttcccca tcggtgatgt cggcgatata ggcgccagca accgcacctg tggcgccggt    3300
gatgccggcc acgatgcgtc cggcgtagag gatctgctca tgtttgacag cttatcatcg    3360
atgcataatg tgcctgtcaa atggacgaag cagggattct gcaaaccccta tgctactccg    3420 tcaagccgtc aattgtctga ttcgttacca attatgacaa cttgacggct acatcattca    3480
ctttttcttc acaaccggca cggaactcgc tcgggctggc cccggtgcat ttttaaata     3540 cccgcgagaa atagagttga tcgtcaaaac caacattgcg accgacgtg gcgataggca    3600 tccgggtggt gctcaaaagc agcttcgcct ggctgatacg ttggtcctcg cgccagctta    3660
```

```
agacgctaat ccctaactgc tggcggaaaa gatgtgacag acgcgacggc gacaagcaaa    3720
catgctgtgc gacgctggcg atatcaaaat tgctgtctgc caggtgatcg ctgatgtact    3780
gacaagcctc gcgtacccga ttatccatcg gtggatggag cgactcgtta atcgcttcca    3840
tgcgccgcag taacaattgc tcaagcagat ttatcgccag cagctccgaa tagcgccctt    3900
ccccttgccc ggcgttaatg atttgcccaa acaggtcgct gaaatgcggc tggtgcgctt    3960
catccgggcg aaagaacccc gtattggcaa atattgacgg ccagttaagc cattcatgcc    4020
agtaggcgcg cggacgaaag taaacccact ggtgatacca ttcgcgagcc tccggatgac    4080
gaccgtagtg atgaatctct cctggcggga acagcaaaat atcacccggt cggcaaacaa    4140
attctcgtcc ctgattttc accacccct gaccgcgaat ggtgagattg agaatataac    4200
ctttcattcc cagcggtcgg tcgataaaaa aatcgagata accgttggcc tcaatcggcg    4260
ttaaacccgc caccagatgg gcattaaacg agtatcccgg cagcagggga tcattttgcg    4320
cttcagccat acttttcata ctcccgccat tcagagaaga aaccaattgt ccatattgca    4380
tcagacattg ccgtcactgc gtcttttact ggctcttctc gctaaccaaa ccggtaaccc    4440
cgcttattaa aagcattctg taacaaagcg ggaccaaagc catgacaaaa acgcgtaaca    4500
aaagtgtcta taatcacggc agaaaagtcc acattgatta tttgcacggc gtcacacttt    4560
gctatgccat agcattttta tccataagat tagcggatcc tacctgacgc tttttatcgc    4620
aactctctac tgtttctcca tacccgtttt tttgggctag cgaattcgag ctcggtacct    4680
ttgaggtggt tatgaaaaaa attgcatgtc tttcagcact ggccgcagtt ctggctttca    4740
ccgcaggtac ttccgtagct ggccagtctg gccagtgtcg tggtgataaa cgtggtcctg    4800
atgaatgtgg agggcagtct gggcagtctg gtgactacaa caaaaaccag tactacggca    4860
tcactgctgt tccggcttac cgcattaacg actgggcaag catctacggt gtagtgggtg    4920
tgggttatgg taaattccag accactgaat acccgaccta caaacacgac accagcgact    4980
acggtttctc ctacggtgcg ggtctgcagt tcaacccgat ggaaaacgtt gctctggact    5040
tctcttacga gcagagccgt attcgtagcg ttgacgtagg cacctggatt ttgtctgttg    5100
gttaccgctt cgggagtaaa tcgcgtcgcg cgacttctac tgtaactggc ggttacgcac    5160
agagcgacgc tcagggccaa atgaacaaaa tgggcggttt caacctgaaa taccgctatg    5220
aagaagacaa cagcccgctg ggtgtgatcg gttctttcac ttacaccgag aaaagccgta    5280
ctgcaagctg tcgtggtgat aaacgtggtc ctgatgaatg ttaataaggc caaggtggcc    5340
aagcttggct gttttggcgg atgagagaag attttcagcc tgatacagat taaatcagaa    5400
cgcagaagcg gtctgataaa acagaatttg cctggcggca gtagcgcggt ggtcccacct    5460
gaccccatgc cgaactcaga agtgaaacgc cgtagcgccg atggtagtgt ggggtctccc    5520
catgcgagag tagggaactg ccaggcatca aataaaacga aaggctcagt cgaaagactg    5580
ggcctttcgt tttatctgtt gtttgtcggt gaacgctctc ctgagtagga caaatccgcc    5640
gggagcggat ttgaacgttg cgaagcaacg gcccggaggg tggcgggcag gacgcccgcc    5700
ataaactgcc aggcatcaaa ttaagcagaa ggccatcctg acggatggcc tttttgcgtt    5760
tctacaaact cttttgttta ttttctaaa tacattcaaa tatgtatccg ctcatgagac    5820
aataccctg ataaatgctt caataatatt gaaaaggaa gagtatgagt attcaacatt    5880
tccgtgtcgc ccttattccc ttttttgcgg cattttgcct tcctgttttt gctcacccag    5940
aaacgctggt gaaagtaaaa gatgctgaag atcagttggg tgca                   5984
```

PROGRAMMABLE DRUG DELIVERY PROFILES OF TUMOR-TARGETED BACTERIA

CROSS REFERENCE TO RELATED APPLICATIONS

This application claims priority to and is a United States National Stage filing inder 35 U.S.C. § 371 of International PCT Application Serial No. PCT/US2013/059832, filed Sep. 13, 2013, which claims priority to U.S. Provisional Application No. 61/700,663, filed Sep. 13, 2012, each of which is incorporated herein by reference in its entirety.

FIELD OF THE INVENTION

This disclosure relates to compositions capable of programmed delivery of therapeutic agents to cancer cells or other cells related to a hyperproliferative disorder in a subject. This disclosure further relates to method of programming at least one bacteria comprising an inducible promoter and a nucleic acid sequence encoding a cellular toxin that modulates the delivery of a therapeutic agent or is itself a therapeutic agent. The bacteria of the invention can be genetically engineered for use in the methods or other aspects of the invention described herein.

BACKGROUND OF THE INVENTION

The engineering of bacteria to controllably deliver therapeutics is an attractive application for synthetic biology. While most synthetic gene networks have been explored within microbes, there is a need for further characterization of in vivo circuit behavior in the context of applications where the host microbes are actively being investigated for efficacy and safety, such as tumor drug delivery. One major hurdle in is that culture-based selective pressures are absent in vivo, leading to strain-dependent instability of plasmid-based networks over time. Here, we experimentally characterize the dynamics of in vivo plasmid instability using attenuated strains of *S. typhimurium* and real-time monitoring of luminescent reporters. Computational modeling described the effects of growth rate and dosage on live-imaging signals generated by internal bacterial populations. This understanding will allow us to harness the transient nature of plasmid-based networks to create tunable temporal release profiles that reduce dosage requirements and increase the safety of bacterial therapies.

Over the past century, the ability of bacteria to accumulate preferentially in tumors has prompted the investigation of the use of a number of strains for cancer therapy, including *C. novyi, E. coli, V. cholorae, B. longum*, and *S. typhimurium* ([3], [12], [2], [24], [15], [21]). Attenuated strains of *S. typhimurium* have generated particular interest as they can innately home in on tumors and colonize a variety of sizes, and have exhibited safety and tolerance in human clinical trials ([22],[5],[19],[8]). *S. typhimurium* were initially shown to have anti-tumor effects through recruitment of the host immune system and competition with cancer cells for nutrients. Subsequently, engineered production of therapeutic cargo was added through simple genetic modifications. While these studies represent important advances in the use of bacteria for tumor therapies, the majority have relied on constitutive, "always on" cargo production ([9],[23], [14], [6]) that typically results in high dosages, off-target effects, and development of host resistance.

As a next step, synthetic biology seeks to add controlled and dynamic production of cargo by utilizing computationally-designed "circuits" that have sophisticated sensing and delivery capability ([7],[4],[17],$_s$[1]). These circuits can be designed to act as delivery systems that sense tumor-specific stimuli and self-regulate cargo production as accessary. Since plasmids are the common framework for synthetic circuits, we begin by characterizing the dynamics of plasmid-based gene expression in vivo by utilizing real-time luminescence imaging, quantitative biodistribution measurement, and computational modeling. Together, these approaches provide a framework for exploiting the inherent instability of plasmid-based networks, which will facilitate the generation of specific temporal release profiles directly within the tumor environment.

SUMMARY OF THE INVENTION

The invention relates to a method of delivering a therapeutic agent to a cancer cell by administering at least one bacterial cell to a subject, the bacterial cell comprising a therapeutic agent operably linked to at least one transcriptional element or promoter, wherein the transcriptional element modulates the expression or secretion of the therapeutic agent in response to the presence of a density or quantity of bacteria comprising the at least one transcriptional element or promoter. In some embodiments, the transcriptional element or promoter is non-constitutive.

The invention relates to a composition comprising at least one non-pathogenic bacterial cell, wherein the non-pathogenic bacterial cell comprises at least a first and a second nucleic acid sequence, the first nucleic acid sequence comprising at least one non-constitutive promoter operably linked to the second nucleic acid sequence, the second nucleic acid encoding at least one therapeutic agent, wherein the non-constitutive promoter is an inducible promoter responsive to at least one stimuli and the at least one stimuli comprises the presence of a certain density or a certain number of bacterial cells comprising the first and second nucleic acid sequences.

In some embodiments, the composition comprises at least one bacterial cell, wherein the at least one non-pathogenic bacterial cell is chosen from one or a combination of bacterial cells of the genera chosen from: *Salmonella, Escherichia, Firmicutes, Bacteroidetes, Lactobacillus, Bifidobacteria*, or *Acidopholus*.

In some embodiments, the composition disclosed herein, wherein the bacterial cell comprises no more than five exogenous nucleic acid sequences that are coding sequences, wherein the first exogenous nucleic acid sequence comprises at least one non-constitutive promoter operably linked to the second exogenous nucleic acid sequence that encodes the at least one therapeutic agent.

In some embodiments, the invention relates to a composition comprising at least one bacterial cell, wherein the bacterial cell comprises a first, a second, and a third exogenous nucleic acid sequence, wherein the first exogenous nucleic acid sequence comprises at least one inducible promoter, the second exogenous nucleic acid sequence encodes at least one therapeutic agent, and the third exogenous nucleic acid sequence encodes at least one amino acid sequence that directs targeting of the at least one therapeutic to a cancer cell or a cell associated with a hyperproliferative disorder. In some embodiments the promoter is operably linked to the nucleic acid sequence encoding a therapeutic agent and/or to the nucleic acid sequence encoding an amino acid that directs targeting of the at least one therapeutic agent to a cancer cell or a cell associated with a hyperprolierative disorder.

In some embodiments, the invention relates to a composition comprising at least one bacterial cell, wherein the bacterial cell comprises a first, a second, and a third exogenous nucleic acid sequence, wherein the first exogenous nucleic acid sequence comprises an inducible promoter, the second exogenous nucleic acid sequence encodes a therapeutic agent, and the third exogenous nucleic acid sequence encodes an amino acid sequence that directs targeting of the at least one therapeutic to the a cancer cell or a cell associated with a hyperproliferative disorder, and wherein the first, second, and third nucleic acid sequences reside on a single DNA plasmid.

In some embodiments, the invention relates to a composition comprising at least one bacterial cell, wherein the at least one bacterial cell comprises either: (a) a first, a second, and a third exogenous nucleic acid sequence, wherein the first exogenous nucleic acid sequence comprises an inducible promoter, the second exogenous nucleic acid sequence encodes a therapeutic agent, and the third exogenous nucleic acid sequence encodes an amino acid sequence that directs targeting of the at least one therapeutic to the a cancer cell or a cell associated with a hyperproliferative disorder, and wherein the first, second, and third nucleic acid sequences reside on at least one DNA plasmid; or (b) a first and a second exogenous nucleic acid sequence, wherein the first exogenous nucleic acid sequence comprises an inducible promoter, and the second exogenous nucleic acid sequence encodes a therapeutic agent, and the third exogenous nucleic acid sequence encodes an amino acid sequence that directs targeting of the at least one therapeutic to the a cancer cell or a cell associated with a hyperproliferative disorder, and wherein the first and second exogenous nucleic acid sequences reside on at least one DNA plasmid.

In some embodiments, the composition comprises at least one bacterial cell comprising a nucleic acid sequence that is an inducible and non-constitutive promoter, wherein the promoter is responsive to a single stimulus, wherein the stimulus comprises the presence of a certain density or a certain number of bacterial cells comprising the first and second exogenous nucleic acid sequences. In some embodiments, the composition disclosed herein, the at least one stimuli are generated naturally by a microenvironment or tissue of a subject. In some embodiments, the microenvironment or tissue of the subject is a solid tumor in the subject.

In some embodiments, the composition disclosed herein, wherein the at least one stimuli comprise the presence of a biofilm of bacteria.

In some embodiments, the composition comprises at least one bacterial cell comprising a nucleic acid sequence that encodes a therapeutic agent, wherein the therapeutic agent is a fusion protein encoded by the second nucleic acid sequence, the fusion protein comprising at least a first and second moiety, wherein the first moiety is a cellular toxin and the second moiety is a targeting sequence. the composition comprises at least one bacterial cell comprising a nucleic acid sequence that encodes a therapeutic agent, wherein the therapeutic agent is a fusion protein encoded by the second nucleic acid sequence, the fusion protein comprising at least a first and second moiety, wherein the first moiety is at least 70% homologous to SEQ ID NO:6 and the second moiety is at least 70% homologous to SEQ ID NO:5.

In some embodiments, the composition comprises at least one bacterial cell comprising a plasmid at least 70%, 75%, 80%, 85%, 90%, 95%, 96%, 97%, 98%, or 99% homologous to SEQ ID NO:1. In some embodiments, the composition comprises at least one bacterial cell comprising a plasmid at least 70%, 75%, 80%, 85%, 90%, 95%, 96%, 97%, 98%, or 99% homologous to SEQ ID NO:7. In some embodiments, a single plasmid encodes all of the exogenous nucleic acid sequences. In some embodiments, the at least one bacterial cells comprises or consists of SEQ ID NO:1 or SEQ ID NO:7.

In some embodiments, the composition comprises at least one bacterial cell comprising one or more exogenous nucleic acid sequences wherein at least one of the exogenous nucleic acid sequences is a coding sequence, and wherein each one or more exogenous nucleic acid sequences reside on a single plasmid.

In some embodiments, the composition comprises at least one bacterial cell comprising one or more exogenous nucleic acid sequences wherein each one or more exogenous nucleic acid sequences reside on a single plasmid consisting of or consisting essentially of SEQ ID NO:1.

In some embodiments, the invention relates to a composition comprising at least one bacteria cell disclosed herein, wherein the at least bacterial cell comprises at least two lux genes operably linked to one or more therapeutic agents. In some embodiments, the one or more therapeutic agents are one or more cellular toxins. In some embodiments, the composition comprises at least one bacterial cell, wherein the at least bacterial cell comprises at least two lux genes and one or more cellular toxins that is are least 70%, 75%, 80%, 85%, 90%, 95%, 96%, 97%, 98%, or 99% homologous to SEQ ID NO:6. In some embodiments, the cellular toxin is an amino acid encoded by a nucleic acid sequence at least 70%, 75%, 80%, 85%, 90%, 95%, 96%, 97%, 98%, or 99% homologous to SEQ ID NO:6 optionally fused to an amino acid encoded by a nucleic acid sequence at least 70%, 75%, 80%, 85%, 90%, 95%, 96%, 97%, 98%, or 99% homologous to SEQ ID NO:5. In some embodiments, the therapeutic agent is linked by a linker amino acid sequence at least 70%, 75%, 80%, 85%, 90%, 95%, 96%, 97%, 98%, or 99% homologous to SEQ ID NO:4.

In some embodiments, the invention relates to a composition comprising at least one bacterial cell disclosed herein, wherein the at least bacterial cell further comprises: (a) at least one exogenous nucleic acid sequence that encodes a marker amino acid sequence, and wherein the at least one exogenous nucleic acid sequences that encode a marker amino acid are optionally operably linked to the inducible promoter; or (b) at least one selectable marker.

In some embodiments, the invention relates to a pharmaceutical composition comprising: (a) the composition comprising any of the compositions disclosed herein, and (b) a pharmaceutically acceptable carrier or a pharmaceutically acceptable salt thereof. In some embodiments, the pharmaceutical composition disclosed herein, further comprises: (c) a chemotherapeutic compound.

In some embodiments, the invention relates to a pharmaceutical composition disclosed herein, wherein the pharmaceutical composition comprises one more radioactive isotopes, optionally incorporated into the at least bacterial cell. In some embodiments, the pharmaceutical composition comprises a therapeutically effective dose of the at least one bacterial cell. As used herein the terms "therapeutically effective dose" means the number of cells per dose administered to a subject in need thereof sufficient in number to ameliorate or reduce the burden of disease symptoms of the subject. In some embodiments, the terms "therapeutically effective dose" means the number of cells per dose administered to a subject in need thereof sufficient in number to reduce the rate of growth of a tumor or cancer cell or cell associated with a hyperproliferative disease, reduce the size of a tumor, or prevent the metastases of a tumor. In some embodiments, the pharmaceutical composition disclosed herein, wherein the therapeutically effective dose is from about $1 \times 10^4$ to about $1 \times 10^7$ bacterial cells. In some embodiments, the therapeutically effective dose is from about $1 \times 10^1$ to about $1 \times 10^7$ bacterial cells. In some embodiments, the therapeutically effective dose is from about $1 \times 10^2$ to about $1 \times 10^7$ bacterial cells. In some embodiments, the therapeutically effective dose is from about $1 \times 10^3$ to about $1 \times 10^7$ bacterial cells. In some embodiments, the therapeutically effective dose is from about $1 \times 10^4$ to about $1 \times 10^7$ bacterial cells. In some embodiments, the therapeutically effective dose is from about $1 \times 10^5$ to about $1 \times 10^7$ bacterial cells. In some embodiments, the therapeutically effective dose is from about $1 \times 10^6$ to about $1 \times 10^7$ bacterial cells.

In some embodiments, the therapeutically effective dose is from about $1 \times 10^1$ to about $1 \times 10^6$ bacterial cells. In some embodiments, the therapeutically effective dose is from about $1 \times 10^2$ to about $1 \times 10^6$ bacterial cells. In some embodiments, the therapeutically effective dose is from about $1 \times 10^3$ to about $1 \times 10^6$ bacterial cells. In some embodiments, the therapeutically effective dose is from about $1 \times 10^4$ to about $1 \times 10^6$ bacterial cells. In some embodiments, the therapeutically effective dose is from about $1 \times 10^5$ to about $1 \times 10^6$ bacterial cells.

In some embodiments, the therapeutically effective dose is from about $1 \times 10^1$ to about $1 \times 10^5$ bacterial cells. In some embodiments, the therapeutically effective dose is from about $1 \times 10^2$ to about $1 \times 10^5$ bacterial cells. In some embodiments, the therapeutically effective dose is from about $1 \times 10^3$ to about $1 \times 10^5$ bacterial cells. In some embodiments, the therapeutically effective dose is from about $1 \times 10^4$ to about $1 \times 10^5$ bacterial cells. In some embodiments, the therapeutically effective dose is from about $1 \times 10^1$ to about $1 \times 10^4$ bacterial cells. In some embodiments, the therapeutically effective dose is from about $1 \times 10^2$ to about $1 \times 10^4$ bacterial cells. In some embodiments, the therapeutically effective dose is from about $1 \times 10^1$ to about $1 \times 10^3$ bacterial cells. In some embodiments, the therapeutically effective dose is from about $1 \times 10^3$ to about $1 \times 10^4$ bacterial cells. In some embodiments, the therapeutically effective dose is from about $1 \times 10^2$ to about $1 \times 10^3$ bacterial cells. In some embodiments, the therapeutically effective dose is from about $1 \times 10^1$ to about $1 \times 10^2$ bacterial cells. In some embodiments, the the therapeutically effective dose is from about $1 \times 10^0$ to about $1 \times 10^2$ bacterial cells. In some embodiments, the therapeutically effective dose is from about $1 \times 10^0$ to about $1 \times 10^8$ bacterial cells. In some embodiments, the therapeutically effective dose is from about $1 \times 10^0$ to about $1 \times 10^9$ bacterial cells. In some embodiments, the therapeutically effective dose of bacterial cells is more than $1 \times 10^9$ bacterial cells. In some embodiments, the therapeutically effective dose of bacterial cells is less than 10 cells.

In some embodiments, a food product comprising the composition comprising at least one non-pathogenic bacterial cell, wherein the non-pathogenic bacterial cell comprises at least a first and a second nucleic acid sequence, the first nucleic acid sequence comprising at least one non-constitutive promoter operably linked to the second nucleic acid sequence, the second nucleic acid encoding at least one therapeutic agent, wherein the non-constitutive promoter is an inducible promoter responsive to at least one stimuli and the at least one stimuli comprises the presence of a certain density or a certain number of bacterial cells comprising the first and second nucleic acid sequences. In some embodiments, the food product further comprises a natural or non-natural food additive.

The invention also relates to a kit comprising the composition disclosed herein, or the pharmaceutical composition disclosed herein, or the food product disclosed herein. In some embodiments, the kit disclosed herein, further comprises a bacterial culture vessel. In some embodiments, the kit disclosed herein, further comprises a bacterial cell growth media.

In some embodiments, the at least one bacterial cell comprises at least a first and a second nucleic acid sequence, the first nucleic acid sequence comprising at least one non-constitutive promoter operably linked to the second nucleic acid sequence, the second nucleic acid encoding at least one therapeutic agent, wherein the non-constitutive promoter is an inducible promoter responsive to at least one stimuli and the at least one stimuli comprises the presence of a certain density or a certain number of bacterial cells comprising the first and second nucleic acid sequences. In some embodiments, the at least one bacterial cell comprises a selectable marker or marker amino acid sequence. In some embodiments, the at least one bacterial cell comprises a marker amino acid sequence that is a luciferase gene or a functional fragment thereof.

In some embodiments, the at least one bacterial cell disclosed herein, wherein the at least one bacterial cell is a non-pathogenic bacterial cell. In some embodiments, the at least one bacterial cell disclosed herein, further comprising: (a) at least a third exogenous nucleic acid sequence that encodes at least one marker amino acid sequence; and (b) at least one selectable marker.

In some embodiments, the at least one bacterial cell comprises is a strain of bacteria chosen from *Salmonella, Escherichia, Firmicutes, Bacteroidetes, Lactobacillus, Bifidobacteria,* or *Acidopholus*. In some embodiments, the at least one bacterial cell disclosed herein, wherein the at least one cell is a strain of *Salmonella typhimurium*. In some embodiments, the at least one bacterium is a non-pathogenic bacterium. In some embodiments, the bacterium is attenuated or rendered non-pathogenic by mutating one or more virulence factors. In some embodiments, the at least one bacterium is chosen from any species listed on Table 1. In some embodiments, the at least one bacterium is chosen from any species listed on Table 1 and the strain is mutated to attenuate one or more virulence factors. In some embodiments, the non-pathogenic bacterium is a pro-biotic bacterium.

In some embodiments, the invention relates to a method of treating or preventing cancer comprising administering to a subject in need thereof the a composition comprising at least one non-pathogenic bacterial cell, wherein the non-pathogenic bacterial cell comprises at least a first and a second nucleic acid sequence, the first nucleic acid sequence comprising at least one inducible and/or non-constitutive promoter operably linked to the second nucleic acid sequence, the second nucleic acid encoding at least one therapeutic agent, wherein the at least one inducible and/or non-constitutive promoter is responsive to at least one stimuli and the at least one stimuli comprises the presence of a certain density or a certain number of bacterial cells comprising the first and second nucleic acid sequences. In some embodiments, the method further comprises a step of administering one or more stimuli external to the subject in order to induce expression of the at least one therapeutic agent in the subject. In some embodiments, the method does not comprise administering any stimuli external to the body of the subject in order to induce expression of the at least one therapeutic agent in the subject. In some embodiments, the method further comprises a step of measuring the presence, absence or quantity of therapeutic agent in the subject one or more times subsequent to administration of the composition disclosed herein, or the pharmaceutical composition disclosed herein, or the food product disclosed herein. In some embodiments, the compositions, pharmaceutical compositions or food products are delivered to a subject in need thereof per os, per anus, per muscosal lavage, via intravenous injection, subcutaneous injection, via any form of injection.

In some embodiments, the invention relates to a method of reducing the growth of a cancer cell, solid tumor, or cell associated with a hyperproliferative disorder comprising administering to a subject in need thereof the composition disclosed herein, or the pharmaceutical composition disclosed herein, or the food product disclosed in paragraph herein. In some embodiments, the method further comprises a step of administering one or more stimuli external to the subject in order to induce expression of the at least one therapeutic agent in the subject.

In some embodiments, the invention relates to a method disclosed herein, wherein the method does not comprise administering any stimuli external to the body of the subject in order to induce expression of the at least one therapeutic agent in the subject. In some embodiments, the invention relates to a method disclosed herein, wherein the method further comprises a step of measuring the presence, absence or quantity of therapeutic agent in the subject one or more times subsequent to administration of the composition disclosed herein, or the pharmaceutical composition disclosed herein, or the food product disclosed herein.

In some embodiments, the invention relates to a method of delivering one or more therapeutic agents to a tumor in a subject comprising administering the composition comprising at least one non-pathogenic bacterial cell, wherein the non-pathogenic bacterial cell comprises at least a first and a second nucleic acid sequence, the first nucleic acid sequence comprising at least one non-constitutive promoter operably linked to the second nucleic acid sequence, the second nucleic acid encoding at least one therapeutic agent, wherein the non-constitutive promoter is an inducible promoter responsive to at least one stimuli and the at least one stimuli comprises the presence of a certain density or a certain number of bacterial cells comprising the first and second nucleic acid sequences; or the pharmaceutical composition disclosed herein, or the food product disclosed herein to the subject in need thereof. In some embodiments, the only stimulus for inducing expression of the therapeutic agent is the density or quantity of bacteria in a given microenvironment where the at least one bacterial cell colonizes. In some embodiments, the microenvironment is chosen from at or around a cancer cell, a cell associated with a hyperproliferative disorder, a solid tumor, or a metastatic tumor, or a grafted tumor.

In some embodiments, the invention relates to a method disclosed herein, wherein the method further comprises a step of administering one or more stimuli external to the subject in order to induce expression of the at least one therapeutic agent in the subject. In some embodiments, the invention relates to a method disclosed herein, wherein the method does not comprise administering any stimuli external to the body of the subject in order to induce expression of the at least one therapeutic agent in the subject. In some embodiments, the invention relates to a method disclosed herein, wherein the method does not comprise administering any light to the body of the subject in order to induce expression of the at least one therapeutic agent in the subject. In some embodiments, the invention relates to a method disclosed herein, wherein the method does not comprise administering any chemical agent to the body of the subject in order to induce expression of the at least one therapeutic agent in the subject prior to, simultaneously with, or subsequent to administration of the at least one bacterial cell.

In some embodiments, the invention relates to any of the methods disclosed herein, wherein the method comprises a step of measuring the presence, absence or quantity of therapeutic agent in the subject in need thereof one or more times subsequent to administration of the composition disclosed in herein, or the pharmaceutical composition disclosed herein, or the food product disclosed herein.

The invention also relates to a method of reducing tolerance to a therapeutic agent in a subject in need thereof comprising administering the composition disclosed in herein, or the pharmaceutical composition disclosed herein, or the food product disclosed herein to the subject in need thereof. In some embodiments, the method of reducing tolerance to a therapeutic agent further comprises a step of administering one or more stimuli external to the subject in order to induce expression of the at least one therapeutic agent in the subject.

In some embodiments, the method of reducing tolerance to a therapeutic agent does not comprise administering any stimuli external to the body of the subject in order to induce expression of the at least one therapeutic agent in the subject.

In some embodiments, the invention also relates to a method of manufacturing the composition disclosed herein, or the pharmaceutical composition disclosed herein, or the food product disclosed herein comprising transforming at least one of nucleic acid comprising at least one inducible and/or non-constitutive promoter into at least one or a combination of bacterial cells. In some embodiments, the method of manufacturing the compositions and food products herein further comprises culturing any of the at least one or a combination of bacterial cells in a tissue culture vessel.

The invention also relates to a pharmaceutical composition comprising the at least one bacterial cell disclosed herein for treatment or prevention of cancer, growth of cells associated with a hyperproliferative disorder, or metastases.

The invention also relates to a pharmaceutical composition comprising the at least one bacterial cell disclosed herein manufactured in a medicament for cancer, growth of cells associated with a hyperproliferative disorder, or metastases.

Embodiments include methods of using tumor-targeted bacteria to identify a therapeutically effective dose of therapeutic agent in a solid tumor, the method comprising administering any of the compositions, pharmaceutical compositions, or food products disclosed herein to a subject in need thereof in some embodiments, the subject is suspected of having or has been diagnosed with cancer or metastatic cancer.

DETAILED DESCRIPTION OF THE INVENTION

Figure 1A:
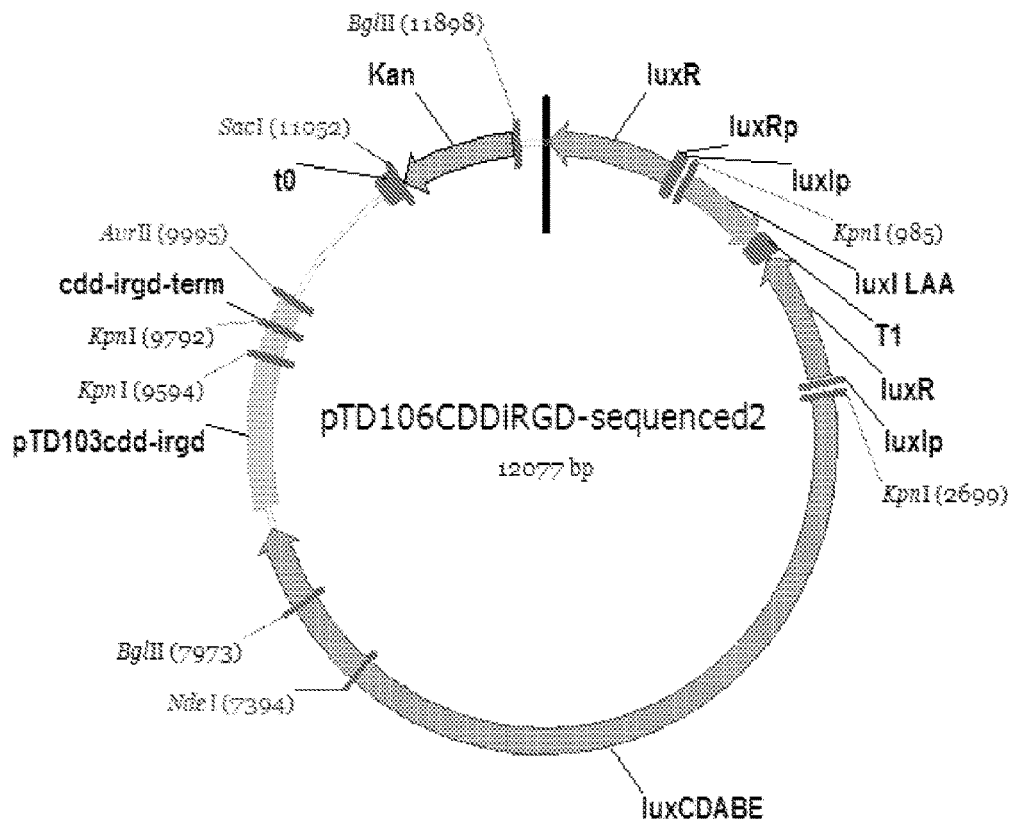
FIG. 1A depicts Plasmid map of the pTD106CDD-iRGD vector. The vector consists of a quorum sensing promoter driving both a luciferase expression cassette (luxCDABE) and a therapeutic (CDD-iRGD). The additional iRGD attached to the CDD gives a stronger internalization of the therapeutic into cells.

Some embodiments relate to bacteria which comprise heterologous nucleic acid sequences. The bacteria colonize tumors. In some embodiments, the non-pathogenic bacteria are non-pathogenic bacteria that colonize tumor cells or cancer cells, or cell associated with a hyperproliferative disorder, and, at a certain concentration or cell density, the bacteria secrete, release, or enhance the activation of a therapeutic agent. In some embodiments, the bacteria that comprise heterologous nucleic acid sequences comprise at least one inducible promoter or non-constitutive promoter. Some embodiments provide compositions comprising at least one bacterial cell disclosed herein.

In some embodiments, the compositions are pharmaceutical compositions that comprise at least one bacterial cell disclosed herein and at least one pharmaceutically acceptable carrier. Some embodiments provide pharmaceutical compositions of the claimed invention that are useful to treat and/or prevent cancer. Some embodiments are useful to treat or prevent metastases. Some embodiments are useful to treat or prevent tumor growth.

Some embodiments provide compositions comprising at least one bacterial cell that comprises one or more exogenous plasmids, wherein at least one plasmid comprises a heterologous nucleic acid sequence that encodes a therapeutic agent operably linked to an non-constitutive and/or inducible promoter; such non-constitutive and/or inducible promoter modulates the expression of the nucleic acid encoding the therapeutic agent in the presence of at least one stimulus. In some embodiments, the inducible and non-constitutive promoter only induces the expression of the nucleic acid encoding the therapeutic agent in the presence of a certain density or number of bacterial cells comprising the inducible promoter and/or the nucleic acid that encodes the therapeutic agent. When such a bacterial cell reproduces in vivo, such as when the bacterial cell colonizes a tumor in an animal, the clonally derived progeny of the at least one bacterial cells may reach a certain density or number that such density or number triggers the expression of the therapeutic agent. The ability of a bacterial cell to modulate expression of a gene in the presence of a certain number or density of cells is quorum sensing. In some embodiments, the non-constitutive or inducible promoter has only a single stimulus that is a certain number or density of cells. In some embodiments, the non-constitutive and/or inducible promoter responds to at least one, two, three, four, five or more stimuli but none of the stimuli require administration or exposure of the stimulus or stimuli external to the subject. In some embodiments, the stimulus or stimuli necessary to induce expression of the nucleic acid encoding the therapeutic agent require exposure to or administration of a cofactor before, simultaneously to, or after administration of the at least one bacterial cell.

In some embodiments, the at least one bacterial cell optionally comprises a nucleic acid sequence that encodes a polarization protein or functional fragment thereof and/or a nucleic acid sequence that encodes a combination of a toxin and an antidote. When such microorganism reproduces in vivo, such as when they are colonizing a tumor in an animal, a greater proportion of the resulting progeny remain plasmid-bearing compared to the proportion of resulting progeny from bacteria which do not comprise a nucleic acid sequence that encodes a polarization protein, or functional fragment thereof and/or a nucleic acid sequence that encode a combination of a toxin and an antidote. The polarization protein, or optionally, the combination of the polarization protein and a toxin and an antidote, reduces plasmid loss that occurs during cell division and facilitates the inclusion of both the plasmids in the at least one bacterial cell and its progeny upon cellular division. This feature of improves therapeutics that use bacteria that target and colonize tumors and release therapeutics or products involved in tumor detection. In some embodiments, the bacteria further comprise a nucleic acid sequence that encodes a protein used in therapeutic methods that cause slowed or inhibit tumor growth or reduce or eliminate tumors.

Specific preferred embodiments of the present invention have been described here in sufficient detail to enable those skilled in the art to practice the full scope of invention. However it is to be understood that many possible variations of the present invention, which have not been specifically described, still fall within the scope of the present invention and the appended claims. Hence these descriptions given herein are added only by way of example and are not intended to limit, in any way, the scope of this invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

The terms "amino acid" refer to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. In some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs including non-natural analogs.

The terms "exogenous gene" means a nucleic acid that has been recombinantly introduced into a cell, which encodes the synthesis of RNA and/or protein. In some embodiments, the exogenous gene is introduced by transformation. In some embodiments, the exogenous gene is introduced into the cell by electroporation. A transformed cell may be referred to as a recombinant cell, into which additional exogenous gene(s) may be introduced. The exogenous gene put into the host species may be taken from a different species (this is called heterologous), or it may naturally occur within the same species (this is homologous as defined below). Therefore, exogenous genes subsume homologous genes that are integrated within or introduced to regions of the genome, episome, or plasmid that differ from the locations where the gene naturally occurs. Multiple copies of the exogenous gene may be introduced into the cell. An exogenous gene may be present in more than one copy within the host cell or transformed cell. In some embodiments, the microorganism comprises between and including 1 and 10,000 copies of the nucleic acid that encodes an exogenous protein. In some embodiments, the microorganism comprises between and including 1 and 1,000 copies of the nucleic acid that encodes an exogenous protein. In some embodiments, the microorganism comprises between and including 1 and 10,000 copies of the nucleic acid that encodes an exogenous protein. In some embodiments, the microorganism comprises between and including 1 and 1,000 copies of the nucleic acid that encodes an exogenous protein. In some embodiments, the microorganism comprises between and including 1 and 500 copies of the nucleic acid that encodes an exogenous protein. In some embodiments, the exogenous gene is maintained by a cell as an insertion into the genome or as an episomal molecule. In some embodiments, the microorganism comprises no more than 1, 2, 3, 4, 5, 6, 7, 8, 9, 10, 20, 30, 40, 50, 60, 70, 80, 90, 100, or 1000 copies of the one or more nucleic acids that encode one or more exogenous proteins.

The terms "functional fragment" means any portion of a polypeptide or nucleic acid sequence from which the respective full-length polypeptide or nucleic acid relates that is of a sufficient length and has a sufficient structure to confer a biological affect that is similar or substantially similar to the full-length polypeptide or nucleic acid upon which the fragment is based. In some embodiments, a functional fragment is a portion of a full-length or wild-type nucleic acid sequence that encodes any one of the nucleic acid sequences disclosed herein, and said portion encodes a polypeptide of a certain length and/or structure that is less than full-length but encodes a domain that still biologically functional as compared to the full-length or wild-type protein. In some embodiments, the functional fragment may have a reduced biological activity, about equivalent biological activity, or an enhanced biological activity as compared to the wild-type or full-length polypeptide sequence upon which the fragment is based. In some embodiments, the functional fragment is derived from the sequence of an organism, such as a human. In such embodiments, the functional fragment may retain 99%, 98%, 97%, 96%, 95%, 94%, 93%, 92%, 91%, or 90% sequence identity to the wild-type human sequence upon which the sequence is derived. In some embodiments, the functional fragment may retain 85%, 80%, 75%, 70%, 65%, or 60% sequence homology to the wild-type sequence upon which the sequence is derived. The present invention also comprises functional fragments of nucleotide sequences that encode a polypeptide capable of enzymatic activity, substrate activity, polarization activity, toxin activity, or antidote to toxin activity as disclosed herein in an animal. In some embodiments, the functional fragment are DNA or amino acid fragments selected from at least one of the various encoding nucleotide sequences of the present invention, including SEQ ID NO: 1, 7, 5, 6, 4, 2, or 3 and can be any of the following described DNA fragments, as it applies to the specific encoding nucleic acid sequence provided herein. In some embodiments, DNA fragments can comprise 30 or more, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, 720 or more, 780 or more, 840 or more, 900 or more, 960 or more, 1020 or more, 1080 or more, 1140 or more, 1200 or more, 1260 or more, 1320 or more, 1380 or more, 1440 or more, 1500 or more, 1560 or more, 1620 or more, 1680 or more, or 1740 or more, 1800 or more, 2000 or more, 2100 or more, 2200 or more, 2300 or more, 2400 or more, 2500 or more, 2600 or more, 2700 or more, 2800 or more, 2900 or more, 3000 or more, 4000 or more, 4500 or more, 5000 or more, 5500 or more, 6000 or more, 6500 or more, 7000 or more, 7500 or more, 8000 or more, 8500 or more, 9000 or more, 9500 or more, 10000 or more, 10100 or more nucleotides. In some embodiments, DNA fragments can comprise coding sequences for accessory proteins such as known ligands to tumor associated antigens expressed on the surface of tumor cells. In some embodiments, DNA fragments can comprise fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 720, fewer than 780, fewer than 840, fewer than 900, fewer than 960, fewer than 1020, fewer than 1080, fewer than 1140, fewer than 1200, fewer than 1260, fewer than 1320, fewer than 1380, fewer than 1440, fewer than 1500, fewer than 1560, fewer than 1620, fewer than 1680, or fewer than 1740, fewer than 1800, fewer than 1900, fewer than 2000, fewer than 2100, fewer than 2200, fewer than 2300, fewer than 2400, fewer than 2500, fewer than 2600, fewer than 2700, fewer than 2800, fewer than 2900, fewer than 3000, fewer than 4000, fewer than 5000, fewer than 6000, fewer than 7000, fewer than 8000, fewer than 9000, or fewer than 10000 nucleotides. In some embodiments, the functional fragments are nucleic acid fragments of SEQ ID NO:1 and include one or more nucleic acid derivatives. In some embodiments, the functional fragments are nucleic acid fragments of SEQ ID NO:1, 2, 3, 7 and include more than about 5, 10, 15, 20, 25, or 30 nucleic acid derivatives.

The terms "hyperproliferative disorder" refer to a disorder characterized by abnormal proliferation, abnormal growth, abnormal senescence, abnormal quiescence, or abnormal removal of cells any or in an organism, and includes include hyperplasias, neoplasias, cancer, fibroproliferative disorders (such as involving connective tissues, as well as other disorders characterized by fibrosis, including for example, rheumatoid arthritis, insulin dependent diabetes mellitus, glomerulonephritis, cirrhosis, and scleroderma), smooth muscle proliferative disorders (such as atherosclerosis and restinosis), chronic inflammation, and epithelial cell proliferative disorders (for example, psoriasis; keratosis; acne; comedogenic lesions; verracous lesions such as verruca plana, plantar warts, verruca acuminata, and other verruciform lesions marked by proliferation of epithelial cells; folliculitis and pseudofolliculitis; keratoacanthoma; callosities; Darier's disease; ichfhyosis; lichen planus; molluscous contagiosum; melasma; Fordyce disease; and keloids or hypertrophic scars). In some embodiments, the hyperproliferative disease is a cancer derived from the gastrointestinal tract or urinary system. In some embodiments, a hyperproliferative disease is a cancer of the adrenal gland, bladder, bone, bone marrow, brain, spine, breast, cervix, gall bladder, ganglia, gastrointestinal tract, stomach, colon, heart, kidney, liver, lung, muscle, ovary, pancreas, parathyroid, penis, prostate, salivary glands, skin, spleen, testis, thymus, thyroid, or uterus. In some embodiments, the term hyperproliferative disease is a cancer chosen from: lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

As used herein, the term "genetic construct" refers to the DNA or RNA molecules that comprise a nucleotide sequence that encodes one or more of the polypeptides. In some embodiments, the genetic construct encodes one or more of the polypeptides described herein. In some embodiments, the nucleotide sequence that encodes a one or more of the polypeptides described herein, or coding sequence, includes initiation and termination signals operably linked to regulatory elements including a bacterial promoter and polyadenylation signal capable of directing expression in the cells of the bacteria in which the nucleic acid molecule is transformed.

The terms "effective amount" refers to an amount of a compound, material, or composition, as described herein effective to achieve a particular biological result such as, but not limited to, biological results disclosed, described, or exemplified herein. Such results may include, but are not limited to colonization of a tumor by administration of a composition disclosed herein, or production of an amount of a therapeutic agent, portion thereof, or a reaction product after exposure of the substrate with an enzyme such that the presence, absence or quantity of substrate, portion thereof, or a reaction product determined by any means suitable in the art. In some embodiments, the biological result is an amount of a substrate, portion thereof, or a reaction product after exposure of the substrate with an enzyme such that the presence, absence or quantity of substrate, portion thereof, or a reaction product determined by visual inspection of urine excreted by a subject administered any one or more compositions disclosed herein. The effective amount of the composition may be dependent on any number of variables, including without limitation, the species, breed, size, height, weight, age, overall health of the subject, the type of formulation, the mode or manner of administration, the type and/or severity of the particular condition being treated.

The terms "electroporation," "electro-permeabilization," or "electro-kinetic enhancement" ("EP") as used interchangeably herein refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, the term "expressible form" refers to gene constructs that contain the necessary regulatory elements operably linked to a coding sequence that encodes one or more proteins described herein, such that, when present in a transformed or transfected cell, the coding sequence will be expressed.

In some embodiments, the compositions, kits, methods comprise at least one non-pathogenic bacteria. As used herein, the term "non-pathogenic" refers to a bacteria that is not capable of causing a disease or disorder in an animal when administered to an animal, including a human. In some embodiments, the microorganism is incapable of causing a disease or disorder when administered to a mammal. In some embodiments, the microorganism is a non-pathogenic microorganism incapable of causing a disease or disorder when administered to a human or domesticated animal (such as a dog, cat, horse, sheep, cow, goat, pig, etc.). In some embodiments, the microorganism is non-pathogenic microorganism incapable of causing a disease or disorder when administered to a human. In some embodiments, the microorganism is non-pathogenic microorganism is chosen from any one of the bacterial species identified in Table 1. In some embodiments, the non-pathogenic microorganism is not at least one of species listed on Table 1. In some embodiments, the non-pathogenic microorganism is an attenuated bacterial strain. In some embodiments, the non-pathogenic microorganism is an attenuated bacterial strain listed on Table 1. In some embodiments, the non-pathogenic microorganism is an attenuated bacterial strain genetically modified to silence, remove, or mutate a virulence factor.

The term "nucleic acid" refers to a molecule comprising two or more linked nucleotides. "Nucleic acid" and "nucleic acid molecule" are used interchangeably and refer to oligoribonucleotides as well as oligodeoxyribonucleotides. The terms also include polynucleosides (i.e., a polynucleotide minus a phosphate) and any other organic base containing nucleic acid. The organic bases include adenine, uracil, guanine, thymine, cytosine and inosine. The nucleic acids may be single or double stranded. The nucleic acid may be naturally or non-naturally occurring. Nucleic acids can be obtained from natural sources, or can be synthesized using a nucleic acid synthesizer (i.e., synthetic). Isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, PNA or LNA, or a combination thereof, as described herein. Non-naturally occurring nucleic acids such as bacterial artificial chromosomes (BACs) can also be used in accordance with some aspects of this invention.

Some aspects of this invention relate to the use of nucleic acid derivatives. The use of certain nucleic acid derivatives may increase the stability of the nucleic acids of the invention by preventing their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages. Nucleic acid derivatives according to some aspects of this invention may contain backbone modifications such as but not limited to phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous. Nucleic acid derivatives according to some aspects of this invention may contain substitutions or modifications in the sugars and/or bases. For example, some nucleic acid derivatives may include nucleic acids having backbone sugars which are covalently attached to low molecular weight organic groups other than a hydroxyl group at the 3' position and other than a phosphate group at the 5' position (e.g., an 2'-O-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. In some embodiments, a nucleic acid may comprise a peptide nucleic acid (PNA), a locked nucleic acid (LNA), DNA, RNA, or a co-nucleic acids of the above such as DNA-LNA co-nucleic acid.

As used herein the term "isolated nucleic acid molecule" refers to a nucleic acid that is not in its natural environment, for example a nucleic acid that has been (i) extracted and/or purified from a cell or microbe, for example, a bacteria or yeast, by methods known in the art, for example, by alkaline lysis of the host cell and subsequent purification of the nucleic acid, for example, by a silica adsorption procedure; (ii) amplified in vitro, for example, by polymerase chain reaction (PCR); (iii) recombinantly produced by cloning, for example, a nucleic acid cloned into an expression vector; (iv) fragmented and size separated, for example, by enzymatic digest in vitro or by shearing and subsequent gel separation; or (v) synthesized by, for example, chemical synthesis. In some embodiments, the term "isolated nucleic acid molecule" refers to (vi) an nucleic acid that is chemically markedly different from any naturally occurring nucleic acid. In some embodiments, an isolated nucleic acid can readily be manipulated by recombinant DNA techniques well known in the art.

Accordingly, a nucleic acid cloned into a vector, or a nucleic acid delivered to a host cell and integrated into the host genome is considered isolated but a nucleic acid in its native state in its natural host, for example, in the genome of the host, is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein.

"Sequence homology" or "sequence identity" or "homologous to" are used herein interchangeably for nucleotides and amino acids sequences determined using FASTA, BLAST and Gapped BLAST (Altschul et al., Nuc. Acids Res., 1997, 25, 3389, which is incorporated herein by reference in its entirety) and PAUP* 4.Ob1O software (D. L. Swofford, Sinauer Associates, Massachusetts). Briefly, the BLAST algorithm, which stands for Basic Local Alignment Search Tool is suitable for determining sequence similarity (Altschul et al., J. Mol. Biol, 1990, 215, 403-410, which is incorporated herein by reference in its entirety). Software for performing BLAST analyses is publicly available through the National Center for Biotechnology Information (http://www.ncbi.nlm.nih.gov). One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001. "Percentage of similarity" or percentage of sequence identity" can be calculated using PAUP* 4.Ob1O software (D. L. Swofford, Sinauer Associates, Massachusetts). The average similarity of the consensus sequence is calculated compared to all sequences in the phylogenic tree. In some embodiments, the compostions disclosed herein comprise nucleic acid sequences that are at least 70%, 75%, 80%, 85%, 90%, 95%, 96%, 97%, 98%, 99% homologous to SEQ ID NO:1, SEQ ID NO: 5, SEQ ID NO: 6, and/or SEQ ID NO:7. In some embodiments, the compostions disclosed herein comprise nucleic acid or amino acid sequences that are at least 70%, 75%, 80%, 85%, 90%, 95%, 96%, 97%, 98%, 99% homologous to SEQ ID NOS:1-7.

As used herein, "conservative" amino acid substitutions may be defined as set out in Tables A, B, or C below. In some embodiments, the at least one bacterial cell of the present invention comprises any of the nucleic acid sequences or amino acid sequences disclosed herein with one or more conservative amino acid or nucleic acid mutations. The mutation may include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A.

TABLE A

Conservative Substitutions I

| Side Chain Characteristics | Amino Acid |
| --- | --- |
| Aliphatic | |
| Non-polar | G A P I L V F |
| Polar - uncharged | C S T M N Q |
| Polar - charged | D E K R |
| Aromatic | H F W Y |
| Other | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | Amino Acid |
| --- | --- |
| Non-polar (hydrophobic) | |
| Aliphatic: | A L I V P. |
| Aromatic: | F W Y |
| Sulfur-containing: | M |
| Borderline: | G Y |
| Uncharged-polar | |
| Hydroxyl: | S T Y |
| Amides: | N Q |
| Sulfhydryl: | C |
| Borderline: | G Y |
| Positively Charged (Basic): | K R H |
| Negatively Charged (Acidic): | D E |

Alternately, exemplary conservative substitutions are set out in Table C.

TABLE C

Conservative Substitutions III

| Original Residue | Exemplary Substitution |
| --- | --- |
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides comprising polypeptide sequences associated with the extracellular matrix described herein are intended to include polypeptides bearing one or more insertions, deletions, or substitutions, or any combination thereof, of amino acid residues as well as modifications other than insertions, deletions, or substitutions of amino acid residues.

The term "subject" is used throughout the specification to describe an animal to whom treatment with the compositions according to the present invention is provided or administered. For treatment of those conditions which are specific for a specific subject, such as a human being or such as a mammal, the term "patient" may be interchangeably used. In some instances in the description of the present invention, the term "patient" will refer to human patients. In some embodiments, the subject may be a mammal to whom the present invention is provided or administered. In some embodiments, the subject may be a domesticated mammal to whom the present invention is provided or administered such as a horse, dog, cat, pig, cow, goat, sheep, llama, or other non-human animal. In some embodiments, the subject is non-human. In some embodiments, the subject is a mammal suspected of having a hyperproliferative disorder. In some embodiments, the subject is an animal diagnosed with cancer and suspected of having cancer.

As used herein, the term "therapeutic agent" is any chemical compound, amino acid sequence, radioisotope, or combination thereof that can be used to reduce symptom burden or correct dysfunctional components of cellular pathways responsible for disease or improve a subject's prognosis or kill a cancer cell or cells. In some embodiments, the therapeutic agent treats or prevents metastatic cancer cell growth. In some embodiments, the therapeutic agent is an amino acid sequence that kills cancer cells or cells associated with a hyperproliferative disease. In some embodiments, the therapeutic agent is an amino acid sequence that enhances the ability of another molecule present in a particular microenvironment to kill cancer cells or cells associated with a hyperproliferative disease. In some embodiments, the therapeutic agent is an amino acid sequence that contains a cellular death domain and/or is a cellular toxin. In some embodiments, the cellular toxin in CDD or an amino acid analog thereof that is 70, 85 80, 85, 90, 95, 96, 97, 98, or 99% homolgous to CDD. In some embodiments, the therapeutic agent comprises a first and second moiety wherein the first moiety comprises one or more amino acid sequences that are cellular toxins and the second moiety comprises one or more targeting sequences. A targeting sequence for purposes of this invention is an amino acid sequence that directs delivery of a therapeutic agent to a target cell or microenvironment within a cell. In some embodiments, the therapeutic agent comprises a linker that fuses the first and second moieties. In some embodiments, the targeting moiety or targeting sequence comprises an amino acid sequence 70, 85 80, 85, 90, 95, 96, 97, 98, or 99% homolgous to iRGD or like proteins. In some embodiments, the therapeutic agent ican kill or enhance killing of colorectal cancer cells and/or ovarian cancer cells. In some embodiments, the at least one bacterial cell is administered sequentially, simultaneously, or subsequently to dosing with one or more of the following chemotherapeutic agents:
Trabectedin®
Belotecan®
Cisplatin®
Carboplatin®
Bevacizumab®
Pazopanib®
Colorectal Cancer:
5-Fluorouracil
Capecitabine®
Irinotecan®
Oxaliplatin®

In some embodiments, pharmaceutical compositions of the present invention comprise at least one bacterial cell disclosed herein, a pharmaceutical acceptable carrier, and at least one additional therapeutic agent. Combination products are contemplated by this invention. Many therapeutic agents are known. For instance, in some embodiments, the pharmaceutical compositions of the claimed invention comprise at least one additional therapeutic agent comprising any of the agents disclosed in U.S. Pat. Nos. 8,343,498, 6,849,272, 8,257,714, 8,466,110, 7,655,444, 6,693,112, 6,428,968, and 5,633,274, each of which are incorporated herein by reference in their entireties.

As used herein, the term "promoter" means at least a first nucleic acid sequence that regulates or mediates transcription of a second nucleic acid sequence. In some embodiments, the second nucleic acid sequence encodes a cellular toxin or an amino acid sequence that enhances cellular toxicity of a microenvironment in the absence or presence of a substance being secreted by a cell. In some embodiments, the second nucleic acid sequence encodes a cellular toxin or an amino acid sequence that enhances cellular toxicity of a microenvironment in the absence or presence of a substance being secreted by a cancer cell or cell associated with a hyperproliferative disorder. For purposes of the invention, a promoter may comprise nucleic acid sequences near the start site of transcription that are required for proper function of the promoter. As an example, a TATA element for a promoter of polymerase II type. Promoters of the present invention can include distal enhancer or repressor elements that may lie in positions from about 1 to about 5,000 base pairs from the initiation site. Promoters of the present invention can include distal enhancer or repressor elements that may lie in positions from about 1 to about 10,000 base pairs or more from the initiation site. Promoters of the present invention can include distal enhancer or repressor elements that may lie in positions from about 1 to about 1,000 base pairs from the initiation site. Promoters of the present invention can include distal enhancer or repressor elements that may lie in positions from about 1 to about 500 base pairs from the initiation site. The term "inducible promoter" refers to an operable linkage between a promoter and a nucleic acid sequence, whereby the promoter mediates the nucleic acid transcription in the presence or absence of at least one specific stimulus. In some embodiments, the inducible promoter mediates transcription of a nucleic acid sequence in the presence or absence of at least one, two, three, four, or five or more stimuli. In some embodiments, the one or more stimuli are not external stimuli in reference to the body of the subject to whom the at least one bacterial cell or compositions disclosed herein are administered. In some embodiments, the one or more stimuli are natural stimuli secreted or presented by the subject to whom the disclosed compositions or at least one bacterial cells are administered. In some embodiments, the at least one stimuli do not comprise light or a chemical molecule administered to the body of a subject before, simultaneously with, or after administration of the disclosed compositions or at least one bacterial cell. In some embodiments, the at least one stimuli is not administered to the body of a subject before, simultaneously with, or after administration of the disclosed compositions or at least one bacterial cell, but is a product or molecule found in the subject of a patient. In some embodiments, the none of the stimuli are administered to the body of a subject before, simultaneously with, or after administration of the disclosed compositions or at least one bacterial cell, but rather the stimulus is a product or molecule found in the subject of a patient. In some embodiments, the only stimulus of the promoter is presence of a certain density of bacteria found in the subject of a patient.

In some embodiments, the only stimulus of the promoter is presence of a certain density of bacteria found in the subject of a patient.

In some embodiments, the inducible promoter mediates transcription of a nucleic acid that enhances cellular toxicity either by encoding an amino acid that is toxic to a cell or encoding an amino acid sequence that increases the toxicity of a microenvironment in which the at least one bacterial cell colonizes and grows. In some embodiments, the inducible promoter mediates transcription of a nucleic acid that enhances cellular toxicity either by encoding an amino acid that is toxic to a cell or encoding an amino acid sequence that increases the toxicity of a microenvironment in the absence of presence of a cellular factor natively produced by the body of the subject. In some embodiments, the at least one specific stimulus is a certain density of bacteria carrying the inducible promoter in a tissue of a subject. In some embodiments, the at least one specific stimulus is the presence of absence of a cofactor. In some embodiments, the at least one specific stimulus is the presence of absence of a cofactor that is a tumor associated antigen. In some embodiments, the inducible promoter does not require any external stimulus other than the presence of a certain density of bacteria within a cofactor which can be added to the environment of the composition comprising the nucleic acid sequence that contains the inducible promoter. An "operable linkage" refers to an operative connection between nucleic acid sequences, such as for example between a control sequence (e.g. a promoter) and another nucleic acid sequence that codes for a protein i.e. a coding sequence. If a promoter can regulate transcription of an exogenous nucleic acid sequence then it is in operable linkage with the gene.

Bacterial Strains

The invention relates to bacterial cells comprising any one or more of the nucleic acid sequences of the disclosed herein. In some embodiments, the at least one bacterial cell comprises one or combination of any two or more bacterial species chosen from Table 1. In some embodiments, the bacteria are non-pathogenic. In some embodiments, the bacteria are attenuated. In some embodiments, the bacteria are attenuate and non-pathogenic. One of ordinary skill in the art would know how to attenuate a pathogenic bacteria to create non-pathogenic bacteria. In some embodiments, the bacteria are attenuated by removing, knocking out, or mutating a virulence gene such as altering genetic components of the bacterial secretion system. In some embodiments, at least one bacterial cell is a Mach1 (*E. coli* strain), *E. coli* Nissle, *E. coli* DH5alpha, or *S. Typhimurium* (strains SL7207, ELH430, ELH1301). In other embodiments, the bacterial strain is chosen from: *Bifidobacterium*, *Vibrio fischeri*, and *Bifidolongum*.

In some embodiments, the invention relates to a composition comprising at least one bacterial cell that comprises a first nucleic acid sequence that encodes a therapeutic amino acid sequence or functional fragment thereof operably linked to a second nucleic acid sequence that comprise one or more inducible promoters or functional fragments thereof operably linked to the first nucleic acid sequence, wherein the inducible promoter or functional fragment thereof mediates the non-constitutive expression of the first nucleic acid sequence. In some embodiments, the invention relates to a composition comprising at least one bacterial cell that comprises a first nucleic acid sequence that encodes a therapeutic amino acid sequence or functional fragment thereof operably linked to a second nucleic acid sequence encoding one or more inducible promoters or functional fragments thereof, wherein the inducible promoter or functional fragment thereof is a non-constitutive promoter that responds only to a single stimulus. In some embodiments, the invention relates to a composition comprising at least one bacterial cell that comprises a first nucleic acid sequence that encodes a therapeutic amino acid sequence or functional fragment thereof operably linked to a second nucleic acid sequence encoding one or more inducible promoters or functional fragments thereof, wherein the inducible promoter or functional fragment thereof is a non-constitutive promoter that mediates expression of the first nucleic acid sequence only in the presence or absence of a certain density of a bacterial cells comprising the first and second nucleic acid sequences.

In some embodiments, the invention relates to a composition comprising at least one bacterial cell that comprises a first nucleic acid sequence encoding an death domain or functional fragment thereof operably linked to a second nucleic acid sequence comprising one or more inducible promoters or functional fragments thereof, wherein the inducible promoter or functional fragments thereof are non-constitutive promoter. In some embodiments, the invention relates to a composition comprising at least one bacterial cell that comprises a first nucleic acid sequence encoding an death domain or functional fragment thereof operably linked to a second nucleic acid sequence encoding one or more inducible promoters or functional fragments thereof, wherein the inducible promoter is a non-constitutive promoter and responds to the density of bacteria in a tissue.

Some embodiments of the invention further comprise a third nucleic acid sequence encoding a bacterial toxin or functional fragment thereof, and a fourth nucleic acid sequence encoding an antidote to the bacterial toxin. In order to manufacture or produce such a non-pathogenic microorganism, one of ordinary skill in the art would contact the microorganism with a composition comprising each of the first, second, third, or fourth nucleic acid sequences. Methods to deliver expression vectors or expression constructs into microbes, for example, into non-pathogenic bacteria, are well known to those of skill in the art. Nucleic acids, including expression vectors, can be delivered to prokaryotic microbes by various methods well known to those of skill in the relevant biological arts. Methods for the delivery of nucleic acids to a microbe in accordance to some aspects of this invention, include, but are not limited to, different chemical, electrochemical and biological approaches, for example, heat shock transformation, electroporation, transfection, for example liposome-mediated transfection, DEAE-Dextran-mediated transfection or calcium phosphate transfection. In some embodiments, a nucleic acid construct, for example an expression construct comprising any combination of the first, second, third, and/or fourth nucleic acid sequences disclosed herein, is introduced into the host microbe using a vehicle, or vector, for transferring genetic material. Vectors for transferring genetic material to microbes are well known to those of skill in the art and include, for example, plasmids, artificial chromosomes, and viral vectors. Methods for the construction of nucleic acid constructs, including expression constructs comprising constitutive or inducible heterologous promoters, knockout and knockdown constructs, as well as methods and vectors for the delivery of a nucleic acid or nucleic acid construct to a microbe are well known to those of skill in the art, and are described, for example, in J. Sambrook and D. Russell, Molecular Cloning: A Laboratory Manual, Cold Spring Harbor Laboratory Press; 3rd edition (Jan. 15, 2001); David C. Amberg, Daniel J. Burke; and Jeffrey N. Strathern, Methods in Yeast Genetics: A Cold Spring Harbor Laboratory Course Manual, Cold Spring Harbor Laboratory Press (April 2005); John N. Abelson, Melvin I. Simon, Christine Guthrie, and Gerald R. Fink, Guide to Yeast Genetics and Molecular Biology, Part A, Volume 194 (Methods in Enzymology Series, 194), Academic Press (Mar. 11, 2004); Christine Guthrie and Gerald R. Fink, Guide to Yeast Genetics and Molecular and Cell Biology, Part B, Volume 350 (Methods in Enzymology, Vol 350), Academic Press; 1st edition (Jul. 2, 2002); Gregory N. Stephanopoulos, Aristos A. Aristidou and Jens Nielsen, Metabolic Engineering: Principles and Methodologies, Academic Press; 1 edition (Oct. 16, 1998); and Christina Smolke, The Metabolic Pathway Engineering Handbook: Fundamentals, CRC Press; 1 edition (Jul. 28, 2009), all of which are incorporated by reference herein in their entireties.

Some aspects of this invention relate to cultures of genetically modified microbes provided herein. In some embodiments, the culture comprises a genetically modified microbe provided herein and a medium, for example, a liquid medium. In some embodiments, the culture comprises a genetically modified microbe provided herein and a carbon source, for example, a carbohydrate source, or an organic acid or salt thereof. In some embodiments, the culture comprises a genetically modified microbe provided herein and a salt and/or buffer establishing conditions of salinity, osmolarity, and pH, that are amenable to survival, growth, and/or catalytic activity of the encoded enzyme. In some embodiments, the culture comprises an additional component, for example, an additive. Non-limiting examples of additives are nutrients, amino acids, albumin, growth factors, enzyme inhibitors (for example protease inhibitors), fatty acids, lipids, hormones (e.g., dexamethasone and gibberellic acid), trace elements, inorganic compounds (e.g., reducing agents, such as manganese), redox-regulators (e.g., antioxidants), stabilizing agents (e.g., dimethylsulfoxide), polyethylene glycol, polyvinylpyrrolidone (PVP), gelatin, antibiotics (e.g., Brefeldin A), salts (e.g., NaCl), chelating agents (e.g., EDTA, EGTA), and enzymes (e.g., cellulase, dispase, hyaluronidase, or DNase). In some embodiments, the culture may comprise a drug inducing or inhibiting transcription from a conditional or inducible promoter, for example doxicycline, tetracycline, tamoxifen, IPTG, hormones, or metal ions. While the specific culture conditions, for example, the concentration of the carbon source, will depend upon the respective engineered microorganism to be cultured, general methods and culture conditions for the generation of microbial cultures are well known to those of skill in the art, and are described, for example, in J. Sambrook and D. Russell, Molecular Cloning: A Laboratory Manual, Cold Spring Harbor Laboratory Press; 3rd edition (Jan. 15, 2001); David C. Amberg, Daniel J. Burke; and Jeffrey N. Strathern, Methods in Yeast Genetics: A Cold Spring Harbor Laboratory Course Manual, Cold Spring Harbor Laboratory Press (April 2005); John N. Abelson, Melvin I. Simon, Christine Guthrie, and Gerald R. Fink, Guide to Yeast Genetics and Molecular Biology, Part A, Volume 194 (Methods in Enzymology Series, 194), Academic Press (Mar. 11, 2004), all of which are incorporated by reference herein.

In some embodiments, the genetically modified non-pathogenic microbe or microorganism exhibits a growth advantage over wild type microbes of the same kind and/or over other microbes, for example, microbes commonly found to contaminate microbial cultures for scaling up production of cultures to large volumes. In some embodiments, the growth and/or proliferation advantage of an engineered microbe provided by aspects of this invention translates into the possibility of using non-sterile culturing and fermentation conditions for production, because the problem of culture overgrowth by contaminating microbes is mitigated or completely abolished. In some embodiments, an engineered microbe provided by aspects of this invention is cultured under non-sterile conditions. For example, in some embodiments, non-sterilized feedstock, non-sterilized culture media, non-sterilized supplements, or a non-sterilized bioreactor (e.g. an open reactor under non-sterile conditions) is used for microorganism division.

A variety of different microbes can be genetically modified according to some aspects of this invention and used for scale-up and/or isolation for eventual animal ingestion, for example, various strains of non-pathogenic E. coli. In some embodiments, the invention provides for a composition comprising one or a combination of non-pathogenic bacteria chosen from: probiotic bacteria is chosen from Salmanella spp., Escherichia spp., Firmicutes spp., Bacteroidetes spp., Lactobacillus spp., Bifidobacteria spp., or Acidopholus spp. In some embodiments, the probiotic is selected from Lactobacillus, Bifidobacteria, and Acidopholus. In some embodiments, the bacteria is harvested from a human or animal sample and transformed as described herein. with our system. The samples may be from stool samples (probiotics) or human/mouse tumor samples (bacteria that have potential to be very tumor selective). In some embodiments, the non-pathogenic microorganism is E. coli Nissle 1917 (EcN). In some embodiments, the non-pathogenic microorganism is a strain of E. coli but not the Nissle 1917 (EcN). In some embodiments, the compositions, pharmaceutical compositions, kits or cells disclosed herein comprise at least one E. coli strain Mach1. Expanding upon this we have shown the E. coli Nissle, E. coli DH5alpha, and S. Typhimurium. In some embodiments, the compositions, pharmaceutical compositions, kits or cells disclosed herein comprise at least one bacterial cell chosen from SL7207, ELH430, and ELH130 strains of S. Typhimurium. In some embodiments, the compositions, pharmaceutical compositions, kits or cells disclosed herein comprise at least one bacterial cell chosen from Salmonella spp., Escherichia spp., Firmicutes spp., Bacteroidetes spp., Lactobacillus spp., Bifidobacteria spp., or Acidopholus spp.

The present invention relates to compositions comprising any one or combination of non-pathogenic bacteria disclosed herein wherein at least one of the bacteria comprises a first, second, third, and/or fourth nucleic acid sequences disclosed herein either alone or in combination. In some embodiments, the invention relates to compositions comprising any one or combination of non-pathogenic bacteria disclosed herein wherein at least one of the bacteria comprises a nucleotide sequence encoding a mutated virulence factor. For instance, in some embodiments, the non-pathogenic microorganism comprises a mutation in its Type I, II, III, IV, V, or VI secretion system which does not allow transport of host toxins and/or host immunogenic proteins out of the cell.

In some embodiments, the invention relates to a system comprising at least one of the bacterial cells disclosed herein and bacterial growth media. In some embodiments, the invention relates to a system comprising at least one of the bacterial cells disclosed herein and a cell culture vessel or bioreactor.

In some embodiments, the invention relates to a system comprising at least one of the bacterial cells disclosed herein, bacterial growth media, and a cell culture vessel or bioreactor. fermentation processes for large-scale microbe cell division may be carried out in bioreactors, isolated and then resuspended in an amount or dosage form disclosed herein. As used herein, the terms "bioreactor" and "fermentor", which are interchangeably used, refer to an enclosure, or partial enclosure, in which a biological and/or chemical reaction takes place, at least part of which involves a living organism or part of a living organism. A "large-scale bioreactor" or "industrial-scale bioreactor" is a bioreactor that is used to generate large volumes of non-pathogenic bacteria for large scale isolation. Large scale bioreactors typically have volumes in the range of liters, hundreds of liters, thousands of liters, or more.

Other examples of bacteria that can be modified for use in the invention include food-grade bacterial strains. In some embodiments, the non-pathogenic bacteria is chosen from the bacterials strains identified in Humarán et al., *Microbial Cell Factories* 2011, 10(Suppl 1):S4; Shrivastava et al., *PlosOne*, August 2008, Volume 3, Issue 8: e2955; and T. Danino et al., *ACS Synth. Biol.* 2012, 1, 465-470, each of which are incorporated by reference in their entireties.

The invention relates to compositions comprising any of the bacteria disclosed herein, wherein the compositions are in a solid or liquid dosage form an wherein the bacteria are in an amount effective to colonize a tumor. The invention relates to compositions comprising any of the bacteria disclosed herein, wherein the compositions are in a solid or liquid dosage form an wherein the bacteria are in an amount effective to colonize a tumor upon administration of the compositions or bacteria to the subject in need thereof. The invention relates to compositions comprising any of the bacteria disclosed herein, wherein the compositions are in a solid or liquid dosage form an wherein the bacteria are in an effective amount to colonize a tumor and adequate produce enzyme or substrate in quantities detectable in urine. The invention relates to compositions comprising any of the non-pathogenic bacteria disclosed herein, wherein the compositions are in a solid or liquid dosage form an wherein the bacteria are in an effective amount to colonize a tumor and adequate produce enzyme or substrate in quantities detectable in urine by visual inspection. The invention relates to compositions comprising any of the non-pathogenic bacteria disclosed herein wherein the compositions are in a solid or liquid dosage form. In addition to the compositions disclosed in either solid or liquid form, the formulations and compositions of the present invention may also contain optional ingredients to enhance the characteristics of the solid dosage form, maintain the integrity of bacteria (in dried, lyophilized, dormant or sporulated forms) during the formulation process, and/or enhance the safety of the formulation. Any additional components may be compatible with the other ingredients in the formulations of the invention, in particular the active ingredients, and may be inert. If inert, the additional component does not adversely affect the osmolarity, osmolality, or isotoncity of the formulations or interfere, to a measureable degree, with the biological function of the non-pathogenic microorganism. Additional optional ingredients that may be used in the formulations of the invention include, for example, coatings, diluents, binders, glidants, lubricants, colors, disintegrants, flavors, sweeteners, polymers or waxes.

Non-limiting examples of diluents include various types of starch, cellulose, crystalline cellulose, microcrystalline cellulose, lactose, fructose, sucrose, mannitol or other sugar alcohols, kaolin, calcium phosphate or sulfate, inorganic salts such as sodium chloride and powdered sugar. Powdered cellulose derivatives are also useful. In some embodiments of the invention, the formulation does not include a diluent.

Lubricants, for example, may be included in the formulations of the invention. Such lubricants include, but are not limited to, magnesium stearate, potassium stearate, talc, stearic acid, sodium lauryl sulphate, and paraffin. In some embodiments of the invention, the colonic purgative formulation further comprises magnesium stearate. Lubricants serve to facilitate the manufacturing of a solid dosage form. In some embodiments of the invention, the formulation does not comprise a lubricant.

Additional suitable ingredients also include, but are not limited to, carriers, such as sodium citrate and dicalcium phosphate; fillers or extenders, such as stearates, silicas, gypsum, starches, lactose, sucrose, glucose, mannitol, talc, and silicic acid; binders, such as hydroxypropyl methylcellulose, hydroxymethyl-cellulose, alginates, gelatin, polyvinyl pyrrolidone, sucrose, and *acacia*; humectants, such as glycerol; disintegrating agents, such as agar, calcium carbonate, potato and tapioca starch, alginic acid, certain silicates, colloidal silicon dioxide, sodium starch glycolate, crospovidone, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; stabilizers, such as fumaric acid; coloring agents; buffering agents; dispersing agents; preservatives; organic acids; and organic bases.

In some embodiments of the instant invention, the tablet or capsules may also include inert dispersal agents which will facilitate dissolution of the a solid dosage form of the non-pathogenic bacteria in the stomach of the patient. Preferably, the dispersal agent is a pharmaceutically acceptable dispersant and is one which also produces no appreciable osmotic effects. Examples of acceptable dispersants include microcrystalline cellulose (which is also useful as a compacting agent) and anhydrous lactose. In some embodiments, the dispersal agent is AC-DI-SOL, a cross-linked starch.

In some embodiments of the present invention, the formulation or composition may also include a buffering agent to minimize any acid imbalance which may accompany ingestion of the compositions disclosed herein. Suitable buffering agents include magnesium hydroxide, aluminum hydroxide, calcium carbonate and magnesium carbonate. In some embodiments, the formulation does not include a buffering agent.

In some embodiments of the invention, an additional component in the formulations of the invention may function to maintain the electrolyte balance in a subject after ingestion of a liquid dosage form of the compositions disclosed herein. For example, formulations of the invention may further comprise calcium, phosphate, potassium, magnesium, other anions, or salts thereof.

In some embodiments, the composition comprises at least one bacterium that comprises stably transfected nucleic acid molecules. In some embodiment, the nucleic acid molecules are DNA or RNA. In some embodiments, the nucleic acid molecules are DNA plasmids.

Culture System

The invention generally relates to a culture system that comprises at least one culture vessel comprising any one or combination of bacteria or compositions disclosed herein. Microbial culturing in the present invention is performed both for the sake of implementing genetic modifications, and for scaled up production of the bacteria disclosed herein. In some embodiments, the invention relates to the method of culturing at least one bacterium disclosed herein comprising inoculating a growth medium with the at least one bacterium disclosed herein.

Microbial culturing with the aim of genetic manipulation is generally performed at a small benchtop scale and often under conditions that select for genetically modified traits. Microbial culturing aimed at the commercial production of bacteria suitable for use in a subject can be performed in bioreactors at much greater scale (e.g., 1 L, 10 L, 500 L, 1,000 L 5,000 L, 10,000 L, 50,000 L, 100,000 L bioreactor volumes and higher). In certain embodiments the bacteria of the present invention are grown in a liquid media inside a bioreactor using the methods of the invention. In some embodiments of the present invention steel fermentors 50,000 liter and greater in volume are utilized. In some embodiments of the present invention egg-shape or cylindrical digestrors 3,000,000 liters and greater in volume are utilized. In some embodiments, the bioreactor comprising the microorganism does not allow light to penetrate its interior.

The bioreactor or fermentor is used to culture cells through the various phases of their physiological cycle. A bioreactor is utilized for the cultivation of cells, which may be maintained at particular phases in their growth curve. Generally the control of growth conditions including dissolved carbon dioxide, oxygen, and other gases such as hydrogen, as well as other dissolved nutrients, trace elements, temperature and pH are facilitated in a bioreactor.

Nutrient media as well as gases can be added to the bioreactor as either a batch addition, or periodically, or in response to a detected depletion or programmed set point, or continuously over the period the culture is grown and/or maintained. For certain embodiments, the bioreactor at inoculation is filled with a starting batch of nutrient media and/or gases at the beginning of growth, and no additional nutrient media and/or gases is added after inoculation. For certain embodiments, nutrient media and/or gases are added periodically after inoculation. For certain embodiments, nutrient media and/or gas is added after inoculation in response to a detected depletion of nutrient and/or gas. For certain embodiments, nutrient media and/or gas is added continuously after inoculation.

In some embodiments, the bioreactors comprise a mechanisms to mix of the nutrient media that include but are not limited to spinning stir bars, blades, impellers, or turbines, spinning, rocking, or turning vessels, gas lifts and sparging. The culture media may be mixed continuously or intermittently.

The ports that are standard in bioreactors may be utilized to deliver, or withdraw, gases, liquids, solids, and/or slurries, into the bioreactor vessel enclosing the microbes of the present invention. Many bioreactors have multiple ports for different purposes (e.g. ports for media addition, gas addition, probes for pH and DO, sampling), and a given port may be used for various purposes during the course of a fermentation run. As an example, a port might be used to add nutrient media to the bioreactor at one point in time and at another time might be used for sampling. Preferably, the multiple use of a sampling port can be performed without introducing contamination or invasive species into the growth environment. A valve or other actuator enabling control of the sample flow or continuous sampling can be provided to a sampling port. For certain embodiments the bioreactors are equipped with at least one port suitable for culture inoculation that can additionally serve other uses including the addition of media or gas. Bioreactors ports enable control of the gas composition and flow rate into the culture environment. For example the ports can be used as gas inlets into the bioreactor through which gases are pumped. For some embodiments gases that may be pumped into a bioreactor include hydrogen gas, CO2, air, air/$CO_2$ mixtures, ammonia, nitrogen, noble gases, such as argon, as well as other gases. Raising the gas flow rate into a bioreactor can enhance mixing of the culture and produce turbulence if the gas inlet is positioned under the surface of the liquid media such that gas bubbles or sparges up through the media. In some embodiments, a bioreactor comprises gas outlet ports for gas escape and pressure release. In some embodiments, gas inlets and outlets are preferably equipped with check valves to prevent gas backflow.

The nucleic acid sequences of the present invention may be components of one, two or more, three or more, four or more than three different plasmid molecules. Each individual nucleica acid sequence may reside on its own nucleic acid molecule or plasmid. In some embodiments, each exogenous nucleic acid resides on a single DNA plasmid. In some embodiments, the nucleic acid sequence that is an inducible promoter comprises at least one, two, three, four or more exogenous nucleic acid sequences whose presence individually or in combination control the expression of one or more coding sequences. In some embodiments, the coding sequence is a therapeutic agent, cell death amino acid sequence, cancer cell targeting sequence (e.g. ligand of a tumor associated antigen), or a selectable marker or marker amino acid sequence. Example of marker amino acid sequences comprise amino acid sequences that, upon exposure to a light, emit a detectable wavelength of light. One of ordinary skill in the art can measure the emission of light from the marker amino acid sequence by known techniques such as fluorescent microscopy, FRET or other, wavelength detection equipment.

Kits

In some embodiments, the present disclosure provides kits for cell administration and treatment of cancer in a subject in need thereof comprising at least one bacterial cell disclosed herein. In some embodiments, the kit comprises cell growth media. In some embodiments, the kit comprises cell growth media in a separate vessel from the at least one bacterial cell. In some embodiments, the kit further comprises cells of the cell type of interest. In some embodiments, the kits provide Methods The present invention relates to methods of treating and preventing cancer. In some embodiments, the methods comprise the step of administering the pharmaceutical compositions, compositions or food disclosed herein to treat or prevent cancer of the adrenal gland, bladder, bone, bone marrow, brain, spine, breast, cervix, gall bladder, ganglia, gastrointestinal tract, stomach, colon, heart, kidney, liver, lung, muscle, ovary, pancreas, parathyroid, penis, prostate, salivary glands, skin, spleen, testis, thymus, thyroid, or uterus. In some embodiments, the methods comprise the step of administering a therapeutically effective dose of at least one bacterial cell as a component of the pharmaceutical compositions, compositions or food disclosed herein to treat or prevent cancer of the adrenal gland, bladder, bone, bone marrow, brain, spine, breast, cervix, gall bladder, ganglia, gastrointestinal tract, stomach, colon, heart, kidney, liver, lung, muscle, ovary, pancreas, parathyroid, penis, prostate, salivary glands, skin, spleen, testis, thymus, thyroid, or uterus. In some embodiments, the methods comprise the step of administering a therapeutically effective dose of the pharmaceutical compositions, compositions or food disclosed herein to treat or prevent cancer of the adrenal gland, bladder, bone, bone marrow, brain, spine, breast, cervix, gall bladder, ganglia, gastrointestinal tract, stomach, colon, heart, kidney, liver, lung, muscle, ovary, pancreas, parathyroid, penis, prostate, salivary glands, skin, spleen, testis, thymus, thyroid, or uterus. In some embodiments, the methods comprise the step of administering a therapeutically effective dose of at least one bacterial cell as a component of the pharmaceutical compositions, compositions or food disclosed herein to treat or prevent the growth or spread of metastatic cancer. In some embodiments, the invention relates to any of the disclosed methods comprising the step of administering a therapeutically effective dose of at least one bacterial cell as a component of the pharmaceutical compositions, compositions or food disclosed herein.

Embodiments include methods of using tumor-targeted bacteria to identify a therapeutically effective dose of therapeutic agent in a solid tumor, the method comprising administering any of the compositions, pharmaceutical compositions, or food products disclosed herein to a subject in need thereof. In some embodiments, the subject is suspected of having or has been diagnosed with cancer or metastatic cancer.

Embodiments also include methods of using tumor-targeted bacteria to deliver a timed therapeutically effective dose of therapeutic agent in regular intervals in a solid tumor, the method comprising administering any of the compositions, pharmaceutical compositions, or food products disclosed herein to a subject in need thereof. In some embodiments, the subject is suspected of having or has been diagnosed with cancer or metastatic cancer. In some embodiments, the methods herein comprise administering one or more stimuli that activate the promoter sequence or sequences and induce expression of one or more coding sequence on the one or more nucleic acid sequences residing in the at least one bacterial cell. Based upon the time administration of the one or more stimuli, bacteria that colonize cancer cells, solid tumors, or cells associated with hyperproliferative disorders may release, secrete, or express cellular toxins, therapeutic agents, or amino acids comprising one or more cell death domains.

The invention also relates to a method of predicting the quantitative expression or dosage of a therapeutic agent in a subject, the method comprising: administering any of the compositions, pharmaceutical compositions or food stuff disclosed herein.

REFERENCES

Danino et al., ACS Synthetic Biology, 2012, 1, pages 465-470.

[1] J. C. Anderson, E. J. Clarke, A. P. Arkin, and C. A. Voigt. Environmentally controlled invasion of cancer cells by engineered bacteria. *Journal of molecular biology*, 355 (4):619-627, 2006.

[2] M. Cronin, A. R. Akin, S. A. Collins, J. Meganck, J. B. Kim, C. K. Baban, S. A. Joyce, G. M. van Dam, N. Zhang, D. van Sinderen, et. al. High resolution in vivo bioluminescent imaging for the study of bacterial tumour targeting, *PloS one*, 7(1):e30940, 2012.

[3] L. H. Dang, C. Bettegowda, D. L. Huso, K. W. Kinzler, and B. Vogelstein. Combination bacteriolytic therapy for the treatment of experimental tumors. *Proceedings of the National Academy of Sciences of the United States of America*, 98(26):15155, 2001.

[4] T. Danino, O. Mondragón-Palomino, L. Tsimring, and J. Hasty. A synchronized quorum of genetic clocks. *Nature*, 463(7279):326-330, 2010, PMID:20090747.

[5] N. S. Forbes. Engineering the perfect (bacterial) cancer therapy. *Nature Reviews Cancer*, 10(11):785-794, 2010.

[6] H. Guo, J. Zhang, and C. Inal. Targeting tumor gene by shrna-expressing *salmonella*-mediated mai. *Gene therapy*, 18(1):95-105, 2010.

[7] J. Hasty, D. McMillen, and J. J. Collins. Engineered gene circuits. *Nature*, 420(6912):224-230, 2002.

[8] D. M. Heimann and S. A. Rosenberg. Continuous intravenous administration of live genetically modified *salmonella typhimurium* in patients with metastatic melanoma. *Journal of immunotherapy* (Hagerstown, Md.: 1997), 26(2):179, 2003.

[9] R. M. Hoffman. Tumor-seeking *salmonella* amino acid auxotrophs. *Current Opinion in Biotechnology*, 2011.

[10] E. L. Hohmann, C. A. Oletta, and S. I. Miller. Evaluation of a phop/phoq-deleted, aroa-deleted live oral *salmonella typhi* vaccine strain in human volunteers. *Vaccine*, 14(1):19-24, 1996.

[11] X. Huang and C. S. Brazel. On the importance and mechanisms of burst release in matrix-controlled drug delivery systems. *Journal of Controlled Release*, 73(2): 121-136, 2001.

[12] S. Leschner, K. Westphal, N. Dietrich, N. Viegas, J. Jablonska, M. Lyszkiewicz, S. Lienenklaus, W. Falk, N. Gekara, H. Loessner, et al. Tumor invasion of *salmonella enterica* serovar *typhimurium* is accompanied by strong hemorrhage promoted by tnf-α. *PloS one*, 4(8):e6692, 2009.

[13] Z. Lm, X. Luo, M. Feng, Z. Li, M. Ittensohn, M. Trailsmith, D. Bermudes, S L Lin, I C King, et al. Tumor amplified protein expression therapy: *Salmonella* as a tumor-selective protein delivery vector. *Oncology Research Featuring Preclinical and Clinical Cancer Therapeutics*, 12(3):127-135, 2001.

[14] V. H. Nguyen, H. S. Kim, J. M. Ha, Y. Hong, H. E. Choy, and J. J. Min. Genetically engineered *salmonella typhimurium* as an imageable therapeutic probe for cancer. *Cancer research*, 70(1):18, 2010.

[15] J. M. Pawelek, K. B. Low, and D. Bermudes. Tumor-targeted *salmonella* as a novel anticancer vector. *Cancer research*, 57(20):4537, 1997.

[16] D. C. Pecota, C. S. Kim, K. Wu, K. Gerdes, and T. K. Wood. Combining the hok/sok, parde, and pnd postsegregational killer loci to enhance plasmid stability. *Applied and environmental microbiology*, 63(5):1917-1924, 1997.

[17] A. Prindle, P. Samayoa, I. Razinkov, T. Danino, L. S. Tsimring, and J. Hasty. A sensing array of radically coupled genetic/biopixels/'. *Nature*, 2011.

[18] F. M. Stewart and B. R. Levin. The population biology of bacterial plasmids: a priori conditions for the existence of conjugationally transmitted factors. *Genetics*, 87(2): 209-228, 1977.

[19] J. F. Toso, V. J. Gill, P. Hwu, F. M. Marincola, N. P. Restifo, D. J. Schwartzentruber, R. M. Sherry, S. L. Topalian, J. C. Yang, F. Stock, et al. Phase i study of the intravenous administration of attenuated *salmonella typhimurium* to patients with metastatic melanoma. *Journal of clinical oncology*, 20(1):142, 2002.

[20] D. Q. Xu, L. Zhang, D. J. Kopecko, L. Gao, Y. Shao, B. Guo, and L. Zhao. Bacterial delivery of sirnas: a new approach to solid tumor therapy. *Methods in Molecular Biology*, 487:161-187, 2009.

[21] A. Y. Yong, S. Shabahang, T. M. Timiryasova, Q. Zhang, R. Beltz, I. Gentschev, W. Goebel, and A. A. Szalay. Visualization of tumors and metastases in live animals with bacteria and vaccinia virus encoding light-emitting proteins. *Nature biotechnology,* 22(3):313-320, 2004.

[22] M. Zhao, M. Yang, X. M. Li, P. Jiang, E. Baranov, S. Li, M. Xu, S. Penman, and R. M. Hoffman. Tumor-targeting bacterial therapy with amino acid auxotrophs of gfp-expressing *salmonella typhimurium. Proceedings of the National Academy of Sciences of the United States of America,* 102(3):755, 2005.

[23] M. Zhao, M. Yang, H. Ma, X. Li, X. Tan, S. Li, Z. Yang, and R. M. Hoffman. Targeted therapy with a *salmonella typhimurium* leucine-arginine auxotroph cures orthotopic human breast tumors in nude mice. *Cancer research,* 66(15):7647, 2006.

[24] S. Zhou, M. Zhang, and J. Wang. Tumor-targeted delivery of tat-apoptin fusion gene using *escherichia coli* nissle 1917 to colorectal cancer. *Medical Hypotheses,* 76(4):533-534, 2011.

Any and all journal articles, patent applications, issued patents, or other cited references disclosed herein are incorporated by reference in their respective entireties.

EXAMPLES

Example 1

A single plasmid, p-TD106-DD was generated by subcloning coding sequences into a synthesized DNA molecule by known molecular biology techniques. We transformed the DNA into bacteria to use for quorum sensing as means to deliver therapeutic payloads to a cancer cell. A restriction enzyme map of the plasmid is depicted in FIG. 1A. The sequence of the plasmid (SEQ ID NO:1) follows:

```
ctcgagttaattttaaagtatgggcaatcaattgctcctgttaaaattgctttagaaatactttggcagcggtttgttgtattgagtttc
atttgcgcattggttaaatggaaagtgacagtacgctcactgcagcctaatattttgaaatatcccaagagcttttccttcgcatgccc
acgctaaacattcttttctcttttggttaaatcgttgtttgatttattatttgctatatttattttcgataattatcaactagagaagg
aacaattaatggtatgttcatacacgcatgtaaaaataaactatctatatagttgtcttttctgaatgtgcaaaactaagcattccgaag
ccattgttagccgtatgaatagggaaactaaacccagtgataagacctgatgttttcgcttcttaattacatttggagatttttattta
cagcattgttttcaaatatattccaattaattggtgaatgattggagttagaataatctactataggatcatatttattaaattagcgtc
atcataatattgcctccatttttagggtaattatctagaattgaaatatcagatttaaccatagaatgaggataaatgatcgcgagtaaa
taatattcacaatgtaccatttagtcatatcagataagcattgattaatatcattattgcttctacaagctttaattttattaattattc
tgtatgtgtcgtcggcatttatgttttcatacccatctctttatccttacctattgtttgtcgcaagttttgcgtgttatatatcattaa
aacggtaatggattgacatttgattctaataaattggattttgtcacactattgtatcgctgggaatacaattacttaacataagcacct
gtaggatcgtacaggtttacgcaagaaatggttgttatagtcgaatgaattcattaaagaggagaaaggtaccatgactataatgataa
aaaaatcggattttttggcaattccatcggaggagtataaaggtattctaagtcttcgttatcaagtgtttaagcaaagacttgagtggga
cttagttgtagaaaataaccttgaatcagatgagtatgataactcaaatgcagaatatatttatgcttgtgatgatactgaaaatgtaagt
ggatgctggcgtttattacctacaacaggtgattatatgctgaaaagtgttttcctgaattgcttggtcaacagagtgctcccaaagatc
ctaatatagtcgaattaagtcgttttgctgtaggtaaaaatagctcaaagataaataactctgctagtgaaattacaatgaaactatttga
agctatatataaacacgctgttagtcaaggtattacagaatatgtaacagtaacatcaacagcaatagagcgattttaaagcgtattaaa
gttccttgtcatcgtattggagacaaagaaattcatgtattaggtgatactaaatcggttgtattgtctatgcctattaatgaacagttta
aaaaagcagtcttaaatgcagcgaacgacgaaaattacgcccttgcagcgtaaacgcgtgctagaggcatcaaataaaacgaaaggctcag
tcgaaagactgggcctttcgttttatctgttgtttgtcggtgaacgctctcctgagtaggacaaatccgccgccctagacctagcatttt
aaagtatgggcaatcaattgctcctgttaaaattgctttagaaatactttggcagcggtttgttgtattgagtttcatttgcgcattggtt
aaatggaaagtgacagtacgctcactgcagcctaatattttgaaatatcccaagagcttttccttcgcatgcccacgctaaacattctt
tttctcttttggttaaatcgttgtttgatttattatttgctatatttattttcgataattatcaactagagaaggaacaattaatggtat
gttcatacacgcatgtaaaaataaactatctatatagttgtcttttctgaatgtgcaaaactaagcattccgaagccattgttagccgta
tgaatagggaaactaaacccagtgataagacctgatgttttcgcttcttaattacatttggagatttttatttacagcattgttttcaa
atatattccaattaattggtgaatgattggagttagaataatctactataggatcatatttattaaattagcgtcatcataatattgcct
ccatttttagggtaattatctagaattgaaatatcagatttaaccatagaatgaggataaatgatcgcgagtaaataatattcacaatgt
accatttagtcatatcagataagcattgattaatatcattattgcttctacaagctttaattttattaattattctgtatgtgtcgtcgg
catttatgttttcatacccatctctttatccttacctattgtttgtcgcaagttttgcgtgttatatatcattaaaacggtaatggattg
acatttgattctaataaattggattttgtcacactattgtatcgctgggaatacaattacttaacataagcacctgtaggatcgtacagg
```

-continued

```
tttacgcaagaaaatggtttgttatagtcgaatgaattcattaaagaggagaaaggtaccatgactaaaaaaatttcattcattattaacg
gccaggttgaaatcttttcccgaaagtgatgatttagtgcaatccattaattttggtgataatagtgtttacctgccaatattgaatgactc
tcatgtaaaaaacattattgattgtaatggaaataacgaattacggttgcataacattgtcaattttctctatacggtagggcaaagatgg
aaaaatgaagaatactcaagacgcaggacatacattcgtgacttaaaaaaatatatgggatattcagaagaaatggctaagctagaggcca
attggatatctatgattttatgttctaaaggcggcctttatgatgttgtagaaaatgaacttggttctcgccatatcatggatgaatggct
acctcaggatgaaagttatgttcgggcttttccgaaaggtaaatctgtacatctgttggcaggtaatgttccattatctgggatcatgtct
atattacgcgcaattttaactaagaatcagtgtattataaaaacatcgtcaaccgatccttttaccgctaatgcattagcgttaagtttta
ttgatgtagaccctaatcatccgataacgcgctctttatctgttatatattggccccaccaaggtgatacatcactcgcaaaagaaattat
gcgacatgcggatgttattgtcgcttggggagggccagatgcgattaattgggcggtagagcatgcgccatcttatgctgatgtgattaaa
tttggttctaaaaagagtcttttgcattatcgataatcctgttgatttgacgtccgcagcgacaggtgcggctcatgatgtttgtttttacg
atcagcgagcttgtttttctgcccaaaacatatattacatgggaaatcattatgaggaatttaagttagcgttgatagaaaaacttaatct
atatgcgcatatattaccgaatgccaaaaaagattttgatgaaaaggcggcctattctttagttcaaaaagaaagcttgtttgctggatta
aaagtagaggtggatattcatcaacgttggatgattattgagtcaaatgcaggtgtggaatttaatcaaccacttggcagatgtgtgtacc
ttcatcacgtcgataatattgagcaaatattgccttatgttcaaaaaaataagacgcaaaccatatctattttccttgggagtcatcatt
taaatatcgagatgcgttagcattaaaaggtgcggaaaggattgtagaagcaggaatgaataacatatttcgagttggtggatctcatgac
ggaatgagaccgttgcaacgattagtgacatatatttctcatgaaaggccatctaactatacggctaaggatgttgcggttgaaatagaac
agactcgattcctgaagaagataagttccttgtatttgtcccataataggtaaaagtatggaaaatgaatcaaaatataaaaccatcgac
cacgttatttgtgttgaaggaaataaaaaaattcatgtttgggaaacgctgccagaagaaaacagcccaaagagaaagaatgccattatta
ttgcgtctggttttgcccgcaggatggatcattttgctggtctggcggaatatttatcgcggaatggatttcatgtgatccgctatgattc
gcttcaccacgttggattgagttcagggacaattgatgaatttacaatgtctataggaaagcagagcttgttagcagtggttgattggtta
actacacgaaaaataaataacttcggtatgttggcttcaagcttatctgcgcggatagcttatgcaagcctatctgaaatcaatgcttcgt
ttttaatcaccgcagtcggtgttgttaacttaagatattctcttgaaagagctttagggtttgattatctcagtctacccattaatgaatt
gccggataatctagattttgaaggccataaattgggtgctgaagtctttgcgagagattgtcttgattttggttgggaagatttagcttct
acaattaataacatgatgtatcttgatataccgtttattgcttttactgcaaataacgataattgggtcaagcaagatgaagttatcacat
tgttatcaaatattcgtagtaatcgatgcaagatatattctttgttaggaagttcgcatgacttgagtgaaaatttagtggtcctgcgcaa
ttttttatcaatcggttacgaaagccgctatcgcgatggataatgatcatctggatattgatgttgatattactgaaccgtcatttgaacat
ttaactattgcgacagtcaatgaacgccgaatgagaattgagattgaaaatcaagcaatttctctgtcttaaaatctattgagatattcta
tcactcaaatagcaatataaggactctctatgaaatttggaaacttttttgcttacataccaacctccccaattttctcaaacagaggtaat
gaaacgtttggttaaattaggtcgcatctctgaggagtgtggttttgataccgtatggttactggagcatcatttcacggagtttggtttg
cttggtaacccttatgtcgctgctgcatatttacttggcgcgactaaaaaattgaatgtaggaactgccgctattgttcttcccacagccc
atccagtacgccaacttgaagatgtgaatttattggatcaaatgtcaaaaggacgatttcggtttggtatttgccgagggctttacaacaa
ggactttcgcgtattcggcacagatatgaataacagtcgcgccttagcggaatgctggtacgggctgataaagaatggcatgacagaggga
tatatggaagctgataatgaacatatcaagttccataaggtaaaagtaaaccccgcggcgtatagcagaggtggcgcaccggtttatgtgg
tggctgaatcagcttcgacgactgagtgggctgctcaatttggcctaccgatgatattaagttggattataaatactaacgaaaagaaagc
acaacttgagctttataatgaagtggctcaagaatatgggcacgatattcataatatcgaccattgcttatcatatataacatctgtagat
catgactcaattaaagcgaaagagatttgccggaaatttctggggcattggtatgattcttatgtgaatgctacgactatttttgatgatt
cagaccaaacaagaggttatgatttcaataaagggcagtggcgtgactttgtattaaaaggacataaagatactaatcgccgtattgatta
cagttacgaaatcaatcccgtgggaacgccgcaggaatgtattgacataattcaaaaagacattgatgctacaggaatatcaaatatttgt
tgtggatttgaagctaatggaacagtagacgaaattattgcttccatgaagctcttccagtctgatgtcatgccattcttaaagaaaaac
aacgttcgctattatattagctaaggagaaagaaatgaaatttggattgttcttccttaacttcatcaattcaacaactgttcaagaacaa
agtatagttcgcatgcaggaaataacggagtatgttgataagttgaattttgaacagattttagtgtatgaaaatcatttttcagataatg
```

-continued

```
gtgttgtcggcgctcctctgactgtttctggttttctgctcggtttaacagagaaaattaaaattggttcattaaatcacatcattacaac
tcatcatcctgtcgccatagcggaggaagcttgcttattggatcagttaagtgaagggagatttattttagggtttagtgattgcgaaaaa
aaagatgaaatgcatttttttaatcgcccggttgaatatcaacagcaactatttgaagagtgttatgaaatcattaacgatgctttaacaa
caggctattgtaatccagataacgattttatagcttccctaaaatatctgtaaatccccatgcttatacgccaggcggacctcggaaata
tgtaacagcaaccagtcatcatattgttgagtgggcggccaaaaaaggtattcctctcatctttaagtgggatgattctaatgatgttaga
tatgaatatgctgaaagatataaagccgttgcgataaatatgacgttgacctatcagagatagaccatcagttaatgatattagttaact
ataacgaagatagtaataaagctaaacaagagacgcgtgcatttattagtgattatgttcttgaaatgcaccctaatgaaaatttcgaaaa
taaacttgaagaaataattgcagaaaacgctgtcggaaattatacggagtgtataactgcggctaagttggcaattgaaaagtgtggtgcg
aaaagtgtattgctgtcctttgaaccaatgaatgatttgatgagccaaaaaaatgtaatcaatattgttgatgataatattaagaagtacc
acatggaatatacctaatagatttcgagttgcagcgaggcggcaagtgaacgaatccccaggagcatagataactatgtgactggggtgag
tgaaagcagccaacaaagcagcagcttgaaagatgaagggtataaaagagtatgacagcagtgctgccatactttctaatattatcttgag
gagtaaaacaggtatgacttcatatgttgataaacaagaaattacagcaagctcagaaattgatgatttgatttttttcgagcgatccatta
gtgtggtcttacgacgagcaggaaaaaatcagaaagaaacttgtgcttgatgcatttcgtaatcattataaacattgtcgagaatatcgtc
actactgtcaggcacacaaagtagatgacaatattacggaaattgatgacatacctgtattcccaacatcggttttttaagtttactcgctt
attaacttctcaggaaaacgagattgaaagttggtttaccagtagcggcacgaatggtttaaaaagtcaggtggcgcgtgacagattaagt
attgagagactcttaggctctgtgagttatggcatgaaatatgttggtagttggtttgatcatcaaatagaattagtcaatttgggaccag
atagatttaatgctcataatatttggtttaaatatgttatgagtttggtggaattgttatatcctacgacatttaccgtaacagaagaacg
aatagattttgttaaaacattgaatagtcttgaacgaataaaaaatcaagggaaagatctttgtcttattggttcgccatactttattat
ttactctgccattatatgaaagataaaaaaatctcattttctggagataaaagcctttatatcataaccggaggcggctggaaaagttacg
aaaaagaatctctgaaacgtgatgatttcaatcatctttttatttgatactttcaatctcagtgatattagtcagatccgagatatatttaa
tcaagttgaactcaacacttgtttctttgaggatgaaatgcagcgtaaacatgttccgccgtgggtatatgcgcgagcgcttgatcctgaa
acgttgaaacctgtacctgatggaacgccgggggttgatgagttatatggatgcgtcagcaaccagttatccagcatttattgttaccgatg
atgtcgggataattagcagagaatatggtaagtatcccggcgtgctcgttgaaattttacgtcgcgtcaatacgaggacgcagaaagggtg
tgctttaagcttaaccgaagcgtttgatagttgataaacgcgtgctagaggcatcaaataaaacgaaaggctcagtcgaaagactgggcct
ttcgttttatctgttgtttgtcggtgaacgctctcctgagtaggacaaatccgccgcctagctaattttaaagtatgggcaatcaattgc
tcctgttaaaattgctttagaaatactttggcagcggtttgttgtattgagtttcatttgcgcattggttaaatggaaagtgacagtacgc
tcactgcagcctaatatttttgaaatatcccaagagcttttccttcgcatgcccacgctaaacattcttttttctctttttggttaaatcgt
tgtttgatttattatttgctatatttatttttcgataattatcaactagagaaggaacaattaatggtatgttcatacacgcatgtaaaaa
taaactatctatatagttgtctttttctgaatgtgcaaaactaagcattccgaagccattgttagccgtatgaatagggaaactaaaccca
gtgataagacctgatgttttcgcttctttaattacatttggagatttttttatttacagcattgttttcaaatatattccaattaattggtg
aatgattggagttagaataatctactataggatcatattttattaaattagcgtcatcataatattgcctccattttttagggtaattatc
tagaattgaaatatcagatttaaccatagaatgaggataaatgatcgcgagtaaataatattcacaatgtaccattttagtcatatcgat
aagcattgattaatatcattattgcttctacaagctttaattttattaattattctgtatgtgtcgtcggcatttatgttttttcatcccca
tctctttatccttacctattgtttgtcgcaagttttgcgtgttatatatcattaaaacggtaatggattgacatttgattctaataaattg
gattttttgtcacactattgtatcgctgggaatacaattacttaacataagcacctgtaggatcgtacaggtttacgcaagaaaatggttg
ttatagtcgaatgaattcattaaagaggagaaaggtaccatgccctccaaatccttggttatggaatatttggctcatcccagtcacactcg
gcttggctgttggagttgcttgtggcatgtgcctgggctggagccttcgagtatgctttgggatgctccccaaaagcaagacgagcaagac
acacacagatactgaaagtgaagcaagcatcttgggagacagctctcgaggtaccggcggcggcagcctgggcgatccgaacagcggctgc
cgcggcgataaaggcccggattgctaaaagcttaattagctgatctagacgcgtgctagaggcatcaaataaaacgaaaggctcagtcgaa
agactgggcctttcgttttatctgttgtttgtcggtgaacgctctcctgagtaggacaaatccgccgccctagacctaggggatatattcc
```

-continued

```
gcttcctcgctcactgactcgctacgctcggtcgttcgactgcggcgagcggaaatggcttacgaacggggcggagatttcctggaagatg ccaggaagatacttaacagggaagtgagagggccgcggcaaagccgttttccataggctccgcccccctgacaagcatcacgaaatctga cgctcaaatcagtggtggcgaaacccgacaggactataaagataccaggcgtttccccctggcggctccctcgtgcgctctcctgttcctg cctttcggtttaccggtgtcattccgctgttatggccgcgtttgtctcattccacgcctgacactcagttccgggtaggcagttcgctcca agctggactgtatgcacgaaccccccgttcagtccgaccgctgcgccttatccggtaactatcgtcttgagtccaacccggaaagacatgc aaaagcaccactggcagcagccactggtaattgatttagaggagttagtcttgaagtcatgcgccggttaaggctaaactgaaaggacaag ttttggtgactgcgctcctccaagccagttacctcggttcaaagagttggtagctcagagaaccttcgaaaaaccgccctgcaaggcggtt ttttcgttttcagagcaagagattacgcgcagaccaaaacgatctcaagaagatcatcttattaatcagataaaatatttctagatttcag tgcaatttatctcttcaaatgtagcacctgaagtcagccccatacgatataagttgttactagtgcttggattctcaccaataaaaaacgc ccggcggcaaccgagcgttctgaacaaatccagatggagttctgaggtcattactggatctatcaacaggagtccaagcactcacgttaag ggattttggtcatgactagtgcttggattctcaccaataaaaaacgcccggcggcaaccgagcgttctgaacaaatccagatggagttctg aggtcattactggatctatcaacaggagtccaagcgagctctcgaacccagagtcccgctcagaagaactcgtcaagaaggcgatagaag gcgatgcgctgcgaatcggagcggcgataccgtaaagcacgaggaagcggtcagcccattcgccgccaagctcttcagcaatatcacggg tagccaacgctatgtcctgatagcggtccgccacacccagccggccacagtcgatgaatccagaaaagcggccattttccaccatgatatt cggcaagcaggcatcgccatgggtcacgacgagatcctcgccgtcgggcatgcgcgccttgagcctggcgaacagttcggctggcgcgagc ccctgatgctcttcgtccagatcatcctgatcgacaagaccggcttccatccgagtacgtgctcgctcgatgcgatgtttcgcttggtggt cgaatgggcaggtagccggatcaagcgtatgcagccgccgcattgcatcagccatgatggatactttctcggcaggagcaaggtgagatga caggagatcctgccccggcacttcgcccaatagcagccagtcccttcccgcttcagtgacaacgtcgagcacagctgcgcaaggaacgccc gtcgtggccagccacgatagccgcgctgcctcgtcctgcagttcattcagggcaccggacaggtcggtcttgacaaaaagaaccgggcgcc cctgcgctgacagccggaacacggcggcatcagagcagccgattgtctgttgtgcccagtcatagccgaatagcctctccacccaagcggc cggagaacctgcgtgcaatccatcttgttcaatcatgcgaaacgatcctcatcctgtctcttgatcagatcttgatccctgcgccatcag atccttggcggcaagaaagccatccagtttactttgcagggcttcccaaccttaccagagggcgcccagctggcaattccgacgtctaag aaaccattattatcatgacattaacctataaaaataggcgtatcacgaggccctttcgtcttcac
```

Embodiments of the invention optionally include at least one bacterial cells comprising a plasmid optionally including one or more of the following sequences:

SEQ ID NO: 2
luxR:
```
attttttaaagtatgggcaatcaattgctcctgttaaaattgctttagaaatactttggcagcggtttgttgtattgagtttcatttgc gcattggttaaatggaaagtgacagtacgctcactgcagcctaatatttttgaaatatcccaagagcttttccttcgcatgcccacg ctaaacattctttttctcttttggttaaatcgttgtttgatttattatttgctatatttatttttcgataattatcaactagagaagg aacaattaatggtatgttcatacacgcatgtaaaaataaactatctatatagttgtcttttctgaatgtgcaaaactaagcattccg aagccattgttagccgtatgaatagggaaactaaacccagtgataagacctgatgttttcgcttctttaattacatttggagattttt tatttacagcattgttttcaaatatattccaattaattggtgaatgattggagttagaataatctactataggatcatatttttattaa attagcgtcatcataatattgcctccattttttagggtaattatctagaattgaaatatcagatttaaccatagaatgaggataaatg atcgcgagtaaataatattcacaatgtaccatttagtcatatcagataagcattgattaatatcattattgcttctacaagctttaa ttttattaattattctgtatgtgtcgtcggcatttatgttttcatacccatctctttatccttacctattgtttgtcgcaagttttg cgtgttatatcattaaaacggtaatggattgacatttgattctaataaattggattttgtcac
```

SEQ ID NO: 3
luxI:
```
atgactataatgataaaaaaatcggatttttttggcaattccatcggaggagtataaaggtattctaagtcttcgttatcaagtgttta agcaaagacttgagtgggacttagttgtagaaaataaccttgaatcagatgagtatgataactcaaatgcagaatatatttatgcttg
```

-continued
tgatgatactgaaaatgtaagtggatgctggcgtttattacctacaacaggtgattatatgctgaaaagtgtttttcctgaattgctt ggtcaacagagtgctcccaaagatcctaatatagtcgaattaagtcgttttgctgtaggtaaaaatagctcaaagataaataactctg ctagtgaaattacaatgaaactatttgaagctatatataaacacgctgttagtcaaggtattacagaatatgtaacagtaacatcaac agcaatagagcgattttttaaagcgtattaaagttccttgtcatcgtattggagacaaagaaattcatgtattaggtgatactaaatcg gttgtattgtctatgcctattaatgaacagtttaaaaaagcagtcttaaatgcagcgaacgacgaaaattacgcccttgcagcg SEQ ID NO: 4
linker cdd to irgd:
GGGGSGGGGSGGGGSLGDPNSGCRGDKGPDC SEQ ID NO: 5
iRGD:
ggcggcggcggcagcggcggcggcggcagcggcggcggcggcagcctgggcgatccgaacagcggctgccgcggcgataaaggcccgg attgctaa SEQ ID NO: 6
CDD:
atgccctccaaatccttggttatggaatatttggctcatcccagtacactcggcttggctgttggagttgcttgtggcatgtgcctgg gctggagccttcgagtatgctttgggatgctcccaaaagcaagacgagcaagacacacacagatactgaaagtgaagcaagcatctt gggagacagc In some embodiments, the at least one bacterial cell comprises SEQ ID NO:7 or a nucleci acid sequence 70%, 75%, 80%, 85%, 90%, 95%, 96%, 97%, 98%, or 99% homolgous to SEQ ID NO:7.

SEQ ID NO: 7 is plasmid pB33eCPX-NC-IRGD
gcaaactattaactggcgaactactactctagcttcccggcaacaattaatagactggatggaggcggataaagttgcaggaccac ttctgcgctcggcccttccggctggctggtttattgctgataaatctggagccggtgagcgtgggtctcgcggtatcattgcagcac tggggccagatggtaagccctcccgtatcgtagttatctacacgacggggagtcaggcaactatggatgaacgaaatagacagatcg ctgagataggtgcctcactgattaagcattggtaactgtcagaccaagtttactcatatatactttagattgatttacgcgccctgt agcggcgcattaagcgcggcgggtgtggtggttacgcgcagcgtgaccgctacacttgccagcgccctagcgcccgctcctttcgct ttcttcccttcctttctcgccacgttcgccggctttccccgtcaagctctaaatcggggggctccctttagggttccgatttagtgct ttacggcacctcgaccccaaaaaacttgatttgggtgatggttcacgtagtgggccatcgccctgatagacggttttttcgcccttg acgttggagtccacgttctttaatagtggactcttgttccaaacttgaacaacactcaaccctatctcgggctattcttttgattta taagggattttgccgatttcggcctattggttaaaaaatgagctgatttaacaaaaatttaacgcgaattttaacaaaatattacgt ttacaatttaaaaggatctaggtgaagatccttttgataatctcatgaccaaaatcccttaacgtgagttttcgttccactgagcg tcagaccccgtagaaaagatcaaaggatcttcttgagatcctttttttctgcgcgtaatctgctgcttgcaaacaaaaaaaccaccg ctaccagcggtggtttgtttgccggatcaagagctaccaactctttttccgaaggtaactggcttcagcagagcgcagataccaaat actgtccttctagtgtagccgtagttaggccaccacttcaagaactctgtagcaccgcctacatacctcgctctgctaatcctgtta ccagtcaggcatttgagaagcacacggtcacactgcttccggtagtcaataaaccggtaaaccagcaatagacataagcggctattt aacgaccctgccctgaaccgacgaccgggtcgaatttgctttcgaatttctgccattcatccgcttattatcacttattcaggcgta gcaccaggcgtttaagggcaccaataactgccttaaaaaaattacgccccgccctgccactcatcgcagtactgttgtaattcatta agcattctgccgacatggaagccatcacagacggcatgatgaacctgaatcgccagcggcatcagcaccttgtcgccttgcgtataa tatttgcccatggtgaaaacggggggcgaagaagttgtccatattggccacgtttaaatcaaaactggtgaaactcacccagggattg gctgagacgaaaaacatattctcaataaaccctttagggaaataggccaggttttcaccgtaacacgccacatcttgcgaatatatg tgtagaaactgccggaaatcgtcgtggtattcactccagagcgatgaaaacgtttcagtttgctcatggaaaacggtgtaacaaggg tgaacactatcccatatcaccagctcaccgtattcattgccatacggaattccggatgagcattcatcaggcgggcaagaatgtgaa taaaggccggataaaacttgtgcttatttttctttacggtctttaaaaaggccgtaatatccagctgaacggtctggttataggtac -continued

```
attgagcaactgactgaaatgcctcaaaatgttctttacgatgccattgggatatatcaacggtggtatatccagtgatttttttct
ccatttttagcttccttagctcctgaaaatctcgataactcaaaaaatacgcccggtagtgatcttatttcattatggtgaaagttgg
aacctcttacgtgccgatcaacgtctcattttcgccaaaagttggcccagggcttcccggtatcaacagggacaccaggatttattt
attctgcgaagtgatcttccgtcacaggtattttattcggcgcaaagtgcgtcgggtgatgctgccaacttactgatttagtgtatga
tggtgtttttgaggtgctccagtggcttctgtttctatcagctgtccctcctgttcagctactgacggggtggtgcgtaacggcaaa
agcaccgccggacatcagcgctagcggagtgtatactggcttactatgttggcactgatgagggtgtcagtgaagtgcttcatgtgg
caggagaaaaaggctgcaccggtgcgtcagcagaatatgtgatacaggatatattccgcttcctcgctcactgactcgctacgctc
ggtcgttcgactgcggcgagcggaaatggcttacgaacggggcggagatttcctggaagatgccaggaagatacttaacagggaagt
gagagggccgcggcaaagccgttttttccataggctccgcccccctgacaagcatcacgaaatctgacgctcaaatcagtggtggcga
aacccgacaggactataaagataccaggcgtttccccctggcggctccctcgtgcgctctcctgttcctgccttccggtttaccggt
gtcattccgctgttatggccgcgtttgtctcattccacgcctgacactcagttccgggtaggcagttcgctccaagctggactgtat
gcacgaaccccccgttcagtccgaccgctgcgccttatccggtaactatcgtcttgagtccaacccggaaagacatgcaaaagcacc
actggcagcagccactggtaattgatttagaggagttagtcttgaagtcatgcgccggttaaggctaaactgaaaggacaagttttg
gtgactgcgctcctccaagccagttacctcggttcaaagagttggtagctcagagaaccttcgaaaaaccgccctgcaaggcggttt
tttcgttttcagagcaagagattacgcgcagaccaaaacgatctcaagaagatcatcttattaatcagataaaatatttgctcatga
gcccgaagtggcgagcccgatcttccccatcggtgatgtcggcgatataggcgccagcaaccgcacctgtggcgccggtgatgccgg
ccacgatgcgtccggcgtagaggatctgctcatgtttgacagcttatcatcgatgcataatgtgcctgtcaaatggacgaagcaggg
attctgcaaaccctatgctactccgtcaagccgtcaattgtctgattcgttaccaattatgacaacttgacggctacatcattcact
ttttcttcacaaccggcacggaactcgctcgggctggccccggtgcattttttaaatacccgcgagaaatagagttgatcgtcaaaa
ccaacattgcgaccgacggtggcgataggcatccgggtggtgctcaaaagcagcttcgcctggctgatacgttggtcctcgcgccag
cttaagacgctaatccctaactgctggcgaaaagatgtgacagacgcgacggcgacaagcaaacatgctgtgcgacgctggcgata
tcaaaattgctgtctgccaggtgatcgctgatgtactgacaagcctcgcgtacccgattatccatcggtggatggagcgactcgtta
atcgcttccatgcgccgcagtaacaattgctcaagcagatttatcgccagcagctccgaatagcgcccttcccctttgcccggcgtta
atgatttgcccaaacaggtcgctgaaatgcggctggtgcgcttcatccgggcgaaagaacccgtattggcaaatattgacggccag
ttaagccattcatgccagtaggcgcgcggacgaaagtaaacccactggtgataccattcgcgagcctccggatgacgaccgtagtga
tgaatctctcctggcgggaacagcaaaatatcacccggtcggcaaacaaattctcgtccctgattttttcaccaccccctgaccgcga
atggtgagattgagaatataacctttcattcccagcggtcggtcgataaaaaaatcgagataaccgttggcctcaatcggcgttaaa
cccgccaccagatgggcattaaacgagtatcccggcagcaggggatcattttgcgcttcagccatacttttctactcccgccattc
agagaagaaaccaattgtccatattgcatcagacattgccgtcactgcgtcttttactggctcttctcgctaaccaaaccggtaacc
ccgcttattaaaagcattctgtaacaaagcgggaccaaagccatgacaaaaacgcgtaacaaaagtgtctataatcacggcagaaaa
gtccacattgattatttgcacggcgtcacactttgctatgccatagcattttttatccataagattagcggatcctacctgacgcttt
ttatcgcaactctctactgtttctccatacccgttttttgggctagcgaattcgagctcggtacctttgaggtggttatgaaaaaa
attgcatgtctttcagcactggccgcagttctggctttcaccgcaggtacttccgtagctggccagtctggccagtgtcgtggtgat
aaacgtggtcctgatgaatgtggagggcagtctgggcagtctggtgactacaacaaaaaccagtactacggcatcactgctggtccg
gcttaccgcattaacgactgggcaagcatctacggtgtagtgggtgtgggttatggtaaattccagaccactgaatacccgacctac
aaacacgacaccagcgactacggtttctcctacggtgcgggtctgcagttcaacccgatggaaaacgttgctctggacttctcttac
gagcagagccgtattcgtagcgttgacgtaggcacctggattttgtctgttggttaccgcttcgggagtaaatcgcgtcgcgcgact
tctactgtaactggcggttacgcacagagcgacgctcagggccaaatgaacaaaatgggcggtttcaacctgaaataccgctatgaa
gaagacaacagcccgctgggtgtgatcggttctttcacttacaccgagaaagccgtactgcaagctgtcgtggtgataaacgtggt
cctgatgaatgttaataaggccaaggtggccaagcttggctgttttggcggatgagagaagattttcagcctgatacagattaaatc
agaacgcagaagcggtctgataaaacagaatttgcctggcggcagtagcgcggtggtcccacctgaccccatgccgaactcagaagt
```

-continued

```
gaaacgccgtagcgccgatggtagtgtggggtctccccatgcgagagtagggaactgccaggcatcaaataaaacgaaaggctcagt cgaaagactgggcctttcgttttatctgttgtttgtcggtgaacgctctcctgagtaggacaaatccgccgggagcggatttgaacg ttgcgaagcaacggcccggagggtggcgggcaggacgcccgccataaactgccaggcatcaaattaagcagaaggccatcctgacgg atggccttttgcgtttctacaaactcttttgtttattttctaaatacattcaaatatgtatccgctcatgagacaataaccctga taaatgcttcaataatattgaaaaaggaagagtatgagtattcaacatttccgtgtcgcccttattccttttttgcggcattttgc cttcctgttttgctcacccagaaacgctggtgaaagtaaaagatgctgaagatcagttgggtgca
```

Figure 1B:
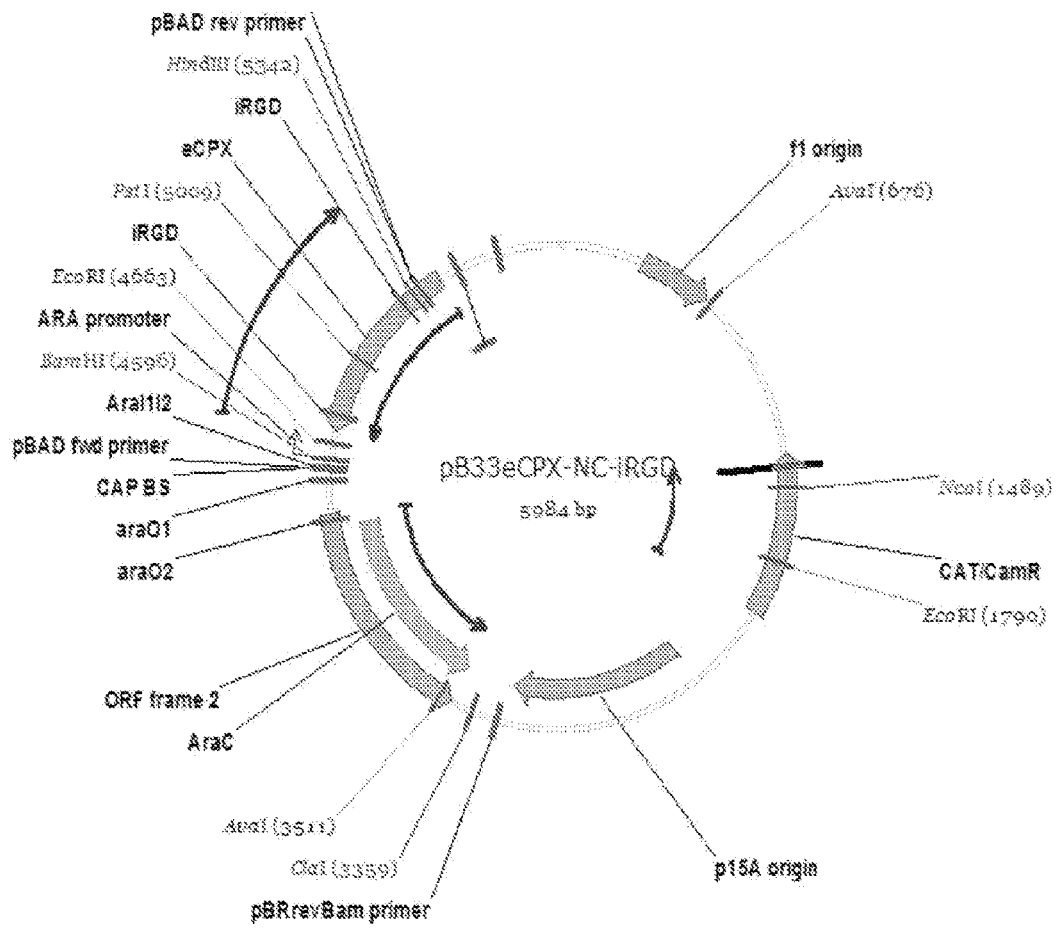
FIG. 1B depicts plasmid pB33eCPX-NC-IRGD.

The restriction map of SEQ ID NO:7 is depicted in FIG. 1B.

Example 2

Synthetic biology seeks to add controlled and dynamic production of cargo by utilizing computationally-designed "circuits" that have sophisticated sensing and delivery capability These circuits can be designed to act as delivery systems that sense tumor-specific stimuli and self-regulate cargo production as accessary. Since plasmids are the common framework for synthetic circuits, we begin by characterizing the dynamics of plasmid-based gene expression in an in vivo mouse model by utilizing real-time luminescence imaging, quantitative biodistribution measurement, and computational modeling. Together, these approaches provide a framework for exploiting the inherent instability of plasmid-based networks, which will facilitate the generation of specific temporal release profiles directly within the tumor environment.

In the context of drug delivery, a critical parameter is the rate at which a device releases drug into the surrounding environment. For instance, materials have been investigated that generate "burst", "delayed", or "sustained" release characteristics. The transient plasmid-based system we have developed here can generate a similar variety of expression dynamics. For instance, Strain A produces an expression profile analogous to, burst release due to its fast growth rate and high rate of plasmid loss. In contrast, Strain B yields a sustained release profile owing to its slow growth rate and moderate rate of plasmid loss. Bacteria are unique in the context of drug-delivery vehicles in that they produce their own cargo, in contrast to other devices that are pre-loaded and depleted. This allows them to deliver a time-varying concentration of cargo in a designed profile directly on site. In the future, this work will enable a variety of drug-release profiles from engineered bacteria for therapeutic applications.

Developing both experimental and computational techniques in concert will be critical to engineering in vivo genetic circuits. Computational modeling can rapidly probe system parameters to explore potential outputs but must remain closely tied to experimental results to remain relevant. On the other hand, in vivo experiments present the most direct application of engineered circuits, but involve long timescales and the results often difficult to interpret. Here, we have utilized plasmid instability to generate transient expression profiles in tumor environments. In our computational model, we can predict how dosage, strain growth rate, and plasmid loss rate combine to yield differing expression dynamics. Then, these designs can be implemented experimentally by varying plasmid type, copy number, and maintenance system or by modifying the strain growth rate. Building on this platform, future applications will include engineered gene circuits that further extend the range of expression dynamics, sensing tumor-specific stimuli and self-regulating cargo production.

Materials and Methods

*S. typhimurium* strains Strain A (SL1344 PhoPQ-) and Strain B (SL1344 PhoPQ-aroA-) were provided by Elizabeth Hohmann (MGH) ([10]). The constitutive plasmid bearing luxCDABE genes was received as a gift ([12]). On the day of injection, bacteria containing plasmids were diluted 1/1000× into fresh LB media (Difco, 0.22 um filtered) with antibiotics (Ampicillin 10 ug/mL) and grown up to OD600=0.4-0.6. Cells were then prepared by washing 4 times with PBS (0.22 um filtered) and measured for $OD_{600}$. Colony counts were performed on the preparation as a calibration and cells were prepared at various concentrations for 1004 injections.

Subcutaneous human xenograft tumors were generated by injecting $5 \times 10^6$ OVCAR-8 cells (NCI DCTD Tumor Repository, Frederick, Md.) bilaterally into the hind flanks of 4-week old female Ncr/Nu mice. Cells were grown to 80-100% confluency in RPMI1640 media supplemented with 10% fetal bovine serum and antibiotics (100 I.U./mL penicillin and 100 µg/mL streptomycin) before injection. Cells were pelleted, resuspended in phenol, red-free DMEM with 15% reduced growth factor Matrigel (BD Biosciences). Tumors were allowed to grow for 10-20 days until tumor diameters of 200-400 mm were reached.

Colony counts were measured by dissecting tumors and organs from mice, homogenizing using a Tissue-Tearor (BioSpec), and plating serial dilutions on LB and LB Ampicillin plates. Prior to imaging, mice were anesthetized with 2-3% isoflurane. IVIS signals were measured using the IVIS Spectrum imaging system (Caliper Life Sciences) with 1-60 second exposure times, and Living Image software (Caliper Life Sciences) was used for analysis. Data where the tumor had ulcerated or had low signal (maximum of trajectory did not reach above $10^6$ radiance, or approximately 5-10× initial background) were not included.

In FIG. 2: Tumor homing bacteria and dosage variation. (a) *S. typhimurium* are injected via tail-vein into nude mice and localize to subcutaneous tumors where they replicate. (b) Dosages between $10^4$ and $5 \times 10^6$ bacteria are injected into mice and IVIS images were taken after 24 hours. Higher initial dosages show an increasing signal and a minimum value of $5 \times 10^5$ bacteria required to visualize tumor colonization at 24 hours. (c) Sequence of IVIS images for strain Strain A at $10^6$ dosage over the course of 60 hours. (d) Total flux of left (light grey) and right (dark grey) tumors as a function of time normalized to the maximum value across the trajectory. The IVIS signal rises due to rapid bacterial growth and then decays due to plasmid loss and luciferase instability.

Figure 2A:
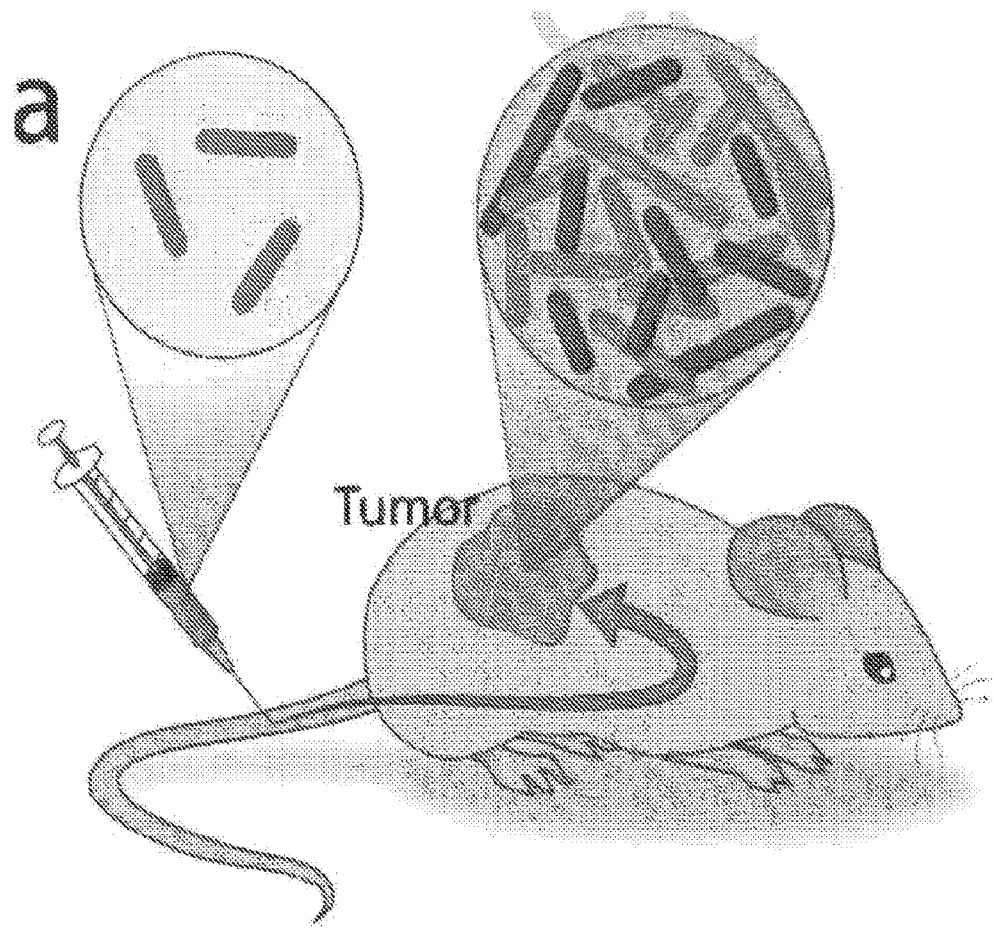
FIG. 2 depicts a schematic of an embodiment. (2A) Schematic showing programmed bacteria being introduced systemically via tail-vein injection in a mouse model. (2B) Variable dosage of bacteria yield different peak onset times of therapeutic agent expression. (2C, 2D) The bacterial cells at different dosages produce dynamioc and temporal expression profiles in vivo.
Figure 2B:
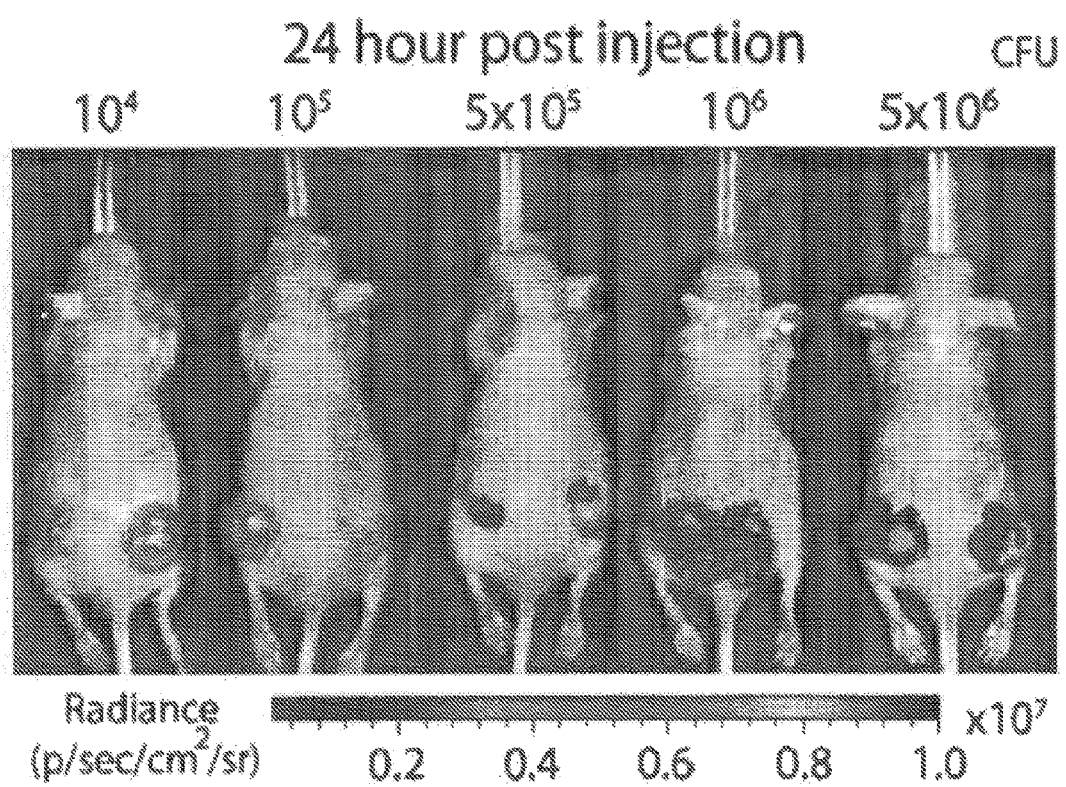

These circuits can be designed to act as delivery systems that sense tumor-specific stimuli and self-regulate cargo production as accessary. Since plasmids are the common framework for synthetic circuits, we begin by characterizing the dynamics of plasmid-based gene expression in an in vivo mouse model by utilizing real-time luminescence imaging, quantitative biodistribution measurement, and computational modeling. Together, these approaches provide a framework for exploiting the inherent instability of plasmid-based networks, which will facilitate the generation of specific temporal release profiles directly within the tumor environment We began by transforming two different attenuated strains of S. typhimurium with a constitutively expressed luciferase (luxCDABE) plasmid to allow for real-time monitoring of luminescence with an in vivo imaging system (IVIS). Strain A (ELH430:SL1344 phoPQ-) is attenuated for the PhoPQ regulon which is known to activate a number of genes related to virulence while Strain B (ELH1301:SL1344 phoPQ-aroA-) contains an additional aromatic amino acid synthesis mutation which effectively allows it to grow only in nutrient-rich environments. Importantly, while these strains are derived from the same parent (SL1344), their growth rates, and therefore plasmid-loss characteristics, differ significantly. To investigate the in vivo gene expression dynamics of these strains, we generated model xenograft tumors in mice by subcutaneous injection of a human ovarian cancer cell line (OVCAR-8). After measurable tumors were established, bacterial strains were injected intravenously via tail vein (FIG. 2 A) with dosages varying from $10^4$ to $5 \times 10^6$ bacteria. Once injected, bacteria specifically colonized tumors at a rate proportional to the dosage administered, as measured by IVIS signal at 24 hours post-injection (FIG. 2B).

Figure 2C:
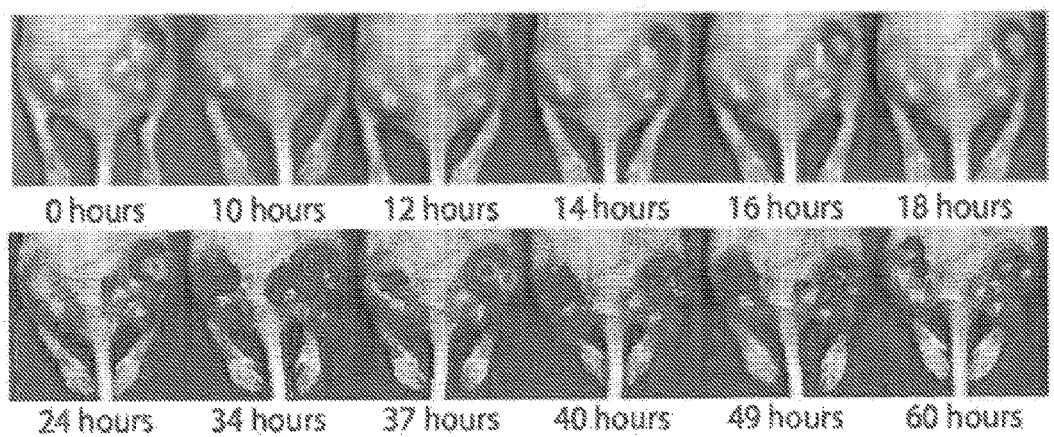
Figure 2D:
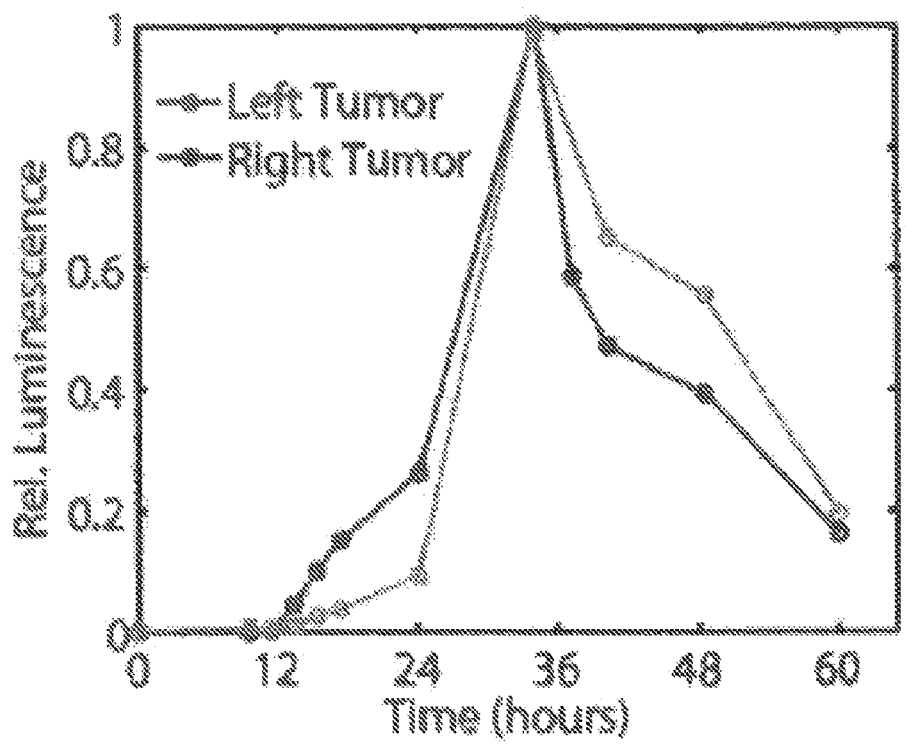

We then monitored tumor signal over the course of 60 hours using time-lapse IVIS imaging (FIG. 2C,D). These trajectories followed the specific pattern of an initial steep increase followed by a gradual decrease back to baseline (FIG. 2D). We hypothesized that this waveform was the result of the initial exponential growth of plasmid-containing bacteria followed by increasing rates of plasmid loss in the absence of antibiotic selection. Eventually, the rate of luciferase production by the remaining plasmid-containing bacteria is overtaken by luciferase decay, and signal begins to decline. To test this hypothesis, we counted the number of plasmid-containing and non-plasmid containing bacteria in tumors over time by observing bacterial growth on selective media. FIG. 3: Characterization of Strain A and Strain B IVIS Profiles.

Figure 3A:
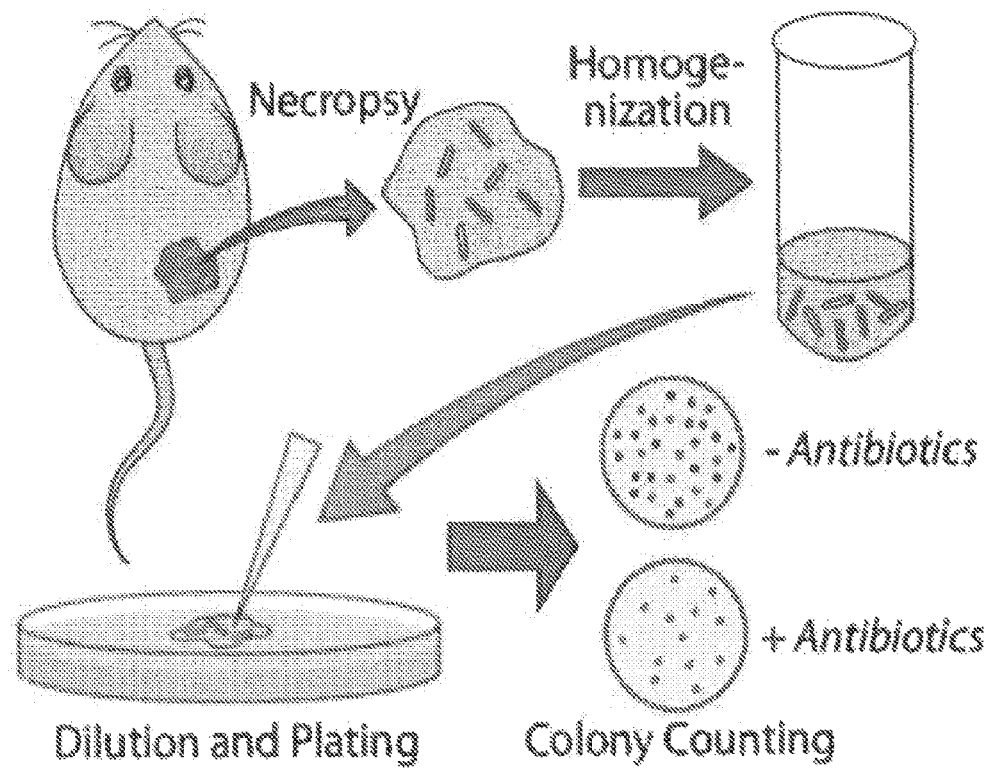
FIG. 3 depicts the population dynamics of bacteria inside tumor environments. (3A) Schematic showing tumor extraction, homogenization and plating to count internal populations of bacteria. Plating on antibiotics reveals the number of plasmid-containing bacteria while plating without antibiotics gives the total number of bacteria. (3B) Measured number of positive and negative containing bacteria per organ calculated for plasmid containing bacteria (light grey) and non-plasmid containing bacteria (dark grey). Bacteria with the plasmid reach a steady state around 24 hours while the non-plasmid bacteria continue to grow. (3C) Percentage of cells containing the plasmid as a function of time showing a constant loss rate over the course of 72 hours. (3D) Ratio for total number of bacteria in the tumor vs. the spleen. This number is typically reported as a measure of specificity of the tumor-targeting strain.
Figure 3B:
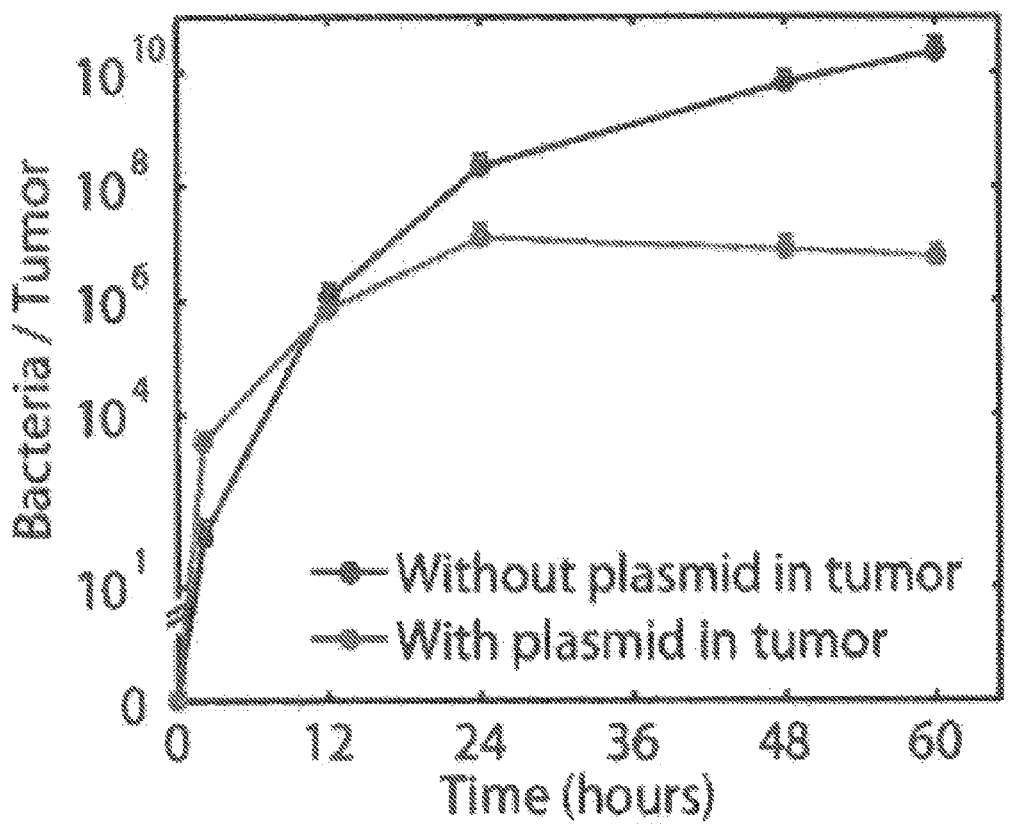

Each measurement was compared to counts taken in the spleen, a control tissue where there is a stable sub-population as the bacteria accumulate but do not grow or die. At each time point, organs were excised from the mouse and then homogenized and plated with or without antibiotic selection (FIG. 3A, n=3-5 tumors). Colony counting on these plates yielded an accurate measure of the plasmid-state of the bacterial population over time (FIG. 3B). After 2 hours, roughly $3 \times 10^3$ plasmid-containing bacteria reside in the tumor, or about 0.3% of the injected dose. After 12 hours, plasmid-containing bacteria grow to a level of $10^6$, and the number of non plasmid-containing bacteria reaches a similar level. This corresponds to a doubling time of approximately 75 minutes. Growth rate declined further over time, presumably due to nutrient limitation, ultimately resulting in a 300 minute doubling time for non-plasmid containing bacteria (FIG. 3B).

Figure 3C:
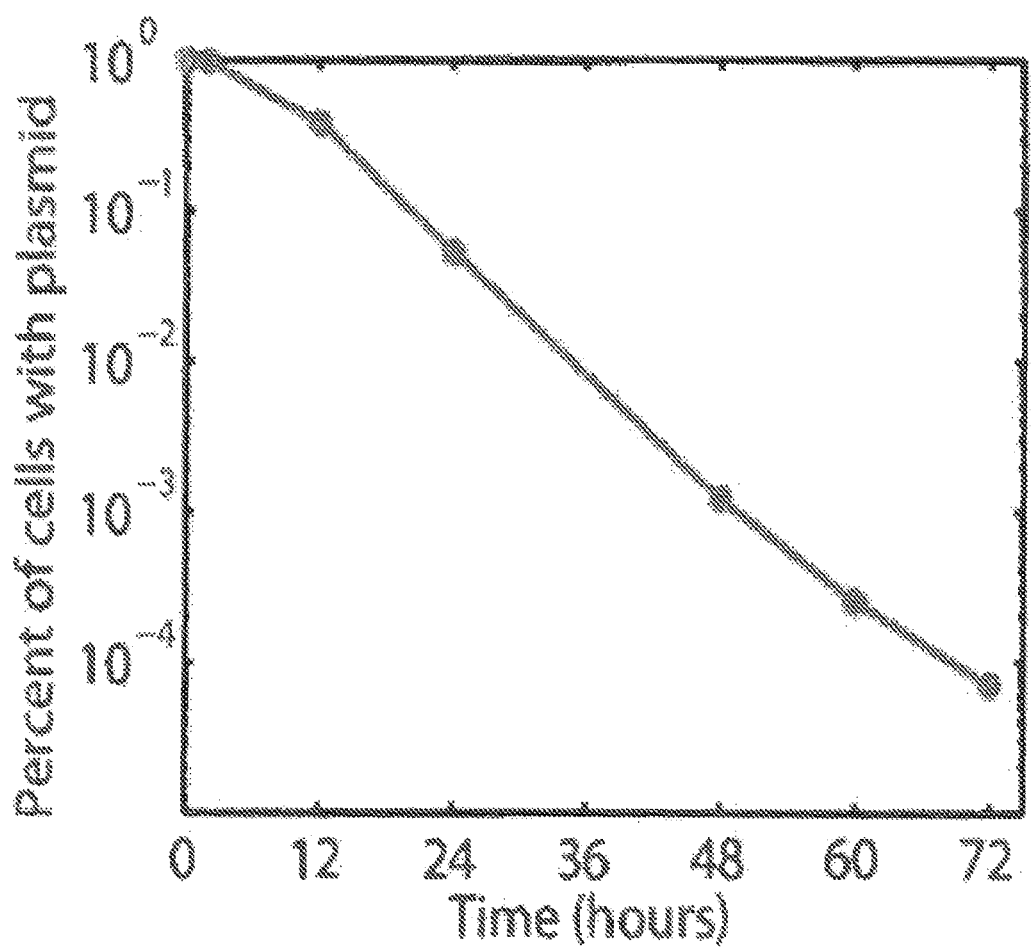

While the total population of bacteria grew throughout the course of the experiment (60 hours), the number of plasmid-containing bacteria reaches a maximum at 24 hours (FIG. 3B). By taking the ratio of these populations, we can calculate the percentage of plasmid-containing bacteria over time (FIG. 3C). After 12 hours, roughly 50% of the population retains the plasmid, a fraction that drops to 10% after 24 hours (FIG. 3C). The slope of this line remains constant throughout the 60-hour experiment and represents the rate of plasmid loss in the tumor environment.

Figure 3D:
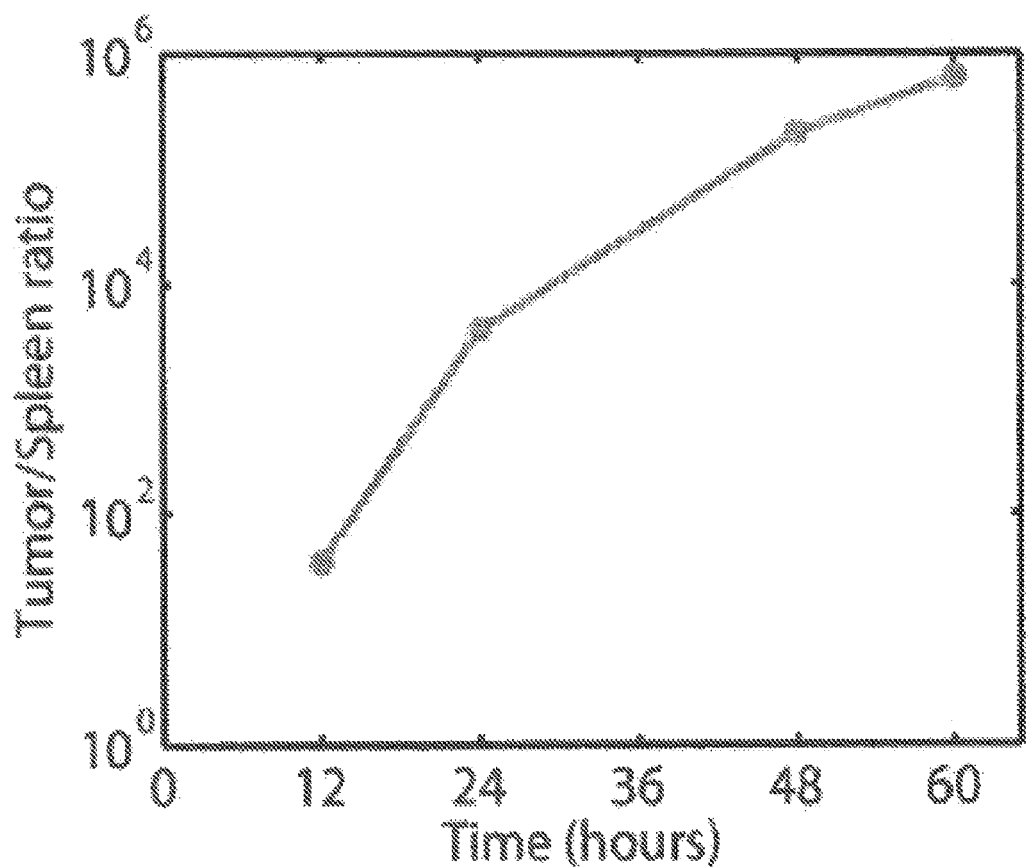

The tumor-spleen ratio is commonly reported as a characteristic measure of specificity and tumor-homing ability for a given strain. Bacteria accumulate in the spleen from the initial dosing yet do not subsequently grow and divide. Given that we observed essentially no increase in the bacterial count in the spleen throughout the duration of our experiments, the tumor-spleen ratio increased over time (FIG. 3D). Since this ratio is typically reported as a fixed number in the literature, its time-dependence may help to explain the wide range of reported values.

Example 3

Modeling Bacterial Dynamics Inside of Tumor Environments

Figure 4A:
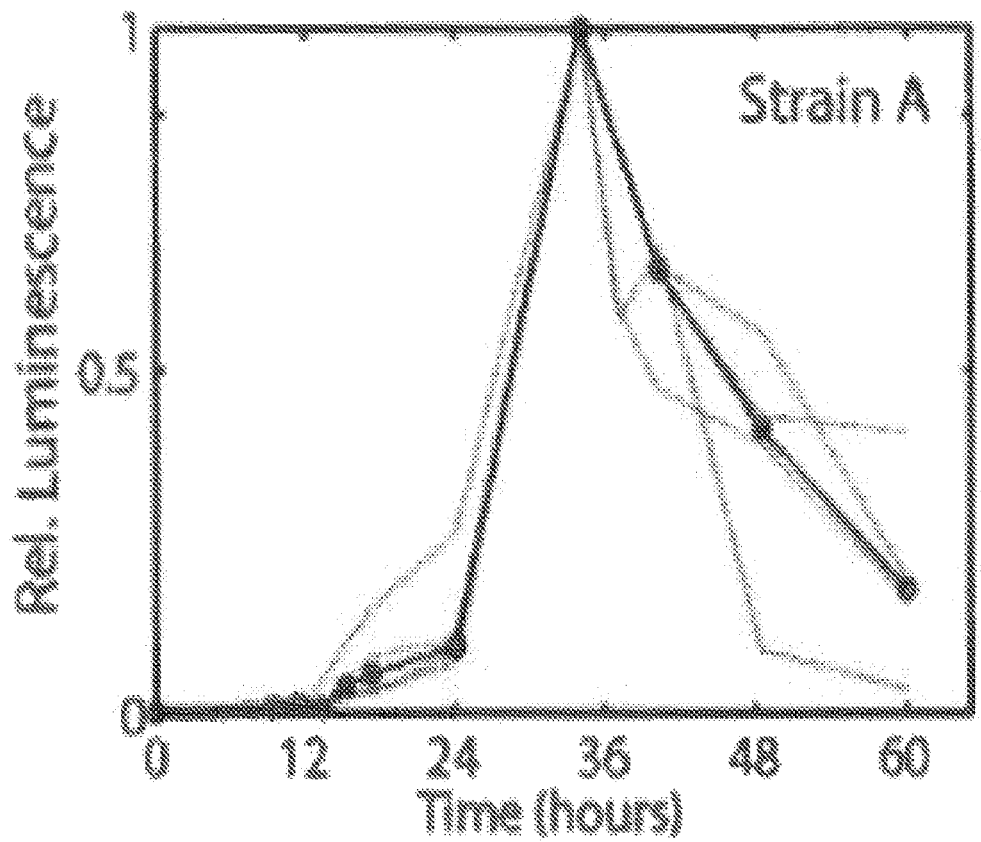
FIG. 4 depicts Characterization of Strain A and Strain B in vivo expression profiles. (4A and 4B) Time-course trajectories for Strain A (4A) and Strain B (4B) over the course of 60 hours normalized to their maximum value across the trajectory. Light grey lines indicate individual trajectories and the solid black line indicates the average trajectories. (4C, Left Panel) Full-width at half-maximum and the area (4C, Right Panel) under the curve for the average trajectory of both strains. These parameters characterize the dosage and duration of transient gene-expression.
Figure 4B:
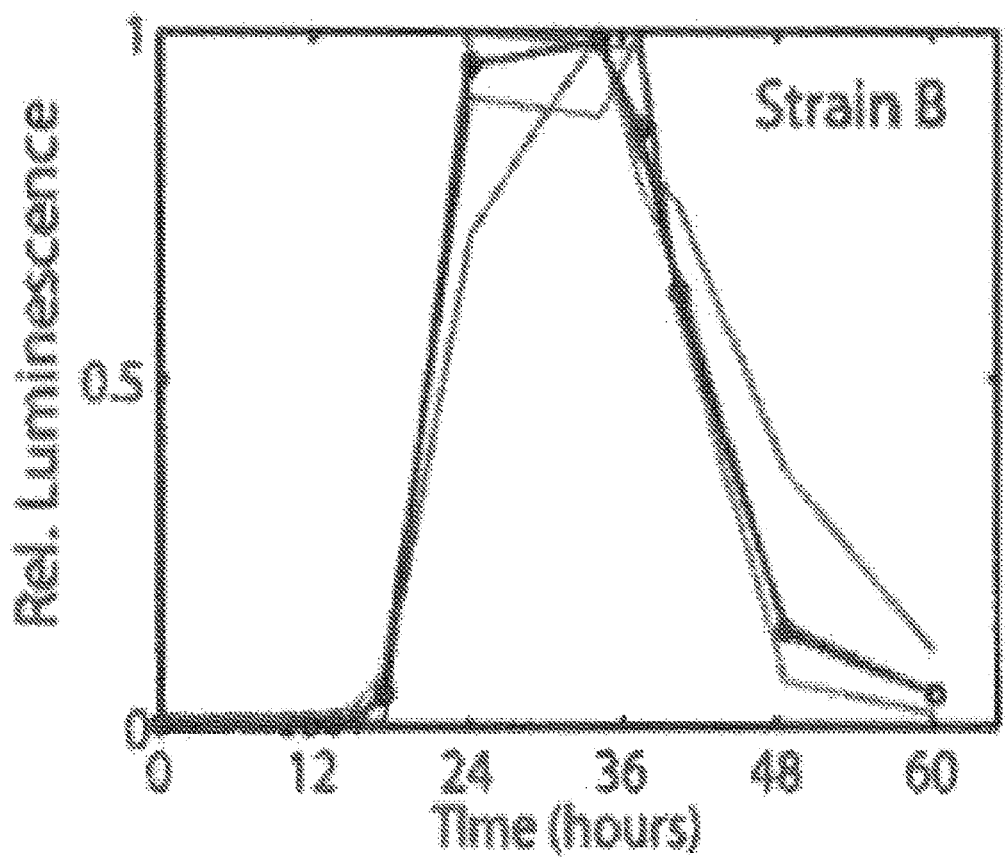
Figure 4C:
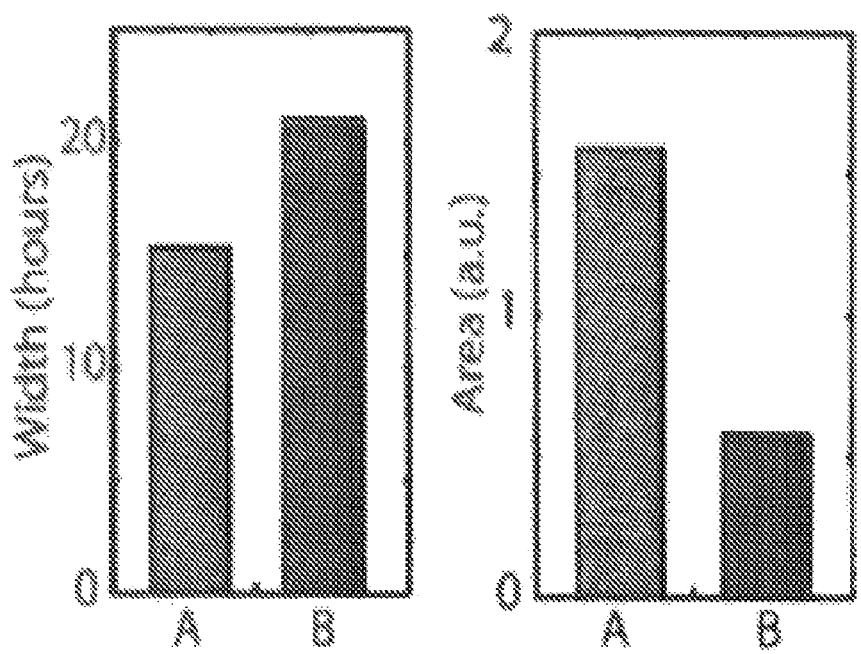

The tumor-spleen ratio is commonly reported as a characteristic measure of specificity and tumor-homing ability for a given strain. Bacteria accumulate in the spleen from the initial dosing yet do not subsequently grow and divide. Given that we observed essentially no increase in the bacterial count in the spleen throughout the duration of our experiments, the tumor-spleen ratio increased over time (FIG. 3d). Since this ratio is typically reported as a fixed number in the literature, its time-dependence may help to explain the wide range of reported values. To explore how bacterial growth rate affects the dynamics of plasmid instability over time, we injected two groups of mice with Strain A and B (at a dosage of $10^6$) and monitored their signal over the course of 60 h. The two strains displayed markedly different profiles, with Strain A peaking and decaying sharply and the slower growing Strain B peaking broadly over a longer period of time before decaying (FIG. 4a,4b). We plot the average trajectories for Strains A and B on an absolute luminescence scale in FIG. 4c for comparison. To quantify these differences, we measured the width at half-maximum and total area under each curve for the average trajectories (FIG. 4d). These measurements illustrate that Strain A produces more luminescence quickly while Strain B produces less luminescence over a longer period of time (FIG. 4d). Additionally, to confirm that signal intensity is a representative measure of the population of plasmid-containing bacteria, we compared counts of antibiotic resistant bacteria with absolute IVIS values at the 72-h time point and found them to be highly correlated (R=0.832).

Figure 5A:
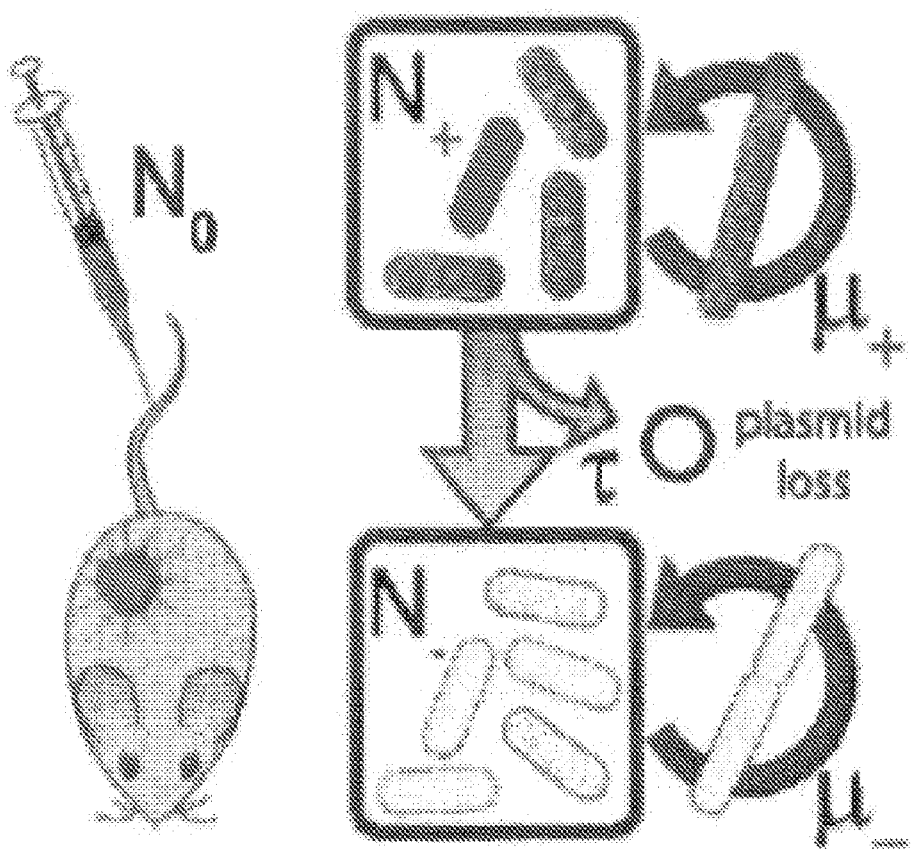
FIG. 5 depicts computational modeling of bacterial dynamics inside of tumor environments. (5A) Schematic of mathematical model. Bacteria containing plasmids are injected at a dosage $N_0$. Plasmids are lost from cells at a rate x and growth of resulting plasmid containing and non-containing cells continues at $\mu+$ and $\mu-$, respectively. (5B) Modeling results (solid lines) for the number of plasmid containing (dark grey) and non-plasmid containing (light grey) bacterial population data from FIG. 3B. Open circles indicate experimental points. (5C) Typical rime course of an IVIS trajectory indicating parameters $\omega$ and area for characterizing transient gene expression. The relative IVIS trajectory is typically measured experimentally due to mouse-to-mouse variability while the absolute IVIS trajectories are used to calculate $\omega$ and area. (5D, 5E, 5F, 5G) The effect of growth rate on transient gene expression. Decreasing growth rate shifts the absolute IVIS signals to a lower value and longer peak times and therefore increasing co and decreasing the area under the curve. (5H, 5I, 5J, 5K) The effect of initial dosage on transient gene expression. Increasing the dosage shifts the absolute IVIS signals to a higher level, increasing the area under the curve, but does not change the relative IVIS trajectory shape or $\omega$ value.

Developing a fully tunable dynamic expression platform will require a more complete understanding of the underlying processes. Plasmid-loss dynamics have been well described in a variety of in vitro and in vivo contexts; however, modeling of population or gene-expression dynamics has not yet been studied for in vivo tumor environments. Specifically, we hope to learn how expression dynamics are dictated by the rates of growth and plasmid-loss for a given strain. To accomplish this, we developed an ordinary differential equation (ODE) model describing internal plasmid and non-plasmid-containing bacteria and their respective expression of luciferase signal (FIG. 5a). Initially, $N_0$ bacteria are injected. These plasmid-containing bacteria replicate and lose their plasmids at rate $\tau$, resulting in populations of plasmid ($N^+$) and non-plasmid ($N^-$) containing bacteria that continue to grow at rates $\mu+$ and $\mu-$, respectively (FIG. 5a). Both populations grow exponentially for 24 h until available nutrients become limiting, a process modeled by including a finite quantity of tumor substrate that is consumed according to Michaelis-Menten kinetics. The tumor environment is also spatially restrictive of bacterial growth, with bacteria in the center consuming nutrients more slowly than bacteria on the rapidly growing periphery. Thus, despite a nearly constant population of plasmid-containing bacteria, IVIS signal fails to increase after 24 h since most of these bacteria reside in the non-growing center of the colony. We accounted for this behavior by limiting the amount of bacteria that can consume the tumor substrate, which effectively limits plasmid-containing bacterial growth and allows luciferase decay to dominate.

Figure 5B:
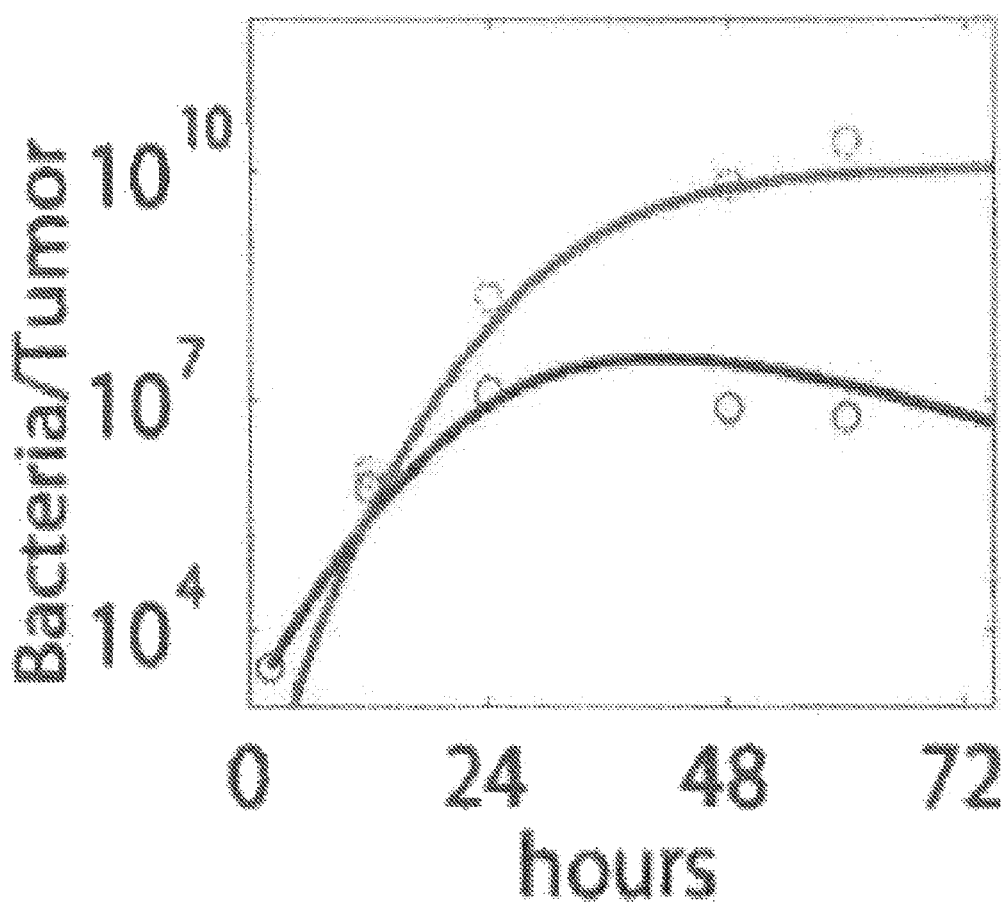
Figure 5C:
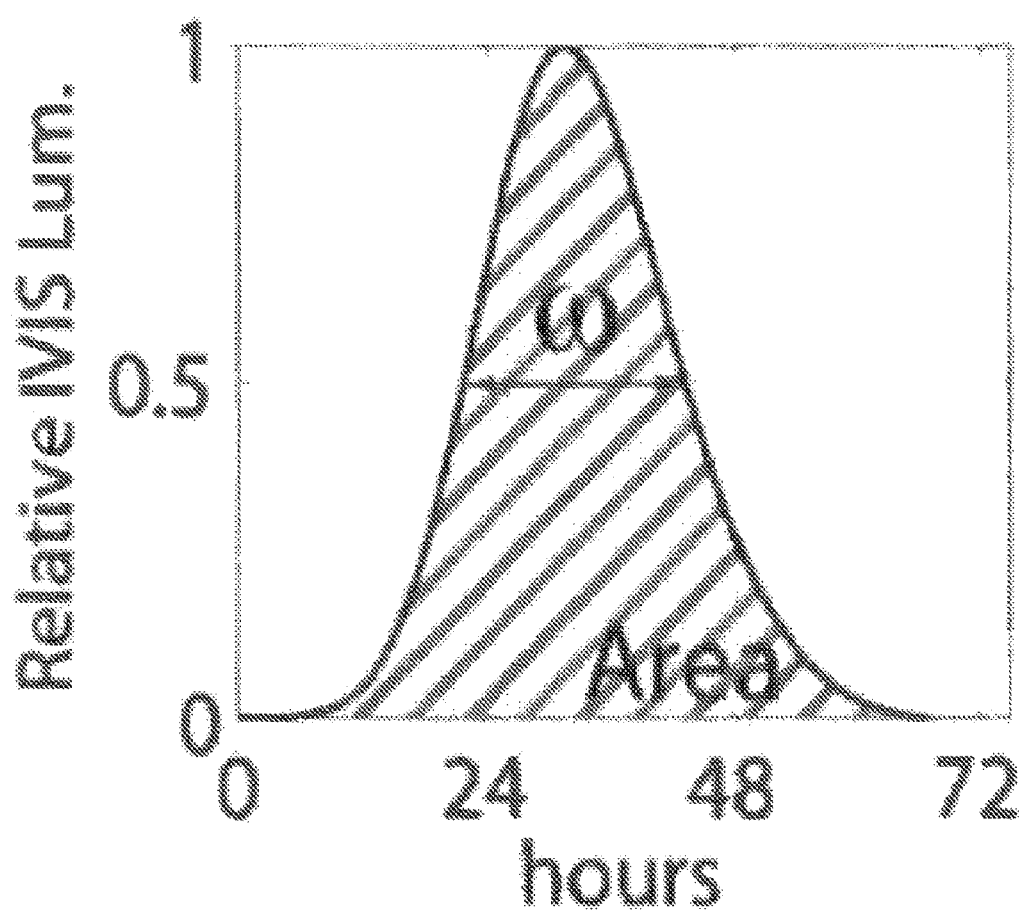
Figure 5D:
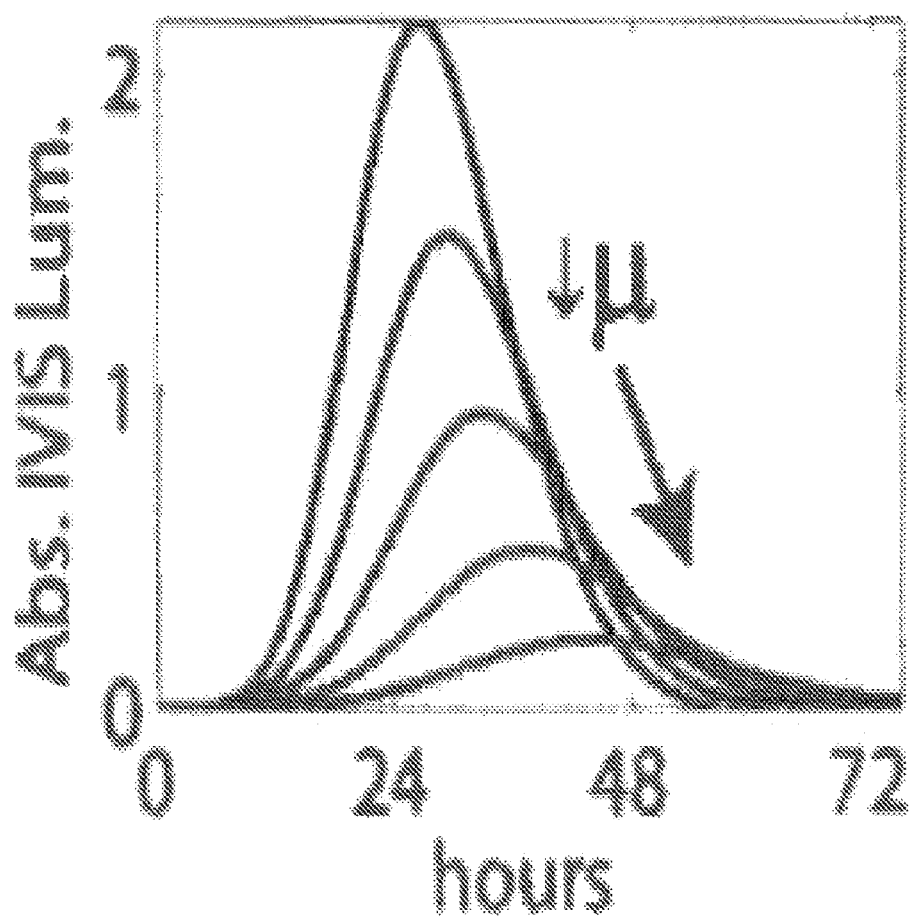
Figure 5E:
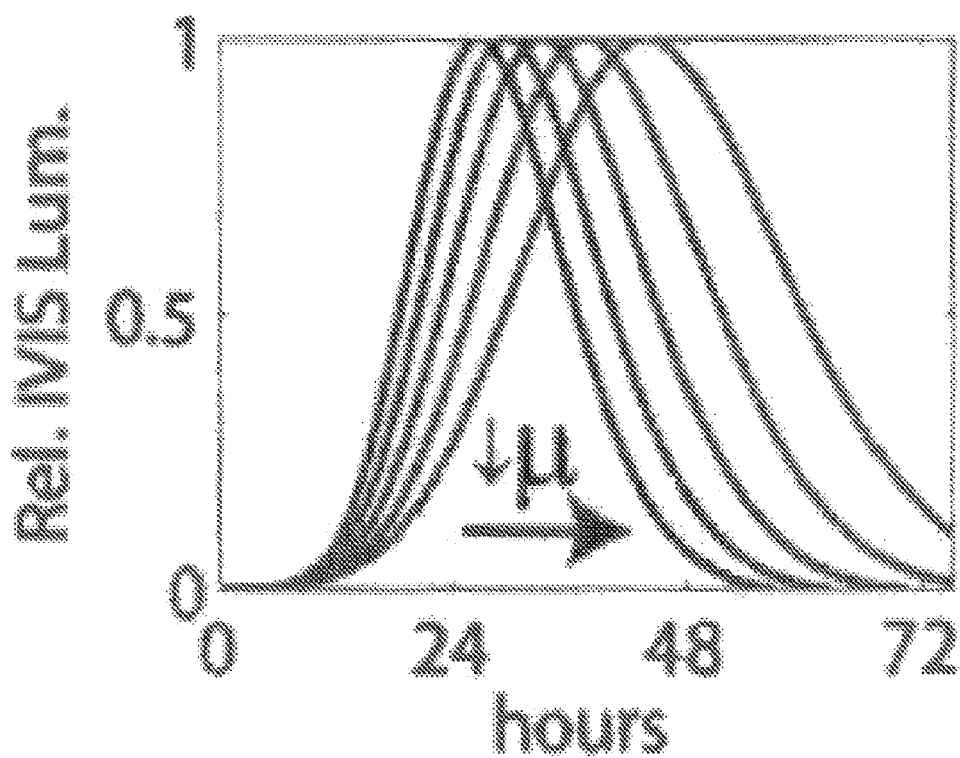
Figure 5F:
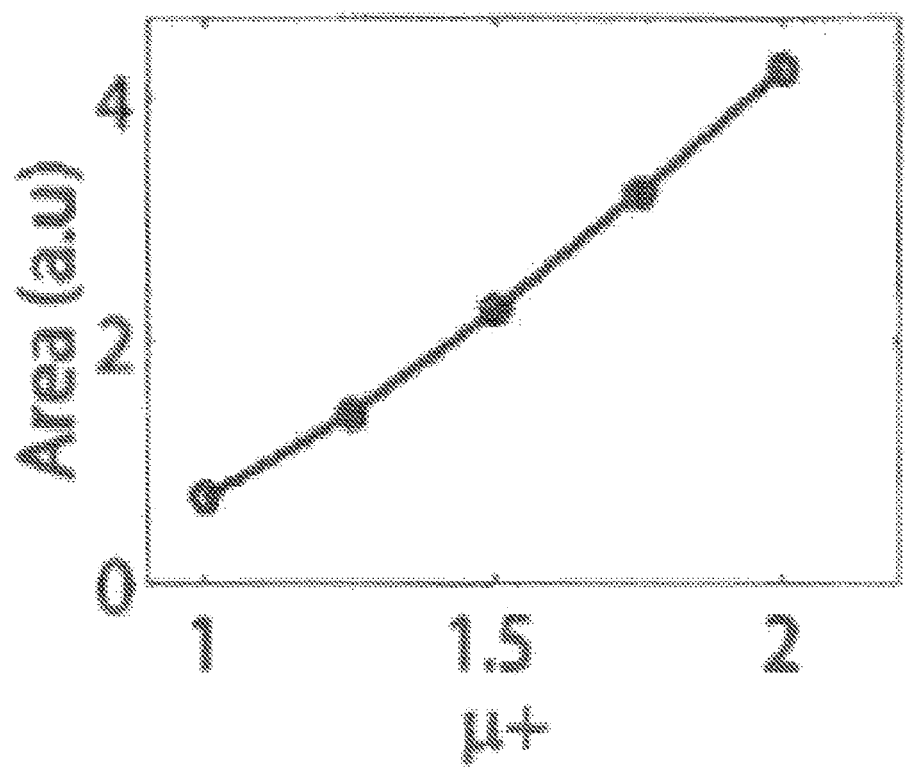
Figure 5G:
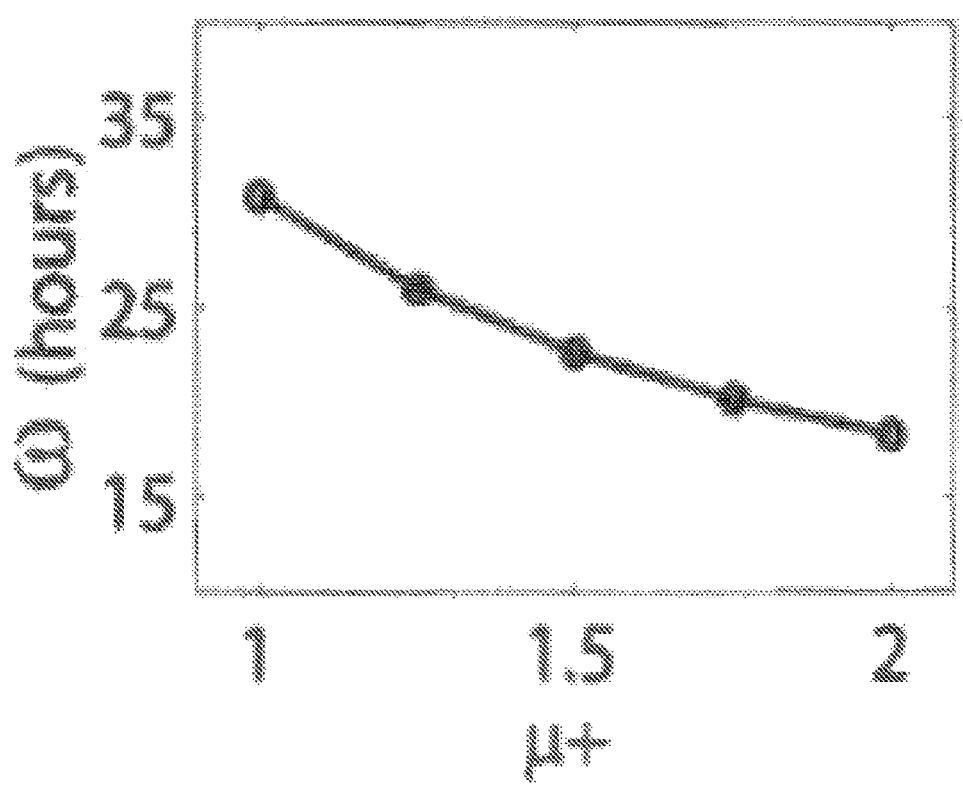
Figure 5H:
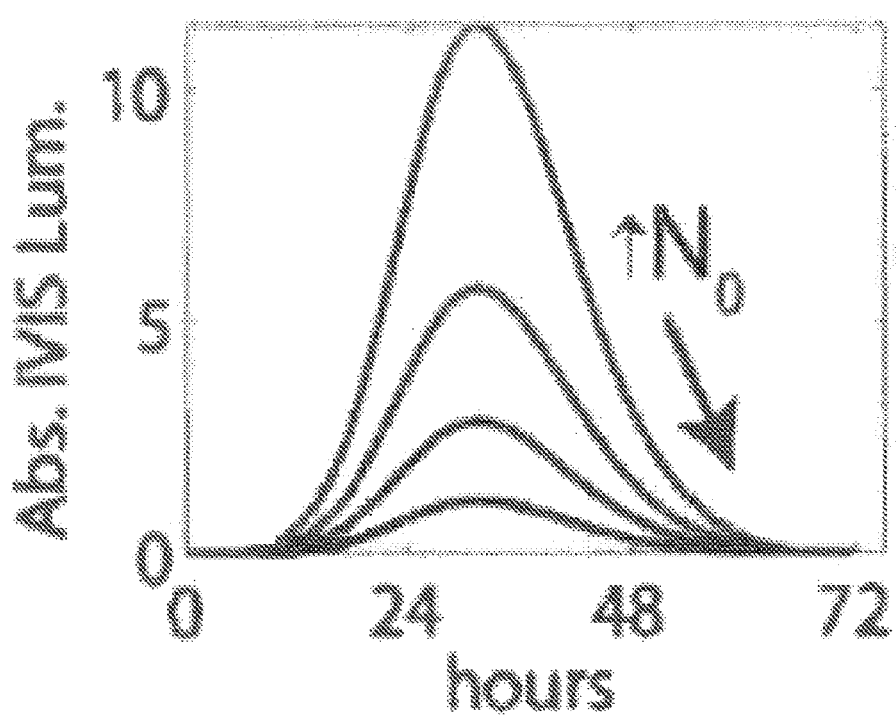
Figure 5I:
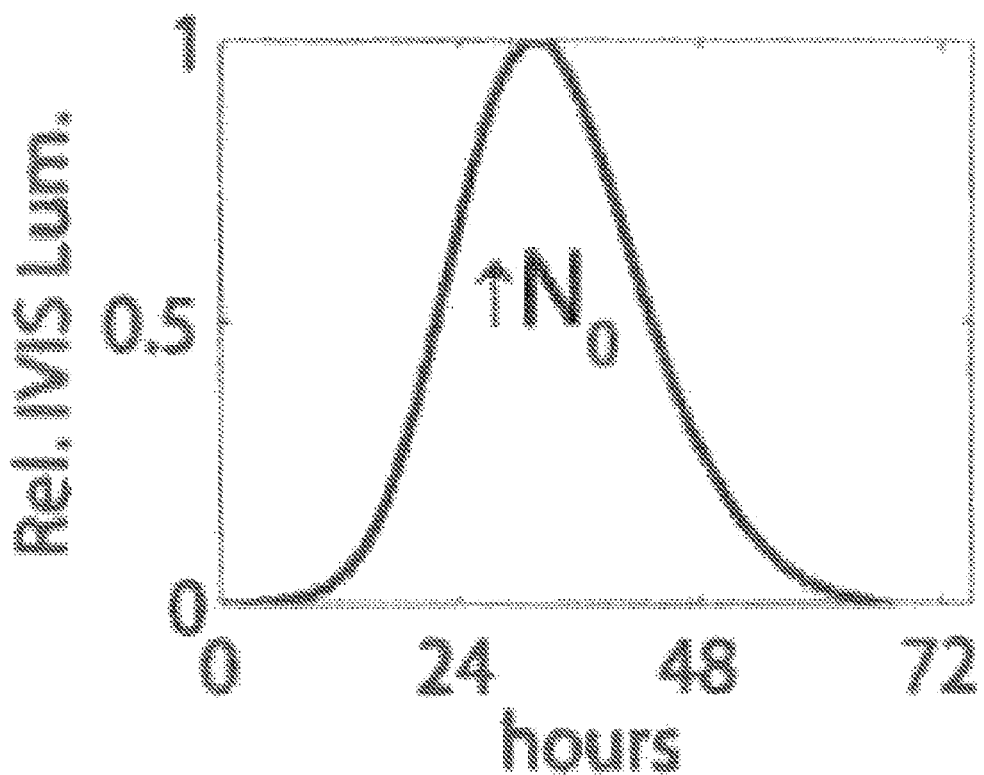
Figure 5J:
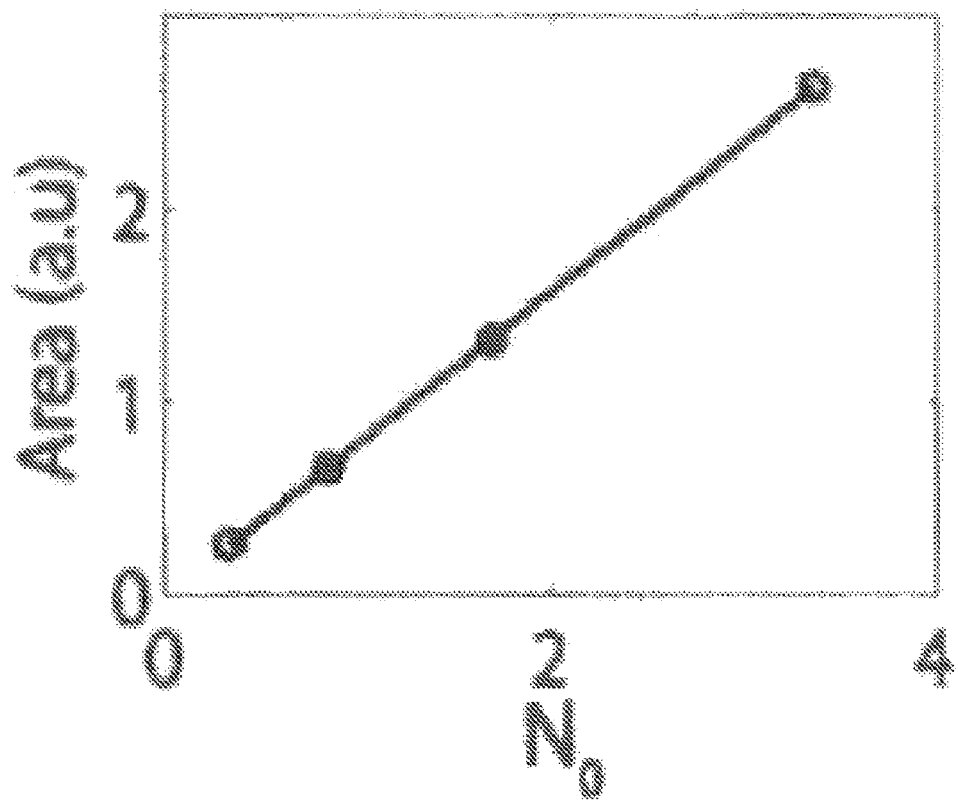
Figure 5K:
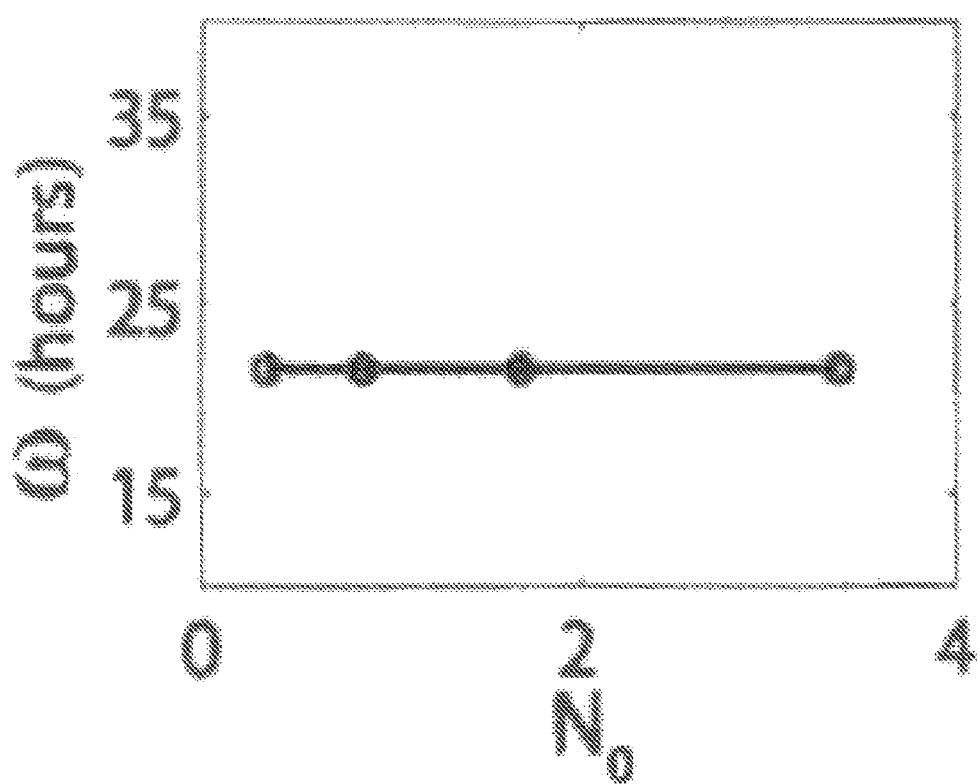

Our ODE model produced dynamics that were consistent with our experimental observations, where IVIS signal is taken to be proportional to the plasmid-containing population (FIG. 5b). We define the full-width at half-maximum, ω, and area under the curve as important parameters that characterize the duration and magnitude of dosage, respectively (FIG. 5c). To understand how to tune in vivo expression profiles according to these parameters, we varied growth rate and dosage level and modeled the effects on IVIS signal in each case (FIGS. 5d,5e, 5f, 5g and 5h, 5i, 5j, 5k). Lower growth rates yield IVIS curves that are shifted toward later times with broader widths and lower areas (FIG. 5d,5e, 5f, 5g). In contrast, larger initial dosages result in a linear increase of IVIS signal that increases area but does not alter the width (FIG. 5h, 5i, 5j, 5k). The latter linear increase in area as a function of dosage is reflective of doses much lower than the carrying capacity of the system. Finally, decreasing the plasmid-loss rate resulted in an increase in area under the curve as well as a slight shift in the width and time to peak of the gene expression profile.

These effects correlate with experimental observations that can be explained based on differences in strain growth rate. Since plasmids are lost during cell division, the faster a cell replicates, the more frequently it loses plasmid. Thus, the faster growing Strain A accumulates luciferase quickly but loses a comparatively larger fraction of plasmids per day, resulting in higher IVIS values that peak at earlier time points than Strain B (FIG. 4a,b). In contrast, Strain B grows more slowly, producing less luciferase but maintaining its plasmids much longer, yielding a broader expression profile compared to Strain A (FIG. 4a,b).

In the context of drug delivery, a critical parameter is the rate at which a device releases drug into the surrounding environment. For instance, materials have been investigated that generate "burst", "delayed", or "sustained" release characteristics. The transient plasmid-based system we have developed here can generate a similar variety of expression dynamics. For instance, Strain A produces an expression profile analogous to burst release due to its fast growth rate and high rate of plasmid loss. In contrast, Strain B yields a sustained release profile owing to its slow growth rate and moderate rate of plasmid loss. Bacteria are unique in the context of drug-delivery vehicles in that they produce their own cargo, in contrast to other devices that are preloaded and depleted. This difference allows them to deliver a time-varying concentration of cargo in a designed profile directly on site. In the future, this work will enable a variety of drug-release profiles from engineered bacteria for therapeutic applications.

Developing both experimental and computational techniques in concert will be critical to engineering in vivo genetic circuits. Computational modeling can rapidly probe system parameters to explore potential outputs but must remain closely tied to experimental results to remain relevant. On the other hand, in vivo experiments present the most direct application of engineered circuits, but involve long time scales and the results are often difficult to interpret. Here, we have utilized plasmid instability to generate transient expression profiles in tumor environments. In our computational model, we can predict how dosage, strain growth rate, and plasmid loss rate combine to yield differing expression dynamics. Subsequently, these designs can be implemented experimentally by varying plasmid type, copy number, and maintenance system or by modifying the strain growth rate. Building on this platform, future applications will include engineered gene circuits that further extend the range of expression dynamics, sensing tumor-specific stimuli and self-regulating cargo production.

Computational models are further explained by way of functions that can be used to determine rate of plasmid loss in a function of concentration of substrate for bacterial growth. Our ordinary differential equation model is presented below in non-dimensional form. The model describes the dynamics of two populations of bacteria, those containing the luminescent plasmid (n+) and those who have lost the plasmid (n−). The two populations grow inside the tumor environment and consume a substrate (S) which is in limited supply.

$$\frac{dn^+}{dt} = (1-\tau)\mu^+ n^+ - \gamma_+ n_+ \quad (1)$$

$$\frac{dn^-}{dt} = \mu^- n^- + \tau\mu^+ n^+ - \gamma_- n_- \quad (2)$$

$$\frac{dS}{dt} = -\left[\frac{\mu^- n^-}{A^-} - \frac{\mu^+ n^+}{A^+}\right]\left[\frac{1}{1+q\cdot(n_-+n_+)}\right] \quad (3)$$

$$\mu^+ = \frac{\mu^+_{max} S}{K+S} \quad (4)$$

$$\mu^- = \frac{\mu^-_{max} S}{K+S}$$

The parameters above are τ, the rate at which cells lose plasmid, μ+max and μ−max, the maximal growth of plasmid and non-plasmid containing cells respectively. K, the Michaelis-saturation constant of growth rate, A+ and A−, the depletion rate constants of substrate S by μ + and μ−cells. γ+ and γ−, the death rates of the bacteria, and q, the rate at which tumor substrate depletion is limited by the maximal amount of cells. This last term is to account for the fact that a limited number of bacteria (those on the outward growing rim) can contribute to the decay of the tumor substrate. The model is non-dimensionalized by hours, 1 bacteria, and a substrate concentration of μM.

The total in vivo system (IVIS) signal is reflective of the number of luciferase enzymes and hence the number of actively expressing luciferase bacteria. As an approximation to this signal, we modeled the signal to be proportional to the number of plasmid containing cells (dominant contribution to the IVIS signal) minus the first-order decay of the luciferase enzyme. We assume that each bacterium containing a plasmid contributes equally to the IVIS signal although there is likely variability due to the distribution of plasmids per cell in a population as well as contributions from non-plasmid containing bacteria where luciferase is not yet significantly diluted. Another approximation in the IVIS signal arises in that plasmid-containing bacteria initially populate the tumor core and express luciferase, but as bacteria grow radially to a larger population, less nutrients are left for the bacteria in the center to express any of the luxCDABE genes (either luciferase or luciferin substrates), which are the main contributors to the IVIS signal. This results in colony counts reaching a nearly steady-state as a function of time but expression level plateauing, causing an decay in IVIS signal due luciferase instability.

Figure 9A:
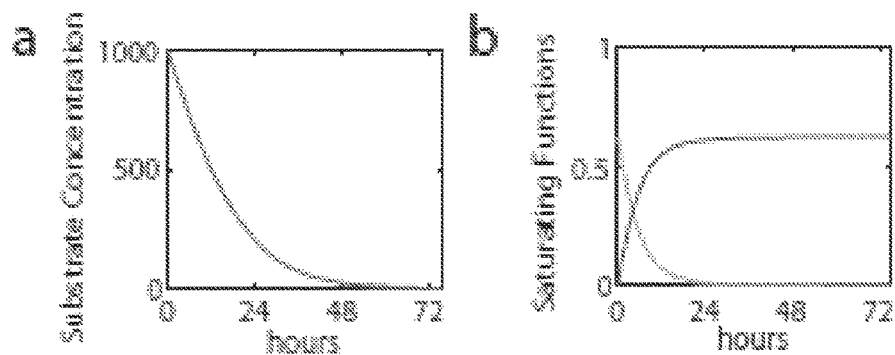
Figure 9B:
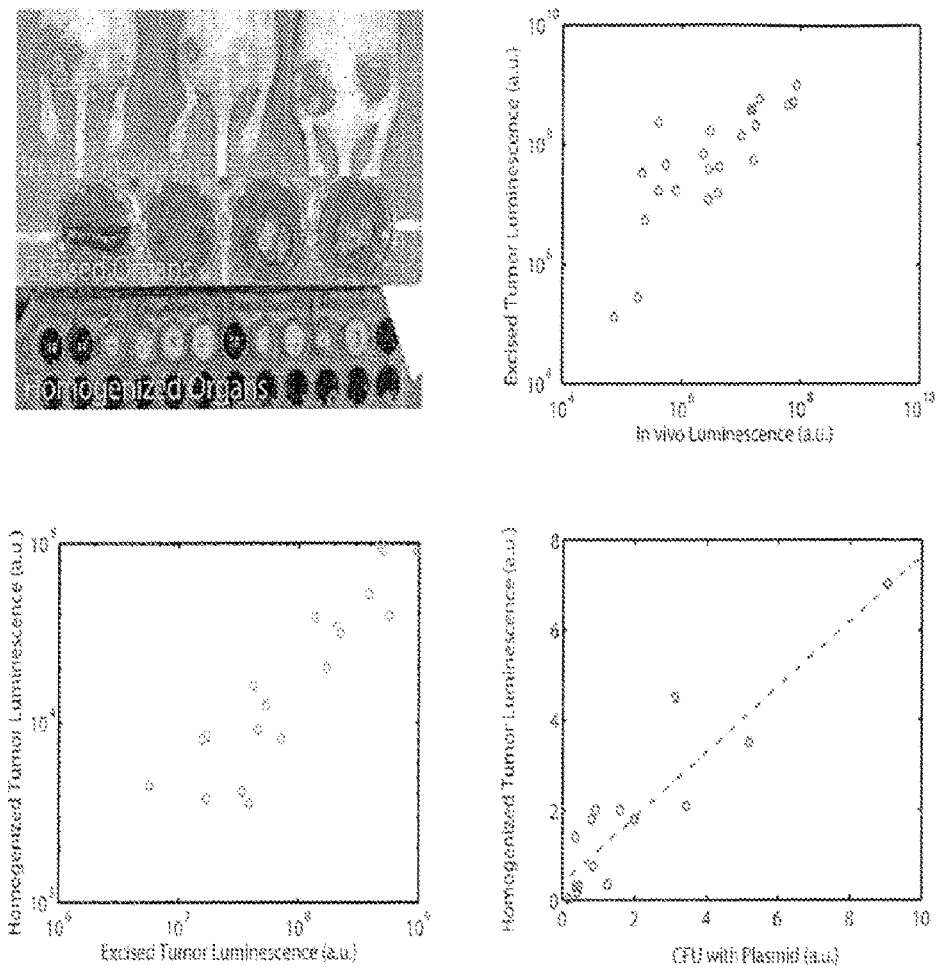
Figure 9C:
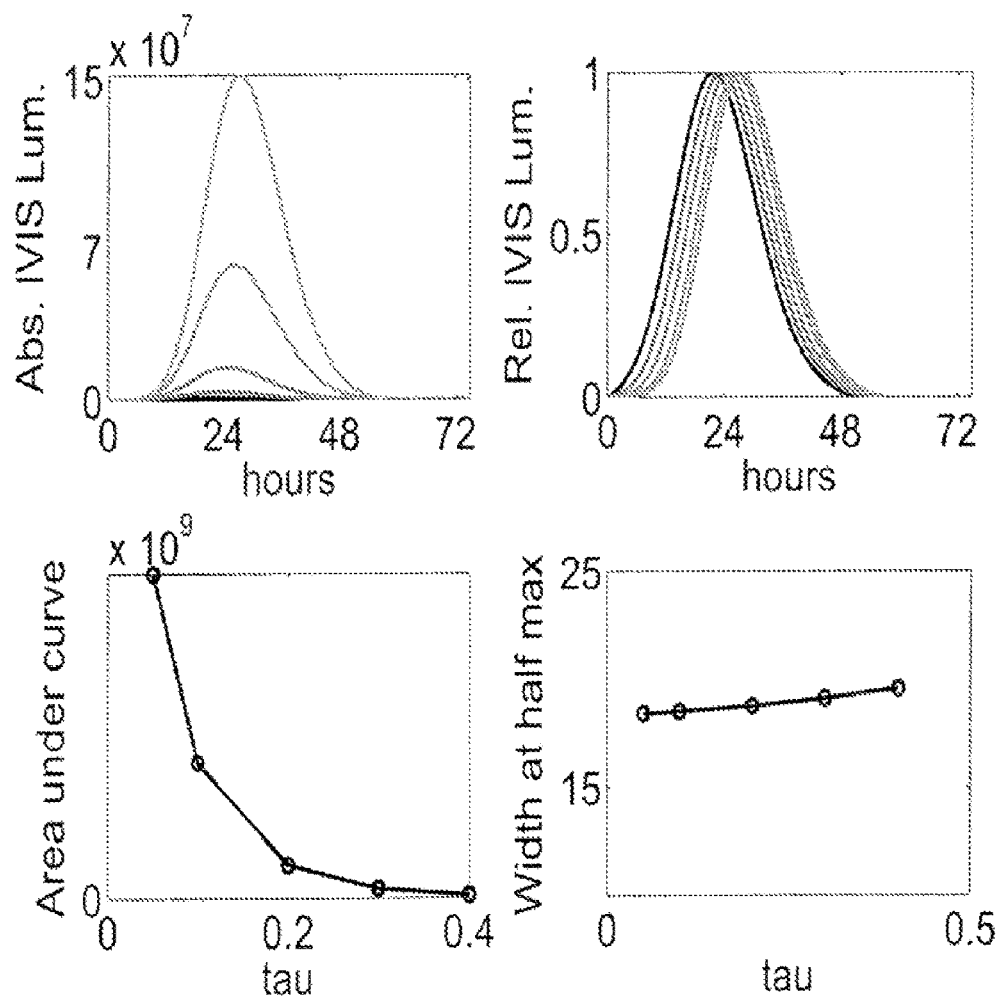

The rate of change of the luciferase enzymes is given by:

$$\frac{dL}{dt} = Bn + \mu + (1 - \tau - \gamma + /\mu +) - \gamma_L L$$

where B represents the number of rate of expression of luciferase per cell and gL represents the luciferase decay. The IVIS signal (I) is proportional to the luciferase signal, i.e., $I = \chi L$, which scales parameters B and $\gamma_L$ accordingly. The value of k contains physical properties 1 such as the permittivity of skin to luciferase enzymes and number of photons emitted per enzyme. The lumped parameters chosen for the data presented in FIGS. 9A, 9B, and 9C are: t=0.2, kB=10, A+=A-=0.01, K=1000, kgL=0.3, g-=0.001, g+=0.075, q=1.6 with initial conditions n+=3365, n-=0, I=0, S=1000. Supplementary FIG. 9 shows the substrate (all of Eq 3), growth rate for plasmid containing cells (Eq 4, light grey), and substrate limitation function (right bracket Eq 3, dark grey) as a function of time.

Example 4

Dose limiting toxicity of bacterial therapies is considered to be an important factor which limits the ability of bacteria to colonize tumors. Here we constructed a plasmid which expresses iRGD, a peptide known to internalize or internalize conjugated nanoparticles into tumors. We genetically expressed iRGD as a fusion to a receptor of an outer-membrane protein known as eCPX at both the N and C terminus. The expression of eCPX-iRGD depicted in FIG. 1B is controlled by induction with arabinose, which allows us to tune the level of iRGD expressed on the surface of the bacterial cells.

Figure 7:
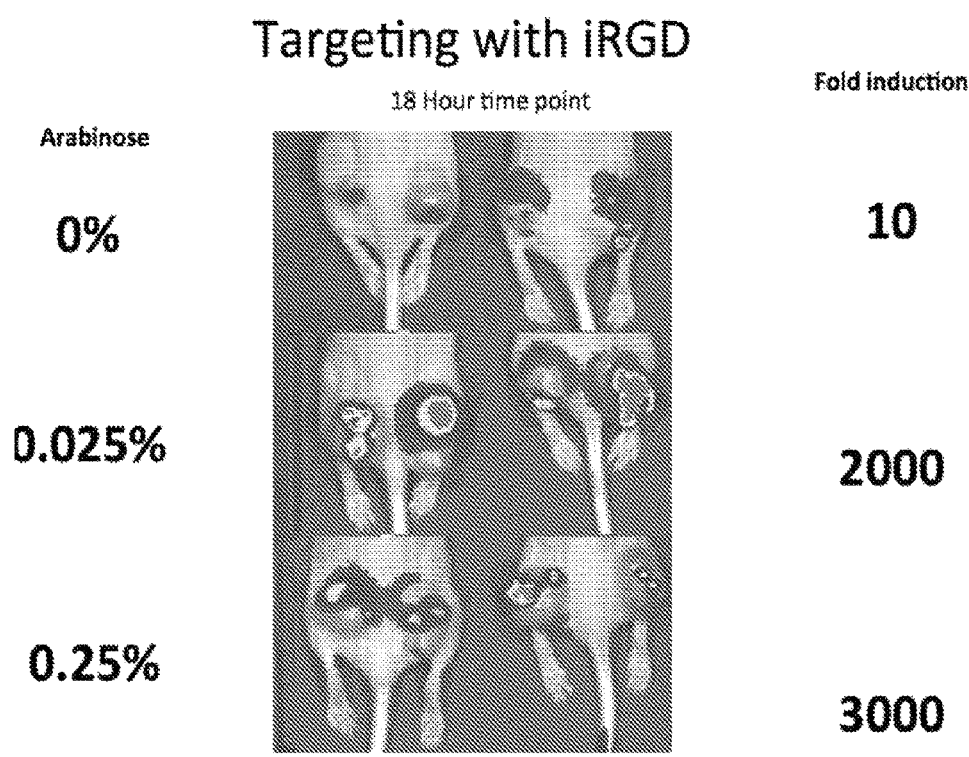

FIG. 7 depicts IVIS imaging of mice bearing subcutaneous ovarian cancer cell lines that have been injected with $1 \times 10^6$ bacteria. Bacteria were grown in different concentrations of arabinose beforehand, giving the bacteria different levels of expression of eCPX-iRGD on their outer surfaces. An 8× increase is shown when an optimal level of arabinose is induced. This experiment demonstrates that cancer cell toxicity can be induced and controlled by tuning the bacteria with a stimulus after transformation of a plasmid with an inducible promoter.

Figure 6:
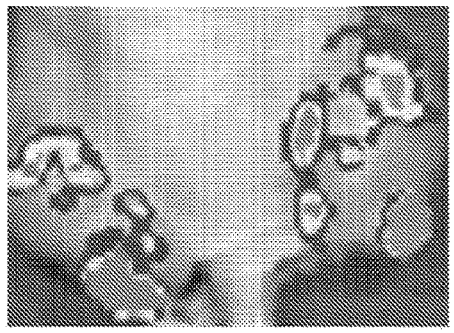
Figure 6:
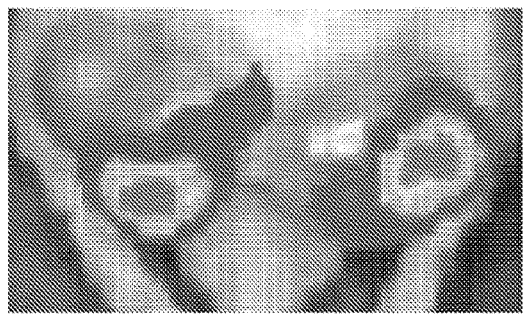

Quorum Sensing bacteria injected intravenously into nude mice bearing OVCAR-8 xenograft hind flank tumors at a concentration of $1 \times 10^6$ bacteria comprising the pTD106CDD plasmid construct (FIG. 1A) are depicted in FIG. 6. A patchy spatial pattern is seen for luciferase expression from quorum sensing, due to the QS system only turning on in the densest parts of the tumor. In comparison the constitutively expressing luciferase plasmid appears to be more uniform. Using quorum sensing inhibitors in the drinking water for mice, we've seen that no luciferase expression appears, while adding AHL, a quorum sensing inducer, can shift the pattern from patchy to uniform.

Figure 8:
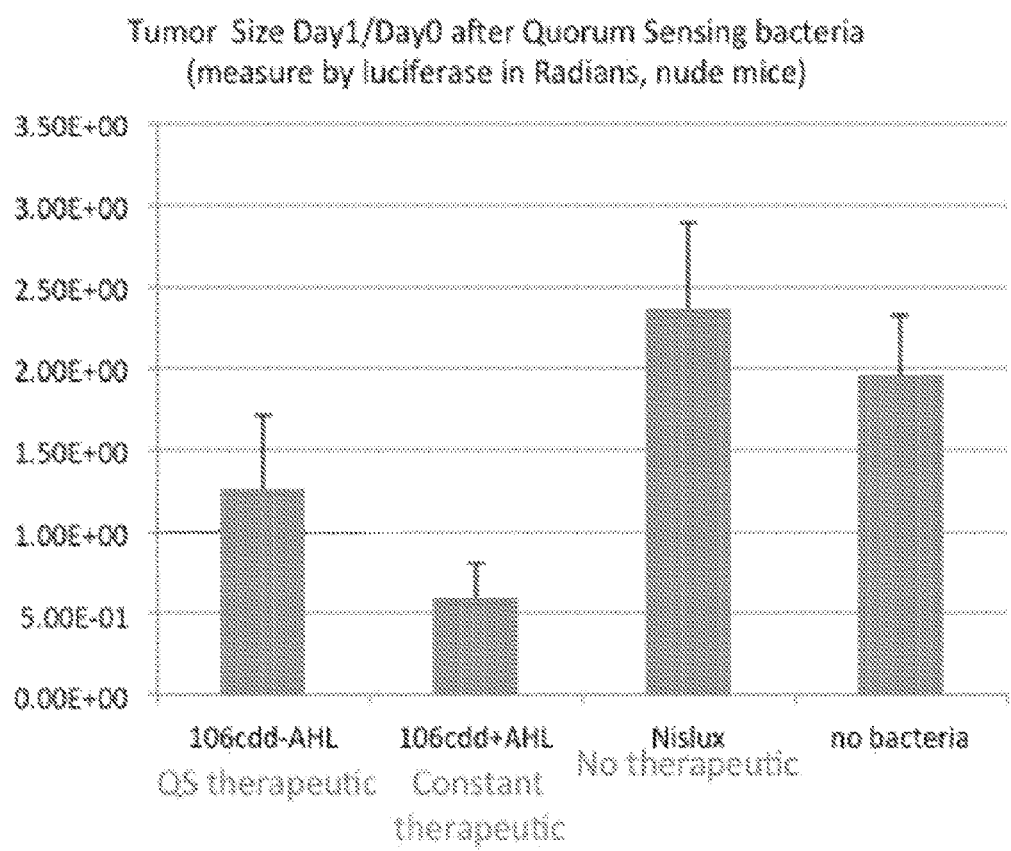

FIG. 8 depicts signal intensity from therapeutic effect of quorum sensing circuit. After 1 day, the relative tumor size is measured by IVIS imaging. Using our pTD106CDD construct, we've shown quorum sensing prevents increase of the tumor size. Inducing our pTD106CDD system with AHL, we see a decrease in tumor size, indicating stronger expression. As controls, tumors with either no bacteria or no therapeutic continue to grow. the bacterial cells described in FIG. 6.

Programming drug expression and release can lead to more efficacious and safe therapies from live bacteria or other vectors. Here we employed a quorum sensing approach as an example of how programming bacteria can make improvements over current methods. Quorum sensing (QS) is a system bacteria use to trigger behavior when a colony reaches a certain level. We programmed our bacteria to produce a therapeutic called CDD, Cell Death Domain, which is a previously known peptide that causes cell death by apoptosis, upon reaching a quorum. CDD is a toxic peptide that would not be possible to administer systemically, thus a programmed delivery vehicle would be necessary to get it to the tumo. Our QS system ensures that many bacteria have to be present to produce CDD, and since bacterial therapies can have bacteria lodged in other organs, this allows for only the high concentration of bacteria seen in the tumor to produce CDD locally in the tumor, reducing systemic side effects. In addition, QS produces drugs with a different dynamical program, which is more in a burst fashion, while previous methods only used a constitutive always-ON method of production. This can potentially have implications in generating less drug resistance, since longer, constant exposures to a drug often lead to tumor drug resistance.

TABLE 1

| Genus: *Salmonella* | |
|---|---|
| *Salmonella bongori* | *Salmonella enterica* subsp. *enterica* serovar 1,4,(5),12:i:- |
| *Salmonella bongori* N268-08 | *Salmonella enterica* subsp. *enterica* serovar 3,10:e,h:- |
| *Salmonella bongori* NCTC 12419 | *Salmonella enterica* subsp. *enterica* serovar 3,10:l,v:e,n,x |
| *Salmonella bongori* serovar 40:z35:- | *Salmonella enterica* subsp. *enterica* serovar 4,12:-:- |
| *Salmonella bongori* serovar 40:z35:- str. 95-0123 | *Salmonella enterica* subsp. *enterica* serovar 4,12:a:- |
| *Salmonella bongori* serovar 48:i:- | *Salmonella enterica* subsp. *enterica* serovar 4,12:i:- |
| *Salmonella bongori* serovar 48:z35:- | *Salmonella enterica* subsp. *enterica* serovar 4,12:r:- |
| *Salmonella bongori* serovar 48:z41:-- | *Salmonella enterica* subsp. *enterica* serovar 4,5,12:b:- |
| *Salmonella bongori* serovar 48:z41:-- str. RKS3044 | *Salmonella enterica* subsp. *enterica* serovar 4,[5],12:i:- |
| *Salmonella bongori* serovar 60:z41:- | *Salmonella enterica* subsp. *enterica* serovar 4,[5],12:r:- |
| *Salmonella bongori* serovar 66:z35:- | *Salmonella enterica* subsp. *enterica* serovar 4,[5]:b:- |
| *Salmonella bongori* serovar 66:z41:- | *Salmonella enterica* subsp. *enterica* serovar 6,7:-:- |
| *Salmonella bongori* serovar 66:z41:- str. SA19983605 | *Salmonella enterica* subsp. *enterica* serovar 6,7:-:1,5 |
| *Salmonella enterica* | *Salmonella enterica* subsp. *enterica* serovar 6,7:-:1,w |
| *Salmonella enterica* subsp. *arizonae* | *Salmonella enterica* subsp. *enterica* serovar 6,7:d:- |
| *Salmonella enterica* subsp. *arizona* serovar Untypable str. 73711 | *Salmonella enterica* subsp. *enterica* serovar 6,7:k:- |
| *Salmonella enterica* subsp. *arizonae* serovar 17:z29:- | *Salmonella enterica* subsp. *enterica* serovar 6,7:l,v:- |
| *Salmonella enterica* subsp. *arizonae* serovar 18:z4,z23:- | *Salmonella enterica* subsp. *enterica* serovar 8,(20):-:z6 |

TABLE 1-continued

| | |
|---|---|
| *Salmonella enterica* subsp. *arizonae* serovar 41:z4,z23:- | *Salmonella enterica* subsp. *enterica* serovar 8,(20):i:- |
| *Salmonella enterica* subsp. *arizonae* serovar 48:z4,z23:- | *Salmonella enterica* subsp. *enterica* serovar 9,12:-:- |
| *Salmonella enterica* subsp. *arizonae* serovar 53:-:- | *Salmonella enterica* subsp. *enterica* serovar 9,12:l,v:- |
| *Salmonella enterica* subsp. *arizonae* serovar 53:g,z51:- | *Salmonella enterica* subsp. *enterica* serovar Abaetetuba |
| *Salmonella enterica* subsp. *arizonae* serovar 56:z4,z23:- | *Salmonella enterica* subsp. *enterica* serovar Aberdeen |
| *Salmonella enterica* subsp. *arizonae* serovar 62:z36:- | *Salmonella enterica* subsp. *enterica* serovar Abony |
| *Salmonella enterica* subsp. *arizonae* serovar 62:z4,z23:- | *Salmonella enterica* subsp. *enterica* serovar Abortus |
| *Salmonella enterica* subsp. *arizonae* str. SARC 5 | *Salmonella enterica* subsp. *enterica* serovar Abortusequi |
| *Salmonella enterica* subsp. *diarizonae* | *Salmonella enterica* subsp. *enterica* serovar Abortusovis |
| *Salmonella enterica* subsp. *diarizonae* serovar 'OMG' l,v:1,5 | *Salmonella enterica* subsp. *enterica* serovar Adelaide |
| *Salmonella enterica* subsp. *diarizonae* serovar 35:i:z35 | *Salmonella enterica* subsp. *enterica* serovar Aesch |
| *Salmonella enterica* subsp. *diarizonae* serovar 38:z10:z53 | *Salmonella enterica* subsp. *enterica* serovar Agama |
| *Salmonella enterica* subsp. *diarizonae* serovar 38[k]:z35:- | *Salmonella enterica* subsp. *enterica* serovar Agona |
| *Salmonella enterica* subsp. *diarizonae* serovar 42:l,v:1,5,7 | *Salmonella enterica* subsp. *enterica* serovar Alabama |
| *Salmonella enterica* subsp. *diarizonae* serovar 42:l,v:e,n,x,z15 | *Salmonella enterica* subsp. *enterica* serovar Alachua |
| *Salmonella enterica* subsp. *diarizonae* serovar 47:k:z35 | *Salmonella enterica* subsp. *enterica* serovar Albany |
| *Salmonella enterica* subsp. *diarizonae* serovar 47:l,v 'HMG' | *Salmonella enterica* subsp. *enterica* serovar Altona |
| *Salmonella enterica* subsp. *diarizonae* serovar 47:l,v:1,5,(7) | *Salmonella enterica* subsp. *enterica* serovar Amsterdam |
| *Salmonella enterica* subsp. *diarizonae* serovar 48:i:z | *Salmonella enterica* subsp. *enterica* serovar Anatum |
| *Salmonella enterica* subsp. *diarizonae* serovar 48:k:z35 | *Salmonella enterica* subsp. *enterica* serovar Ank |
| *Salmonella enterica* subsp. *diarizonae* serovar 50:1,2,3:k:z | *Salmonella enterica* subsp. *enterica* serovar Antsalova |
| *Salmonella enterica* subsp. *diarizonae* serovar 50:k:z | *Salmonella enterica* subsp. *enterica* serovar Apapa |
| *Salmonella enterica* subsp. *diarizonae* serovar 50:l,v:e,n,x,z15 | *Salmonella enterica* subsp. *enterica* serovar Aqua |
| *Salmonella enterica* subsp. *diarizonae* serovar 50:r:1,5 | *Salmonella enterica* subsp. *enterica* serovar Arechavaleta |
| *Salmonella enterica* subsp. *diarizonae* serovar 58:z52:z35 | *Salmonella enterica* subsp. *enterica* serovar Arizona |
| *Salmonella enterica* subsp. *diarizonae* serovar 59:z10:- | *Salmonella enterica* subsp. *enterica* serovar Augustenborg |
| *Salmonella enterica* subsp. *diarizonae* serovar 59:z10:z53 | *Salmonella enterica* subsp. *enterica* serovar Austin |
| *Salmonella enterica* subsp. *diarizonae* serovar 60:r:e,n,x,z15 | *Salmonella enterica* subsp. *enterica* serovar Azteca |
| *Salmonella enterica* subsp. *diarizonae* serovar 60:r:enxz15 | *Salmonella enterica* subsp. *enterica* serovar Baildon |
| *Salmonella enterica* subsp. *diarizonae* serovar 60:z52:1,5 | *Salmonella enterica* subsp. *enterica* serovar Banana |
| *Salmonella enterica* subsp. *diarizonae* serovar 60:z55:e,n,x | *Salmonella enterica* subsp. *enterica* serovar Bangkok |
| *Salmonella enterica* subsp. *diarizonae* serovar 61:-:1,5,7 | *Salmonella enterica* subsp. *enterica* serovar Bangui |
| *Salmonella enterica* subsp. *diarizonae* serovar 61:c:1,5,(7) | *Salmonella enterica* subsp. *enterica* serovar Bardo |
| *Salmonella enterica* subsp. *diarizonae* serovar 61:k:1,5,7 | *Salmonella enterica* subsp. *enterica* serovar Bareilly |
| *Salmonella enterica* subsp. *diarizonae* serovar 61:k:1,5,77 | *Salmonella enterica* subsp. *enterica* serovar Barranquilla |
| *Salmonella enterica* subsp. *diarizonae* serovar 65:c:1,5,7 | *Salmonella enterica* subsp. *enterica* serovar Bergen |
| *Salmonella enterica* subsp. *diarizonae* serovar 65:c:z | *Salmonella enterica* subsp. *enterica* serovar Berta |
| *Salmonella enterica* subsp. *diarizonae* serovar O61:k:1,5 | *Salmonella enterica* subsp. *enterica* serovar Binza |
| *Salmonella enterica* subsp. *diarizonae* str. 01-005 | *Salmonella enterica* subsp. *enterica* serovar Bispebjerg |
| *Salmonella enterica* subsp. *diarizonae* str. 36806 | *Salmonella enterica* subsp. *enterica* serovar Bissau |
| *Salmonella enterica* subsp. *diarizonae* str. ATCC BAA-1579 | *Salmonella enterica* subsp. *enterica* serovar Blegdam |
| *Salmonella enterica* subsp. *enterica* str. 77231 | *Salmonella enterica* subsp. *enterica* serovar Blockley |
| *Salmonella enterica* subsp. *enterica* | *Salmonella enterica* subsp. *enterica* serovar Bonariensis |
| *Salmonella enterica* subsp. *enterica* serovar '02-6026 18:1 v-z-Arizona' | *Salmonella enterica* subsp. *enterica* serovar Bonn |
| | *Salmonella enterica* subsp. *enterica* serovar Borreze |
| *Salmonella enterica* subsp. *enterica* serovar Bovismorbificans | *Salmonella enterica* subsp. *enterica* serovar Hvittingfoss |
| *Salmonella enterica* subsp. *enterica* serovar Braenderup | *Salmonella enterica* subsp. *enterica* serovar Idikan |
| *Salmonella enterica* subsp. *enterica* serovar Brandenburg | *Salmonella enterica* subsp. *enterica* serovar India |
| *Salmonella enterica* subsp. *enterica* serovar Bredeney | *Salmonella enterica* subsp. *enterica* serovar Indiana |
| *Salmonella enterica* subsp. *enterica* serovar Bron | *Salmonella enterica* subsp. *enterica* serovar Infantis |
| *Salmonella enterica* subsp. *enterica* serovar Brunei | *Salmonella enterica* subsp. *enterica* serovar Inverness |
| *Salmonella enterica* subsp. *enterica* serovar Bsilla | *Salmonella enterica* subsp. *enterica* serovar Isangi |
| *Salmonella enterica* subsp. *enterica* serovar Budapest | *Salmonella enterica* subsp. *enterica* serovar Istanbul |
| *Salmonella enterica* subsp. *enterica* serovar Bury | *Salmonella enterica* subsp. *enterica* serovar Itami |
| *Salmonella enterica* subsp. *enterica* serovar California | *Salmonella enterica* subsp. *enterica* serovar Javiana |
| *Salmonella enterica* subsp. *enterica* serovar Canada | *Salmonella enterica* subsp. *enterica* serovar Jericho |
| *Salmonella enterica* subsp. *enterica* serovar Caracas | *Salmonella enterica* subsp. *enterica* serovar Johannesburg |
| *Salmonella enterica* subsp. *enterica* serovar Carrau | *Salmonella enterica* subsp. *enterica* serovar Kahla |
| *Salmonella enterica* subsp. *enterica* serovar Cerro | *Salmonella enterica* subsp. *enterica* serovar Kedougou |
| *Salmonella enterica* subsp. *enterica* serovar Champaign | *Salmonella enterica* subsp. *enterica* serovar Kentucky |
| *Salmonella enterica* subsp. *enterica* serovar Chester | *Salmonella enterica* subsp. *enterica* serovar Keurmassar |
| *Salmonella enterica* subsp. *enterica* serovar Chincol | *Salmonella enterica* subsp. *enterica* serovar Kiambu |
| *Salmonella enterica* subsp. *enterica* serovar Chingola | *Salmonella enterica* subsp. *enterica* serovar Kiel |
| *Salmonella enterica* subsp. *enterica* serovar Choleraesuis | *Salmonella enterica* subsp. *enterica* serovar Kinshasa |
| *Salmonella enterica* subsp. *enterica* serovar Coeln | *Salmonella enterica* subsp. *enterica* serovar Kintambo |
| *Salmonella enterica* subsp. *enterica* serovar Concord | *Salmonella enterica* subsp. *enterica* serovar Kisangani |
| *Salmonella enterica* subsp. *enterica* serovar Coogee | *Salmonella enterica* subsp. *enterica* serovar Kitenge |
| *Salmonella enterica* subsp. *enterica* serovar Copenhagen | *Salmonella enterica* subsp. *enterica* serovar Koessen |
| *Salmonella enterica* subsp. *enterica* serovar Corvallis | *Salmonella enterica* subsp. *enterica* serovar Kottbus |
| *Salmonella enterica* subsp. *enterica* serovar Crossness | *Salmonella enterica* subsp. *enterica* serovar Krefeld |
| *Salmonella enterica* subsp. *enterica* serovar Cubana | *Salmonella enterica* subsp. *enterica* serovar Kundunchi |
| *Salmonella enterica* subsp. *enterica* serovar Dakar | *Salmonella enterica* subsp. *enterica* serovar Kunzendorf |
| *Salmonella enterica* subsp. *enterica* serovar Decatur | *Salmonella enterica* subsp. *enterica* serovar Lansing |
| *Salmonella enterica* subsp. *enterica* serovar Derby | *Salmonella enterica* subsp. *enterica* serovar Lexington |
| *Salmonella enterica* subsp. *enterica* serovar Djakarta | *Salmonella enterica* subsp. *enterica* serovar Lille |
| *Salmonella enterica* subsp. *enterica* serovar Doom | *Salmonella enterica* subsp. *enterica* serovar Limete |
| *Salmonella enterica* subsp. *enterica* serovar Dowd | *Salmonella enterica* subsp. *enterica* serovar Lindenburg |
| *Salmonella enterica* subsp. *enterica* serovar Dublin | *Salmonella enterica* subsp. *enterica* serovar Litchfield |
| *Salmonella enterica* subsp. *enterica* serovar Duesseldorf | *Salmonella enterica* subsp. *enterica* serovar Liverpool |
| *Salmonella enterica* subsp. *enterica* serovar Duisburg | *Salmonella enterica* subsp. *enterica* serovar Livingstone |

TABLE 1-continued

| | |
|---|---|
| *Salmonella enterica* subsp. *enterica* serovar Durban | *Salmonella enterica* subsp. *enterica* serovar Lomita |
| *Salmonella enterica* subsp. *enterica* serovar Eastbourne | *Salmonella enterica* subsp. *enterica* serovar London |
| *Salmonella enterica* subsp. *enterica* serovar Edinburgh | *Salmonella enterica* subsp. *enterica* serovar Macclesfield |
| *Salmonella enterica* subsp. *enterica* serovar Emek | *Salmonella enterica* subsp. *enterica* serovar Madelia |
| *Salmonella enterica* subsp. *enterica* serovar Enteritidis | *Salmonella enterica* subsp. *enterica* serovar Madjorio |
| *Salmonella enterica* subsp. *enterica* serovar Epinay | *Salmonella enterica* subsp. *enterica* serovar Manchester |
| *Salmonella enterica* subsp. *enterica* serovar Eschberg | *Salmonella enterica* subsp. *enterica* serovar Manhattan |
| *Salmonella enterica* subsp. *enterica* serovar Essen | *Salmonella enterica* subsp. *enterica* serovar Maracaibo |
| *Salmonella enterica* subsp. *enterica* serovar Etterbeek | *Salmonella enterica* subsp. *enterica* serovar Maregrosso |
| *Salmonella enterica* subsp. *enterica* serovar Farsta | *Salmonella enterica* subsp. *enterica* serovar Marrtens |
| *Salmonella enterica* subsp. *enterica* serovar Fischerhuette | *Salmonella enterica* subsp. *enterica* serovar Matopeni |
| *Salmonella enterica* subsp. *enterica* serovar Fischerkietz | *Salmonella enterica* subsp. *enterica* serovar Mbandaka |
| *Salmonella enterica* subsp. *enterica* serovar Flottbek | *Salmonella enterica* subsp. *enterica* serovar Meleagridis |
| *Salmonella enterica* subsp. *enterica* serovar Freetown | *Salmonella enterica* subsp. *enterica* serovar Mgulani |
| *Salmonella enterica* subsp. *enterica* serovar Fresno | *Salmonella enterica* subsp. *enterica* serovar Miami |
| *Salmonella enterica* subsp. *enterica* serovar Fulica | *Salmonella enterica* subsp. *enterica* serovar Michigan |
| *Salmonella enterica* subsp. *enterica* serovar Gallinarum | *Salmonella enterica* subsp. *enterica* serovar Mikawasima |
| *Salmonella enterica* subsp. *enterica* serovar Gallinarum/pullorum | *Salmonella enterica* subsp. *enterica* serovar Milwaukee |
| *Salmonella enterica* subsp. *enterica* serovar Gamaba | *Salmonella enterica* subsp. *enterica* serovar Minneapolis |
| *Salmonella enterica* subsp. *enterica* serovar Gaminara | *Salmonella enterica* subsp. *enterica* serovar Minnesota |
| *Salmonella enterica* subsp. *enterica* serovar Garoli | *Salmonella enterica* subsp. *enterica* serovar Mississippi |
| *Salmonella enterica* subsp. *enterica* serovar Gatuni | *Salmonella enterica* subsp. *enterica* serovar Molade |
| *Salmonella enterica* subsp. *enterica* serovar Give | *Salmonella enterica* subsp. *enterica* serovar Monophasic |
| *Salmonella enterica* subsp. *enterica* serovar Glostrup | *Salmonella enterica* subsp. *enterica* serovar Monschaui |
| *Salmonella enterica* subsp. *enterica* serovar Goettingen | *Salmonella enterica* subsp. *enterica* serovar Montevideo |
| *Salmonella enterica* subsp. *enterica* serovar Goldcoast | *Salmonella enterica* subsp. *enterica* serovar Moscow |
| *Salmonella enterica* subsp. *enterica* serovar Grumpensis | *Salmonella enterica* subsp. *enterica* serovar Muenchen |
| *Salmonella enterica* subsp. *enterica* serovar Gueuletapee | *Salmonella enterica* subsp. *enterica* serovar Muenster |
| *Salmonella enterica* subsp. *enterica* serovar Hadar | *Salmonella enterica* subsp. *enterica* serovar Mygdal |
| *Salmonella enterica* subsp. *enterica* serovar Haifa | *Salmonella enterica* subsp. *enterica* serovar Naestved |
| *Salmonella enterica* subsp. *enterica* serovar Hartford | *Salmonella enterica* subsp. *enterica* serovar Napoli |
| *Salmonella enterica* subsp. *enterica* serovar Havana | *Salmonella enterica* subsp. *enterica* serovar Nchanga |
| *Salmonella enterica* subsp. *enterica* serovar Heidelberg | *Salmonella enterica* subsp. *enterica* serovar Neukoelln |
| *Salmonella enterica* subsp. *enterica* serovar Hessarek | *Salmonella enterica* subsp. *enterica* serovar Newbrunswick |
| *Salmonella enterica* subsp. *enterica* serovar Hillingdon | *Salmonella enterica* subsp. *enterica* serovar Newington |
| *Salmonella enterica* subsp. *enterica* serovar Newlands | *Salmonella enterica* subsp. *enterica* serovar Tennessee |
| *Salmonella enterica* subsp. *enterica* serovar Newmexico | *Salmonella enterica* subsp. *enterica* serovar Tennyson |
| *Salmonella enterica* subsp. *enterica* serovar Newport | *Salmonella enterica* subsp. *enterica* serovar Texas |
| *Salmonella enterica* subsp. *enterica* serovar Ngili | *Salmonella enterica* subsp. *enterica* serovar Thompson |
| *Salmonella enterica* subsp. *enterica* serovar Niarembe | *Salmonella enterica* subsp. *enterica* serovar Tinda |
| *Salmonella enterica* subsp. *enterica* serovar Nima | *Salmonella enterica* subsp. *enterica* serovar Togba |
| *Salmonella enterica* subsp. *enterica* serovar Nitra | *Salmonella enterica* subsp. *enterica* serovar Tonev |
| *Salmonella enterica* subsp. *enterica* serovar Norwich | *Salmonella enterica* subsp. *enterica* serovar Toronto |
| *Salmonella enterica* subsp. *enterica* serovar Nottingham | *Salmonella enterica* subsp. *enterica* serovar Toulon |
| *Salmonella enterica* subsp. *enterica* serovar O rough | *Salmonella enterica* subsp. *enterica* serovar Travis |
| *Salmonella enterica* subsp. *enterica* serovar O rough O:r:1,2 | *Salmonella enterica* subsp. *enterica* serovar Tripoli |
| *Salmonella enterica* subsp. *enterica* serovar O7:Hc:1,5 | *Salmonella enterica* subsp. *enterica* serovar Tshiongwe |
| *Salmonella enterica* subsp. *enterica* serovar O7:Hh:1,5 | *Salmonella enterica* subsp. *enterica* serovar Tucson |
| *Salmonella enterica* subsp. *enterica* serovar Ohio | *Salmonella enterica* subsp. *enterica* serovar Typhi |
| *Salmonella enterica* subsp. *Enterica* serovar Onderstepoort | *Salmonella enterica* subsp. *enterica* serovar Typhimurium |
| *Salmonella enterica* subsp. *enterica* serovar Oranienburg | *Salmonella enterica* subsp. *enterica* serovar Typhisuis |
| *Salmonella enterica* subsp. *enterica* serovar Ordonez | *Salmonella enterica* subsp. *enterica* serovar Uganda |
| *Salmonella enterica* subsp. *enterica* serovar Orion | *Salmonella enterica* subsp. *enterica* serovar Untypable str. 75788 |
| *Salmonella enterica* subsp. *enterica* serovar Oslo | *Salmonella enterica* subsp. *enterica* serovar Untypable str. 77116 |
| *Salmonella enterica* subsp. *enterica* serovar Osnabrueck | *Salmonella enterica* subsp. *enterica* serovar Untypable str. 77132 |
| *Salmonella enterica* subsp. *enterica* serovar Othmarschen | *Salmonella enterica* subsp. *enterica* serovar Untypable str. 77528 |
| *Salmonella enterica* subsp. *enterica* serovar Ouakam | *Salmonella enterica* subsp. *enterica* serovar Untypable str. 81146 |
| *Salmonella enterica* subsp. *enterica* serovar Overvecht | *Salmonella enterica* subsp. *enterica* serovar Untypable str. 83332 |
| *Salmonella enterica* subsp. *enterica* serovar Panama | *Salmonella enterica* subsp. *enterica* serovar Untypable str. 83987 |
| *Salmonella enterica* subsp. *enterica* serovar Paratyphi A | *Salmonella enterica* subsp. *enterica* serovar Untypable str. 91013 |
| *Salmonella enterica* subsp. *enterica* serovar Paratyphi B | *Salmonella enterica* subsp. *enterica* serovar Untypable str. 91510 |
| *Salmonella enterica* subsp. *enterica* serovar Paratyphi C | *Salmonella enterica* subsp. *enterica* serovar Untypable str. 92055 |
| *Salmonella enterica* subsp. *enterica* serovar Pensacola | *Salmonella enterica* subsp. *enterica* serovar Uphill |
| *Salmonella enterica* subsp. *enterica* serovar Poano | *Salmonella enterica* subsp. *enterica* serovar Urbana |
| *Salmonella enterica* subsp. *enterica* serovar Poeseldorf | *Salmonella enterica* subsp. *enterica* serovar Utrecht |
| *Salmonella enterica* subsp. *enterica* serovar Pomona | *Salmonella enterica* subsp. *enterica* serovar Vellore |
| *Salmonella enterica* subsp. *enterica* serovar Poona | *Salmonella enterica* subsp. *enterica* serovar Virchow |
| *Salmonella enterica* subsp. *enterica* serovar Portedeslilas | *Salmonella enterica* subsp. *enterica* serovar Virginia |
| *Salmonella enterica* subsp. *enterica* serovar Potsdam | *Salmonella enterica* subsp. *enterica* serovar Wagenia |
| *Salmonella enterica* subsp. *enterica* serovar Pullorum | *Salmonella enterica* subsp. *enterica* serovar Wandsworth |
| *Salmonella enterica* subsp. *enterica* serovar Putten | *Salmonella enterica* subsp. *enterica* serovar Wangata |
| *Salmonella enterica* subsp. *enterica* serovar Quebec | *Salmonella enterica* subsp. *enterica* serovar Washington |
| *Salmonella enterica* subsp. *enterica* serovar Rachaburi | *Salmonella enterica* subsp. *enterica* serovar Waycross |
| *Salmonella enterica* subsp. *enterica* serovar Reading | *Salmonella enterica* subsp. *enterica* serovar Weltevreden |
| *Salmonella enterica* subsp. *enterica* serovar Richmond | *Salmonella enterica* subsp. *enterica* serovar Weslaco |
| *Salmonella enterica* subsp. *enterica* serovar Rissen | *Salmonella enterica* subsp. *enterica* serovar Westhampton |
| *Salmonella enterica* subsp. *enterica* serovar Rosenberg | *Salmonella enterica* subsp. *enterica* serovar Wien |
| *Salmonella enterica* subsp. *enterica* serovar Rostock | *Salmonella enterica* subsp. *enterica* serovar Worthington |
| *Salmonella enterica* subsp. *enterica* serovar Rubislaw | *Salmonella enterica* subsp. *enterica* serovar York |
| *Salmonella enterica* subsp. *enterica* serovar Saintpaul | *Salmonella enterica* subsp. *enterica* serovar Yovokome |

TABLE 1-continued

| | |
|---|---|
| *Salmonella enterica* subsp. *enterica* serovar Salford | *Salmonella enterica* subsp. *enterica* serovar Zaiman |
| *Salmonella enterica* subsp. *enterica* serovar Sandiego | *Salmonella enterica* subsp. *enterica* serovar Zanzibar |
| *Salmonella enterica* subsp. *enterica* serovar Sangera | *Salmonella enterica* subsp. *enterica* str. 01-11525 |
| *Salmonella enterica* subsp. *enterica* serovar Sanjuan | *Salmonella enterica* subsp. *enterica* str. 09-06166 |
| *Salmonella enterica* subsp. *enterica* serovar Sanktgeorg | *Salmonella enterica* subsp. *enterica* str. 11-01213 |
| *Salmonella enterica* subsp. *enterica* serovar Sarajane | *Salmonella enterica* subsp. *enterica* str. 11-01214 |
| *Salmonella enterica* subsp. *enterica* serovar Schleissheim | *Salmonella enterica* subsp. *enterica* str. 11-01216-1 |
| *Salmonella enterica* subsp. *enterica* serovar Schwarzengrund | *Salmonella enterica* subsp. *enterica* str. 609458-2604314_2-2 |
| *Salmonella enterica* subsp. *enterica* serovar Sendai | *Salmonella enterica* subsp. *enterica* str. 85356 |
| *Salmonella enterica* subsp. *enterica* serovar Senftenberg | *Salmonella enterica* subsp. *enterica* str. CFSAN004167 |
| *Salmonella enterica* subsp. *enterica* serovar Setubal | *Salmonella enterica* subsp. *enterica* str. S703 |
| *Salmonella enterica* subsp. *enterica* serovar Shomron | *Salmonella enterica* subsp. *enterica* str. xld |
| *Salmonella enterica* subsp. *enterica* serovar Simsbury | *Salmonella enterica* subsp. *houtenae* |
| *Salmonella enterica* subsp. *enterica* serovar Singapore | *Salmonella enterica* subsp. *houtenae* serovar 1,40:g,z51:- |
| *Salmonella enterica* subsp. *enterica* serovar Sloterdijk | *Salmonella enterica* subsp. *houtenae* serovar 1,40:z4,z24:- |
| *Salmonella enterica* subsp. *enterica* serovar Soahanina | *Salmonella enterica* subsp. *houtenae* serovar 16:z4,z32:- |
| *Salmonella enterica* subsp. *enterica* serovar Soerenga | *Salmonella enterica* subsp. *houtenae* serovar 16:z4,z32:-- |
| *Salmonella enterica* subsp. *enterica* serovar Stanley | *Salmonella enterica* subsp. *houtenae* serovar 40:z4,z24:- |
| *Salmonella enterica* subsp. *enterica* serovar Stanleyville | *Salmonella enterica* subsp. *houtenae* serovar 43:z4,z23:- |
| *Salmonella enterica* subsp. *enterica* serovar Stellingen | *Salmonella enterica* subsp. *houtenae* serovar 44:a:- |
| *Salmonella enterica* subsp. *enterica* serovar Stourbridge | *Salmonella enterica* subsp. *houtenae* serovar 44:z4,z23:- |
| *Salmonella enterica* subsp. *enterica* serovar Taksony | *Salmonella enterica* subsp. *houtenae* serovar 45a,b:g,z51:- |
| *Salmonella enterica* subsp. *enterica* serovar Tallahassee | *Salmonella enterica* subsp. *houtenae* serovar 48:g,z51:- |
| *Salmonella enterica* subsp. *enterica* serovar Tejas | *Salmonella enterica* subsp. *houtenae* serovar 50:g,z51:- |
| *Salmonella enterica* subsp. *enterica* serovar Telaviv | *Salmonella enterica* subsp. *houtenae* serovar 6,7:z4,z24:- |
| *Salmonella enterica* subsp. *houtenae* serovar Houten | *Salmonella* sp. APK1 |
| *Salmonella enterica* subsp. *houtenae* str. ATCC BAA-1580 | *Salmonella* sp. ATK1 |
| *Salmonella enterica* subsp. *houtenae* str. ATCC BAA-1581 | *Salmonella* sp. AV(2010) |
| *Salmonella enterica* subsp. *indica* | *Salmonella* sp. BSCC 29 |
| *Salmonella enterica* subsp. *indica* serovar 1,6,14,25:a:e,n,x | *Salmonella* sp. BV10 |
| *Salmonella enterica* subsp. *indica* serovar 11:b:1,7 | *Salmonella* sp. BV34 |
| *Salmonella enterica* subsp. *indica* serovar 11:b:e,n,x | *Salmonella* sp. BV37 |
| *Salmonella enterica* subsp. *indica* serovar 45:a:e,n,x | *Salmonella* sp. Bz21 |
| *Salmonella enterica* subsp. *indica* serovar 6,14,25:z10:1,(2),7 | *Salmonella* sp. CASMBAUKKAGK2 |
| *Salmonella enterica* subsp. *indica* serovar 6,7:z41:1,7 | *Salmonella* sp. CDC 156-87 |
| *Salmonella enterica* subsp. *indica* str. ATCC BAA-1576 | *Salmonella* sp. CMCC50041 |
| *Salmonella enterica* subsp. *indica* str. ATCC BAA-1578 | *Salmonella* sp. Co9901 |
| *Salmonella enterica* subsp. *salamae* | *Salmonella* sp. Co9936 |
| *Salmonella enterica* subsp. *salamae* serovar 1,4,12,27:a:e,n,x | *Salmonella* sp. Co9937 |
| *Salmonella enterica* subsp. *salamae* serovar 1,4,12,27:b:e,n,x | *Salmonella* sp. CRMB13 |
| *Salmonella enterica* subsp. *salamae* serovar 1,40:z10:e,n,x | *Salmonella* sp. CRMB68 |
| *Salmonella enterica* subsp. *salamae* serovar 1,9,12:d:e,n,x | *Salmonella* sp. CRTB1 |
| *Salmonella enterica* subsp. *salamae* serovar 1,9,12:l,w:e,n,x | *Salmonella* sp. CRTB29 |
| *Salmonella enterica* subsp. *salamae* serovar 11:l,z28:e,n,x | *Salmonella* sp. CRTB7 |
| *Salmonella enterica* subsp. *salamae* serovar 35:g,z62:e,n,x | *Salmonella* sp. D187-2 |
| *Salmonella enterica* subsp. *salamae* serovar 35:m,t:e,n,x | *Salmonella* sp. D194-1 |
| *Salmonella enterica* subsp. *salamae* serovar 4,12,27:i:z35 | *Salmonella* sp. D194-2 |
| *Salmonella enterica* subsp. *salamae* serovar 4,12:z:1,7 | *Salmonella* sp. D76 |
| *Salmonella enterica* subsp. *salamae* serovar 40:z10:e,n,x | *Salmonella* sp. DAP8 |
| *Salmonella enterica* subsp. *salamae* serovar 42:f,g,t:-- | *Salmonella* sp. DSPV 002PSA |
| *Salmonella enterica* subsp. *salamae* serovar 42:l,v:e,n,x,z15 | *Salmonella* sp. ES-B43 |
| *Salmonella enterica* subsp. *salamae* serovar 48:d:z6 | *Salmonella* sp. H16-244 |
| *Salmonella enterica* subsp. *salamae* serovar 55:k:z39 | *Salmonella* sp. H17-62 |
| *Salmonella enterica* subsp. *salamae* serovar 56:z1:enx | *Salmonella* sp. H3 |
| *Salmonella enterica* subsp. *salamae* serovar 57:z42:1,6:z53 | *Salmonella* sp. H48 |
| *Salmonella enterica* subsp. *salamae* serovar 58:l,z13,z28:z6 | *Salmonella* sp. ICMP 15669 |
| *Salmonella enterica* subsp. *salamae* serovar 6,7:l,w:1,5,7 | *Salmonella* sp. Inspire71 |
| *Salmonella enterica* subsp. *salamae* serovar 9,12:d:e,n,x | *Salmonella* sp. Inspire72 |
| *Salmonella enterica* subsp. *salamae* serovar 9,12:l,v:e,n,x | *Salmonella* sp. Inspire73 |
| *Salmonella enterica* subsp. *salamae* serovar Greenside | *Salmonella* sp. Inspire74 |
| *Salmonella enterica* subsp. *salamae* serovar Sofia | *Salmonella* sp. Inspire75 |
| *Salmonella enterica* subsp. *salamae* str. 3588/07 | *Salmonella* sp. JPunk1-2 |
| *Salmonella enterica* subsp. *salamae* str. ATCC BAA-1582 | *Salmonella* sp. LCN1-13 |
| *Salmonella enterica* subsp. *salamae* str. ATCC BAA-1583 | *Salmonella* sp. LFW070403 |
| *Salmonella enterica* subsp. *salamae* str. DMA-1 | *Salmonella* sp. Lorraine road_2007_01 |
| *Salmonella enterica* subsp. VII | *Salmonella* sp. Lorraine road_2007_03 |
| *Salmonella enterica* VII 1,40:g,z51:-- | *Salmonella* sp. Lorraine road_2007_07 |
| *Salmonella enterica* VII 40:z4,z24:-- | *Salmonella* sp. Lorraine road_2007_08 |
| *Salmonella subterranea* | *Salmonella* sp. Lorraine road_2007_14 |
| *Salmonella* sp. | *Salmonella* sp. Lorraine road_2007_16 |
| *Salmonella* sp. 'group B' | *Salmonella* sp. Lorraine road_2007_17 |
| *Salmonella* sp. 10 | *Salmonella* sp. Lorraine road_2007_19 |
| *Salmonella* sp. 14 | *Salmonella* sp. M9 |
| *Salmonella* sp. 2 | *Salmonella* sp. M9397 |
| *Salmonella* sp. 30 | *Salmonella* sp. MRT3 |
| *Salmonella* sp. 40 | *Salmonella* sp. Pratt ave_2007_03 |
| *Salmonella* sp. 4063 | *Salmonella* sp. Pratt ave_2007_06 |
| *Salmonella* sp. 4064 | *Salmonella* sp. Pratt ave_2007_10 |
| *Salmonella* sp. 4065 | *Salmonella* sp. Pratt ave_2007_11 |
| *Salmonella* sp. 4066 | *Salmonella* sp. Pratt ave_2007_12 |

TABLE 1-continued

| | |
|---|---|
| *Salmonella* sp. 4071 | *Salmonella* sp. Pratt ave_2007_14 |
| *Salmonella* sp. 4072 | *Salmonella* sp. Pratt ave_2007_15 |
| *Salmonella* sp. 4182 | *Salmonella* sp. Pratt ave_2007_16 |
| *Salmonella* sp. 45 | *Salmonella* sp. RG-14/07 |
| *Salmonella* sp. 467 | *Salmonella* sp. RPWA1.6 |
| *Salmonella* sp. 53 | *Salmonella* sp. RV_A06_3c |
| *Salmonella* sp. 56 | *Salmonella* sp. s010 |
| *Salmonella* sp. 577 | *Salmonella* sp. s084 |
| *Salmonella* sp. 6R | *Salmonella* sp. S126 |
| *Salmonella* sp. 77 | *Salmonella* sp. S138 |
| *Salmonella* sp. 85MP | *Salmonella* sp. S14 |
| *Salmonella* sp. 8R | *Salmonella* sp. S191 |
| *Salmonella* sp. 9 | *Salmonella* sp. S1a |
| *Salmonella* sp. 96A-29192 | *Salmonella* sp. SAM2 |
| *Salmonella* sp. AHL 6 | *Salmonella* sp. sc-S |
| *Salmonella* sp. SSBC3 | *Salmonella* sp. Trautman ave_2007_26 |
| *Salmonella* sp. STM13 | *Salmonella* sp. Trautman ave_2007_27 |
| *Salmonella* sp. T1a | *Salmonella* sp. Trautman ave_2007_28 |
| *Salmonella* sp. TC67 | *Salmonella* sp. Trautman ave_2007_29 |
| *Salmonella* sp. TR-95 | *Salmonella* sp. Vetaran hospital_2007_03 |
| *Salmonella* sp. Trautman ave_2007_01 | *Salmonella* sp. Vetaran hospital_2007_20 |
| *Salmonella* sp. Trautman ave_2007_02 | *Salmonella* sp. Veteran hospital_2007_01 |
| *Salmonella* sp. Trautman ave_2007_03 | *Salmonella* sp. Veteran hospital_2007_02 |
| *Salmonella* sp. Trautman ave_2007_04 | *Salmonella* sp. Veteran hospital_2007_07 |
| *Salmonella* sp. Trautman ave_2007_05 | *Salmonella* sp. Veteran hospital_2007_08 |
| *Salmonella* sp. Trautman ave_2007_06 | *Salmonella* sp. Veteran hospital_2007_11 |
| *Salmonella* sp. Trautman ave_2007_07 | *Salmonella* sp. Veteran hospital_2007_14 |
| *Salmonella* sp. Trautman ave_2007_08 | *Salmonella* sp. VI11 |
| *Salmonella* sp. Trautman ave_2007_09 | *Salmonella* sp. VII |
| *Salmonella* sp. Trautman ave_2007_10 | *Salmonella* sp. WT |
| *Salmonella* sp. Trautman ave_2007_11 | *Salmonella* sp. XJ-ZG1 |
| *Salmonella* sp. Trautman ave_2007_12 | *Salmonella* sp. YLA4 |
| *Salmonella* sp. Trautman ave_2007_13 | *Salmonella* sp. YLD3 |
| *Salmonella* sp. Trautman ave_2007_14 | *Salmonella* sp. ZKC20 |
| *Salmonella* sp. Trautman ave_2007_15 | *Salmonella* sp. ZZ-4 |
| *Salmonella* sp. Trautman ave_2007_16 | environmental samples |
| *Salmonella* sp. Trautman ave_2007_17 | *Salmonella* sp. enrichment culture clone CL107 |
| *Salmonella* sp. Trautman ave_2007_18 | *Salmonella* sp. enrichment culture clone NEP50 |
| *Salmonella* sp. Trautman ave_2007_19 | *Salmonella* sp. enrichment culture clone NJ-8 |
| *Salmonella* sp. Trautman ave_2007_20 | *Salmonella* sp. enrichment culture clone TB43_1 |
| *Salmonella* sp. Trautman ave_2007_21 | *Salmonella* sp. enrichment culture clone TB43_2 |
| *Salmonella* sp. Trautman ave_2007_22 | *Salmonella* sp. enrichment culture clone TB43_3 |
| *Salmonella* sp. Trautman ave_2007_23 | *Salmonella* sp. enrichment culture clone TB43_4 |
| *Salmonella* sp. Trautman ave_2007_24 | uncultured *Salmonella* sp. |
| *Salmonella* sp. Trautman ave_2007_25 | |

Genus: *Escherichia*

| | |
|---|---|
| *Escherichia albertii* | *Escherichia coli* 10.0833 |
| *Escherichia albertii* B090 | *Escherichia coli* 10.0869 |
| *Escherichia albertii* B156 | *Escherichia coli* 13B01 |
| *Escherichia albertii* NBRC 107761 | *Escherichia coli* 1412 |
| *Escherichia albertii* TW07627 | *Escherichia coli* 14A |
| *Escherichia albertii* TW08933 | *Escherichia coli* 19B05 |
| *Escherichia albertii* TW11588 | *Escherichia coli* 113290 |
| *Escherichia albertii* TW15818 | *Escherichia coli* 113302 |
| *Escherichia coli* | *Escherichia coli* 113303 |
| *Escherichia coli* 0.1288 | *Escherichia coli* 1303 |
| *Escherichia coli* #1/H766 | *Escherichia coli* 2.3941 |
| *Escherichia coli* 'BL21-Gold(DE3)pLysS AG' | *Escherichia coli* 2.4168 |
| *Escherichia coli* 08BKT055439 | *Escherichia coli* 2.4174 |
| *Escherichia coli* 08BKT77219 | *Escherichia coli* 201600.1 |
| *Escherichia coli* 0.1197 | *Escherichia coli* 20B05 |
| *Escherichia coli* 07798 | *Escherichia coli* 2254-75 (11a) |
| *Escherichia coli* 101-1 | *Escherichia coli* 229_11 |
| *Escherichia coli* 110957 | *Escherichia coli* 2362-75 |
| *Escherichia coli* 09BKT078844 | *Escherichia coli* 23B03 |
| *Escherichia coli* 1.0080 | *Escherichia coli* 24B05 |
| *Escherichia coli* 1.2264 | *Escherichia coli* 2534-86 |
| *Escherichia coli* 1.2741 | *Escherichia coli* 2719100 |
| *Escherichia coli* 09BKT024447 | *Escherichia coli* 2720900 |
| *Escherichia coli* 09BKT076207 | *Escherichia coli* 179100 |
| *Escherichia coli* 0.1304 | *Escherichia coli* 179550 |
| *Escherichia coli* 151_06 | *Escherichia coli* 180050 |
| *Escherichia coli* 1520 | *Escherichia coli* 180200 |
| *Escherichia coli* 174750 | *Escherichia coli* 180600 |
| *Escherichia coli* 174900 | *Escherichia coli* 1827-70 |
| *Escherichia coli* 178200 | *Escherichia coli* 199900.1 |
| *Escherichia coli* 178850 | *Escherichia coli* 2733950 |
| *Escherichia coli* 178900 | *Escherichia coli* 2735000 |
| *Escherichia coli* 112469215-isolate1 | *Escherichia coli* 2741950 |

TABLE 1-continued

| | |
|---|---|
| *Escherichia coli* 112469218-isolate1 | *Escherichia coli* 2747800 |
| *Escherichia coli* 10.0562 | *Escherichia coli* 2749250 |
| *Escherichia coli* 10.0821 | *Escherichia coli* 2756500 |
| *Escherichia coli* 2762100 | *Escherichia coli* 2860650 |
| *Escherichia coli* 2770900 | *Escherichia coli* 2861200 |
| *Escherichia coli* 2780750 | *Escherichia coli* 55989 |
| *Escherichia coli* 2785200 | *Escherichia coli* 576-1 |
| *Escherichia coli* 2788150 | *Escherichia coli* 5905 |
| *Escherichia coli* 2845350 | *Escherichia coli* 6.0172 |
| *Escherichia coli* 2845650 | *Escherichia coli* 6.168 |
| *Escherichia coli* 2846750 | *Escherichia coli* 7.1485 |
| *Escherichia coli* 2846750-DM-A | *Escherichia coli* 7.1495 |
| *Escherichia coli* 2846750-DM-B | *Escherichia coli* 7.1575 |
| *Escherichia coli* 2846750-DM-B-A | *Escherichia coli* 7.3192 |
| *Escherichia coli* 2846750-DM-B-B | *Escherichia coli* 75 |
| *Escherichia coli* 2848050 | *Escherichia coli* 754_10 |
| *Escherichia coli* 2850400 | *Escherichia coli* 79 |
| *Escherichia coli* 2850750 | *Escherichia coli* 8.0416 |
| *Escherichia coli* 2851500 | *Escherichia coli* 8.0566 |
| *Escherichia coli* 2853500 | *Escherichia coli* 8.0569 |
| *Escherichia coli* 1E14 | *Escherichia coli* 8.0586 |
| *Escherichia coli* 2.0731 | *Escherichia coli* 8.2256 |
| *Escherichia coli* 2.0966 | *Escherichia coli* 8.2524 |
| *Escherichia coli* 2.3916 | *Escherichia coli* 83972 |
| *Escherichia coli* 2862600 | *Escherichia coli* 85.0143 |
| *Escherichia coli* 2864350 | *Escherichia coli* 85.1284 |
| *Escherichia coli* 2865200 | *Escherichia coli* 8624 |
| *Escherichia coli* 2866350 | *Escherichia coli* 87-1713 (10i) |
| *Escherichia coli* 2722950 | *Escherichia coli* 88.0221 |
| *Escherichia coli* 2726800 | *Escherichia coli* 88.1042 |
| *Escherichia coli* 2726950 | *Escherichia coli* 88.1467 |
| *Escherichia coli* 2729250 | *Escherichia coli* 88817 (10j) |
| *Escherichia coli* 2729250-DM-A | *Escherichia coli* 89.0511 |
| *Escherichia coli* 2729250-DM-B | *Escherichia coli* 9.0111 |
| *Escherichia coli* 2729250-DM-B-A | *Escherichia coli* 9.1649 |
| *Escherichia coli* 2729250-DM-B-B | *Escherichia coli* 2866450 |
| *Escherichia coli* 2730350 | *Escherichia coli* 908616 |
| *Escherichia coli* 2730450 | *Escherichia coli* 908624 |
| *Escherichia coli* 2731150 | *Escherichia coli* 908632 |
| *Escherichia coli* 2866550 | *Escherichia coli* 908658 |
| *Escherichia coli* 2866750 | *Escherichia coli* 908675 |
| *Escherichia coli* 2867750 | *Escherichia coli* 908691 |
| *Escherichia coli* 2871950 | *Escherichia coli* 909945-2 |
| *Escherichia coli* 2872000 | *Escherichia coli* 53638 |
| *Escherichia coli* 2872800 | *Escherichia coli* 541-1 |
| *Escherichia coli* 2875000 | *Escherichia coli* 541-15 |
| *Escherichia coli* 2875150 | *Escherichia coli* 5412 |
| *Escherichia coli* 2886-75 | *Escherichia coli* 93-001 |
| *Escherichia coli* 290_10 | *Escherichia coli* 93-111 |
| *Escherichia coli* 3.0190 | *Escherichia coli* 93.0055 |
| *Escherichia coli* 3.2303 | *Escherichia coli* 93.0056 |
| *Escherichia coli* 3.2608 | *Escherichia coli* 93.0624 |
| *Escherichia coli* 3.3884 | *Escherichia coli* 94.0618 |
| *Escherichia coli* 3.4870 | *Escherichia coli* 95.0183 |
| *Escherichia coli* 3.4871 | *Escherichia coli* 95.0941 |
| *Escherichia coli* 3003 | *Escherichia coli* 95.0943 |
| *Escherichia coli* 3006 | *Escherichia coli* 95.1288 |
| *Escherichia coli* 3030-1 | *Escherichia coli* 95JB1 |
| *Escherichia coli* 3350-73 (13a) | *Escherichia coli* 95NR1 |
| *Escherichia coli* 3431 | *Escherichia coli* 96.0107 |
| *Escherichia coli* 371_08 | *Escherichia coli* 96.0109 |
| *Escherichia coli* 4.0522 | *Escherichia coli* 96.0427 |
| *Escherichia coli* 4.0967 | *Escherichia coli* 96.0428 |
| *Escherichia coli* 4_1_47FAA | *Escherichia coli* 96.0497 |
| *Escherichia coli* 5.0588 | *Escherichia coli* 96.0932 |
| *Escherichia coli* 5.0959 | *Escherichia coli* 96.0939 |
| *Escherichia coli* 5.2219 | *Escherichia coli* 96.154 |
| *Escherichia coli* 5.2239 | *Escherichia coli* 97.0003 |
| *Escherichia coli* 5.2246 | *Escherichia coli* 97.0007 |
| *Escherichia coli* 5.3169 | *Escherichia coli* 97.0010 |
| *Escherichia coli* 536 | *Escherichia coli* 97.0246 |
| *Escherichia coli* 2854350 | *Escherichia coli* 97.0259 |
| *Escherichia coli* 2860050 | *Escherichia coli* 97.0264 |
| *Escherichia coli* 97.1742 | *Escherichia coli* C40_11 |
| *Escherichia coli* 98NK2 | *Escherichia coli* C418_89 |
| *Escherichia coli* 99.0670 | *Escherichia coli* C458_10 |
| *Escherichia coli* 99.0672 | *Escherichia coli* C488_07 |
| *Escherichia coli* 99.0678 | *Escherichia coli* C496_10 |
| *Escherichia coli* 99.0713 | *Escherichia coli* C497_10 |
| *Escherichia coli* 99.0741 | *Escherichia coli* C527_94 |

TABLE 1-continued

| | |
|---|---|
| *Escherichia coli* 99.0814 | *Escherichia coli* C54-58 (1b) |
| *Escherichia coli* 99.0815 | *Escherichia coli* C581_05 |
| *Escherichia coli* 99.0816 | *Escherichia coli* C586_05 |
| *Escherichia coli* 99.0839 | *Escherichia coli* C58_11 |
| *Escherichia coli* 99.0848 | *Escherichia coli* C595_09 |
| *Escherichia coli* 99.1753 | *Escherichia coli* C639_08 |
| *Escherichia coli* 99.1762 | *Escherichia coli* C652_10 |
| *Escherichia coli* 99.1775 | *Escherichia coli* C654_09 |
| *Escherichia coli* 99.1781 | *Escherichia coli* C666_01 |
| *Escherichia coli* 99.1793 | *Escherichia coli* C691-71 (14b) |
| *Escherichia coli* 99.1805 | *Escherichia coli* C717_10 |
| *Escherichia coli* A-03_34 | *Escherichia coli* C725_88 |
| *Escherichia coli* A25922R | *Escherichia coli* C732_98 |
| *Escherichia coli* A35218R | *Escherichia coli* C743_03 |
| *Escherichia coli* A9619-c2 (11c) | *Escherichia coli* C751_03 |
| *Escherichia coli* AA86 | *Escherichia coli* C77_08 |
| *Escherichia coli* AB42410445-isolate1 | *Escherichia coli* C78_09C |
| *Escherichia coli* AB42554418-isolate1 | *Escherichia coli* C792_92 |
| *Escherichia coli* AB42602061-isolate1 | *Escherichia coli* C796_10 |
| *Escherichia coli* AB43739056-isolate1 | *Escherichia coli* C799_92 |
| *Escherichia coli* ABU 83972 | *Escherichia coli* C79_08 |
| *Escherichia coli* AD30 | *Escherichia coli* C807_09 |
| *Escherichia coli* ADL-218 | *Escherichia coli* C80_08 |
| *Escherichia coli* ADL-223 | *Escherichia coli* C824_10 |
| *Escherichia coli* ADL-226 | *Escherichia coli* C82_11 |
| *Escherichia coli* ADL-304 | *Escherichia coli* C838_10 |
| *Escherichia coli* ADL-305 | *Escherichia coli* C842_97 |
| *Escherichia coli* ADL-306 | *Escherichia coli* C844_97 |
| *Escherichia coli* ADL-307 | *Escherichia coli* ADL-309 |
| *Escherichia coli* ADL-308 | *Escherichia coli* ADL-310 |
| *Escherichia coli* 9.1796 | *Escherichia coli* ADL-311 |
| *Escherichia coli* 90.0039 | *Escherichia coli* ADL-312 |
| *Escherichia coli* 90.0091 | *Escherichia coli* ADL-313 |
| *Escherichia coli* 90.2281 | *Escherichia coli* ADL-314 |
| *Escherichia coli* 900105 (10e) | *Escherichia coli* ADL-316 |
| *Escherichia coli* 902034 (7b) | *Escherichia coli* ADL-324 |
| *Escherichia coli* 907357 | *Escherichia coli* ADL-327 |
| *Escherichia coli* 907391 | *Escherichia coli* AI27 |
| *Escherichia coli* 907446 | *Escherichia coli* APEC IMT5155 |
| *Escherichia coli* 907672 | *Escherichia coli* APEC O1 |
| *Escherichia coli* 907700 | *Escherichia coli* APEC O78 |
| *Escherichia coli* 907701 | *Escherichia coli* ARL10/167 |
| *Escherichia coli* 907710 | *Escherichia coli* ARS4.2123 |
| *Escherichia coli* 907713 | *Escherichia coli* ATCC 25922 |
| *Escherichia coli* 907715 | *Escherichia coli* ATCC 35150 |
| *Escherichia coli* 907779 | *Escherichia coli* B |
| *Escherichia coli* 907889 | *Escherichia coli* B str. REL606 |
| *Escherichia coli* 907892 | *Escherichia coli* B str. REL607 |
| *Escherichia coli* 908519 | *Escherichia coli* B-04_28 |
| *Escherichia coli* 908521 | *Escherichia coli* B088 |
| *Escherichia coli* 908522 | *Escherichia coli* B093 |
| *Escherichia coli* 908524 | *Escherichia coli* B102 |
| *Escherichia coli* 908525 | *Escherichia coli* B103 |
| *Escherichia coli* 908541 | *Escherichia coli* B104 |
| *Escherichia coli* 908555 | *Escherichia coli* B105 |
| *Escherichia coli* 908573 | *Escherichia coli* B106 |
| *Escherichia coli* 908585 | *Escherichia coli* B107 |
| *Escherichia coli* C33_11 | *Escherichia coli* B108 |
| *Escherichia coli* C341_10 | *Escherichia coli* B109 |
| *Escherichia coli* C343_08 | *Escherichia coli* B112 |
| *Escherichia coli* C347_93 | *Escherichia coli* B113 |
| *Escherichia coli* C353_09 | *Escherichia coli* B114 |
| *Escherichia coli* C354_03B | *Escherichia coli* B1167 |
| *Escherichia coli* 909957 | *Escherichia coli* BIDMC 39 |
| *Escherichia coli* 910096-2 | *Escherichia coli* BIDMC 6 |
| *Escherichia coli* 92.0144 (F03) | *Escherichia coli* BIDMC 9 |
| *Escherichia coli* 929-78 | *Escherichia coli* BL21 |
| *Escherichia coli* B185 | *Escherichia coli* BL21(DE3) |
| *Escherichia coli* B26-1 | *Escherichia coli* BWH 24 |
| *Escherichia coli* B26-2 | *Escherichia coli* BWH 32 |
| *Escherichia coli* B28-1 | *Escherichia coli* BWH 34 |
| *Escherichia coli* B28-2 | *Escherichia coli* BWH 40 |
| *Escherichia coli* B29-1 | *Escherichia coli* C |
| *Escherichia coli* B29-2 | *Escherichia coli* ATCC 8739 |
| *Escherichia coli* B354 | *Escherichia coli* C-04_22 |
| *Escherichia coli* B36-1 | *Escherichia coli* C-34666 |
| *Escherichia coli* B36-2 | *Escherichia coli* C1214_90 |
| *Escherichia coli* B367 | *Escherichia coli* C1244_91 |
| *Escherichia coli* B40-1 | *Escherichia coli* C12_92 |
| *Escherichia coli* B40-2 | *Escherichia coli* C154_11 |

TABLE 1-continued

| | |
|---|---|
| *Escherichia coli* B41 | *Escherichia coli* C155_11 |
| *Escherichia coli* B49-1 | *Escherichia coli* C157_11 |
| *Escherichia coli* B49-2 | *Escherichia coli* C161_11 |
| *Escherichia coli* B5-1 | *Escherichia coli* C166_11 |
| *Escherichia coli* B5-2 | *Escherichia coli* C170_11 |
| *Escherichia coli* B574 | *Escherichia coli* C186-61 (10h) |
| *Escherichia coli* B671 | *Escherichia coli* C2139_99 |
| *Escherichia coli* B7-1 | *Escherichia coli* C213_10 |
| *Escherichia coli* B7-2 | *Escherichia coli* C238_91 |
| *Escherichia coli* B706 | *Escherichia coli* C240-52 (9c) |
| *Escherichia coli* B799 | *Escherichia coli* C260_92 |
| *Escherichia coli* B7A | *Escherichia coli* C262_10 |
| *Escherichia coli* B83 | *Escherichia coli* C283_09 |
| *Escherichia coli* B84 | *Escherichia coli* C295_10 |
| *Escherichia coli* B85 | *Escherichia coli* C309-64 (10g) |
| *Escherichia coli* B86 | *Escherichia coli* DH5 [alpha] |
| *Escherichia coli* B89 | *Escherichia coli* DSM 30083 = JCM 1649 |
| *Escherichia coli* B90 | *Escherichia coli* E-01_37 |
| *Escherichia coli* B91 | *Escherichia coli* E1002 |
| *Escherichia coli* B92 | *Escherichia coli* E101 |
| *Escherichia coli* B921 | *Escherichia coli* E110019 |
| *Escherichia coli* B93 | *Escherichia coli* E1114 |
| *Escherichia coli* B94 | *Escherichia coli* E1118 |
| *Escherichia coli* B95 | *Escherichia coli* E1167 |
| *Escherichia coli* Bal225 | *Escherichia coli* E128010 |
| *Escherichia coli* BCE001_MS16 | *Escherichia coli* E1492 |
| *Escherichia coli* BCE002_MS12 | *Escherichia coli* E1520 |
| *Escherichia coli* BCE006_MS-23 | *Escherichia coli* E1777 |
| *Escherichia coli* BCE007_MS-11 | *Escherichia coli* E2265 |
| *Escherichia coli* BCE008_MS-01 | *Escherichia coli* E24377A |
| *Escherichia coli* BCE008_MS-13 | *Escherichia coli* E267 |
| *Escherichia coli* BCE011_MS-01 | *Escherichia coli* E482 |
| *Escherichia coli* BCE019_MS-13 | *Escherichia coli* E560 |
| *Escherichia coli* BCE030_MS-09 | *Escherichia coli* E704 |
| *Escherichia coli* BCE032-DM-A | *Escherichia coli* E74/68 |
| *Escherichia coli* BCE032-DM-B | *Escherichia coli* E851/71 |
| *Escherichia coli* BCE032-DM-B-A | *Escherichia coli* Ec 11-9450 |
| *Escherichia coli* BCE032-DM-B-B | *Escherichia coli* Ec 11-9941 |
| *Escherichia coli* BCE032_MS-12 | *Escherichia coli* Ec 11-9990 |
| *Escherichia coli* BCE034_MS-14 | *Escherichia coli* EC096/10 |
| *Escherichia coli* Bd5610_99 | *Escherichia coli* Ec11-4986 |
| *Escherichia coli* BIDMC 15 | *Escherichia coli* EC1734 |
| *Escherichia coli* BIDMC 17A | *Escherichia coli* EC1735 |
| *Escherichia coli* BIDMC 17B | *Escherichia coli* EC1736 |
| *Escherichia coli* BIDMC 19A | *Escherichia coli* EC1737 |
| *Escherichia coli* BIDMC 19B | *Escherichia coli* EC1738 |
| *Escherichia coli* BIDMC 19C | *Escherichia coli* EC1845 |
| *Escherichia coli* BIDMC 20A | *Escherichia coli* EC1846 |
| *Escherichia coli* BIDMC 20B | *Escherichia coli* EC1847 |
| *Escherichia coli* BIDMC 2B | *Escherichia coli* EC1848 |
| *Escherichia coli* BIDMC 3 | *Escherichia coli* EC1849 |
| *Escherichia coli* BIDMC 37 | *Escherichia coli* EC1850 |
| *Escherichia coli* BIDMC 38 | *Escherichia coli* EC1856 |
| *Escherichia coli* EC1862 | *Escherichia coli* FRIK920 |
| *Escherichia coli* EC1863 | *Escherichia coli* FVEC1302 |
| *Escherichia coli* EC1864 | *Escherichia coli* FVEC1412 |
| *Escherichia coli* EC1865 | *Escherichia coli* FVEC1465 |
| *Escherichia coli* EC1866 | *Escherichia coli* G5101 |
| *Escherichia coli* EC1868 | *Escherichia coli* G58-1 |
| *Escherichia coli* EC1869 | *Escherichia coli* GEMS_EPEC1 |
| *Escherichia coli* EC1870 | *Escherichia coli* H001 |
| *Escherichia coli* EC302/04 | *Escherichia coli* H120 |
| *Escherichia coli* EC4013 | *Escherichia coli* H16 |
| *Escherichia coli* EC4100B | *Escherichia coli* H185 |
| *Escherichia coli* EC4196 | *Escherichia coli* H218 |
| *Escherichia coli* EC4203 | *Escherichia coli* H220 |
| *Escherichia coli* EC4402 | *Escherichia coli* H223 |
| *Escherichia coli* EC4421 | *Escherichia coli* H252 |
| *Escherichia coli* EC4422 | *Escherichia coli* H260 |
| *Escherichia coli* EC4436 | *Escherichia coli* C87_11 |
| *Escherichia coli* EC4437 | *Escherichia coli* C887_10 |
| *Escherichia coli* EC4439 | *Escherichia coli* C900_01 |
| *Escherichia coli* EC4448 | *Escherichia coli* C93_11 |
| *Escherichia coli* EC96038 | *Escherichia coli* C9_92 |
| *Escherichia coli* ECA-0157 | *Escherichia coli* CB7326 |
| *Escherichia coli* ECA-727 | *Escherichia coli* B15 |
| *Escherichia coli* ECC-1470 | *Escherichia coli* B17 |
| *Escherichia coli* ECC-Z | *Escherichia coli* B171 |
| *Escherichia coli* EcNDM1 | *Escherichia coli* B175 |
| *Escherichia coli* ED1a | *Escherichia coli* CE418 |

TABLE 1-continued

| | |
|---|---|
| *Escherichia coli* EDM106 | *Escherichia coli* CE516 |
| *Escherichia coli* EDM116 | *Escherichia coli* CE549 |
| *Escherichia coli* EDM530 | *Escherichia coli* CFT073 |
| *Escherichia coli* Envira 10/1 | *Escherichia coli* chi7122 |
| *Escherichia coli* Envira 8/11 | *Escherichia coli* cloneA_i1 |
| *Escherichia coli* EPEC 32/73 | *Escherichia coli* Combat2D2 |
| *Escherichia coli* EPEC C342-62 | *Escherichia coli* CUMT8 |
| *Escherichia coli* EPEC11 | *Escherichia coli* D-04_27 |
| *Escherichia coli* EPECa12 | *Escherichia coli* DEC10A |
| *Escherichia coli* EPECa14 | *Escherichia coli* DEC10B |
| *Escherichia coli* ER2796 | *Escherichia coli* DEC10C |
| *Escherichia coli* ES699 | *Escherichia coli* DEC10D |
| *Escherichia coli* ETEC 1392/75 | *Escherichia coli* DEC10E |
| *Escherichia coli* ETEC DS168-1 | *Escherichia coli* DEC10F |
| *Escherichia coli* ETEC H10407 | *Escherichia coli* DEC11A |
| *Escherichia coli* H10407_1968 | *Escherichia coli* DEC11B |
| *Escherichia coli* H10407_1970 | *Escherichia coli* DEC11C |
| *Escherichia coli* ETEC TW03439 | *Escherichia coli* DEC11D |
| *Escherichia coli* ETEC TW03452 | *Escherichia coli* DEC11E |
| *Escherichia coli* ETEC TW03574 | *Escherichia coli* DEC12A |
| *Escherichia coli* ETEC TW03576 | *Escherichia coli* DEC12B |
| *Escherichia coli* ETEC TW03585 | *Escherichia coli* DEC12C |
| *Escherichia coli* ETEC TW03741 | *Escherichia coli* DEC12D |
| *Escherichia coli* ETEC TW14691 | *Escherichia coli* DEC12E |
| *Escherichia coli* ETEC WS1896A | *Escherichia coli* DEC13A |
| *Escherichia coli* ETEC WS2068A | *Escherichia coli* DEC13B |
| *Escherichia coli* ETEC WS3080A | *Escherichia coli* DEC13C |
| *Escherichia coli* F11 | *Escherichia coli* DEC13D |
| *Escherichia coli* F18+ | *Escherichia coli* DEC13E |
| *Escherichia coli* F576 | *Escherichia coli* DEC14A |
| *Escherichia coli* FDA504 | *Escherichia coli* DEC14B |
| *Escherichia coli* FDA505 | *Escherichia coli* DEC14C |
| *Escherichia coli* FDA506 | *Escherichia coli* DEC14D |
| *Escherichia coli* FDA507 | *Escherichia coli* DEC15A |
| *Escherichia coli* FDA517 | *Escherichia coli* DEC15B |
| *Escherichia coli* FREP | *Escherichia coli* DEC15C |
| *Escherichia coli* FRIK1985 | *Escherichia coli* DEC15D |
| *Escherichia coli* FRIK1990 | *Escherichia coli* DEC15E |
| *Escherichia coli* FRIK1996 | *Escherichia coli* DEC1A |
| *Escherichia coli* FRIK1997 | *Escherichia coli* DEC1B |
| *Escherichia coli* FRIK1999 | *Escherichia coli* DEC1C |
| *Escherichia coli* FRIK2001 | *Escherichia coli* DEC1D |
| *Escherichia coli* FRIK523 | *Escherichia coli* DEC1E |
| *Escherichia coli* DEC2A | *Escherichia coli* HVH 223 (4-2976528) |
| *Escherichia coli* DEC2B | *Escherichia coli* HVH 225 (4-1273116) |
| *Escherichia coli* DEC2C | *Escherichia coli* HVH 227 (4-2277670) |
| *Escherichia coli* DEC2D | *Escherichia coli* HVH 228 (4-7787030) |
| *Escherichia coli* DEC2E | *Escherichia coli* HVH 23 (4-6066488) |
| *Escherichia coli* DEC3A | *Escherichia coli* HVH 24 (4-5985145) |
| *Escherichia coli* DEC3B | *Escherichia coli* HVH 25 (4-5851939) |
| *Escherichia coli* DEC3C | *Escherichia coli* HVH 26 (4-5703913) |
| *Escherichia coli* DEC3D | *Escherichia coli* HVH 27 (4-7449267) |
| *Escherichia coli* DEC3E | *Escherichia coli* HVH 28 (4-0907367) |
| *Escherichia coli* DEC3F | *Escherichia coli* HVH 29 (4-3418073) |
| *Escherichia coli* DEC4A | *Escherichia coli* HVH 3 (4-7276001) |
| *Escherichia coli* DEC4B | *Escherichia coli* HVH 30 (4-2661829) |
| *Escherichia coli* DEC4C | *Escherichia coli* HVH 31 (4-2602156) |
| *Escherichia coli* DEC4D | *Escherichia coli* HVH 32 (4-3773988) |
| *Escherichia coli* DEC4E | *Escherichia coli* HVH 33 (4-2174936) |
| *Escherichia coli* DEC4F | *Escherichia coli* HVH 35 (4-2962667) |
| *Escherichia coli* DEC5A | *Escherichia coli* HVH 36 (4-5675286) |
| *Escherichia coli* DEC5B | *Escherichia coli* HVH 37 (4-2773848) |
| *Escherichia coli* DEC5C | *Escherichia coli* HVH 38 (4-2774682) |
| *Escherichia coli* DEC5D | *Escherichia coli* HVH 39 (4-2679949) |
| *Escherichia coli* DEC5E | *Escherichia coli* HVH 4 (4-7276109) |
| *Escherichia coli* DEC6A | *Escherichia coli* HVH 40 (4-1219782) |
| *Escherichia coli* DEC6B | *Escherichia coli* HVH 41 (4-2677849) |
| *Escherichia coli* DEC6C | *Escherichia coli* HVH 42 (4-2100061) |
| *Escherichia coli* DEC6D | *Escherichia coli* HVH 43 (4-2173468) |
| *Escherichia coli* DEC6E | *Escherichia coli* HVH 44 (4-2298570) |
| *Escherichia coli* DEC7A | *Escherichia coli* HVH 45 (4-3129918) |
| *Escherichia coli* DEC7B | *Escherichia coli* HVH 46 (4-2758776) |
| *Escherichia coli* DEC7C | *Escherichia coli* HVH 48 (4-2658593) |
| *Escherichia coli* DEC7D | *Escherichia coli* HVH 5 (4-7148410) |
| *Escherichia coli* DEC7E | *Escherichia coli* HVH 50 (4-2593475) |
| *Escherichia coli* DEC8A | *Escherichia coli* HVH 51 (4-2172526) |
| *Escherichia coli* DEC8B | *Escherichia coli* HVH 53 (4-0631051) |
| *Escherichia coli* DEC8C | *Escherichia coli* HVH 54 (4-2723514) |
| *Escherichia coli* DEC8D | *Escherichia coli* HVH 55 (4-2646161) |
| *Escherichia coli* DEC8E | *Escherichia coli* HVH 56 (4-2153033) |

TABLE 1-continued

| | |
|---|---|
| *Escherichia coli* DEC9A | *Escherichia coli* HVH 58 (4-2839709) |
| *Escherichia coli* DEC9B | *Escherichia coli* HVH 59 (4-1119338) |
| *Escherichia coli* DEC9C | *Escherichia coli* HVH 6 (3-8296502) |
| *Escherichia coli* DEC9D | *Escherichia coli* HVH 61 (4-2736020) |
| *Escherichia coli* DEC9E | *Escherichia coli* HVH 63 (4-2542528) |
| *Escherichia coli* DH1 | *Escherichia coli* HVH 65 (4-2262045) |
| *Escherichia coli* HVH 199 (4-5670322) | *Escherichia coli* HVH 68 (4-0888028) |
| *Escherichia coli* HVH 2 (4-6943160) | *Escherichia coli* HVH 69 (4-2837072) |
| *Escherichia coli* HVH 20 (4-5865042) | *Escherichia coli* HVH 7 (4-7315031) |
| *Escherichia coli* HVH 200 (4-4449924) | *Escherichia coli* HVH 70 (4-2963531) |
| *Escherichia coli* HVH 201 (4-4459431) | *Escherichia coli* HVH 73 (4-2393174) |
| *Escherichia coli* HVH 202 (4-3163997) | *Escherichia coli* HVH 74 (4-1034782) |
| *Escherichia coli* HVH 203 (4-3126218) | *Escherichia coli* HVH 76 (4-2538717) |
| *Escherichia coli* HVH 204 (4-3112802) | *Escherichia coli* HVH 77 (4-2605759) |
| *Escherichia coli* HVH 205 (4-3094677) | *Escherichia coli* HVH 78 (4-2735946) |
| *Escherichia coli* HVH 206 (4-3128229) | *Escherichia coli* HVH 79 (4-2512823) |
| *Escherichia coli* HVH 207 (4-3113221) | *Escherichia coli* HVH 80 (4-2428830) |
| *Escherichia coli* HVH 208 (4-3112292) | *Escherichia coli* HVH 82 (4-2209276) |
| *Escherichia coli* HVH 209 (4-3062651) | *Escherichia coli* HVH 83 (4-2051087) |
| *Escherichia coli* HVH 21 (4-4517873) | *Escherichia coli* HVH 84 (4-1021478) |
| *Escherichia coli* HVH 210 (4-3042480) | *Escherichia coli* HVH 85 (4-0792144) |
| *Escherichia coli* HVH 211 (4-3041891) | *Escherichia coli* HVH 86 (4-7026218) |
| *Escherichia coli* HVH 212 (3-9305343) | *Escherichia coli* HVH 87 (4-5977630) |
| *Escherichia coli* HVH 213 (4-3042928) | *Escherichia coli* HVH 88 (4-5854636) |
| *Escherichia coli* HVH 214 (4-3062198) | *Escherichia coli* HVH 89 (4-5885604) |
| *Escherichia coli* HVH 215 (4-3008371) | *Escherichia coli* HVH 9 (4-6942539) |
| *Escherichia coli* HVH 216 (4-3042952) | *Escherichia coli* HVH 90 (4-3191362) |
| *Escherichia coli* HVH 217 (4-1022806) | *Escherichia coli* HVH 91 (4-4638751) |
| *Escherichia coli* HVH 218 (4-4500903) | *Escherichia coli* HVH 92 (4-5930790) |
| *Escherichia coli* HVH 22 (4-2258986) | *Escherichia coli* HVH 93 (4-5851025) |
| *Escherichia coli* HVH 220 (4-5876842) | *Escherichia coli* HVH 95 (4-6074464) |
| *Escherichia coli* HVH 221 (4-3136817) | *Escherichia coli* HVH 96 (4-5934869) |
| *Escherichia coli* HVH 222 (4-2977443) | *Escherichia coli* HVH 97 (4-6859038) |
| *Escherichia coli* HVH 98 (4-5799287) | *Escherichia coli* KTE115 |
| *Escherichia coli* HVH 99 (4-6745172) | *Escherichia coli* KTE116 |
| *Escherichia coli* IAI1 | *Escherichia coli* KTE117 |
| *Escherichia coli* IAI39 | *Escherichia coli* KTE118 |
| *Escherichia coli* IHE3034 | *Escherichia coli* KTE119 |
| *Escherichia coli* IMT8073 | *Escherichia coli* KTE12 |
| *Escherichia coli* J53 | *Escherichia coli* KTE120 |
| *Escherichia coli* J96 | *Escherichia coli* KTE121 |
| *Escherichia coli* JB1-95 | *Escherichia coli* KTE122 |
| *Escherichia coli* JC2722 | *Escherichia coli* KTE123 |
| *Escherichia coli* JC5048 | *Escherichia coli* KTE124 |
| *Escherichia coli* JCL16 | *Escherichia coli* KTE125 |
| *Escherichia coli* JCMA | *Escherichia coli* KTE126 |
| *Escherichia coli* Jurua 18/11 | *Escherichia coli* KTE127 |
| *Escherichia coli* Jurua 20/10 | *Escherichia coli* KTE128 |
| *Escherichia coli* K-12 | *Escherichia coli* KTE129 |
| *Escherichia coli* BW25113 | *Escherichia coli* KTE13 |
| *Escherichia coli* BW2952 | *Escherichia coli* KTE130 |
| *Escherichia coli* BW38028 | *Escherichia coli* KTE131 |
| *Escherichia coli* LW1655F+ | *Escherichia coli* KTE132 |
| *Escherichia coli* MC1061 | *Escherichia coli* KTE133 |
| *Escherichia coli* NC-7 | *Escherichia coli* KTE134 |
| *Escherichia coli* str. K-12 substr. DH10B | *Escherichia coli* KTE135 |
| *Escherichia coli* str. K-12 substr. MDS42 | *Escherichia coli* KTE136 |
| *Escherichia coli* str. K-12 substr. MG1655 | *Escherichia coli* KTE137 |
| *Escherichia coli* str. K-12 substr. W3110 | *Escherichia coli* KTE138 |
| *Escherichia coli* K1 | *Escherichia coli* KTE139 |
| *Escherichia coli* K2 | *Escherichia coli* KTE14 |
| *Escherichia coli* K71 | *Escherichia coli* KTE140 |
| *Escherichia coli* KD1 | *Escherichia coli* KTE141 |
| *Escherichia coli* KD2 | *Escherichia coli* KTE142 |
| *Escherichia coli* KO11FL | *Escherichia coli* KTE143 |
| *Escherichia coli* KOEGE 10 (25a) | *Escherichia coli* KTE144 |
| *Escherichia coli* KOEGE 118 (317a) | *Escherichia coli* KTE145 |
| *Escherichia coli* KOEGE 131 (358a) | *Escherichia coli* KTE146 |
| *Escherichia coli* KOEGE 3 (4a) | *Escherichia coli* KTE147 |
| *Escherichia coli* KOEGE 30 (63a) | *Escherichia coli* KTE148 |
| *Escherichia coli* KOEGE 32 (66a) | *Escherichia coli* KTE149 |
| *Escherichia coli* KOEGE 33 (68a) | *Escherichia coli* KTE15 |
| *Escherichia coli* KOEGE 40 (102a) | *Escherichia coli* KTE150 |
| *Escherichia coli* KOEGE 43 (105a) | *Escherichia coli* KTE153 |
| *Escherichia coli* KOEGE 44 (106a) | *Escherichia coli* KTE154 |
| *Escherichia coli* KOEGE 56 (169a) | *Escherichia coli* KTE155 |
| *Escherichia coli* KOEGE 58 (171a) | *Escherichia coli* KTE156 |
| *Escherichia coli* KOEGE 61 (174a) | *Escherichia coli* KTE157 |
| *Escherichia coli* KOEGE 62 (175a) | *Escherichia coli* KTE158 |
| *Escherichia coli* KOEGE 68 (182a) | *Escherichia coli* KTE159 |

TABLE 1-continued

| | |
|---|---|
| *Escherichia coli* KOEGE 7 (16a) | *Escherichia coli* KTE16 |
| *Escherichia coli* KOEGE 70 (185a) | *Escherichia coli* KTE160 |
| *Escherichia coli* KOEGE 71 (186a) | *Escherichia coli* KTE161 |
| *Escherichia coli* KOEGE 73 (195a) | *Escherichia coli* KTE162 |
| *Escherichia coli* KOEGE 77 (202a) | *Escherichia coli* KTE163 |
| *Escherichia coli* KTE1 | *Escherichia coli* KTE165 |
| *Escherichia coli* KTE10 | *Escherichia coli* KTE166 |
| *Escherichia coli* KTE100 | *Escherichia coli* KTE167 |
| *Escherichia coli* KTE101 | *Escherichia coli* KTE168 |
| *Escherichia coli* KTE102 | *Escherichia coli* KTE169 |
| *Escherichia coli* KTE103 | *Escherichia coli* KTE17 |
| *Escherichia coli* KTE104 | *Escherichia coli* KTE170 |
| *Escherichia coli* KTE105 | *Escherichia coli* KTE171 |
| *Escherichia coli* KTE106 | *Escherichia coli* KTE172 |
| *Escherichia coli* KTE107 | *Escherichia coli* KTE173 |
| *Escherichia coli* KTE108 | *Escherichia coli* KTE174 |
| *Escherichia coli* KTE109 | *Escherichia coli* KTE175 |
| *Escherichia coli* KTE11 | *Escherichia coli* KTE176 |
| *Escherichia coli* KTE110 | *Escherichia coli* KTE177 |
| *Escherichia coli* KTE111 | *Escherichia coli* KTE178 |
| *Escherichia coli* KTE112 | *Escherichia coli* KTE179 |
| *Escherichia coli* KTE113 | *Escherichia coli* KTE18 |
| *Escherichia coli* KTE114 | *Escherichia coli* KTE180 |
| *Escherichia coli* KTE181 | *Escherichia coli* H489 |
| *Escherichia coli* KTE182 | *Escherichia coli* H494 |
| *Escherichia coli* KTE183 | *Escherichia coli* H504 |
| *Escherichia coli* KTE184 | *Escherichia coli* H588 |
| *Escherichia coli* KTE185 | *Escherichia coli* H591 |
| *Escherichia coli* KTE186 | *Escherichia coli* H593 |
| *Escherichia coli* KTE187 | *Escherichia coli* H605 |
| *Escherichia coli* KTE188 | *Escherichia coli* H617 |
| *Escherichia coli* KTE189 | *Escherichia coli* H660 |
| *Escherichia coli* KTE19 | *Escherichia coli* H730 |
| *Escherichia coli* KTE190 | *Escherichia coli* H736 |
| *Escherichia coli* KTE191 | *Escherichia coli* HB101 |
| *Escherichia coli* KTE192 | *Escherichia coli* HM26 |
| *Escherichia coli* KTE193 | *Escherichia coli* HM27 |
| *Escherichia coli* KTE194 | *Escherichia coli* HM46 |
| *Escherichia coli* KTE195 | *Escherichia coli* HM605 |
| *Escherichia coli* KTE196 | *Escherichia coli* HM65 |
| *Escherichia coli* KTE197 | *Escherichia coli* HM69 |
| *Escherichia coli* KTE198 | *Escherichia coli* HP20A2007 |
| *Escherichia coli* KTE199 | *Escherichia coli* HUSEC41 |
| *Escherichia coli* KTE2 | *Escherichia coli* HVH 1 (4-6876161) |
| *Escherichia coli* KTE20 | *Escherichia coli* HVH 10 (4-6832164) |
| *Escherichia coli* KTE200 | *Escherichia coli* HVH 100 (4-2850729) |
| *Escherichia coli* KTE201 | *Escherichia coli* HVH 101 (4-6859844) |
| *Escherichia coli* KTE202 | *Escherichia coli* HVH 102 (4-6906788) |
| *Escherichia coli* KTE203 | *Escherichia coli* HVH 103 (4-5904188) |
| *Escherichia coli* KTE204 | *Escherichia coli* HVH 104 (4-6977960) |
| *Escherichia coli* KTE205 | *Escherichia coli* HVH 105 (4-6748473) |
| *Escherichia coli* KTE206 | *Escherichia coli* HVH 106 (4-6881831) |
| *Escherichia coli* KTE207 | *Escherichia coli* HVH 107 (4-5860571) |
| *Escherichia coli* KTE208 | *Escherichia coli* HVH 108 (4-6924867) |
| *Escherichia coli* KTE209 | *Escherichia coli* HVH 109 (4-6977162) |
| *Escherichia coli* KTE21 | *Escherichia coli* HVH 110 (4-6978754) |
| *Escherichia coli* KTE210 | *Escherichia coli* HVH 111 (4-7039018) |
| *Escherichia coli* KTE211 | *Escherichia coli* HVH 112 (4-5987253) |
| *Escherichia coli* KTE212 | *Escherichia coli* HVH 113 (4-7535473) |
| *Escherichia coli* KTE213 | *Escherichia coli* HVH 114 (4-7037740) |
| *Escherichia coli* KTE214 | *Escherichia coli* HVH 115 (4-4465989) |
| *Escherichia coli* KTE215 | *Escherichia coli* HVH 115 (4-4465997) |
| *Escherichia coli* KTE216 | *Escherichia coli* HVH 116 (4-6879942) |
| *Escherichia coli* KTE217 | *Escherichia coli* HVH 117 (4-6857191) |
| *Escherichia coli* KTE218 | *Escherichia coli* HVH 118 (4-7345399) |
| *Escherichia coli* KTE219 | *Escherichia coli* HVH 119 (4-6879578) |
| *Escherichia coli* KTE22 | *Escherichia coli* HVH 12 (4-7653042) |
| *Escherichia coli* KTE220 | *Escherichia coli* HVH 120 (4-6978681) |
| *Escherichia coli* KTE221 | *Escherichia coli* HVH 121 (4-6877826) |
| *Escherichia coli* KTE222 | *Escherichia coli* HVH 122 (4-6851606) |
| *Escherichia coli* KTE223 | *Escherichia coli* HVH 125 (4-2634716) |
| *Escherichia coli* KTE224 | *Escherichia coli* HVH 126 (4-6034225) |
| *Escherichia coli* KTE225 | *Escherichia coli* HVH 127 (4-7303629) |
| *Escherichia coli* KTE226 | *Escherichia coli* HVH 128 (4-7030436) |
| *Escherichia coli* KTE227 | *Escherichia coli* HVH 13 (4-7634056) |
| *Escherichia coli* KTE228 | *Escherichia coli* HVH 130 (4-7036876) |
| *Escherichia coli* KTE229 | *Escherichia coli* HVH 132 (4-6876862) |
| *Escherichia coli* KTE23 | *Escherichia coli* HVH 133 (4-4466519) |
| *Escherichia coli* H263 | *Escherichia coli* HVH 134 (4-6073441) |
| *Escherichia coli* H288 | *Escherichia coli* HVH 135 (4-4449320) |

TABLE 1-continued

| | |
|---|---|
| *Escherichia coli* H296 | *Escherichia coli* HVH 136 (4-5970458) |
| *Escherichia coli* H299 | *Escherichia coli* HVH 137 (4-2124971) |
| *Escherichia coli* H30 | *Escherichia coli* HVH 138 (4-6066704) |
| *Escherichia coli* H305 | *Escherichia coli* HVH 139 (4-3192644) |
| *Escherichia coli* H378 | *Escherichia coli* HVH 140 (4-5894387) |
| *Escherichia coli* H383 | *Escherichia coli* HVH 141 (4-5995973) |
| *Escherichia coli* H386 | *Escherichia coli* HVH 142 (4-5627451) |
| *Escherichia coli* H397 | *Escherichia coli* HVH 143 (4-5674999) |
| *Escherichia coli* H413 | *Escherichia coli* HVH 144 (4-4451937) |
| *Escherichia coli* H420 | *Escherichia coli* HVH 145 (4-5672112) |
| *Escherichia coli* H442 | *Escherichia coli* HVH 146 (4-3189767) |
| *Escherichia coli* H454 | *Escherichia coli* HVH 147 (4-5893887) |
| *Escherichia coli* H461 | *Escherichia coli* HVH 148 (4-3192490) |
| *Escherichia coli* HVH 149 (4-4451880) | *Escherichia coli* MP021552.12 |
| *Escherichia coli* HVH 150 (4-3258106) | *Escherichia coli* MP021552.7 |
| *Escherichia coli* HVH 151 (4-5755573) | *Escherichia coli* MP021552.8 |
| *Escherichia coli* HVH 152 (4-3447545) | *Escherichia coli* MP021561.2 |
| *Escherichia coli* HVH 153 (3-9344314) | *Escherichia coli* MP021561.3 |
| *Escherichia coli* HVH 154 (4-5636698) | *Escherichia coli* MP021566.1 |
| *Escherichia coli* HVH 155 (4-4509048) | *Escherichia coli* MP 1 |
| *Escherichia coli* HVH 156 (4-3206505) | *Escherichia coli* MS 107-1 |
| *Escherichia coli* HVH 157 (4-3406229) | *Escherichia coli* MS 110-3 |
| *Escherichia coli* HVH 158 (4-3224287) | *Escherichia coli* MS 115-1 |
| *Escherichia coli* HVH 159 (4-5818141) | *Escherichia coli* MS 116-1 |
| *Escherichia coli* HVH 16 (4-7649002) | *Escherichia coli* MS 117-3 |
| *Escherichia coli* HVH 160 (4-5695937) | *Escherichia coli* MS 119-7 |
| *Escherichia coli* HVH 161 (4-3119890) | *Escherichia coli* MS 124-1 |
| *Escherichia coli* HVH 162 (4-5627982) | *Escherichia coli* MS 145-7 |
| *Escherichia coli* HVH 163 (4-4697553) | *Escherichia coli* MS 146-1 |
| *Escherichia coli* HVH 164 (4-5953081) | *Escherichia coli* MS 153-1 |
| *Escherichia coli* HVH 167 (4-6073565) | *Escherichia coli* MS 16-3 |
| *Escherichia coli* HVH 169 (4-1075578) | *Escherichia coli* MS 175-1 |
| *Escherichia coli* HVH 17 (4-7473087) | *Escherichia coli* MS 182-1 |
| *Escherichia coli* HVH 170 (4-3026949) | *Escherichia coli* MS 185-1 |
| *Escherichia coli* HVH 171 (4-3191958) | *Escherichia coli* MS 187-1 |
| *Escherichia coli* HVH 172 (4-3248542) | *Escherichia coli* MS 196-1 |
| *Escherichia coli* HVH 173 (3-9175482) | *Escherichia coli* MS 198-1 |
| *Escherichia coli* HVH 175 (4-3405184) | *Escherichia coli* MS 200-1 |
| *Escherichia coli* HVH 176 (4-3428664) | *Escherichia coli* MS 21-1 |
| *Escherichia coli* HVH 177 (4-2876612) | *Escherichia coli* MS 45-1 |
| *Escherichia coli* HVH 178 (4-3189163) | *Escherichia coli* MS 57-2 |
| *Escherichia coli* HVH 18 (4-8589585) | *Escherichia coli* MS 60-1 |
| *Escherichia coli* HVH 180 (4-3051617) | *Escherichia coli* MS 69-1 |
| *Escherichia coli* HVH 182 (4-0985554) | *Escherichia coli* MS 78-1 |
| *Escherichia coli* HVH 183 (4-3205932) | *Escherichia coli* MS 79-10 |
| *Escherichia coli* HVH 184 (4-3343286) | *Escherichia coli* MS 84-1 |
| *Escherichia coli* HVH 185 (4-2876639) | *Escherichia coli* MS 85-1 |
| *Escherichia coli* HVH 186 (4-3405044) | *Escherichia coli* N1 |
| *Escherichia coli* HVH 187 (4-4471660) | *Escherichia coli* NA114 |
| *Escherichia coli* HVH 188 (4-2356988) | *Escherichia coli* NC101 |
| *Escherichia coli* HVH 189 (4-3220125) | *Escherichia coli* NCCP 15653 |
| *Escherichia coli* HVH 19 (4-7154984) | *Escherichia coli* NCCP 15655 |
| *Escherichia coli* HVH 190 (4-3255514) | *Escherichia coli* NCCP 15656 |
| *Escherichia coli* HVH 191 (3-9341900) | *Escherichia coli* NCCP15647 |
| *Escherichia coli* HVH 192 (4-3054470) | *Escherichia coli* NCCP15648 |
| *Escherichia coli* HVH 193 (4-3331423) | *Escherichia coli* NCCP15657 |
| *Escherichia coli* HVH 194 (4-2356805) | *Escherichia coli* NCCP15658 |
| *Escherichia coli* HVH 195 (3-7155360) | *Escherichia coli* NCTC 86 |
| *Escherichia coli* HVH 196 (4-4530470) | *Escherichia coli* NDM1Dok01 |
| *Escherichia coli* HVH 197 (4-4466217) | *Escherichia coli* NE037 |
| *Escherichia coli* HVH 198 (4-3206106) | *Escherichia coli* NE098 |
| *Escherichia coli* MA6 | *Escherichia coli* NE1487 |
| *Escherichia coli* MC19 | *Escherichia coli* Nissle 1917 |
| *Escherichia coli* MC21 | *Escherichia coli* NT:H19 |
| *Escherichia coli* MC23 | *Escherichia coli* NT:H40 |
| *Escherichia coli* MC6002 | *Escherichia coli* NU14 |
| *Escherichia coli* MC6003 | *Escherichia coli* O08 |
| *Escherichia coli* MG1657 | *Escherichia coli* O10 |
| *Escherichia coli* MGR194 | *Escherichia coli* O10 str. Bi8337-41 |
| *Escherichia coli* MP020940.1 | *Escherichia coli* O101:H33 |
| *Escherichia coli* MP020980.1 | *Escherichia coli* O103 |
| *Escherichia coli* MP020980.2 | *Escherichia coli* O103 str. RM10042 |
| *Escherichia coli* MP021017.1 | *Escherichia coli* O103 str. RM8385 |
| *Escherichia coli* MP021017.10 | *Escherichia coli* O103:H2 |
| *Escherichia coli* MP021017.11 | *Escherichia coli* E22 |
| *Escherichia coli* MP021017.12 | *Escherichia coli* O103:H2 str. 12009 |
| *Escherichia coli* MP021017.2 | *Escherichia coli* O103:H2 str. CVM9450 |
| *Escherichia coli* MP021017.3 | *Escherichia coli* O103:H25 |
| *Escherichia coli* MP021017.4 | *Escherichia coli* O103:H25 str. 6582 |
| *Escherichia coli* MP021017.5 | *Escherichia coli* O103:H25 str. CVM9340 |

TABLE 1-continued

*Escherichia coli* MP021017.6
*Escherichia coli* MP021017.9
*Escherichia coli* MP021552.11
*Escherichia coli* O104:H12
*Escherichia coli* O104:H21
*Escherichia coli* O104:H21 str. CFSAN002236
*Escherichia coli* O104:H21 str. CFSAN002237
*Escherichia coli* O104:H4
*Escherichia coli* O104:H4 str. 01-09591
*Escherichia coli* O104:H4 str. 04-8351
*Escherichia coli* O104:H4 str. 09-7901
*Escherichia coli* O104:H4 str. 11-02030
*Escherichia coli* O104:H4 str. 11-02033-1
*Escherichia coli* O104:H4 str. 11-02092
*Escherichia coli* O104:H4 str. 11-02093
*Escherichia coli* O104:H4 str. 11-02281
*Escherichia coli* O104:H4 str. 11-02318
*Escherichia coli* O104:H4 str. 11-02913
*Escherichia coli* O104:H4 str. 11-03439
*Escherichia coli* O104:H4 str. 11-03943
*Escherichia coli* O104:H4 str. 11-04080
*Escherichia coli* O104:H4 str. 11-3677
*Escherichia coli* O104:H4 str. 11-3798
*Escherichia coli* O104:H4 str. 11-4404
*Escherichia coli* O104:H4 str. 11-4522
*Escherichia coli* O104:H4 str. 11-4623
*Escherichia coli* O104:H4 str. 11-4632 C1
*Escherichia coli* O104:H4 str. 11-4632 C2
*Escherichia coli* O104:H4 str. 11-4632 C3
*Escherichia coli* O104:H4 str. 11-4632 C4
*Escherichia coli* O104:H4 str. 11-4632 C5
*Escherichia coli* O104:H4 str. 2009EL-2050
*Escherichia coli* O104:H4 str. 2009EL-2071
*Escherichia coli* O104:H4 str. 2011C-3493
*Escherichia coli* O104:H4 str. C227-11
*Escherichia coli* O104:H4 str. C236-11
*Escherichia coli* O104:H4 str. C237-11
*Escherichia coli* O104:H4 str. E101/11
*Escherichia coli* O104:H4 str. E103/11
*Escherichia coli* O104:H4 str. E107/11
*Escherichia coli* O104:H4 str. E112/10
*Escherichia coli* O104:H4 str. E83/11
*Escherichia coli* O104:H4 str. E84/11
*Escherichia coli* O104:H4 str. E90/11
*Escherichia coli* O104:H4 str. E92/11
*Escherichia coli* O104:H4 str. E94/11
*Escherichia coli* O104:H4 str. Ec11-4984
*Escherichia coli* O104:H4 str. Ec11-4986
*Escherichia coli* O104:H4 str. Ec11-4987
*Escherichia coli* O104:H4 str. Ec11-4988
*Escherichia coli* O104:H4 str. Ec11-5536
*Escherichia coli* O104:H4 str. Ec11-5537
*Escherichia coli* O104:H4 str. Ec11-5538
*Escherichia coli* O104:H4 str. Ec11-5603
*Escherichia coli* O104:H4 str. Ec11-5604
*Escherichia coli* O104:H4 str. Ec11-6006
*Escherichia coli* O104:H4 str. Ec11-9450
*Escherichia coli* O104:H4 str. Ec11-9941
*Escherichia coli* O104:H4 str. Ec11-9990
*Escherichia coli* O104:H4 str. Ec12-0465
*Escherichia coli* O104:H4 str. Ec12-0466
*Escherichia coli* O104:H4 str. GOS1
*Escherichia coli* O104:H4 str. GOS2
*Escherichia coli* O104:H4 str. H112180280
*Escherichia coli* O104:H4 str. H112180282
*Escherichia coli* O104:H4 str. H112180283
*Escherichia coli* O104:H4 str. H112180540
*Escherichia coli* O104:H4 str. H112180541
*Escherichia coli* O104:H4 str. LB226692
*Escherichia coli* O104:H4 str. ON2010
*Escherichia coli* O104:H4 str. ON2011
*Escherichia coli* O104:H4 str. TY-2482
*Escherichia coli* O108:H25
*Escherichia coli* O145:H28 str. RM13516
*Escherichia coli* O145:NM
*Escherichia coli* O145:NM str. 2012C-4474
*Escherichia coli* O145:NM str. 2012C-4477
*Escherichia coli* O145:NM str. 2012C-4478
*Escherichia coli* O145:NM str. 2012C-4479
*Escherichia coli* O145:NM str. 2012C-4480

*Escherichia coli* O103:H25 str. NIPH-11060424
*Escherichia coli* O103:HNM
*Escherichia coli* O103:K+
*Escherichia coli* O109:H9
*Escherichia coli* O10:K5(L):H4
*Escherichia coli* O10:K5(L):H4 str. ATCC 23506
*Escherichia coli* O11
*Escherichia coli* O11 str. Bi632-42
*Escherichia coli* O111
*Escherichia coli* O111 str. RM9322
*Escherichia coli* O111:B4
*Escherichia coli* O111:H−
*Escherichia coli* O111:H− str. 11128
*Escherichia coli* O111:H11
*Escherichia coli* O111:H11 str. CFSAN001630
*Escherichia coli* O111:H11 str. CVM9455
*Escherichia coli* O111:H11 str. CVM9534
*Escherichia coli* O111:H11 str. CVM9545
*Escherichia coli* O111:H11 str. CVM9553
*Escherichia coli* O111:H19
*Escherichia coli* O111:H2
*Escherichia coli* O111:H21
*Escherichia coli* O111:H21 str. 226
*Escherichia coli* O111:H8
*Escherichia coli* O111:H8 str. 1074
*Escherichia coli* O111:H8 str. 9662
*Escherichia coli* O111:H8 str. CFSAN001632
*Escherichia coli* O111:H8 str. CVM9570
*Escherichia coli* O111:H8 str. CVM9574
*Escherichia coli* O111:H8 str. CVM9602
*Escherichia coli* O111:H8 str. CVM9634
*Escherichia coli* O111:NM
*Escherichia coli* O113
*Escherichia coli* O113:H19
*Escherichia coli* O113:H21
*Escherichia coli* O113:H21 str. CL-3
*Escherichia coli* O115:H−
*Escherichia coli* O115:HMN
*Escherichia coli* O115:K+
*Escherichia coli* O117:K1:H7
*Escherichia coli* O119:H6
*Escherichia coli* O119:UT
*Escherichia coli* O120:HNM
*Escherichia coli* O121
*Escherichia coli* O121 str. RM8352
*Escherichia coli* O121:H19
*Escherichia coli* O121:H19 str. 9918
*Escherichia coli* O121:H19 str. MT#2
*Escherichia coli* O121:H46
*Escherichia coli* O124:H−
*Escherichia coli* O124:H40
*Escherichia coli* O126:H27
*Escherichia coli* O127:B8
*Escherichia coli* O127:H21
*Escherichia coli* O127:H27
*Escherichia coli* O127:H27 str. C43/90
*Escherichia coli* O127:H6
*Escherichia coli* O127:H6 str. E2348/69
*Escherichia coli* O127a:H6
*Escherichia coli* O128:H2
*Escherichia coli* O131:H25
*Escherichia coli* O136:H−
*Escherichia coli* O138:NM
*Escherichia coli* O13:H11
*Escherichia coli* O142:H6
*Escherichia coli* O145
*Escherichia coli* O145 str. RM9872
*Escherichia coli* O145:H−
*Escherichia coli* O145:H28
*Escherichia coli* O145:H28 str. 4865/96
*Escherichia coli* O145:H28 str. RM12581
*Escherichia coli* O145:H28 str. RM12761
*Escherichia coli* O145:H28 str. RM13514
*Escherichia coli* O157:H7 str. Sakai
*Escherichia coli* O157:H7 str. SS17
*Escherichia coli* O157:H7 str. SS52
*Escherichia coli* O157:H7 str. TW14359
*Escherichia coli* O157:H7 str. TW14588
*Escherichia coli* O157:H7 str. ZAP430
*Escherichia coli* O157:H9

TABLE 1-continued

| | |
|---|---|
| *Escherichia coli* O145:NM str. 8235 | *Escherichia coli* O157:HNM |
| *Escherichia coli* O149:H10 | *Escherichia coli* O157:NM |
| *Escherichia coli* O153:H21 | *Escherichia coli* O15:H34 |
| *Escherichia coli* O153:H7 | *Escherichia coli* O15:NM |
| *Escherichia coli* O154:H9 | *Escherichia coli* O16 |
| *Escherichia coli* O157 | *Escherichia coli* O16 str. F11119-41 |
| *Escherichia coli* 3.4880 | *Escherichia coli* O169:H− |
| *Escherichia coli* 7.1982 | *Escherichia coli* O17 |
| *Escherichia coli* 95.0083 | *Escherichia coli* O17 str. K12a |
| *Escherichia coli* ATCC 700728 | *Escherichia coli* O174:H21 |
| *Escherichia coli* O157 str. NCCP15738 | *Escherichia coli* O177:H11 |
| *Escherichia coli* O157 str. NCCP15739 | *Escherichia coli* O18 |
| *Escherichia coli* PA11 | *Escherichia coli* O18 str. F10018-41 |
| *Escherichia coli* PA13 | *Escherichia coli* O180:H− |
| *Escherichia coli* PA19 | *Escherichia coli* O19 |
| *Escherichia coli* PA35 | *Escherichia coli* O19 str. F8188-41 |
| *Escherichia coli* O157:12 | *Escherichia coli* O20 |
| *Escherichia coli* O157:H− | *Escherichia coli* O20 str. P7a |
| *Escherichia coli* O157:H− str. 493-89 | *Escherichia coli* O23 |
| *Escherichia coli* O157:H− str. H 2687 | *Escherichia coli* O23 str. P7a |
| *Escherichia coli* O157:H12 | *Escherichia coli* O25 |
| *Escherichia coli* O157:H16 | *Escherichia coli* O25 str. E39a |
| *Escherichia coli* O157:H37 | *Escherichia coli* O25b:H4 |
| *Escherichia coli* O157:H39 | *Escherichia coli* O25b:H4-ST131 str. EC958 |
| *Escherichia coli* O157:H43 | *Escherichia coli* O25b:ST131 |
| *Escherichia coli* O157:H43 str. T22 | *Escherichia coli* O26 |
| *Escherichia coli* O157:H45 | *Escherichia coli* O26 str. RM10386 |
| *Escherichia coli* O157:H7 | *Escherichia coli* O26 str. RM8426 |
| *Escherichia coli* O157:H7 str. 1044 | *Escherichia coli* O26:H− |
| *Escherichia coli* O157:H7 str. 1125 | *Escherichia coli* O26:H11 |
| *Escherichia coli* O157:H7 str. 121 | *Escherichia coli* O26:H11 str. 10140 |
| *Escherichia coli* O157:H7 str. 262 | *Escherichia coli* O26:H11 str. 11368 |
| *Escherichia coli* O157:H7 str. 611 | *Escherichia coli* O26:H11 str. 6629 |
| *Escherichia coli* O157:H7 str. EC10 | *Escherichia coli* O26:H11 str. CFSAN001629 |
| *Escherichia coli* O157:H7 str. EC1212 | *Escherichia coli* O26:H11 str. CVM10021 |
| *Escherichia coli* O157:H7 str. EC4009 | *Escherichia coli* O26:H11 str. CVM10026 |
| *Escherichia coli* O157:H7 str. EC4024 | *Escherichia coli* O26:H11 str. CVM10030 |
| *Escherichia coli* O157:H7 str. EC4042 | *Escherichia coli* O26:H11 str. CVM10224 |
| *Escherichia coli* O157:H7 str. EC4045 | *Escherichia coli* O26:H11 str. CVM9942 |
| *Escherichia coli* O157:H7 str. EC4076 | *Escherichia coli* O26:H11 str. CVM9952 |
| *Escherichia coli* O157:H7 str. EC4084 | *Escherichia coli* O26:H11:K60 |
| *Escherichia coli* O157:H7 str. EC4113 | *Escherichia coli* O26:NM |
| *Escherichia coli* O157:H7 str. EC4115 | *Escherichia coli* O27 |
| *Escherichia coli* O157:H7 str. EC4127 | *Escherichia coli* O27 str. E47a |
| *Escherichia coli* O157:H7 str. EC4191 | *Escherichia coli* O28ac:H− |
| *Escherichia coli* O157:H7 str. EC4192 | *Escherichia coli* O29 |
| *Escherichia coli* O157:H7 str. EC4196 | *Escherichia coli* O29 str. Su4338-41 |
| *Escherichia coli* O157:H7 str. EC4205 | *Escherichia coli* O30 |
| *Escherichia coli* O157:H7 str. EC4206 | *Escherichia coli* O30 str. P2a |
| *Escherichia coli* O157:H7 str. EC4401 | *Escherichia coli* O32:H37 |
| *Escherichia coli* O157:H7 str. EC4486 | *Escherichia coli* O32:H37 str. P4 |
| *Escherichia coli* O157:H7 str. EC4501 | *Escherichia coli* O33 |
| *Escherichia coli* O157:H7 str. EC508 | *Escherichia coli* O33 str. E40 |
| *Escherichia coli* O157:H7 str. EC536 | *Escherichia coli* O34 |
| *Escherichia coli* O157:H7 str. EC869 | *Escherichia coli* O34 str. H304 |
| *Escherichia coli* O157:H7 str. EDL933 | *Escherichia coli* O41:H− |
| *Escherichia coli* O157:H7 str. F8092B | *Escherichia coli* O42:H37 |
| *Escherichia coli* O157:H7 str. FRIK2000 | *Escherichia coli* O44:H18 |
| *Escherichia coli* O157:H7 str. FRIK966 | *Escherichia coli* 042 |
| *Escherichia coli* O157:H7 str. G5101 | *Escherichia coli* O45:H2 |
| *Escherichia coli* O157:H7 str. GZ-021210/cattle | *Escherichia coli* O45:H2 str. 03-EN-705 |
| *Escherichia coli* O157:H7 str. H093800014 | *Escherichia coli* O45:NM |
| *Escherichia coli* O157:H7 str. LSU-61 | *Escherichia coli* O45:NM str. G4 |
| *Escherichia coli* O5 | *Escherichia coli* P0298942.7 |
| *Escherichia coli* O5 str. U1-41 | *Escherichia coli* P0298942.8 |
| *Escherichia coli* O5:K4(L):H4 str. ATCC 23502 | *Escherichia coli* P0298942.9 |
| *Escherichia coli* O51:H− | *Escherichia coli* P0299438.10 |
| *Escherichia coli* O55:H2 | *Escherichia coli* P0299438.11 |
| *Escherichia coli* O55:H51 | *Escherichia coli* P0299438.2 |
| *Escherichia coli* O55:H6 | *Escherichia coli* P0299438.3 |
| *Escherichia coli* O55:H7 | *Escherichia coli* P0299438.4 |
| *Escherichia coli* O55:H7 str. 3256-97 | *Escherichia coli* P0299438.5 |
| *Escherichia coli* O55:H7 str. CB9615 | *Escherichia coli* P0299438.6 |
| *Escherichia coli* O55:H7 str. RM12579 | *Escherichia coli* P0299438.7 |
| *Escherichia coli* O55:H7 str. USDA 5905 | *Escherichia coli* P0299438.8 |
| *Escherichia coli* O5:H− | *Escherichia coli* P0299438.9 |
| *Escherichia coli* O6 | *Escherichia coli* P0299483.1 |
| *Escherichia coli* O6 str. Bi7458-41 | *Escherichia coli* P0299483.2 |
| *Escherichia coli* O63:H6 | *Escherichia coli* P0299483.3 |
| *Escherichia coli* O63:HNM | *Escherichia coli* P02997067.6 |

TABLE 1-continued

| | |
|---|---|
| *Escherichia coli* O6:HNM | *Escherichia coli* P0299917.1 |
| *Escherichia coli* O70:NM | *Escherichia coli* P0299917.10 |
| *Escherichia coli* O75:H2 | *Escherichia coli* P0299917.2 |
| *Escherichia coli* O78:H9 | *Escherichia coli* P0299917.3 |
| *Escherichia coli* IMT2125 | *Escherichia coli* P0299917.4 |
| *Escherichia coli* O7:K1 | *Escherichia coli* P0299917.5 |
| *Escherichia coli* O7:K1 str. CE10 | *Escherichia coli* P0299917.6 |
| *Escherichia coli* O8 | *Escherichia coli* P0299917.7 |
| *Escherichia coli* O8 str. G3404-41 | *Escherichia coli* P0299917.8 |
| *Escherichia coli* O83:H1 | *Escherichia coli* P0299917.9 |
| *Escherichia coli* O83:H1 str. NRG 857C | *Escherichia coli* P0301867.1 |
| *Escherichia coli* O84:H- | *Escherichia coli* P0301867.11 |
| *Escherichia coli* O86a:H34 | *Escherichia coli* P0301867.13 |
| *Escherichia coli* O86a:H40 | *Escherichia coli* P0301867.2 |
| *Escherichia coli* O9 | *Escherichia coli* P0301867.3 |
| *Escherichia coli* O9 str. Bi316-42 | *Escherichia coli* P0301867.4 |
| *Escherichia coli* O90:H8 | *Escherichia coli* P0301867.5 |
| *Escherichia coli* O91 | *Escherichia coli* P0301867.7 |
| *Escherichia coli* O91 str. RM7190 | *Escherichia coli* P0301867.8 |
| *Escherichia coli* O91:H21 | *Escherichia coli* P0301904.3 |
| *Escherichia coli* O91:H21 str. B2F1 | *Escherichia coli* P0302293.10 |
| *Escherichia coli* O9:H51 | *Escherichia coli* P0302293.2 |
| *Escherichia coli* OK1114 | *Escherichia coli* P0302293.3 |
| *Escherichia coli* OK1180 | *Escherichia coli* P0302293.4 |
| *Escherichia coli* OK1357 | *Escherichia coli* P0302293.6 |
| *Escherichia coli* ONT:H- | *Escherichia coli* P0302293.7 |
| *Escherichia coli* ONT:H10 | *Escherichia coli* P0302293.8 |
| *Escherichia coli* ONT:H25 | *Escherichia coli* P0302293.9 |
| *Escherichia coli* ONT:H33 | *Escherichia coli* P0302308.1 |
| *Escherichia coli* ONT:H33 str. C48/93 | *Escherichia coli* P0302308.10 |
| *Escherichia coli* OP50 | *Escherichia coli* P0302308.11 |
| *Escherichia coli* Orough:H12 | *Escherichia coli* P0302308.12 |
| *Escherichia coli* Orough:H19 | *Escherichia coli* P0302308.13 |
| *Escherichia coli* Orough:H34 | *Escherichia coli* P0302308.14 |
| *Escherichia coli* Orough:H37 | *Escherichia coli* P0302308.2 |
| *Escherichia coli* Orough:H9 | *Escherichia coli* P0302308.3 |
| *Escherichia coli* OUT:H12 | *Escherichia coli* P0302308.4 |
| *Escherichia coli* OUT:H18 | *Escherichia coli* P0302308.5 |
| *Escherichia coli* OUT:H45 | *Escherichia coli* P0304777.1 |
| *Escherichia coli* OUT:H6 | *Escherichia coli* P0304777.10 |
| *Escherichia coli* OUT:H7 | *Escherichia coli* P0304777.11 |
| *Escherichia coli* OUT:HNM | *Escherichia coli* P0304777.12 |
| *Escherichia coli* OUT:NM | *Escherichia coli* P0304777.13 |
| *Escherichia coli* P0298942.1 | *Escherichia coli* P0304777.14 |
| *Escherichia coli* P0298942.10 | *Escherichia coli* P0304777.15 |
| *Escherichia coli* P0298942.11 | *Escherichia coli* P0304777.2 |
| *Escherichia coli* P0298942.12 | *Escherichia coli* P0304777.3 |
| *Escherichia coli* P0298942.14 | *Escherichia coli* P0304777.4 |
| *Escherichia coli* P0298942.15 | *Escherichia coli* P0304777.5 |
| *Escherichia coli* P0298942.2 | *Escherichia coli* P0304777.7 |
| *Escherichia coli* P0298942.3 | *Escherichia coli* P0304777.8 |
| *Escherichia coli* P0298942.4 | *Escherichia coli* P0304777.9 |
| *Escherichia coli* P0298942.6 | *Escherichia coli* P0304799.3 |
| *Escherichia coli* P0304816.1 | *Escherichia coli* PA49 |
| *Escherichia coli* P0304816.10 | *Escherichia coli* PA6 |
| *Escherichia coli* P0304816.11 | *Escherichia coli* PA7 |
| *Escherichia coli* P0304816.12 | *Escherichia coli* PA8 |
| *Escherichia coli* P0304816.13 | *Escherichia coli* PA9 |
| *Escherichia coli* P0304816.14 | *Escherichia coli* PB10 |
| *Escherichia coli* P0304816.15 | *Escherichia coli* PBA1 |
| *Escherichia coli* P0304816.2 | *Escherichia coli* PBA5 |
| *Escherichia coli* P0304816.3 | *Escherichia coli* PBA9 |
| *Escherichia coli* P0304816.4 | *Escherichia coli* PBB13 |
| *Escherichia coli* P0304816.5 | *Escherichia coli* PBB4 |
| *Escherichia coli* P0304816.6 | *Escherichia coli* PBB5 |
| *Escherichia coli* P0304816.7 | *Escherichia coli* PBB6 |
| *Escherichia coli* P0304816.8 | *Escherichia coli* PBC20 |
| *Escherichia coli* P0304816.9 | *Escherichia coli* PBC22 |
| *Escherichia coli* P0305260.1 | *Escherichia coli* PBC3 |
| *Escherichia coli* P0305260.10 | *Escherichia coli* PBC6 |
| *Escherichia coli* P0305260.11 | *Escherichia coli* PBC7 |
| *Escherichia coli* P0305260.12 | *Escherichia coli* PBD1 |
| *Escherichia coli* P0305260.13 | *Escherichia coli* PBD11 |
| *Escherichia coli* P0305260.15 | *Escherichia coli* PBD16 |
| *Escherichia coli* P0305260.2 | *Escherichia coli* PBD19 |
| *Escherichia coli* P0305260.3 | *Escherichia coli* PBD2 |
| *Escherichia coli* P0305260.4 | *Escherichia coli* PBD20 |
| *Escherichia coli* P0305260.5 | *Escherichia coli* PBD21 |
| *Escherichia coli* P0305260.6 | *Escherichia coli* PBD22 |
| *Escherichia coli* P0305260.7 | *Escherichia coli* PBD24 |

TABLE 1-continued

| | |
|---|---|
| *Escherichia coli* P0305260.8 | *Escherichia coli* PBD3 |
| *Escherichia coli* P0305260.9 | *Escherichia coli* PBD7 |
| *Escherichia coli* p0305293.1 | *Escherichia coli* PCN009 |
| *Escherichia coli* p0305293.10 | *Escherichia coli* PCN033 |
| *Escherichia coli* p0305293.11 | *Escherichia coli* PCN042 |
| *Escherichia coli* p0305293.12 | *Escherichia coli* PCN079 |
| *Escherichia coli* p0305293.13 | *Escherichia coli* PCN097 |
| *Escherichia coli* p0305293.14 | *Escherichia coli* PMV-1 |
| *Escherichia coli* p0305293.15 | *Escherichia coli* PS |
| *Escherichia coli* p0305293.2 | *Escherichia coli* PUTI459 |
| *Escherichia coli* p0305293.3 | *Escherichia coli* R424 |
| *Escherichia coli* p0305293.4 | *Escherichia coli* R527 |
| *Escherichia coli* p0305293.5 | *Escherichia coli* R529 |
| *Escherichia coli* p0305293.6 | *Escherichia coli* RDEC-1 (10f) |
| *Escherichia coli* p0305293.7 | *Escherichia coli* REL606 |
| *Escherichia coli* p0305293.8 | *Escherichia coli* RN587/1 |
| *Escherichia coli* p0305293.9 | *Escherichia coli* RS218 |
| *Escherichia coli* P12b | *Escherichia coli* S17 |
| *Escherichia coli* P4-96 | *Escherichia coli* S88 |
| *Escherichia coli* P4-NR | *Escherichia coli* SCD1 |
| *Escherichia coli* PA10 | *Escherichia coli* SCD2 |
| *Escherichia coli* PA14 | *Escherichia coli* SCI-07 |
| *Escherichia coli* PA15 | *Escherichia coli* SE11 |
| *Escherichia coli* PA2 | *Escherichia coli* SE15 |
| *Escherichia coli* PA22 | *Escherichia coli* SEPT362 |
| *Escherichia coli* PA23 | *Escherichia coli* SEQ895 |
| *Escherichia coli* PA24 | *Escherichia coli* SMS-3-5 |
| *Escherichia coli* PA25 | *Escherichia coli* STEC_7v |
| *Escherichia coli* PA28 | *Escherichia coli* STEC_94C |
| *Escherichia coli* PA3 | *Escherichia coli* STEC_B2F1 |
| *Escherichia coli* PA31 | *Escherichia coli* STEC_C165-02 |
| *Escherichia coli* PA32 | *Escherichia coli* STEC_DG131-3 |
| *Escherichia coli* PA33 | *Escherichia coli* STEC_EH250 |
| *Escherichia coli* PA34 | *Escherichia coli* STEC_H.I.8 |
| *Escherichia coli* PA38 | *Escherichia coli* STEC_MHI813 |
| *Escherichia coli* PA39 | *Escherichia coli* STEC_O31 |
| *Escherichia coli* PA4 | *Escherichia coli* STEC_S1191 |
| *Escherichia coli* PA40 | *Escherichia coli* STHG79 |
| *Escherichia coli* PA41 | *Escherichia coli* str. 'clone D i14' |
| *Escherichia coli* PA42 | *Escherichia coli* str. 'clone D i2' |
| *Escherichia coli* PA45 | *Escherichia coli* str. Deng |
| *Escherichia coli* PA47 | *Escherichia coli* SWW33 |
| *Escherichia coli* PA48 | *Escherichia coli* T1282_01 |
| *Escherichia coli* T1840_97 | *Escherichia coli* TW10491 |
| *Escherichia coli* T234_00 | *Escherichia coli* TW10503 |
| *Escherichia coli* T408 | *Escherichia coli* TW10509 |
| *Escherichia coli* T426 | *Escherichia coli* TW10512 |
| *Escherichia coli* T924_01 | *Escherichia coli* TW10518 |
| *Escherichia coli* TA004 | *Escherichia coli* TW10519 |
| *Escherichia coli* TA007 | *Escherichia coli* TW10523 |
| *Escherichia coli* TA008 | *Escherichia coli* TW10526 |
| *Escherichia coli* TA014 | *Escherichia coli* TW10530 |
| *Escherichia coli* TA024 | *Escherichia coli* TW10537 |
| *Escherichia coli* TA054 | *Escherichia coli* TW10545 |
| *Escherichia coli* TA103 | *Escherichia coli* TW10547 |
| *Escherichia coli* TA124 | *Escherichia coli* TW10564 |
| *Escherichia coli* TA141 | *Escherichia coli* TW10568 |
| *Escherichia coli* TA143 | *Escherichia coli* TW10595 |
| *Escherichia coli* TA144 | *Escherichia coli* TW10598 |
| *Escherichia coli* TA155 | *Escherichia coli* TW10619 |
| *Escherichia coli* TA206 | *Escherichia coli* TW10664 |
| *Escherichia coli* TA249 | *Escherichia coli* TW10722 |
| *Escherichia coli* TA255 | *Escherichia coli* TW10738 |
| *Escherichia coli* TA271 | *Escherichia coli* TW10742 |
| *Escherichia coli* TA280 | *Escherichia coli* TW10747 |
| *Escherichia coli* TA435 | *Escherichia coli* TW10785 |
| *Escherichia coli* TA445 | *Escherichia coli* TW10818 |
| *Escherichia coli* TA447 | *Escherichia coli* TW10828 |
| *Escherichia coli* TA464 | *Escherichia coli* TW10880 |
| *Escherichia coli* ThroopD | *Escherichia coli* TW10894 |
| *Escherichia coli* TOP2386 | *Escherichia coli* TW10899 |
| *Escherichia coli* TOP2396-1 | *Escherichia coli* TW11039 |
| *Escherichia coli* TOP2396-2 | *Escherichia coli* TW11606 |
| *Escherichia coli* TOP2396-3 | *Escherichia coli* TW11638 |
| *Escherichia coli* TOP2515 | *Escherichia coli* TW11651 |
| *Escherichia coli* TOP2522-1 | *Escherichia coli* TW11666 |
| *Escherichia coli* TOP2522-3 | *Escherichia coli* TW11681 |
| *Escherichia coli* TOP2652 | *Escherichia coli* TW11685 |
| *Escherichia coli* TOP2662-1 | *Escherichia coli* TW11690 |
| *Escherichia coli* TOP2662-2 | *Escherichia coli* KTE230 |

TABLE 1-continued

| | |
|---|---|
| *Escherichia coli* TOP2662-3 | *Escherichia coli* KTE231 |
| *Escherichia coli* TOP2662-4 | *Escherichia coli* KTE232 |
| *Escherichia coli* TOP291 | *Escherichia coli* KTE233 |
| *Escherichia coli* TOP293-1 | *Escherichia coli* KTE234 |
| *Escherichia coli* TOP293-2 | *Escherichia coli* KTE235 |
| *Escherichia coli* TOP293-3 | *Escherichia coli* KTE236 |
| *Escherichia coli* TOP293-4 | *Escherichia coli* KTE237 |
| *Escherichia coli* TOP379 | *Escherichia coli* KTE24 |
| *Escherichia coli* TOP382-1 | *Escherichia coli* KTE240 |
| *Escherichia coli* TOP382-2 | *Escherichia coli* KTE25 |
| *Escherichia coli* TOP382-3 | *Escherichia coli* KTE26 |
| *Escherichia coli* TOP498 | *Escherichia coli* KTE27 |
| *Escherichia coli* TOP550-1 | *Escherichia coli* KTE28 |
| *Escherichia coli* TOP550-2 | *Escherichia coli* KTE29 |
| *Escherichia coli* TOP550-3 | *Escherichia coli* KTE3 |
| *Escherichia coli* TOP550-4 | *Escherichia coli* KTE31 |
| *Escherichia coli* TT12B | *Escherichia coli* KTE33 |
| *Escherichia coli* TW00353 | *Escherichia coli* KTE34 |
| *Escherichia coli* TW06591 | *Escherichia coli* KTE35 |
| *Escherichia coli* TW07509 | *Escherichia coli* KTE36 |
| *Escherichia coli* TW07793 | *Escherichia coli* KTE37 |
| *Escherichia coli* TW07945 | *Escherichia coli* KTE38 |
| *Escherichia coli* TW09098 | *Escherichia coli* KTE39 |
| *Escherichia coli* TW09109 | *Escherichia coli* KTE4 |
| *Escherichia coli* TW09195 | *Escherichia coli* KTE40 |
| *Escherichia coli* TW10119 | *Escherichia coli* KTE41 |
| *Escherichia coli* TW10245 | *Escherichia coli* KTE42 |
| *Escherichia coli* TW10246 | *Escherichia coli* KTE43 |
| *Escherichia coli* TW10470 | *Escherichia coli* KTE44 |
| *Escherichia coli* TW10481 | *Escherichia coli* KTE45 |
| *Escherichia coli* TW10483 | *Escherichia coli* KTE46 |
| *Escherichia coli* TW10484 | *Escherichia coli* KTE47 |
| *Escherichia coli* TW10485 | *Escherichia coli* KTE48 |
| *Escherichia coli* HS | *Escherichia coli* LT-62 |
| *Escherichia coli* HT115 | *Escherichia coli* LT-68 |
| *Escherichia coli* HUSEC2001 | *Escherichia coli* LY180 |
| *Escherichia coli* HUSEC2011 | *Escherichia coli* M056 |
| *Escherichia coli* KTE52 | *Escherichia coli* M1 |
| *Escherichia coli* KTE53 | *Escherichia coli* M10 |
| *Escherichia coli* KTE54 | *Escherichia coli* M11 |
| *Escherichia coli* KTE55 | *Escherichia coli* M114 |
| *Escherichia coli* KTE56 | *Escherichia coli* M12 |
| *Escherichia coli* KTE57 | *Escherichia coli* M13 |
| *Escherichia coli* KTE58 | *Escherichia coli* M14 |
| *Escherichia coli* KTE59 | *Escherichia coli* M15 |
| *Escherichia coli* KTE6 | *Escherichia coli* M16 |
| *Escherichia coli* KTE60 | *Escherichia coli* M17 |
| *Escherichia coli* KTE61 | *Escherichia coli* M18 |
| *Escherichia coli* KTE62 | *Escherichia coli* M19 |
| *Escherichia coli* KTE63 | *Escherichia coli* M2 |
| *Escherichia coli* KTE64 | *Escherichia coli* M20 |
| *Escherichia coli* KTE65 | *Escherichia coli* M21 |
| *Escherichia coli* KTE66 | *Escherichia coli* M22 |
| *Escherichia coli* KTE67 | *Escherichia coli* M23 |
| *Escherichia coli* KTE68 | *Escherichia coli* M3 |
| *Escherichia coli* KTE69 | *Escherichia coli* M4 |
| *Escherichia coli* KTE7 | *Escherichia coli* M5 |
| *Escherichia coli* KTE70 | *Escherichia coli* M6 |
| *Escherichia coli* KTE71 | *Escherichia coli* M605 |
| *Escherichia coli* KTE72 | *Escherichia coli* M646 |
| *Escherichia coli* KTE73 | *Escherichia coli* M7 |
| *Escherichia coli* KTE74 | *Escherichia coli* M718 |
| *Escherichia coli* KTE75 | *Escherichia coli* M8 |
| *Escherichia coli* KTE76 | *Escherichia coli* M863 |
| *Escherichia coli* KTE77 | *Escherichia coli* M9 |
| *Escherichia coli* KTE78 | *Escherichia coli* M919 |
| *Escherichia coli* KTE79 | *Escherichia coli* UMEA 3687-1 |
| *Escherichia coli* KTE8 | *Escherichia coli* UMEA 3693-1 |
| *Escherichia coli* KTE80 | *Escherichia coli* UMEA 3694-1 |
| *Escherichia coli* KTE81 | *Escherichia coli* UMEA 3702-1 |
| *Escherichia coli* KTE82 | *Escherichia coli* UMEA 3703-1 |
| *Escherichia coli* KTE83 | *Escherichia coli* UMEA 3705-1 |
| *Escherichia coli* KTE84 | *Escherichia coli* UMEA 3707-1 |
| *Escherichia coli* KTE85 | *Escherichia coli* UMEA 3718-1 |
| *Escherichia coli* KTE86 | *Escherichia coli* UMEA 3805-1 |
| *Escherichia coli* KTE87 | *Escherichia coli* UMEA 3821-1 |
| *Escherichia coli* KTE88 | *Escherichia coli* UMEA 3834-1 |
| *Escherichia coli* KTE89 | *Escherichia coli* UMEA 3889-1 |
| *Escherichia coli* KTE9 | *Escherichia coli* UMEA 3893-1 |
| *Escherichia coli* KTE90 | *Escherichia coli* UMEA 3899-1 |

TABLE 1-continued

| | |
|---|---|
| *Escherichia coli* KTE91 | *Escherichia coli* UMEA 3955-1 |
| *Escherichia coli* KTE93 | *Escherichia coli* UMEA 4075-1 |
| *Escherichia coli* KTE94 | *Escherichia coli* UMEA 4076-1 |
| *Escherichia coli* KTE95 | *Escherichia coli* UMEA 4207-1 |
| *Escherichia coli* KTE96 | *Escherichia coli* UMN026 |
| *Escherichia coli* KTE97 | *Escherichia coli* UMNF18 |
| *Escherichia coli* KTE98 | *Escherichia coli* UMNK88 |
| *Escherichia coli* KTE99 | *Escherichia coli* UTI89 |
| *Escherichia coli* LAU-EC1 | *Escherichia coli* VDP |
| *Escherichia coli* LAU-EC10 | *Escherichia coli* Vir68 |
| *Escherichia coli* LAU-EC2 | *Escherichia coli* VL2732 |
| *Escherichia coli* LAU-EC3 | *Escherichia coli* VL2874 |
| *Escherichia coli* LAU-EC4 | *Escherichia coli* VR50 |
| *Escherichia coli* LAU-EC5 | *Escherichia coli* W |
| *Escherichia coli* LAU-EC6 | *Escherichia coli* W113 |
| *Escherichia coli* LAU-EC7 | *Escherichia coli* W181 |
| *Escherichia coli* LAU-EC8 | *Escherichia coli* W202 |
| *Escherichia coli* LAU-EC9 | *Escherichia coli* W26 |
| *Escherichia coli* LCT-EC106 | *Escherichia coli* Wa1 |
| *Escherichia coli* LCT-EC52 | *Escherichia coli* Wa2 |
| *Escherichia coli* LCT-EC59 | *Escherichia coli* WC1 |
| *Escherichia coli* LF82 | *Escherichia coli* WC2 |
| *Escherichia coli* LT-41 | *Escherichia coli* WV_060327 |
| *Escherichia coli* XH001 | *Escherichia coli* UMEA 3155-1 |
| *Escherichia coli* XH140A | *Escherichia coli* UMEA 3159-1 |
| *Escherichia coli* Xuzhou21 | *Escherichia coli* UMEA 3160-1 |
| *Escherichia coli* TW11694 | *Escherichia coli* UMEA 3161-1 |
| *Escherichia coli* TW11699 | *Escherichia coli* UMEA 3162-1 |
| *Escherichia coli* TW11704 | *Escherichia coli* UMEA 3163-1 |
| *Escherichia coli* TW11728 | *Escherichia coli* UMEA 3172-1 |
| *Escherichia coli* TW11737 | *Escherichia coli* UMEA 3173-1 |
| *Escherichia coli* TW11741 | *Escherichia coli* UMEA 3174-1 |
| *Escherichia coli* TW11756 | *Escherichia coli* UMEA 3175-1 |
| *Escherichia coli* TW11767 | *Escherichia coli* UMEA 3176-1 |
| *Escherichia coli* TW11786 | *Escherichia coli* UMEA 3178-1 |
| *Escherichia coli* TW11816 | *Escherichia coli* UMEA 3180-1 |
| *Escherichia coli* TW11833 | *Escherichia coli* UMEA 3185-1 |
| *Escherichia coli* TW11839 | *Escherichia coli* UMEA 3190-1 |
| *Escherichia coli* TW11890 | *Escherichia coli* UMEA 3193-1 |
| *Escherichia coli* TW11906 | *Escherichia coli* UMEA 3199-1 |
| *Escherichia coli* TW11917 | *Escherichia coli* UMEA 3200-1 |
| *Escherichia coli* TW11950 | *Escherichia coli* UMEA 3201-1 |
| *Escherichia coli* TW11951 | *Escherichia coli* UMEA 3203-1 |
| *Escherichia coli* TW11973 | *Escherichia coli* UMEA 3206-1 |
| *Escherichia coli* TW12001 | *Escherichia coli* UMEA 3208-1 |
| *Escherichia coli* TW12002 | *Escherichia coli* UMEA 3212-1 |
| *Escherichia coli* TW12009 | *Escherichia coli* UMEA 3215-1 |
| *Escherichia coli* TW12014 | *Escherichia coli* UMEA 3216-1 |
| *Escherichia coli* TW12019 | *Escherichia coli* UMEA 3217-1 |
| *Escherichia coli* TW12023 | *Escherichia coli* UMEA 3220-1 |
| *Escherichia coli* TW12033 | *Escherichia coli* UMEA 3221-1 |
| *Escherichia coli* TW12082 | *Escherichia coli* UMEA 3222-1 |
| *Escherichia coli* TW12086 | *Escherichia coli* UMEA 3230-1 |
| *Escherichia coli* TW12093 | *Escherichia coli* UMEA 3233-1 |
| *Escherichia coli* TW12101 | *Escherichia coli* UMEA 3240-1 |
| *Escherichia coli* TW14301 | *Escherichia coli* UMEA 3244-1 |
| *Escherichia coli* TW14313 | *Escherichia coli* UMEA 3252-1 |
| *Escherichia coli* TW14380 | *Escherichia coli* UMEA 3257-1 |
| *Escherichia coli* TW14390 | *Escherichia coli* UMEA 3264-1 |
| *Escherichia coli* TW14397 | *Escherichia coli* UMEA 3268-1 |
| *Escherichia coli* KTE49 | *Escherichia coli* UMEA 3271-1 |
| *Escherichia coli* KTE5 | *Escherichia coli* UMEA 3290-1 |
| *Escherichia coli* KTE50 | *Escherichia coli* UMEA 3292-1 |
| *Escherichia coli* KTE51 | *Escherichia coli* UMEA 3298-1 |
| *Escherichia coli* TW14711 | *Escherichia coli* UMEA 3304-1 |
| *Escherichia coli* TW15901 | *Escherichia coli* UMEA 3314-1 |
| *Escherichia coli* Tx1686 | *Escherichia coli* UMEA 3317-1 |
| *Escherichia coli* TX1999 | *Escherichia coli* UMEA 3318-1 |
| *Escherichia coli* Tx3800 | *Escherichia coli* UMEA 3323-1 |
| *Escherichia coli* UM146 | *Escherichia coli* UMEA 3329-1 |
| *Escherichia coli* UMEA 3014-1 | *Escherichia coli* UMEA 3336-1 |
| *Escherichia coli* UMEA 3022-1 | *Escherichia coli* UMEA 3337-1 |
| *Escherichia coli* UMEA 3033-1 | *Escherichia coli* UMEA 3341-1 |
| *Escherichia coli* UMEA 3041-1 | *Escherichia coli* UMEA 3342-1 |
| *Escherichia coli* UMEA 3052-1 | *Escherichia coli* UMEA 3355-1 |
| *Escherichia coli* UMEA 3053-1 | *Escherichia coli* UMEA 3391-1 |
| *Escherichia coli* UMEA 3065-1 | *Escherichia coli* UMEA 3426-1 |
| *Escherichia coli* UMEA 3087-1 | *Escherichia coli* UMEA 3489-1 |
| *Escherichia coli* UMEA 3088-1 | *Escherichia coli* UMEA 3490-1 |
| *Escherichia coli* UMEA 3097-1 | *Escherichia coli* UMEA 3585-1 |

TABLE 1-continued

| | |
|---|---|
| *Escherichia coli* UMEA 3108-1 | *Escherichia coli* UMEA 3592-1 |
| *Escherichia coli* UMEA 3113-1 | *Escherichia coli* UMEA 3609-1 |
| *Escherichia coli* UMEA 3117-1 | *Escherichia coli* UMEA 3617-1 |
| *Escherichia coli* UMEA 3121-1 | *Escherichia coli* UMEA 3632-1 |
| *Escherichia coli* UMEA 3122-1 | *Escherichia coli* UMEA 3652-1 |
| *Escherichia coli* UMEA 3124-1 | *Escherichia coli* UMEA 3656-1 |
| *Escherichia coli* UMEA 3139-1 | *Escherichia coli* UMEA 3662-1 |
| *Escherichia coli* UMEA 3140-1 | *Escherichia coli* UMEA 3671-1 |
| *Escherichia coli* UMEA 3144-1 | *Escherichia coli* UMEA 3682-1 |
| *Escherichia coli* UMEA 3148-1 | *Escherichia coli* TW14435 |
| *Escherichia coli* UMEA 3150-1 | *Escherichia coli* TW14406 |
| *Escherichia coli* UMEA 3151-1 | *Escherichia coli* TW14425 |
| *Escherichia coli* UMEA 3152-1 | *Escherichia coli* TW14427 |
| *Escherichia faecalis* | *Escherichia* sp. ASG34 |
| *Escherichia fergusonii* | *Escherichia* sp. B1147 |
| *Escherichia fergusonii* ATCC 35469 | *Escherichia* sp. B1225 |
| *Escherichia fergusonii* B253 | *Escherichia* sp. B4 |
| *Escherichia fergusonii* ECD227 | *Escherichia* sp. B49 |
| *Escherichia hermannii* | *Escherichia* sp. B646 |
| *Escherichia hermannii* NBRC 105704 | *Escherichia* sp. B685 |
| *Escherichia senegalensis* | *Escherichia* sp. B827 |
| *Escherichia vulneris* | *Escherichia* sp. BBDP20 |
| *Escherichia vulneris* NBRC 102420 | *Escherichia* sp. BBDP27 |
| *Escherichia* sp. 003.10 | *Escherichia* sp. BV24 |
| *Escherichia* sp. 003.14 | *Escherichia* sp. BV25 |
| *Escherichia* sp. 003.22 | *Escherichia* sp. C013(2010) |
| *Escherichia* sp. 003.23 | *Escherichia* sp. CPD32 |
| *Escherichia* sp. 006.16 | *Escherichia* sp. daliu |
| *Escherichia* sp. 006.18 | *Escherichia* sp. dayi |
| *Escherichia* sp. 006.33 | *Escherichia* sp. DGM MC1E |
| *Escherichia* sp. 1.1-11 | *Escherichia* sp. DGM MC3E |
| *Escherichia* sp. 1.3-02 | *Escherichia* sp. DGM MC4E |
| *Escherichia* sp. 1.9-16 | *Escherichia* sp. DJM1A6 |
| *Escherichia* sp. 104.10 | *Escherichia* sp. DJM1A8 |
| *Escherichia* sp. 105.12 | *Escherichia* sp. DJM1B4 |
| *Escherichia* sp. 105.16 | *Escherichia* sp. DJM1B6 |
| *Escherichia* sp. 105.17 | *Escherichia* sp. DJM1C4 |
| *Escherichia* sp. 105.3 | *Escherichia* sp. DM104 |
| *Escherichia* sp. 105.30 | *Escherichia* sp. DSD31 |
| *Escherichia* sp. 105.6 | *Escherichia* sp. DSP |
| *Escherichia* sp. 115 | *Escherichia* sp. E11118 |
| *Escherichia* sp. 12 | *Escherichia* sp. E1195 |
| *Escherichia* sp. 1_1_43 | *Escherichia* sp. E1196 |
| *Escherichia* sp. 2.2.5-13 | *Escherichia* sp. E1492 |
| *Escherichia* sp. 21CR | *Escherichia* sp. E24-PCAi-T2P21 |
| *Escherichia* sp. 22 | *Escherichia* sp. E25-PCAi-T2P21 |
| *Escherichia* sp. 23 | *Escherichia* sp. E471 |
| *Escherichia* sp. 23CR | *Escherichia* sp. E472 |
| *Escherichia* sp. 253b | *Escherichia* sp. E5-PCAi-T2P21 |
| *Escherichia* sp. 26N | *Escherichia* sp. E620 |
| *Escherichia* sp. 28N | *Escherichia* sp. E7-PCAi-T2P21 |
| *Escherichia* sp. 3-26(2010) | *Escherichia* sp. E807 |
| *Escherichia* sp. 32 | *Escherichia* sp. EC3 |
| *Escherichia* sp. 33 | *Escherichia* sp. EECC-575 |
| *Escherichia* sp. 34 | *Escherichia* sp. EECC-590 |
| *Escherichia* sp. 3_2_53FAA | *Escherichia* sp. EMB 210 |
| *Escherichia* sp. 4 | *Escherichia* sp. EMB 339 |
| *Escherichia* sp. 4067 | *Escherichia* sp. ES13 |
| *Escherichia* sp. 4094 | *Escherichia* sp. F24-PCAi-T3P21 |
| *Escherichia* sp. 41 | *Escherichia* sp. FH12 |
| *Escherichia* sp. 42 | *Escherichia* sp. FH14 |
| *Escherichia* sp. 43 | *Escherichia* sp. FHM101 |
| *Escherichia* sp. 49 | *Escherichia* sp. FHM102 |
| *Escherichia* sp. 49A | *Escherichia* sp. FHM106 |
| *Escherichia* sp. 4_1_40B | *Escherichia* sp. FHM113 |
| *Escherichia* sp. 4B | *Escherichia* sp. G3 |
| *Escherichia* sp. 54 | *Escherichia* sp. GDR06 |
| *Escherichia* sp. 63 | *Escherichia* sp. H442 |
| *Escherichia* sp. 64 | *Escherichia* sp. H605 |
| *Escherichia* sp. 68 | *Escherichia* sp. HPCKc-45 |
| *Escherichia* sp. 6B | *Escherichia* sp. I6 |
| *Escherichia* sp. 6CR | *Escherichia* sp. ICFP6 |
| *Escherichia* sp. 75R | *Escherichia* sp. II_B13 |
| *Escherichia* sp. 7CR | *Escherichia* sp. July_KB1F3 |
| *Escherichia* sp. 80 | *Escherichia* sp. July_NA2A8 |
| *Escherichia* sp. 88 | *Escherichia* sp. July_TSA2A8 |
| *Escherichia* sp. A422 | *Escherichia* sp. Kaveri_River_12 |
| *Escherichia* sp. A441 | *Escherichia* sp. M1108 |
| *Escherichia* sp. A741 | *Escherichia* sp. M1N2G03 |
| *Escherichia* sp. A94 | *Escherichia* sp. M2T9B5 |

TABLE 1-continued

| | |
|---|---|
| *Escherichia* sp. AF4 | *Escherichia* sp. M863 |
| *Escherichia* sp. AI(2010) | *Escherichia* sp. ML-11 |
| *Escherichia* sp. AJ(2010) | *Escherichia* sp. ML2-46 |
| *Escherichia* sp. MSCB-10 | *Escherichia* sp. ZHS050713 |
| *Escherichia* sp. NBRC 13921 | *Escherichia* sp. ZHS050714 |
| *Escherichia* sp. NII | *Escherichia* sp. ZY-2006a |
| *Escherichia* sp. Nj-91 | *Escherichia* sp. 4 |
| *Escherichia* sp. NMU-ST2 | environmental samples |
| *Escherichia* sp. OES18 | *Escherichia coli* CAG:4 |
| *Escherichia* sp. P14 | *Escherichia* sp. enrichment culture clone 01-084 |
| *Escherichia* sp. PF7 | *Escherichia* sp. enrichment culture clone 02-023 |
| *Escherichia* sp. RL325/96 | *Escherichia* sp. enrichment culture clone 03-018 |
| *Escherichia* sp. S4-AA1-4 | *Escherichia* sp. enrichment culture clone 03-426 |
| *Escherichia* sp. Sam130-5B | *Escherichia* sp. enrichment culture clone 04 |
| *Escherichia* sp. Sam130-6A | *Escherichia* sp. enrichment culture clone 1(2012) |
| *Escherichia* sp. SC-C4-4 | *Escherichia* sp. enrichment culture clone 11(2012) |
| *Escherichia* sp. SDT20 | *Escherichia* sp. enrichment culture clone 12 |
| *Escherichia* sp. Sflu5 | *Escherichia* sp. enrichment culture clone 16 |
| *Escherichia* sp. SI-56 | *Escherichia* sp. enrichment culture clone 17 |
| *Escherichia* sp. SO-A5-32 | *Escherichia* sp. enrichment culture clone 19(2012) |
| *Escherichia* sp. SO-Y1-39 | *Escherichia* sp. enrichment culture clone 23 |
| *Escherichia* sp. SOD-7317 | *Escherichia* sp. enrichment culture clone 3(2012) |
| *Escherichia* sp. Souza-207 | *Escherichia* sp. enrichment culture clone 9(2012) |
| *Escherichia* sp. Souza-273 | *Escherichia* sp. enrichment culture clone AVCTGRB2A |
| *Escherichia* sp. Souza-57 | *Escherichia* sp. enrichment culture clone AVCTGRB2B |
| *Escherichia* sp. SR2-18-f | *Escherichia* sp. enrichment culture clone CMX |
| *Escherichia* sp. SVUB6 | *Escherichia* sp. enrichment culture clone Jdgsrb051 |
| *Escherichia* sp. SW86 | *Escherichia* sp. enrichment culture clone Jdgsrb055 |
| *Escherichia* sp. SWM_Isolation_4 | *Escherichia* sp. enrichment culture clone Jdgsrb056 |
| *Escherichia* sp. SZ-6 | *Escherichia* sp. enrichment culture clone NBAR001 |
| *Escherichia* sp. T2 | *Escherichia* sp. enrichment culture clone NBAR004 |
| *Escherichia* sp. TA04 | *Escherichia* sp. enrichment culture clone NBAR005 |
| *Escherichia* sp. TA290 | *Escherichia* sp. enrichment culture clone NBAR006 |
| *Escherichia* sp. TW09231 | *Escherichia* sp. enrichment culture clone NBAR013 |
| *Escherichia* sp. TW09254 | *Escherichia* sp. enrichment culture clone NBAR015 |
| *Escherichia* sp. TW09266 | *Escherichia* sp. enrichment culture clone NBAR018 |
| *Escherichia* sp. TW09276 | *Escherichia* sp. enrichment culture clone NBAR020 |
| *Escherichia* sp. TW09308 | *Escherichia* sp. enrichment culture clone NBAR022 |
| *Escherichia* sp. TW10509 | *Escherichia* sp. enrichment culture clone NBAR023 |
| *Escherichia* sp. TW11930 | *Escherichia* sp. enrichment culture clone NBAR024 |
| *Escherichia* sp. TW11966 | *Escherichia* sp. enrichment culture clone NX |
| *Escherichia* sp. TW14182 | *Escherichia* sp. enrichment culture clone R__1017-3__OTU3 |
| *Escherichia* sp. TW14263 | *Escherichia* sp. enrichment culture clone R__8m3__OTU3 |
| *Escherichia* sp. TW14264 | *Escherichia* sp. enrichment culture clone SRC_NBA4 |
| *Escherichia* sp. TW14265 | *Escherichia* sp. enrichment culture clone SRC_NBA7 |
| *Escherichia* sp. TW14266 | *Escherichia* sp. enrichment culture clone SRC_NBAS |
| *Escherichia* sp. TW14267 | *Escherichia* sp. enrichment culture clone SunHY |
| *Escherichia* sp. TW15838 | *Escherichia* sp. enrichment culture clone V-S5__1-51 |
| *Escherichia* sp. TX3 | *Escherichia* sp. enrichment culture DGGE band D5 |
| *Escherichia* sp. V2M20 | *Escherichia* sp. oral clone 3RH-30 |
| *Escherichia* sp. V3M66 | uncultured *Escherichia* clone MT9 |
| *Escherichia* sp. VA17 | uncultured *Escherichia* sp. |
| *Escherichia* sp. VF2(2010) | uncultured *Escherichia* sp. FR039 |
| *Escherichia* sp. W8-PCAi-E14 | uncultured *Escherichia* sp. FR040 |
| *Escherichia* sp. Z205 | |

Genus: Firmicutes

| | |
|---|---|
| Bacilli | Lactobacillales |
| Bacillales | Aerococcaceae |
| Alicyclobacillaceae | Carnobacteriaceae |
| Bacillaceae | Enterococcaceae |
| Listeriaceae | Lactobacillaceae |
| Paenibacillaceae | Leuconostocaceae |
| Pasteuriaceae | Streptococcaceae |
| Planococcaceae | unclassified Lactobacillales |
| Sporolactobacillaceae | environmental samples |
| Staphylococcaceae | unclassified Bacilli |
| Thermoactinomycetaceae | Bacilli bacterium 01A |
| unclassified Bacillales | Bacilli bacterium 04A |
| Bacillales incertae sedis | Bacilli bacterium 08A |
| environmental samples | Bacilli bacterium 09A |
| Bacilli bacterium 12B | Clostridia bacterium enrichment culture clone |
| Bacilli bacterium A3-1b | D2CL_Bac_16S_Clone18 |
| Bacilli bacterium AD51 | Clostridia bacterium enrichment culture clone |
| Bacilli bacterium BC6 | D2CL_Bac_16S_Clone19 |
| Bacilli bacterium BG__5a | Clostridia bacterium enrichment culture clone |
| Bacilli bacterium f50-7-u8f | D2CL_Bac_16S_Clone20 |
| Bacilli bacterium JAM-FM0401 | Clostridia bacterium enrichment culture clone HB__114 |
| Bacilli bacterium JGI BulkO13H05 | Clostridia bacterium enrichment culture clone HB__117 |
| Bacilli bacterium JW22.2a | Clostridia bacterium enrichment culture clone HB__90 |

TABLE 1-continued

Bacilli bacterium oral taxon C35
Bacilli bacterium oral taxon C43
Bacilli bacterium PF61
Bacilli bacterium TSW19BA3
bacterium 103NT4
bacterium 105NT4
bacterium 17N1
bacterium 18N1
bacterium 3E1
bacterium 64B4
bacterium 66B4
bacterium 95LM4
bacterium 9B1
bacterium WE1
bacterium WE4
bacterium WN16
environmental samples
Bacilli bacterium enrichment culture clone 1-2-1
Bacilli bacterium enrichment culture clone YFZ9
uncultured Bacilli bacterium
Clostridia
Clostridiales
Caldicoprobacteraceae
Catabacteriaceae
Christensenellaceae
Clostridiaceae
Defluviitaleaceae
Eubacteriaceae
Gracilibacteraceae
Heliobacteriaceae
Lachnospiraceae
Oscillospiraceae
Peptococcaceae
Peptostreptococcaceae
Ruminococcaceae
Syntrophomonadaceae
unclassified Clostridiales
Clostridiales incertae sedis
environmental samples
Halanaerobiales
Halanaerobiaceae
Halobacteroidaceae
unclassified Halanaerobiales
environmental samples
Natranaerobiales
Natranaerobiaceae
environmental samples
Thermoanaerobacterales
Thermoanaerobacteraceae
Thermodesulfobiaceae
unclassified Thermoanaerobacterales
Thermoanaerobacterales Family III. Incertae Sedis
Thermoanaerobacterales Family IV. Incertae Sedis
environmental samples
unclassified Clostridia
unclassified Clostridia (miscellaneous)
environmental samples
Clostridia bacterium enrichment culture clone 40D01
Clostridia bacterium enrichment culture clone BF
Clostridia bacterium enrichment culture clone D2CL_Bac_16S_Clone17
bacterium TC8
blackwater bioreactor bacterium BW21
endosymbiont 'TC1' of *Trimyema compressum*
Firmicutes bacterium 00DQ7
Firmicutes bacterium 00DQ8
Firmicutes bacterium 00DQ9
Firmicutes bacterium 00YDA
Firmicutes bacterium 00YDC
Firmicutes bacterium 00YJS
Firmicutes bacterium 00YK2
Firmicutes bacterium 00YDJ
Firmicutes bacterium 00YDK
Firmicutes bacterium 00YDM
Firmicutes bacterium 00YDS
Firmicutes bacterium 00YDU
Firmicutes bacterium 00YFJ
Firmicutes bacterium 00YFM
Firmicutes bacterium 00YFP
Firmicutes bacterium 00YFR Clostridia bacterium enrichment culture clone L11_1_31
Clostridia bacterium enrichment culture clone L35B_10
Clostridia bacterium enrichment culture clone L35B_105
Clostridia bacterium enrichment culture clone L35B_145
Clostridia bacterium enrichment culture clone L35B_146
Clostridia bacterium enrichment culture clone L35B_152
Clostridia bacterium enrichment culture clone L35B_154
Clostridia bacterium enrichment culture clone L35B_2
Clostridia bacterium enrichment culture clone L35B_30
Clostridia bacterium enrichment culture clone L35B_66
Clostridia bacterium enrichment culture clone L35B_85
Clostridia bacterium enrichment culture clone L35B_89
Clostridia bacterium enrichment culture clone L35B_99
Clostridia bacterium enrichment culture clone L55B-110
Clostridia bacterium enrichment culture clone L55B-127
Clostridia bacterium enrichment culture clone L55B-129
Clostridia bacterium enrichment culture clone L55B-21
Clostridia bacterium enrichment culture clone L55B-30
Clostridia bacterium enrichment culture clone L55B-38
Clostridia bacterium enrichment culture clone L55B-41
Clostridia bacterium enrichment culture clone L55B-44
Clostridia bacterium enrichment culture clone L55B-73
Clostridia bacterium enrichment culture clone L55B-80
Clostridia bacterium enrichment culture clone SIP11D
Clostridia bacterium enrichment culture clone SIP3C
Clostridia bacterium enrichment culture clone SIP4D
Clostridia bacterium enrichment culture clone WIP10m2D
Clostridia bacterium enrichment culture clone WSC-26
Clostridia bacterium enrichment culture clone WSC-8
Clostridia bacterium enrichment culture clone WSC-9
Clostridia bacterium enrichment culture DGGE band 1
Clostridia bacterium enrichment culture RD-M/D-OTU C
uncultured Clostridia bacterium
Erysipelotrichia
Erysipelotrichales
Erysipelotrichaceae
unclassified Erysipelotrichales
environmental samples
environmental samples
Erysipelotrichi bacterium enrichment culture clone Y12
uncultured Erysipelotrichi bacterium
Negativicutes
Selenomonadales
Acidaminococcaceae
Veillonellaceae
environmental samples
environmental samples
uncultured Negativicutes bacterium
Thermolithobacteria
Thermolithobacterales
Thermolithobacteraceae
unclassified Firmicutes sensu stricto
unclassified Firmicutes sensu stricto (miscellaneous)
anaerobic bacterium TOL
bacterial str. vp184
bacterial str. vp188
bacterium ASF500
alkaliphilic *eubacterium* 163-26
anaerobic bacterium 'strain 7'
bacterium CBM5-27
bacterium CBM5-49
Firmicutes bacterium CPB4
Firmicutes bacterium CSC3
Firmicutes bacterium CSC8
Firmicutes bacterium DJF_VP44
Firmicutes bacterium DJF_VR50
Firmicutes bacterium EG14
Firmicutes bacterium EG16
Firmicutes bacterium EG18
Firmicutes bacterium EG20
Firmicutes bacterium EG24
Firmicutes bacterium FA1
Firmicutes bacterium FA1a
Firmicutes bacterium FAB2
Firmicutes bacterium G6-4
Firmicutes bacterium GM12
Firmicutes bacterium GM21
Firmicutes bacterium GM29
Firmicutes bacterium GM64
Firmicutes bacterium AV4-2

TABLE 1-continued

| | |
|---|---|
| Firmicutes bacterium 00YIV | Firmicutes bacterium B4_5 |
| Firmicutes bacterium 00YIZ | Firmicutes bacterium JGI 0000119-C08 |
| Firmicutes bacterium 00YJ3 | Firmicutes bacterium JGI 0000119-P10 |
| Firmicutes bacterium 00YJ4 | Firmicutes bacterium JGI 0001003-N4 |
| Firmicutes bacterium 00YJQ | Firmicutes bacterium JGI 0002005-C11 |
| Firmicutes bacterium 7d3-2 | Firmicutes bacterium JS13 |
| Firmicutes bacterium 7d4-1 | Firmicutes bacterium K-2054 |
| Firmicutes bacterium 7d4-2 | Firmicutes bacterium K-2061 |
| Firmicutes bacterium ADS-1 | Firmicutes bacterium K-2063 |
| Firmicutes bacterium AD3-3 | Firmicutes bacterium HF1 |
| Firmicutes bacterium Apb7 | Firmicutes bacterium HF2 |
| Firmicutes bacterium ASF500 | Firmicutes bacterium HF4 |
| Firmicutes bacterium AV4-1 | Firmicutes bacterium HF5 |
| Firmicutes bacterium 01QG4 | Firmicutes bacterium HF6 |
| Firmicutes bacterium 10827 | Firmicutes bacterium HK1 |
| Firmicutes bacterium 109-1 | Firmicutes bacterium HK11 |
| Firmicutes bacterium 120-6-24 | Firmicutes bacterium HK13 |
| Firmicutes bacterium 1229-1IIA | Firmicutes bacterium HK14 |
| Firmicutes bacterium 1UG | Firmicutes bacterium HK15 |
| Firmicutes bacterium 215-38 | Firmicutes bacterium HK16 |
| Firmicutes bacterium 215-68 | Firmicutes bacterium HK17 |
| Firmicutes bacterium 255-2 | Firmicutes bacterium HK19 |
| Firmicutes bacterium 293-12 | Firmicutes bacterium HK2 |
| Firmicutes bacterium 309-58 | Firmicutes bacterium HK20 |
| Firmicutes bacterium 351UG | Firmicutes bacterium HK21 |
| Firmicutes bacterium 43-3 | Firmicutes bacterium HK22 |
| Firmicutes bacterium 7d15-2 | Firmicutes bacterium HK23 |
| Firmicutes bacterium 7d2-1 | Firmicutes bacterium HK24 |
| Firmicutes bacterium 7d2-2 | Firmicutes bacterium HK25 |
| Firmicutes bacterium 7d3-1 | Firmicutes bacterium HK26 |
| Firmicutes bacterium baku-08 | Firmicutes bacterium HK28 |
| Firmicutes bacterium BAL8 | Firmicutes bacterium HK3 |
| Firmicutes bacterium BAL9 | Firmicutes bacterium HK30 |
| Firmicutes bacterium BC1 | Firmicutes bacterium HK4 |
| Firmicutes bacterium BCOT-15 | Firmicutes bacterium HK6 |
| Firmicutes bacterium BCOT-3 | Firmicutes bacterium HK7 |
| Firmicutes bacterium BCOT-6 | Firmicutes bacterium HK8 |
| Firmicutes bacterium BCOT-9 | Firmicutes bacterium InGrA1 |
| Firmicutes bacterium BD7-1 | Firmicutes bacterium IS2605 |
| Firmicutes bacterium BD7-2 | Firmicutes bacterium IS3105 |
| Firmicutes bacterium BD7-3 | Firmicutes bacterium Jbg1 |
| Firmicutes bacterium BL80 | Firmicutes bacterium Jbg2 |
| Firmicutes bacterium BS-02 | Firmicutes bacterium Jbg3 |
| Firmicutes bacterium Bt aa 02 | Firmicutes bacterium Jbg4 |
| Firmicutes bacterium BTY6 | Firmicutes bacterium Jbg5 |
| Firmicutes bacterium BV9-1 | Firmicutes bacterium Jbg6 |
| Firmicutes bacterium BV9-3a | Firmicutes bacterium Jbg7 |
| Firmicutes bacterium BV9-4a | Firmicutes bacterium JGI 0000059-A33 |
| Firmicutes bacterium canine oral taxon 309 | Firmicutes bacterium JGI 0000059-D05 |
| Firmicutes bacterium CP4.1 | Firmicutes bacterium JGI 0000059-G16 |
| Firmicutes bacterium CP4.3 | Firmicutes bacterium JGI 0000059-H17 |
| Firmicutes bacterium Mexcell3.3 | Firmicutes bacterium K16 |
| Firmicutes bacterium Mexcell7 | Firmicutes bacterium K17 |
| Firmicutes bacterium Mexdtt1 | Firmicutes bacterium K23 |
| Firmicutes bacterium MMD11 | Firmicutes bacterium K24 |
| Firmicutes bacterium MMD12 | Firmicutes bacterium K3 |
| Firmicutes bacterium OR-167 | Firmicutes bacterium K4 |
| Firmicutes bacterium oral taxon A55 | Firmicutes bacterium K7 |
| Firmicutes bacterium oral taxon C68 | Firmicutes bacterium K9 |
| Firmicutes bacterium oral taxon D73 | Firmicutes bacterium Kam1851 |
| Firmicutes bacterium oral taxon F03 | Firmicutes bacterium L10-A08 |
| Firmicutes bacterium oral taxon F06 | Firmicutes bacterium LC 13R |
| Firmicutes bacterium oral taxon G23 | Firmicutes bacterium LM4605 |
| Firmicutes bacterium ORNL_2OR_SB_170 | Firmicutes bacterium LX-B |
| Firmicutes bacterium OS-13B | Firmicutes bacterium LX-D |
| Firmicutes bacterium P1 | Firmicutes bacterium M10-2 |
| Firmicutes bacterium P4 | Firmicutes bacterium M28 |
| Firmicutes bacterium PD5-2 | Firmicutes bacterium M29 |
| Firmicutes bacterium PM1 | Firmicutes bacterium M34 |
| Firmicutes bacterium PM15 | Firmicutes bacterium M38 |
| Firmicutes bacterium PM33 | Firmicutes bacterium M39 |
| Firmicutes bacterium PM39 | Firmicutes bacterium M40 |
| Firmicutes bacterium PM49 | Firmicutes bacterium M42 |
| Firmicutes bacterium PV6-1b | Firmicutes bacterium M53 |
| Firmicutes bacterium PV6-4 | Firmicutes bacterium M71_D119 |
| Firmicutes bacterium R11 | Firmicutes bacterium M71_D94 |
| Firmicutes bacterium R24 | Firmicutes bacterium M71_S54 |
| Firmicutes bacterium RBE2CD-62 | Firmicutes bacterium Macell 1.1 |
| Firmicutes bacterium RD1-3 | Firmicutes bacterium Macell3.1 |
| Firmicutes bacterium RD1-6 | Firmicutes bacterium Mad1 |

TABLE 1-continued

| | |
|---|---|
| Firmicutes bacterium rif200828 | Firmicutes bacterium Mad4 |
| Firmicutes bacterium RV2-2 | Firmicutes bacterium Madtt6 |
| Firmicutes bacterium SC-6EZ3-F-Cy56 | Firmicutes bacterium Madttd2.1 |
| Firmicutes bacterium SC-6EZ3-F-Cy62 | Firmicutes bacterium Madttd2.2 |
| Firmicutes bacterium SCGC AAA028-E02 | Firmicutes bacterium Man17 |
| Firmicutes bacterium SCGC AAA028-K20 | Firmicutes bacterium MCF99 |
| Firmicutes bacterium SCGC AAA041-M19 | Firmicutes bacterium Mecdtt4 |
| Firmicutes bacterium SCGC AAA041-N22 | Firmicutes bacterium Mecdtt5 |
| Firmicutes bacterium SCGC AAA043-A02 | Firmicutes bacterium Mexcdtt7 |
| Firmicutes bacterium SCGC AAA043-F09 | Firmicutes bacterium Mexcell2 |
| Firmicutes bacterium SCGC AAA044-J20 | Firmicutes bacterium TH-G17 |
| Firmicutes bacterium SCGC AAA044-P03 | Firmicutes bacterium TH-H12 |
| Firmicutes bacterium SCGC AAA160-B08 | Firmicutes bacterium TH-H16 |
| Firmicutes bacterium SCGC AAA278-I09 | Firmicutes bacterium TH-N38 |
| Firmicutes bacterium SCGC AAA280-N09 | Firmicutes bacterium TH-N39 |
| Firmicutes bacterium SCGC AAA487-F07 | Firmicutes bacterium TH-S33 |
| Firmicutes bacterium SCGC AAA487-G07 | Firmicutes bacterium TH-S35 |
| Firmicutes bacterium SCGC AB-670-A06 | Firmicutes bacterium TH-S40 |
| Firmicutes bacterium SCGC AB-670-B05 | Firmicutes bacterium TH-S57 |
| Firmicutes bacterium SCGC AB-670-E02 | Firmicutes bacterium TH-S64 |
| Firmicutes bacterium SCGC AB-670-J02 | Firmicutes bacterium TH-S70 |
| Firmicutes bacterium SCGC AB-670-K04 | Firmicutes bacterium TP160 |
| Firmicutes bacterium SCGC AB-670-L02 | Firmicutes bacterium TP271 |
| Firmicutes bacterium SCGC AB-670-O02 | Firmicutes bacterium TP425 |
| Firmicutes bacterium SCGC AB-670-P10 | Firmicutes bacterium TP84 |
| Firmicutes bacterium SCGC AB-674-M10 | Firmicutes bacterium TP86 |
| Firmicutes bacterium SCGC AC-310-C05 | Firmicutes bacterium TP94 |
| Firmicutes bacterium SCGC AC-310-E10 | Firmicutes bacterium UFLA03-11 |
| Firmicutes bacterium SCGC AC-310-F10 | Firmicutes bacterium VAS32 |
| Firmicutes bacterium SCGC AC-310-F16 | Firmicutes bacterium VAS38 |
| Firmicutes bacterium SCGC AC-310-G06 | Firmicutes bacterium VAS39 |
| Firmicutes bacterium SCGC AC-310-G07 | Firmicutes bacterium VAS40 |
| Firmicutes bacterium SCGC AC-310-I07 | Firmicutes bacterium VAS41 |
| Firmicutes bacterium SCGC AC-310-M02 | Firmicutes bacterium VAS48 |
| Firmicutes bacterium SCGC AC-310-M09 | Firmicutes bacterium VAS49 |
| Firmicutes bacterium SCGC AC-310-M17 | Firmicutes bacterium VAS50 |
| Firmicutes bacterium SCGC AC-310-M18 | Firmicutes bacterium VAS51 |
| Firmicutes bacterium SCGC AC-310-N09 | Firmicutes bacterium VAS52 |
| Firmicutes bacterium SCGC AC-310-N17 | Firmicutes bacterium VAS53 |
| Firmicutes bacterium SCGC AC-310-O09 | Firmicutes bacterium VNs03 |
| Firmicutes bacterium K11 | Firmicutes bacterium VNs39 |
| Firmicutes bacterium VNs41 | low G + C Gram-positive bacterium M53 |
| Firmicutes bacterium VNs44 | low G + C Gram-positive bacterium M54 |
| Firmicutes bacterium VNs59 | low G + C Gram-positive bacterium M55 |
| Firmicutes bacterium W-2006 | low G + C Gram-positive bacterium MPD-62 |
| Firmicutes bacterium W-2017 | low G + C Gram-positive bacterium MPD-63 |
| Firmicutes bacterium W-2018 | low G + C Gram-positive bacterium MPD-67 |
| Firmicutes bacterium Wash11.2 | low G + C Gram-positive bacterium MPD-76 |
| Firmicutes bacterium Wash5 | low G + C Gram-positive bacterium R2A161 |
| Firmicutes bacterium WD116 | low G + C Gram-positive bacterium R2A180 |
| Firmicutes bacterium WD117 | low G + C Gram-positive bacterium R2A28 |
| Firmicutes bacterium WD121 | low G + C Gram-positive bacterium S-N(0)-17C |
| Firmicutes bacterium WD3 | low G + C Gram-positive bacterium S-N(1)-3 |
| Firmicutes bacterium WD526 | low G + C Gram-positive bacterium S-St(1)-6A |
| Firmicutes bacterium WD6 | low G + C Gram-positive bacterium S-St(nd)-7D2 |
| Firmicutes bacterium WD80 | low G + C Gram-positive bacterium S-Su(1)-8A |
| Firmicutes bacterium WD83 | low G + C Gram-positive bacterium S-Su(2)-18 |
| Firmicutes bacterium WH009142s | low G + C Gram-positive bacterium S4 |
| Firmicutes bacterium WSF2-15 | low G + C Gram-positive bacterium S5 |
| Firmicutes bacterium X3 | low G + C Gram-positive bacterium SA-5 |
| Firmicutes bacterium YJF1-16 | low G + C Gram-positive bacterium SSCA31 |
| low G + C Gram-positive bacterium B773 | Firmicutes bacterium SCGC AC-310-O15 |
| low G + C Gram-positive bacterium B775 | Firmicutes bacterium SCGC AC-310-O20 |
| low G + C Gram-positive bacterium BAL128 | Firmicutes bacterium SCGC AC-310-O21 |
| low G + C Gram-positive bacterium D-N(0)-4D | Firmicutes bacterium SCGC AC-310-P16 |
| low G + C Gram-positive bacterium D-N(1)-11A | Firmicutes bacterium SCGC AC-699-C23 |
| low G + C Gram-positive bacterium D-N(1)-1B | Firmicutes bacterium SCGC AC-699-M18 |
| low G + C Gram-positive bacterium D-N(1)-1C | Firmicutes bacterium SD1 |
| low G + C Gram-positive bacterium D-N(1)-1D | Firmicutes bacterium SE1905 |
| low G + C Gram-positive bacterium D-N(1)-2A | Firmicutes bacterium SE2005 |
| low G + C Gram-positive bacterium D-N(1)-3C | Firmicutes bacterium SE2105 |
| low G + C Gram-positive bacterium D-N(2)-1A | Firmicutes bacterium SH-4-1 |
| low G + C Gram-positive bacterium D-N(2)-2B | Firmicutes bacterium SH-4-3-1 |
| low G + C Gram-positive bacterium D-N(2)-2C | Firmicutes bacterium SH-5-2 |
| low G + C Gram-positive bacterium D-N(2)-3A | Firmicutes bacterium SL-6 |
| low G + C Gram-positive bacterium D-N(2)-3B2 | Firmicutes bacterium SM22 |
| low G + C Gram-positive bacterium D-St(1)-3 | Firmicutes bacterium SM60 |
| low G + C Gram-positive bacterium D-Su(1)-14A | Firmicutes bacterium SP83 |
| low G + C Gram-positive bacterium D-Su(1)-19B | Firmicutes bacterium SRC01-ECW |
| low G + C Gram-positive bacterium D-Su(1)-21A | Firmicutes bacterium T17b-60 |

TABLE 1-continued

| | |
|---|---|
| low G + C Gram-positive bacterium D-Su(1)-21B | Firmicutes bacterium T17b-64 |
| low G + C Gram-positive bacterium D-Su(1)-21C | Firmicutes bacterium T28-15 |
| low G + C Gram-positive bacterium D-Su(1)-22 | Firmicutes bacterium T28-20a |
| low G + C Gram-positive bacterium D-Su(1)-25 | Firmicutes bacterium T28-9b |
| low G + C Gram-positive bacterium D-Su(1)-4B | Firmicutes bacterium T30b-36 |
| low G + C Gram-positive bacterium D-Su(1)-5 | Firmicutes bacterium TATAC-10 |
| low G + C Gram-positive bacterium D-Su(1)-6B | Firmicutes bacterium TG10 |
| low G + C Gram-positive bacterium D-Su(1)-7B | Firmicutes bacterium TG11 |
| low G + C Gram-positive bacterium D-Su(1)-7C | Firmicutes bacterium TG14 |
| low G + C Gram-positive bacterium D-Su(2)-10 | Firmicutes bacterium TG15 |
| low G + C Gram-positive bacterium HTA1415 | Firmicutes bacterium TG17 |
| low G + C Gram-positive bacterium HTA1416 | Firmicutes bacterium TG18 |
| low G + C Gram-positive bacterium HTA1417 | Firmicutes bacterium TG19 |
| low G + C Gram-positive bacterium HTA1418 | Firmicutes bacterium TG2 |
| low G + C Gram-positive bacterium HTA1420 | Firmicutes bacterium TG20 |
| low G + C Gram-positive bacterium HTA1422 | Firmicutes bacterium TG21 |
| low G + C Gram-positive bacterium HTA426 | Firmicutes bacterium TG24 |
| low G + C Gram-positive bacterium HTA437 | Firmicutes bacterium TG25 |
| low G + C Gram-positive bacterium HTA454 | Firmicutes bacterium TG26 |
| low G + C Gram-positive bacterium HTA462 | Firmicutes bacterium TG27 |
| low G + C Gram-positive bacterium HTA484 | Firmicutes bacterium TG29 |
| low G + C Gram-positive bacterium HTA506 | Firmicutes bacterium TG3 |
| low G + C Gram-positive bacterium HTA563 | Firmicutes bacterium TG30 |
| low G + C Gram-positive bacterium HTE856 | Firmicutes bacterium TG32 |
| low G + C Gram-positive bacterium IRB 1 | Firmicutes bacterium TG34 |
| low G + C Gram-positive bacterium L23 | Firmicutes bacterium TG39 |
| low G + C Gram-positive bacterium LVS-50 | Firmicutes bacterium TG4 |
| low G + C Gram-positive bacterium M33 | Firmicutes bacterium TG6 |
| low G + C Gram-positive bacterium M34 | Firmicutes bacterium TG7 |
| low G + C Gram-positive bacterium M51 | Firmicutes bacterium TG8 |
| low G + C Gram-positive bacterium M52 | Firmicutes bacterium TG9 |
| Firmicutes bacterium TGT3-6A | Firmicutes bacterium CAG:170 |
| Firmicutes bacterium TGT5-5A | Firmicutes bacterium CAG:176 |
| Firmicutes bacterium TGT5-5B | Firmicutes bacterium CAG:194 |
| Firmicutes bacterium TGTM-5A | Firmicutes bacterium CAG:212 |
| Firmicutes bacterium TGTM-5B | Firmicutes bacterium CAG:227 |
| Firmicutes bacterium TH-G1 | Firmicutes bacterium CAG:238 |
| low G + C Gram-positive bacterium zo05 | Firmicutes bacterium CAG:24 |
| low GC Gram-positive bacterium strain AHT28 | Firmicutes bacterium CAG:240 |
| low GC Gram-positive bacterium strain AHT29 | Firmicutes bacterium CAG:270 |
| marine bacterium NBF29 | Firmicutes bacterium CAG:272 |
| marine bacterium NBF32 | Firmicutes bacterium CAG:308 |
| marine bacterium SIMO IS-S76-284 | Firmicutes bacterium CAG:313 |
| marine bacterium SIMO-IS120 | Firmicutes bacterium CAG:321 |
| marine bacterium SIMO-IS131 | Firmicutes bacterium CAG:341 |
| marine bacterium SIMO-IS186 | Firmicutes bacterium CAG:345 |
| marine bacterium SIMO-IS188 | Firmicutes bacterium CAG:41 |
| marine bacterium SIMO-IS189 | Firmicutes bacterium CAG:424 |
| marine bacterium SIMO-IS191 | Firmicutes bacterium CAG:449 |
| marine bacterium SIMO-IS194 | Firmicutes bacterium CAG:460 |
| marine bacterium SIMO-IS197 | Firmicutes bacterium CAG:466 |
| marine bacterium SIMO-IS206 | Firmicutes bacterium CAG:475 |
| marine bacterium SIMO-IS209 | Firmicutes bacterium CAG:534 |
| marine bacterium SIMO-IS212 | Firmicutes bacterium CAG:536 |
| marine bacterium SIMO-IS214 | Firmicutes bacterium CAG:552 |
| marine bacterium SIMO-IS215 | Firmicutes bacterium CAG:555 |
| marine bacterium SIMO-IS216 | Firmicutes bacterium CAG:56 |
| marine firmicute 1P07AA | Firmicutes bacterium CAG:582 |
| marine firmicute HTB096 | Firmicutes bacterium CAG:631 |
| marine firmicute HTB113 | Firmicutes bacterium CAG:646 |
| mixed culture isolate koll13 | Firmicutes bacterium CAG:65 |
| segmented filamentous bacterium | Firmicutes bacterium CAG:791 |
| low G + C Gram-positive bacterium SSCS10 | Firmicutes bacterium CAG:822 |
| low G + C Gram-positive bacterium SSCS20 | Firmicutes bacterium CAG:83 |
| low G + C Gram-positive bacterium SSCS21-2 | Firmicutes bacterium CAG:882 |
| low G + C Gram-positive bacterium SSCS28 | Firmicutes bacterium CAG:884 |
| low G + C Gram-positive bacterium SSCS35 | Firmicutes bacterium CAG:94 |
| low G + C Gram-positive bacterium SSCS42 | Firmicutes bacterium CAG:95 |
| low G + C Gram-positive bacterium SSCT75 | Firmicutes bacterium enrichment culture clone 0-6F07 |
| low G + C Gram-positive bacterium SSCT76 | Firmicutes bacterium enrichment culture clone 106MTBE |
| low G + C Gram-positive bacterium SSCT84-2 | Firmicutes bacterium enrichment culture clone 16695 ECW 20 |
| low G + C Gram-positive bacterium T134 | Firmicutes bacterium enrichment culture clone 16695 ECW 21 |
| low G + C Gram-positive bacterium T135 | Firmicutes bacterium enrichment culture clone 16695 ECW 22 |
| low G + C Gram-positive bacterium T152 | Firmicutes bacterium enrichment culture clone 16695 ECW 24 |
| low G + C Gram-positive bacterium T155 | Firmicutes bacterium enrichment culture clone 16695 ECW 6 |
| low G + C Gram-positive bacterium TR1 | Firmicutes bacterium enrichment culture clone 16695 ECW 8 |
| low G + C Gram-positive bacterium wo11 | Firmicutes bacterium enrichment culture clone 4.17b Bac band 1 |
| low G + C Gram-positive bacterium wo47 | Firmicutes bacterium enrichment culture clone 4.17b Bac band 2 |
| unidentified low G + C gram-positive bacterium RS10 | Firmicutes bacterium enrichment culture clone 4.17b Bac band 3 |
| unidentified low G + C gram-positive bacterium RS13 | Firmicutes bacterium enrichment culture clone 4.17b Bac band 4 |

TABLE 1-continued

| | |
|---|---|
| unidentified low G + C gram-positive bacterium RS16 | Firmicutes bacterium enrichment culture clone A17 |
| unidentified low G + C gram-positive bacterium RS19 | Firmicutes bacterium enrichment culture clone B31179 |
| swine manure bacterium PC9 | Firmicutes bacterium enrichment culture clone BSK 1 |
| thermophilic bacterium JA2 | Firmicutes bacterium enrichment culture clone BSK 108 |
| Firmicutes symbiont of *Osedax* sp. | Firmicutes bacterium enrichment culture clone BSK_11 |
| unidentified bacterium Par64 | Firmicutes bacterium enrichment culture clone BSK_114 |
| unidentified low G + C gram-positive bacterium RS20 | Firmicutes bacterium enrichment culture clone BSK_125 |
| unidentified low G + C gram-positive bacterium RS21 | Firmicutes bacterium enrichment culture clone BSK_23 |
| unidentified low G + C gram-positive bacterium RS21a | Firmicutes bacterium enrichment culture clone BSK_30 |
| unidentified low G + C gram-positive bacterium RS3 | Firmicutes bacterium enrichment culture clone BSK_36 |
| unidentified low G + C gram-positive bacterium RS5 | Firmicutes bacterium enrichment culture clone BSK_37 |
| unidentified low G + C gram-positive bacterium S12 | Firmicutes bacterium enrichment culture clone BSK_40 |
| environmental samples | Firmicutes bacterium enrichment culture clone BSK_41 |
| Firmicutes bacterium CAG:102 | Firmicutes bacterium enrichment culture clone BSK_48 |
| Firmicutes bacterium CAG:103 | Firmicutes bacterium enrichment culture clone BSK_52 |
| Firmicutes bacterium CAG:110 | Firmicutes bacterium enrichment culture clone BSK_58 |
| Firmicutes bacterium CAG:114 | Firmicutes bacterium enrichment culture clone BSK_60 |
| Firmicutes bacterium CAG:124 | Firmicutes bacterium enrichment culture clone BSK_67 |
| Firmicutes bacterium CAG:129 | Firmicutes bacterium enrichment culture clone BSK_88 |
| Firmicutes bacterium CAG:137 | Firmicutes bacterium enrichment culture clone BSK_94 |
| Firmicutes bacterium CAG:145 | Firmicutes bacterium enrichment culture clone BSK_96 |
| Firmicutes bacterium enrichment culture clone BSK_97 | Firmicutes bacterium enrichment culture clone CTBE CDB1009D09 |
| Firmicutes bacterium enrichment culture clone BSK_98 | Firmicutes bacterium enrichment culture clone CTBE CDB1009D10 |
| Firmicutes bacterium enrichment culture clone BSK_99 | Firmicutes bacterium enrichment culture clone CTBE CDB1009D11 |
| Firmicutes bacterium enrichment culture clone CTBE CDB1001A07 | Firmicutes bacterium enrichment culture clone CTBE CDB1009E02 |
| Firmicutes bacterium enrichment culture clone CTBE CDB1001H03 | Firmicutes bacterium enrichment culture clone CTBE CDB1009E03 |
| Firmicutes bacterium enrichment culture clone CTBE CDB1006A02 | Firmicutes bacterium enrichment culture clone CTBE CDB1009E04 |
| Firmicutes bacterium enrichment culture clone CTBE CDB1006A04 | Firmicutes bacterium enrichment culture clone CTBE CDB1009E05 |
| Firmicutes bacterium enrichment culture clone CTBE CDB1006A06 | Firmicutes bacterium enrichment culture clone CTBE CDB1009E06 |
| Firmicutes bacterium enrichment culture clone CTBE CDB1006A07 | Firmicutes bacterium enrichment culture clone CTBE CDB1009E07 |
| Firmicutes bacterium enrichment culture clone CTBE CDB1006A08 | Firmicutes bacterium enrichment culture clone CTBE CDB1009E10 |
| Firmicutes bacterium enrichment culture clone CTBE CDB1006A09 | Firmicutes bacterium enrichment culture clone CTBE CDB1009F03 |
| Firmicutes bacterium enrichment culture clone CTBE CDB1006A10 | Firmicutes bacterium enrichment culture clone CTBE CDB1009F04 |
| Firmicutes bacterium enrichment culture clone CTBE CDB1006B01 | Firmicutes bacterium enrichment culture clone CTBE CDB1009F05 |
| Firmicutes bacterium enrichment culture clone CTBE CDB1006B07 | Firmicutes bacterium enrichment culture clone CTBE CDB1009F06 |
| Firmicutes bacterium enrichment culture clone CTBE CDB1006B10 | Firmicutes bacterium enrichment culture clone CTBE CDB1009F07 |
| Firmicutes bacterium enrichment culture clone CTBE CDB1006B11 | Firmicutes bacterium enrichment culture clone CTBE CDB1009F12 |
| Firmicutes bacterium enrichment culture clone CTBE CDB1006B12 | Firmicutes bacterium enrichment culture clone CTBE CDB1009G02 |
| Firmicutes bacterium enrichment culture clone CTBE CDB1006C06 | Firmicutes bacterium enrichment culture clone CTBE CDB1009G07 |
| Firmicutes bacterium enrichment culture clone CTBE CDB1006C07 | Firmicutes bacterium enrichment culture clone CTBE CDB1009G08 |
| Firmicutes bacterium enrichment culture clone CTBE CDB1006C09 | Firmicutes bacterium enrichment culture clone CTBE CDB1009G12 |
| Firmicutes bacterium enrichment culture clone CTBE CDB1006C10 | Firmicutes bacterium enrichment culture clone CTBE CDB1009H01 |
| Firmicutes bacterium enrichment culture clone CTBE CDB1006C11 | Firmicutes bacterium enrichment culture clone CTBE CDB1009H02 |
| Firmicutes bacterium enrichment culture clone CTBE CDB1006C12 | Firmicutes bacterium enrichment culture clone CTBE CDB1009H04 |
| Firmicutes bacterium enrichment culture clone CTBE CDB1006D05 | Firmicutes bacterium enrichment culture clone CTBE CDB1009H05 |
| Firmicutes bacterium enrichment culture clone CTBE CDB1006D06 | Firmicutes bacterium enrichment culture clone CTBE CDB1009H07 |
| Firmicutes bacterium enrichment culture clone CTBE CDB1006D07 | Firmicutes bacterium enrichment culture clone CTBE CDB1009H09 |
| Firmicutes bacterium enrichment culture clone CTBE CDB1006D08 | Firmicutes bacterium enrichment culture clone CTBE CDB1009H10 |
| Firmicutes bacterium enrichment culture clone CTBE CDB1006D10 | Firmicutes bacterium enrichment culture clone CTBE CDB1010A02 |
| Firmicutes bacterium enrichment culture clone CTBE CDB1006D11 | Firmicutes bacterium enrichment culture clone CTBE CDB1010A03 |
| Firmicutes bacterium enrichment culture clone CTBE CDB1006E04 | Firmicutes bacterium enrichment culture clone CTBE CDB1010A04 |
| Firmicutes bacterium enrichment culture clone CTBE CDB1006E07 | Firmicutes bacterium enrichment culture clone CTBE CDB1010A07 |
| Firmicutes bacterium enrichment culture clone CTBE CDB1006E08 | Firmicutes bacterium enrichment culture clone CTBE CDB1010A08 |
| Firmicutes bacterium enrichment culture clone CTBE CDB1006E09 | Firmicutes bacterium enrichment culture clone CTBE CDB1010A09 |
| Firmicutes bacterium enrichment culture clone CTBE CDB1006E10 | Firmicutes bacterium enrichment culture clone CTBE CDB1010A12 |
| Firmicutes bacterium enrichment culture clone CTBE CDB1006E11 | Firmicutes bacterium enrichment culture clone CTBE CDB1010B02 |
| Firmicutes bacterium enrichment culture clone CTBE CDB1006F02 | Firmicutes bacterium enrichment culture clone CTBE CDB1010B04 |
| Firmicutes bacterium enrichment culture clone CTBE CDB1006F06 | Firmicutes bacterium enrichment culture clone CTBE CDB1010B07 |
| Firmicutes bacterium enrichment culture clone CTBE CDB1006F07 | Firmicutes bacterium enrichment culture clone CTBE CDB1010B10 |
| Firmicutes bacterium enrichment culture clone CTBE CDB1006F08 | Firmicutes bacterium enrichment culture clone CTBE CDB1010B11 |
| Firmicutes bacterium enrichment culture clone CTBE CDB1006F11 | Firmicutes bacterium enrichment culture clone CTBE CDB1010C01 |
| Firmicutes bacterium enrichment culture clone CTBE CDB1006G03 | Firmicutes bacterium enrichment culture clone CTBE CDB1010C02 |
| Firmicutes bacterium enrichment culture clone CTBE CDB1006G06 | Firmicutes bacterium enrichment culture clone CTBE CDB1010C03 |
| Firmicutes bacterium enrichment culture clone CTBE CDB1006G07 | Firmicutes bacterium enrichment culture clone CTBE CDB1010C05 |
| Firmicutes bacterium enrichment culture clone CTBE CDB1006G08 | Firmicutes bacterium enrichment culture clone CTBE CDB1010C06 |
| Firmicutes bacterium enrichment culture clone CTBE CDB1006G10 | Firmicutes bacterium enrichment culture clone CTBE CDB1010C07 |
| Firmicutes bacterium enrichment culture clone CTBE CDB1006H06 | Firmicutes bacterium enrichment culture clone CTBE CDB1010C08 |
| Firmicutes bacterium enrichment culture clone CTBE CDB1006H07 | Firmicutes bacterium enrichment culture clone CTBE CDB1010C11 |
| Firmicutes bacterium enrichment culture clone CTBE CDB1006H08 | Firmicutes bacterium enrichment culture clone CTBE CDB1010C12 |
| Firmicutes bacterium enrichment culture clone CTBE CDB1006H09 | Firmicutes bacterium enrichment culture clone CTBE CDB1010D07 |
| Firmicutes bacterium enrichment culture clone CTBE CDB1006H10 | Firmicutes bacterium enrichment culture clone CTBE CDB1010D08 |
| Firmicutes bacterium enrichment culture clone CTBE CDB1006H11 | Firmicutes bacterium enrichment culture clone CTBE CDB1010D10 |
| Firmicutes bacterium enrichment culture clone CTBE CDB1006H12 | Firmicutes bacterium enrichment culture clone CTBE CDB1010D12 |
| Firmicutes bacterium enrichment culture clone CTBE CDB1009A05 | Firmicutes bacterium enrichment culture clone CTBE CDB1010E04 |
| Firmicutes bacterium enrichment culture clone CTBE CDB1009A08 | Firmicutes bacterium enrichment culture clone CTBE CDB1010E06 |
| Firmicutes bacterium enrichment culture clone CTBE CDB1009A10 | Firmicutes bacterium enrichment culture clone CTBE CDB1010E07 |
| Firmicutes bacterium enrichment culture clone CTBE CDB1009A12 | Firmicutes bacterium enrichment culture clone CTBE CDB1010E10 |
| Firmicutes bacterium enrichment culture clone CTBE CDB1009B03 | Firmicutes bacterium enrichment culture clone CTBE CDB1010E11 |
| Firmicutes bacterium enrichment culture clone CTBE CDB1009B04 | Firmicutes bacterium enrichment culture clone CTBE CDB1010F01 |
| Firmicutes bacterium enrichment culture clone CTBE CDB1009B07 | Firmicutes bacterium enrichment culture clone CTBE CDB1010F03 |

TABLE 1-continued

| | |
|---|---|
| Firmicutes bacterium enrichment culture clone CTBE CDB1009B08 | Firmicutes bacterium enrichment culture clone CTBE CDB1010F04 |
| Firmicutes bacterium enrichment culture clone CTBE CDB1009C03 | Firmicutes bacterium enrichment culture clone CTBE CDB1010F06 |
| Firmicutes bacterium enrichment culture clone CTBE CDB1009C04 | Firmicutes bacterium enrichment culture clone CTBE CDB1010F07 |
| Firmicutes bacterium enrichment culture clone CTBE CDB1009C06 | Firmicutes bacterium enrichment culture clone CTBE CDB1010F08 |
| Firmicutes bacterium enrichment culture clone CTBE CDB1009C08 | Firmicutes bacterium enrichment culture clone CTBE CDB1010G02 |
| Firmicutes bacterium enrichment culture clone CTBE CDB1009C11 | Firmicutes bacterium enrichment culture clone CTBE CDB1010G03 |
| Firmicutes bacterium enrichment culture clone CTBE CDB1009D03 | Firmicutes bacterium enrichment culture clone CTBE CDB1010G05 |
| Firmicutes bacterium enrichment culture clone CTBE CDB1009D04 | Firmicutes bacterium enrichment culture clone CTBE CDB1010G06 |
| Firmicutes bacterium enrichment culture clone CTBE CDB1009D05 | Firmicutes bacterium enrichment culture clone CTBE CDB1010G07 |
| Firmicutes bacterium enrichment culture clone CTBE CDB1009D06 | Firmicutes bacterium enrichment culture clone CTBE CDB1010G12 |
| Firmicutes bacterium enrichment culture clone CTBE CDB1009D08 | Firmicutes bacterium enrichment culture clone CTBE CDB1010H01 |
| Firmicutes bacterium enrichment culture clone CTBE CDB1010H05 | uncultured feedlot manure bacterium A54 |
| Firmicutes bacterium enrichment culture clone CTBE CDB1010H09 | uncultured feedlot manure bacterium A77 |
| Firmicutes bacterium enrichment culture clone CTBE CDB1010H11 | uncultured feedlot manure bacterium A84 |
| Firmicutes bacterium enrichment culture clone DhR^2/LM-A04 | uncultured feedlot manure bacterium B1 |
| Firmicutes bacterium enrichment culture clone E197 | uncultured feedlot manure bacterium B101 |
| Firmicutes bacterium enrichment culture clone E200 | uncultured feedlot manure bacterium B117 |
| Firmicutes bacterium enrichment culture clone J | uncultured feedlot manure bacterium B126 |
| Firmicutes bacterium enrichment culture clone j220 | uncultured feedlot manure bacterium B17 |
| Firmicutes bacterium enrichment culture clone L12 | uncultured feedlot manure bacterium B2 |
| Firmicutes bacterium enrichment culture clone MLSB6m7B | uncultured feedlot manure bacterium B29 |
| Firmicutes bacterium enrichment culture clone MS_LAC_U11 | uncultured feedlot manure bacterium B51 |
| Firmicutes bacterium enrichment culture clone MS_NAP_N15 | uncultured feedlot manure bacterium B56 |
| Firmicutes bacterium enrichment culture clone MS_NAP_N4 | uncultured feedlot manure bacterium B6 |
| Firmicutes bacterium enrichment culture clone otu_F1 | uncultured feedlot manure bacterium B78 |
| Firmicutes bacterium enrichment culture clone phylotype P9 | uncultured feedlot manure bacterium B8 |
| Firmicutes bacterium enrichment culture clone VNABaOS | uncultured feedlot manure bacterium B81 |
| Firmicutes bacterium enrichment culture clone VNBB003 | uncultured feedlot manure bacterium B82 |
| Firmicutes bacterium enrichment culture clone VNBB004 | uncultured feedlot manure bacterium B85 |
| Firmicutes bacterium enrichment culture clone VNC1B071 | uncultured feedlot manure bacterium B87 |
| Firmicutes bacterium enrichment culture clone WSC-21 | uncultured feedlot manure bacterium B90 |
| Firmicutes bacterium enrichment culture clone WSC-32 | uncultured fermented cassava bacterium M10 |
| Firmicutes bacterium oral clone 24-91 | uncultured fermented cassava bacterium M2 |
| hydrogen production community clone HPB-G1-14 | uncultured fermented cassava bacterium M4 |
| metal-contaminated soil clone K20-13 | uncultured fermented cassava bacterium M5 |
| metal-contaminated soil clone K20-14 | uncultured fermented cassava bacterium M6 |
| metal-contaminated soil clone K20-66 | uncultured fermented cassava bacterium M7 |
| uncultured bacterium #0319-23G15 | uncultured fermented cassava bacterium M8 |
| uncultured bacterium #0319-7G4 | uncultured fermented cassava bacterium M9 |
| uncultured bacterium #0319-7J14 | uncultured Firmicutes bacterium |
| uncultured bacterium CLEAR-17 | uncultured hydrocarbon seep bacterium BPC043 |
| uncultured bacterium CLEAR-33 | uncultured hydrocarbon seep bacterium BPC060 |
| uncultured bacterium CLEAR-6 | uncultured hydrocarbon seep bacterium BPC094 |
| uncultured bacterium EKHO-4 | uncultured Low G + C gram positive bacterium Kmlps3-23 |
| uncultured bacterium mle1-9 | uncultured low G + C gram positive bacterium MT35 |
| uncultured bacterium O11D9 | uncultured low G + C gram positive bacterium MT38 |
| uncultured bacterium SCALE-16 | uncultured low G + C gram positive bacterium n35r |
| uncultured bacterium SJA-112 | uncultured low G + C Gram-positive bacterium |
| uncultured bacterium SJA-118 | uncultured low G + C Gram-positive bacterium 102ev |
| uncultured bacterium SJA-131 | uncultured low G + C Gram-positive bacterium 105ev |
| uncultured bacterium SJA-136 | uncultured low G + C Gram-positive bacterium 108ev |
| uncultured bacterium SJA-143 | uncultured low G + C Gram-positive bacterium 10ev |
| uncultured bacterium SJA-173 | uncultured low G + C Gram-positive bacterium 111ev |
| uncultured bacterium SJA-29 | uncultured low G + C Gram-positive bacterium 119ev |
| uncultured bacterium SJA-65 | uncultured low G + C Gram-positive bacterium 121ev |
| uncultured bacterium SJA-84 | uncultured low G + C Gram-positive bacterium 129ev |
| uncultured bacterium tbr1-1 | uncultured low G + C Gram-positive bacterium 12ev |
| uncultured bacterium tbr1-10 | uncultured low G + C Gram-positive bacterium 132ev |
| uncultured bacterium tbr1-8 | uncultured low G + C Gram-positive bacterium 135ev |
| uncultured bacterium tbr1-9 | uncultured low G + C Gram-positive bacterium 13ev |
| uncultured bacterium tbr4-15 | uncultured low G + C Gram-positive bacterium 145ev |
| uncultured bacterium tbr4-78 | uncultured low G + C Gram-positive bacterium 146ev |
| uncultured eubacterium WCHA1-17 | uncultured low G + C Gram-positive bacterium 151ev |
| uncultured eubacterium WCHA1-45 | uncultured low G + C Gram-positive bacterium 178ev |
| uncultured eubacterium WCHA1-53 | uncultured low G + C Gram-positive bacterium 17ev |
| uncultured eubacterium WCHB1-20 | uncultured low G + C Gram-positive bacterium 188ev |
| uncultured eubacterium WCHB1-21 | uncultured low G + C Gram-positive bacterium 208ev |
| uncultured eubacterium WCHB1-49 | uncultured low G + C Gram-positive bacterium 20ev |
| uncultured eubacterium WCHB1-54 | uncultured low G + C Gram-positive bacterium 219ev |
| uncultured eubacterium WCHB1-71 | uncultured low G + C Gram-positive bacterium 225ev |
| uncultured eubacterium WCHB1-77 | uncultured low G + C Gram-positive bacterium 228ev |
| uncultured eubacterium WCHB1-82 | uncultured low G + C Gram-positive bacterium 236ev |
| uncultured eubacterium WCHB1-84 | uncultured low G + C Gram-positive bacterium 243ev |
| uncultured eubacterium WCHB1-89 | uncultured low G + C Gram-positive bacterium 248ev |
| uncultured eubacterium WFeA1-16 | uncultured low G + C Gram-positive bacterium 261ev |
| uncultured eubacterium WsCH1 | uncultured low G + C Gram-positive bacterium 274ev |
| uncultured eubacterium WsCH5 | uncultured low G + C Gram-positive bacterium 275ev |
| uncultured eubacterium WsCH8 | uncultured low G + C Gram-positive bacterium 28ev |
| uncultured feedlot manure bacterium A13 | uncultured low G + C Gram-positive bacterium 291ev |
| uncultured feedlot manure bacterium A18 | |

TABLE 1-continued

| | |
|---|---|
| uncultured feedlot manure bacterium A20 | uncultured low G + C Gram-positive bacterium 29ev |
| uncultured low G + C Gram-positive bacterium 301ev | unidentified rumen bacterium JW19 |
| uncultured low G + C Gram-positive bacterium 303ev | unidentified rumen bacterium JW21 |
| uncultured low G + C Gram-positive bacterium 306ev | unidentified rumen bacterium JW23 |
| uncultured low G + C Gram-positive bacterium 307ev | unidentified rumen bacterium JW24 |
| uncultured low G + C Gram-positive bacterium 310ev | unidentified rumen bacterium JW25 |
| uncultured low G + C Gram-positive bacterium 33ev | unidentified rumen bacterium JW26 |
| uncultured low G + C Gram-positive bacterium 340ev | unidentified rumen bacterium JW28 |
| uncultured low G + C Gram-positive bacterium 355ev | unidentified rumen bacterium JW29 |
| uncultured low G + C Gram-positive bacterium 358ev | unidentified rumen bacterium JW3 |
| uncultured low G + C Gram-positive bacterium 370ev | unidentified rumen bacterium JW32 |
| uncultured low G + C Gram-positive bacterium 371ev | unidentified rumen bacterium JW33 |
| uncultured low G + C Gram-positive bacterium 372ev | unidentified rumen bacterium JW5 |
| uncultured low G + C Gram-positive bacterium 377ev | unidentified rumen bacterium JW6 |
| uncultured low G + C Gram-positive bacterium 380ev | unidentified rumen bacterium RC15 |
| uncultured low G + C Gram-positive bacterium 398ev | unidentified rumen bacterium RC6 |
| uncultured low G + C Gram-positive bacterium 400ev | unidentified rumen bacterium RCP1 |
| uncultured low G + C Gram-positive bacterium 411ev | unidentified rumen bacterium RF3 |
| uncultured low G + C Gram-positive bacterium 414ev | |
| uncultured low G + C Gram-positive bacterium 430ev | |
| uncultured low G + C Gram-positive bacterium 433ev | |
| uncultured low G + C Gram-positive bacterium 437ev | |
| uncultured low G + C Gram-positive bacterium 43ev | |
| uncultured low G + C Gram-positive bacterium 444ev | |
| uncultured low G + C Gram-positive bacterium 48ev | |
| uncultured low G + C Gram-positive bacterium 53ev | |
| uncultured low G + C Gram-positive bacterium 59ev | |
| uncultured low G + C Gram-positive bacterium 5ev | |
| uncultured low G + C Gram-positive bacterium 75ev | |
| uncultured low G + C Gram-positive bacterium 77ev | |
| uncultured low G + C Gram-positive bacterium 78ev | |
| uncultured low G + C Gram-positive bacterium 7ev | |
| uncultured low G + C Gram-positive bacterium 82ev | |
| uncultured low G + C Gram-positive bacterium 91ev | |
| uncultured low G + C Gram-positive bacterium 92ev | |
| uncultured low G + C Gram-positive bacterium 98ev | |
| uncultured low G + C Gram-positive bacterium clone OPB54 | |
| uncultured low G + C Gram-positive bacterium SHD-209 | |
| uncultured Low G + C Gram-positive bacterium Sva0855 | |
| uncultured Low G + C Gram-positive bacterium Sva1064 | |
| uncultured low-GC gram+ bacterium kpa86rc | |
| uncultured marine Gram-positive bacterium DH148-Z18 | |
| uncultured sludge bacterium A28 | |
| uncultured synthetic wastewater bacterium tmbr11-29 | |
| uncultured synthetic wastewater bacterium tmbr11-6 | |
| uncultured synthetic wastewater bacterium tmbr11-7 | |
| uncultured synthetic wastewater bacterium tmbr15-12 | |
| uncultured synthetic wastewater bacterium tmbr15-20 | |
| uncultured synthetic wastewater bacterium tmbr15-26 | |
| unidentified *eubacterium* RB04 | |
| unidentified *eubacterium* RB05 | |
| unidentified *eubacterium* RB07 | |
| unidentified *eubacterium* RB08 | |
| unidentified *eubacterium* RB16 | |
| unidentified *eubacterium* RB17 | |
| unidentified *eubacterium* RB29 | |
| unidentified *eubacterium* RB38 | |
| unidentified low G + C gram-positive bacterium | |
| unidentified oil field bacterium EUBA7 | |
| unidentified oil field bacterium SYNE4 | |
| unidentified rumen bacterium 12-110 | |
| unidentified rumen bacterium 12-116 | |
| unidentified rumen bacterium 12-124 | |
| unidentified rumen bacterium 12-128 | |
| unidentified rumen bacterium 12-74 | |
| unidentified rumen bacterium 12-76 | |
| unidentified rumen bacterium 30-2 | |
| unidentified rumen bacterium 30-20 | |
| unidentified rumen bacterium JW11 | |
| unidentified rumen bacterium JW13 | |
| unidentified rumen bacterium JW18 | |

Genus: Bacteroidetes

| | |
|---|---|
| Bacteroidia | Flavobacteria bacterium PG2S01 |
| Bacteroidales | Flavobacteria bacterium S1-62 |
| Bacteroidaceae | Flavobacteria bacterium SC2 |
| Marinilabiliaceae | Flavobacteria bacterium SC4 |
| Porphyromonadaceae | Flavobacteria bacterium SG-13 |
| Prevotellaceae | Flavobacteria bacterium SG-18 |
| Rikenellaceae | Flavobacteria bacterium SO53PV |

TABLE 1-continued unclassified Bacteroidales
environmental samples
unclassified Bacteroidia
Bacteroidia bacterium canine oral taxon 041
Bacteroidia bacterium canine oral taxon 187
Bacteroidia bacterium canine oral taxon 301
Bacteroidia bacterium canine oral taxon 387
environmental samples
uncultured Bacteroidia bacterium
Cytophagia
Cytophagales
Cyclobacteriaceae
Cytophagaceae
Flammeovirgaceae
unclassified Cytophagales
environmental samples
uncultured Cytophagia bacterium
Flavobacteriia
Flavobacteriales
Blattabacteriaceae
Cryomorphaceae
Flavobacteriaceae
Schleiferiaceae
unclassified Flavobacteriales
environmental samples
unclassified Flavobacteriia
aquatic bacterium STS_R2A_06
Flavobacteria bacterium 'BSD S1 20'
Flavobacteria bacterium 7515
Flavobacteria bacterium 7531
Flavobacteria bacterium 7536
Flavobacteria bacterium 7538
Flavobacteria bacterium 7575
Flavobacteria bacterium 7583
Flavobacteria bacterium 7586
Flavobacteria bacterium b42
Flavobacteria bacterium B6 ZZ-2008
Flavobacteria bacterium BBFL7
Flavobacteria bacterium BR4
Flavobacteria bacterium CC-AMO-30D
Flavobacteria bacterium Ellin6119
Flavobacteria bacterium Ellin6120
Flavobacteria bacterium FB1
Flavobacteria bacterium HMD1033
Flavobacteria bacterium HMD1041
Flavobacteria bacterium HMD1051
Flavobacteria bacterium HTCC2962
Flavobacteria bacterium IAJ6
Flavobacteria bacterium Ib001
Flavobacteria bacterium Ib002
Flavobacteria bacterium Ib003
Flavobacteria bacterium Ib004
Flavobacteria bacterium Ib005
Flavobacteria bacterium Ib006
Flavobacteria bacterium KF030
Flavobacteria bacterium MS024-2A
Flavobacteria bacterium MS024-3C
Flavobacteria bacterium MS190-1F
Flavobacteria bacterium NAMAF006
Sphingobacteriales
Chitinophagaceae
Saprospiraceae
Sphingobacteriaceae
unclassified Sphingobacteriales
Sphingobacteriales genera incertae sedis
environmental samples
unclassified Sphingobacteriia
barley rhizosphere bacterium JJ-1452
barley rhizosphere bacterium JJ-1607
barley rhizosphere bacterium JJ-1618
barley rhizosphere bacterium JJ-1649
barley rhizosphere bacterium JJ-1870
barley rhizosphere bacterium JJ-1894
barley rhizosphere bacterium JJ-2060
barley rhizosphere bacterium JJ-220
barley rhizosphere bacterium JJ-2607
barley rhizosphere bacterium JJ-3208
barley rhizosphere bacterium JJ-3210
barley rhizosphere bacterium JJ-3233
barley rhizosphere bacterium JJ-3427
Flavobacteria bacterium SOMBO59
Flavobacteria bacterium SR3
Flavobacteria bacterium TW-JL-17
Flavobacteria bacterium TW-JL-80
Flavobacteria bacterium UST061013-075
Flavobacteria bacterium UST061013-076
Flavobacteria bacterium Yb001
Flavobacteria bacterium Yb004
Flavobacteria bacterium Yb008
Flavobacteria bacterium Yb009
Flavobacteria bacterium Yb011
Flavobacteria bacterium ZL-3
Flavobacteria bacterium ZL-4
Flavobacteria endosymbiont of *Homalodisca coagulata*
Flavobacteria symbiont 1 of *Acromyrmex otcospinosus*
Flavobacteria symbiont 2 of *Acromyrmex otcospinosus*
Flavobacteria symbiont 3 of *Acromyrmex otcospinosus*
Flavobacteria symbiont 4 of *Acromyrmex otcospinosus*
Flavobacteria symbiont 5 of *Acromyrmex otcospinosus*
Flavobacteriia bacterium hmp_mda_pilot_jcvi_0014
marine bacterium MBIC1357
marine bacterium P99-3
Flavobacteria sp. MaPt5
environmental samples
Flavobacteria bacterium enrichment culture clone SMEC3
Flavobacteria bacterium enrichment culture clone YYS1
Flavobacteria bacterium enrichment culture clone YYS3
Flavobacteriia bacterium enrichment culture clone 1-4-3
Flavobacteriia bacterium enrichment culture clone 2-1-3
Flavobacteriia bacterium enrichment culture clone 2-3-2
Flavobacteriia bacterium enrichment culture clone 2-3-3
Flavobacteriia bacterium enrichment culture clone 2-4-3
Flavobacteriia bacterium enrichment culture clone AB5
uncultured bacterium #0319-8B8
uncultured bacterium #0319-8J1
uncultured bacterium BURTON-13
uncultured bacterium BURTON-18
uncultured bacterium BURTON-20
uncultured bacterium BURTON-28
uncultured bacterium BURTON-31
uncultured bacterium BURTON-38
uncultured bacterium BURTON-44
uncultured bacterium BURTON-50
uncultured bacterium BURTON-52
uncultured bacterium BURTON-55
uncultured bacterium CLEAR-5
uncultured bacterium ORGANIC-5
uncultured bacterium ORGANIC-6
uncultured bacterium ORGANIC-7
uncultured bacterium TAYNAYA-16
uncultured bacterium TAYNAYA-4
uncultured bacterium TAYNAYA-5
uncultured bacterium TAYNAYA-6
uncultured bacterium TAYNAYA-7
uncultured *eubacterium* 4-19
uncultured *eubacterium* 4-36
uncultured Flavobacteriia bacterium
uncultured *flavobacterium* DGGE band PSBAC-1
Sphingobacteriia
*Cardinium* endosymbiont of *Culicoides lungchiensis*
*Cardinium* endosymbiont of *Culicoides ohmorii*
*Cardinium* endosymbiont of *Culicoides peregrinus*
*Cardinium* endosymbiont of *Cybaeota nana*
*Cardinium* endosymbiont of *Cybaeus chauliodous*
*Cardinium* endosymbiont of *Cybaeus chaulodious*
*Cardinium* endosymbiont of *Cybaeus eutypus*
*Cardinium* endosymbiont of *Cybaeus hesper*
*Cardinium* endosymbiont of *Cybaeus morosus*
*Cardinium* endosymbiont of *Cybaeus multnoma*
*Cardinium* endosymbiont of *Cybaeus paralypropriapus*
*Cardinium* endosymbiont of *Cybaeus penedentatus*
*Cardinium* endosymbiont of *Cybaeus reticulatus*
*Cardinium* endosymbiont of *Cybaeus sanbruno*
*Cardinium* endosymbiont of *Cybaeus signifer*
*Cardinium* endosymbiont of *Cybaeus somesbar*
*Cardinium* endosymbiont of *Cybaeus waynei*
*Cardinium* endosymbiont of *Dermanyssus gallinae*
*Cardinium* endosymbiont of *Encarsia hispida*
*Cardinium* endosymbiont of *Encarsia inaron*
*Cardinium* endosymbiont of *Encarsia pergandiella*

TABLE 1-continued

| | |
|---|---|
| barley rhizosphere bacterium JJ-3776 | *Cardinium* endosymbiont of *Eotetranychus suginamensis* |
| barley rhizosphere bacterium JJ-394 | *Cardinium* endosymbiont of *Euides speciosa* |
| barley rhizosphere bacterium JJ-4019 | *Cardinium* endosymbiont of *Formica cinerea* |
| glacier bacterium FJS5 | *Cardinium* endosymbiont of *Harmalia sirokata* |
| marine bacterium MSC1 | *Cardinium* endosymbiont of *Hemiberlesia palmae* |
| Sphingobacteria bacterium 2790 | *Cardinium* endosymbiont of *Holocnemus pluchei* |
| Sphingobacteria bacterium BC4 | *Cardinium* endosymbiont of honey bee mite |
| Sphingobacteria bacterium Ellin6121 | *Cardinium* endosymbiont of *Howardia biclavis* |
| Sphingobacteria bacterium GWS-BW-H154 | *Cardinium* endosymbiont of *Indozuriel dantur* |
| Sphingobacteria bacterium GWS-BW-H159 | *Cardinium* endosymbiont of *Ixodes scapularis* |
| Sphingobacteria bacterium JAM-BA0302 | *Cardinium* endosymbiont of *Leiobunum vittatum* |
| Sphingobacteria bacterium ROi22 | *Cardinium* endosymbiont of *Lepidosaphes pinnaeformis* |
| Sphingobacteria bacterium RYG | *Cardinium* endosymbiont of *Leucaspis pusilla* |
| Sphingobacteria bacterium SH-52 | *Cardinium* endosymbiont of *Nitocra spinipes* |
| Sphingobacteria bacterium SKA50 | *Cardinium* endosymbiont of *Oceanaspidiotus spinosus* |
| Sphingobacteria bacterium SKA51 | *Cardinium* endosymbiont of *Oedothorax gibbosus* |
| Sphingobacteria bacterium WF20 | *Cardinium* endosymbiont of *Oedothorax retusus* |
| Sphingobacteria bacterium WWH129 | *Cardinium* endosymbiont of *Oligonychus ilicis* |
| environmental samples | *Cardinium* endosymbiont of *Palinaspis quohogiformis* |
| Sphingobacteria bacterium enrichment culture clone AB7 | *Cardinium* endosymbiont of *Pallulaspis ephedrae* |
| Sphingobacteria bacterium enrichment culture DGGE band 8 | *Cardinium* endosymbiont of *Panonychus ulmi* |
| Sphingobacteria bacterium enrichment culture DGGE band 9 | *Cardinium* endosymbiont of *Petrobia harti* |
| uncultured Sphingobacteria bacterium | *Cardinium* endosymbiont of *Phalangium opilio* |
| *Sunxiuqinia* | *Cardinium* endosymbiont of *Plagiomerus diaspidis* |
| *Sunxiuqinia elliptica* | *Cardinium* endosymbiont of *Poliaspis media* |
| *Sunxiuqinia* sp. CAU1234 | *Cardinium* endosymbiont of *Protargionia larreae* |
| *Sunxiuqinia* sp. JNU-J035 | *Cardinium* endosymbiont of *Rilaena triangularis* |
| *Sunxiuqinia* sp. JNU-SGY008 | *Cardinium* endosymbiont of *Scaphoideus titanus* |
| *Sunxiuqinia* sp. SCSIO N0430 | *Cardinium* endosymbiont of *Sogatella furcifera* |
| unclassified Bacteroidetes | *Cardinium* endosymbiont of *Tetranychus cinnabarinus* |
| *Bifissio* | *Cardinium* endosymbiont of *Tetranychus puearicola* |
| *Bifissio spartinae* | *Cardinium* endosymbiont of *Tetranychus urticae* |
| environmental samples | *Cardinium* endosymbiont of *Tetranychus urticae* red form A |
| *Candidatus* Amoebophilus | *Cardinium* endosymbiont of *Tetranychus urticae* red form B |
| *Candidatus* Amoebophilus *asiaticus* | *Cardinium* endosymbiont of *Tetranychus urticae* red form C |
| endosymbiont of *Acanthamoeba* sp. (Hungarian isolate) | *Cardinium* endosymbiont of *Unaspis euonymi* |
| environmental samples | *Cardinium* symbiont of *Neoseiulus paspalivorus* |
| *Candidatus* Cardinium | *Candidatus* Cardinium sp. Sigean4 |
| *Candidatus* Cardinium *hertigii* | *Cardinium* endosymbiont of Anyphaenidae sp. |
| *Cardinium* endosymbiont of *Abgrallaspis degenerata* | *Cardinium* endosymbiont of *Aonidomytilus* sp. |
| *Cardinium* endosymbiont of *Aleurodicus dispersus* | *Cardinium* endosymbiont of *Aphytis* sp. |
| *Cardinium* endosymbiont of *Amphitetranychus quercivorus* | *Cardinium* endosymbiont of Araneidae sp. |
| *Cardinium* endosymbiont of *Aspediotus paranerii* | *Cardinium* endosymbiont of *Brevipalpus* sp. |
| *Cardinium* endosymbiont of *Aspidiotus nerii* | *Cardinium* endosymbiont of *Chaetodactylus* sp. |
| *Cardinium* endosymbiont of *Bemisia tabaci* | *Cardinium* endosymbiont of *Leiobunum* sp. |
| *Cardinium* endosymbiont of *Bryobia rubrioculus* | *Cardinium* endosymbiont of *Marietta* sp. |
| *Cardinium* endosymbiont of *Bryobia sarothamni* | *Cardinium* endosymbiont of *Melanaspis* sp. |
| *Cardinium* endosymbiont of *Chionaspis heterophyllae* | *Cardinium* endosymbiont of *Prodigiaspis* sp. |
| *Cardinium* endosymbiont of *Culicoides arakawae* | *Cardinium* endosymbiont of *Pseudoparlatoria* sp. |
| *Cardinium* endosymbiont of *Rilaena* sp. | bacterium Phenol-4 |
| *Cardinium* endosymbiont of *Salticidae* sp. | bacterium SB 12 |
| *Cardinium* endosymbiont of *Tetragnathidae* sp. | bacterium XB45 |
| *Cardinium* endosymbiont of *Theridiidae* sp. | Bacteroidetes bacterium '10.5 MW-13' |
| environmental samples | Bacteroidetes bacterium '10.5 MW-17' |
| *Candidatus* Paenicardinium | Bacteroidetes bacterium '13.5 MW-13' |
| *Candidatus* Paenicardinium *endonii* | Bacteroidetes bacterium '13.5 MW-16' |
| *Marinifilum* | Bacteroidetes bacterium '14.5 MW-30' |
| *Marinifilum fragile* | Bacteroidetes bacterium '5.5 MW-14' |
| *Marinifilum* sp. CECT 7448 | Bacteroidetes bacterium '5.6 MW-6' |
| *Marinifilum* sp. JNU-H032 | Bacteroidetes bacterium '6.5 MW-11' |
| *Marinifilum* sp. JNU-H036 | Bacteroidetes bacterium '7.3 MW-12' |
| *Marinifilum* sp. JNU-J034 | Bacteroidetes bacterium '7.5 MW-10' |
| *Marinifilum* sp. KYW 585 | Bacteroidetes bacterium '7.5 MW-12' |
| environmental samples | Bacteroidetes bacterium '8.3 MW-7' |
| *Prolixibacter* | Bacteroidetes bacterium '9.3 MW-13' |
| *Prolixibacter bellariivorans* | Bacteroidetes bacterium 'Oral Taxon 274' |
| environmental samples | Bacteroidetes bacterium 'PS-7' |
| truffle symbionts | Bacteroidetes bacterium 0-9 |
| *Tuber borchii* symbiont b-10RA | Bacteroidetes bacterium 109-13 |
| *Tuber borchii* symbiont b-17BO | Bacteroidetes bacterium 11B |
| *Tuber borchii* symbiont b-1BO | Bacteroidetes bacterium 13456 |
| *Tuber borchii* symbiont b-Z43 | Bacteroidetes bacterium 1_(MB)_12.9mbsf |
| *Venteria* | Bacteroidetes bacterium 20/6 |
| *Venteria marina* | Bacteroidetes bacterium 215-60 |
| unclassified Bacteroidetes (miscellaneous) | Bacteroidetes bacterium 215-9 |
| abyssal strain AII3 | Bacteroidetes bacterium 23-9 |
| abyssal strain AIII4 | Bacteroidetes bacterium 2bG |
| Antarctic bacterium L2 | Bacteroidetes bacterium 3-6 |
| Antarctic bacterium R-7515 | Bacteroidetes bacterium 37LGx-1 |
| Antarctic bacterium R-7550 | Bacteroidetes bacterium 37LGy-2 |

TABLE 1-continued

| | |
|---|---|
| Antarctic bacterium R-7572 | Bacteroidetes bacterium 4_C16_35 |
| Antarctic bacterium R-7579 | Bacteroidetes bacterium 4F6B |
| Antarctic bacterium R-7666 | Bacteroidetes bacterium 5-4 |
| Antarctic bacterium R-7933 | Bacteroidetes bacterium 5-5 |
| Antarctic bacterium R-8963 | Bacteroidetes bacterium 6E |
| Antarctic bacterium R-9003 | Bacteroidetes bacterium 7-11 |
| Antarctic bacterium R-9033 | Bacteroidetes bacterium 7_(MB)_12.9mbsf |
| Antarctic bacterium R-9217 | Bacteroidetes bacterium 8_(MB)_12.9mbsf |
| Arctic sea ice bacterium AWS-4M1 | Bacteroidetes bacterium A973 |
| Arctic sea ice bacterium AWS-4M3 | Bacteroidetes bacterium ABF3A |
| Arctic sea ice bacterium AWS-4M4 | Bacteroidetes bacterium Acht4 |
| Arctic sea ice bacterium AWS-4M5 | Bacteroidetes bacterium AH23 |
| Arctic sea ice bacterium AWS-4M6 | Bacteroidetes bacterium AH26 |
| Arctic sea ice bacterium AWS-4M7 | Bacteroidetes bacterium AH7 |
| Arctic sea ice bacterium AWS-4M8 | Bacteroidetes bacterium AH8 |
| Arctic sea ice bacterium AWS-4U1 | Bacteroidetes bacterium AK43 6.1 |
| Arctic sea ice bacterium AWS-6B2 | Bacteroidetes bacterium AKB-K1-255 |
| Arctic sea ice bacterium AWS-7B1 | Bacteroidetes bacterium AL33 9.1 |
| Arctic sea ice bacterium AWS-7B3 | Bacteroidetes bacterium AL42 2.1 |
| Arctic sea ice bacterium AWS-7B4 | Bacteroidetes bacterium ALI-INI1 |
| Arctic sea ice bacterium AWS-7B8 | Bacteroidetes bacterium ALI-INI12 |
| bacterium 1.3.10 | Bacteroidetes bacterium ALI-INI24 |
| bacterium 5.3.10 | Bacteroidetes bacterium Ana1 |
| bacterium AG | Bacteroidetes bacterium Ana2 |
| bacterium AH47 | Bacteroidetes bacterium ANT9105 |
| bacterium BA | Bacteroidetes bacterium ANT9285 |
| bacterium BD | Bacteroidetes bacterium ARK10264 |
| bacterium BE | Bacteroidetes bacterium ArSB |
| bacterium D21 | Bacteroidetes bacterium b1b1 |
| bacterium H-S3 | Bacteroidetes bacterium b1b2 |
| bacterium KHN36A | Bacteroidetes bacterium b1b3 |
| bacterium Km1 | Bacteroidetes bacterium BAL102 |
| bacterium Km4 | Bacteroidetes bacterium BAL103 |
| bacterium Km5 | Bacteroidetes bacterium BAL120 |
| bacterium KmC | Bacteroidetes bacterium BAL138 |
| bacterium ML24 | Bacteroidetes bacterium BAL139 |
| bacterium P16L841 | Bacteroidetes bacterium BAL140 |
| bacterium P2G231 | Bacteroidetes bacterium BAL141 |
| bacterium PB90-2 | Bacteroidetes bacterium BAL142 |
| Bacteroidetes bacterium BAL147 | Bacteroidetes bacterium G4 |
| Bacteroidetes bacterium BAL151 | Bacteroidetes bacterium G8_24 |
| Bacteroidetes bacterium BAL151.1 | Bacteroidetes bacterium GCM36 |
| Bacteroidetes bacterium BAL151.2 | Bacteroidetes bacterium GCM63 |
| Bacteroidetes bacterium BAL152 | Bacteroidetes bacterium GCM65 |
| Bacteroidetes bacterium BAL153 | Bacteroidetes bacterium GCM68 |
| Bacteroidetes bacterium BAL154 | Bacteroidetes bacterium GCM69 |
| Bacteroidetes bacterium BAL175 | Bacteroidetes bacterium GM10 |
| Bacteroidetes bacterium BAL176 | Bacteroidetes bacterium GM14 |
| Bacteroidetes bacterium BAL180 | Bacteroidetes bacterium GM19 |
| Bacteroidetes bacterium BAL192 | Bacteroidetes bacterium GM24 |
| Bacteroidetes bacterium BAL210 | Bacteroidetes bacterium GM31 |
| Bacteroidetes bacterium BAL214 | Bacteroidetes bacterium GM34 |
| Bacteroidetes bacterium BAL215 | Bacteroidetes bacterium GM36 |
| Bacteroidetes bacterium BAL216 | Bacteroidetes bacterium GM51 |
| Bacteroidetes bacterium BAL222 | Bacteroidetes bacterium GM57 |
| Bacteroidetes bacterium BAL223 | Bacteroidetes bacterium GM61 |
| Bacteroidetes bacterium BAL224 | Bacteroidetes bacterium GM71 |
| Bacteroidetes bacterium BAL232 | Bacteroidetes bacterium GM80 |
| Bacteroidetes bacterium BAL240 | Bacteroidetes bacterium GMD13F04 |
| Bacteroidetes bacterium BAL241 | Bacteroidetes bacterium GMD15A07 |
| Bacteroidetes bacterium BAL242 | Bacteroidetes bacterium GMD16C04 |
| Bacteroidetes bacterium BAL254 | Bacteroidetes bacterium GMD16C10 |
| Bacteroidetes bacterium BAL256 | Bacteroidetes bacterium GMD37F7 |
| Bacteroidetes bacterium BAL257 | Bacteroidetes bacterium GMD38C4 |
| Bacteroidetes bacterium BAL268 | Bacteroidetes bacterium GMDJE10E6 |
| Bacteroidetes bacterium BAL269 | Bacteroidetes bacterium GMDsbC3 |
| Bacteroidetes bacterium BAL273 | Bacteroidetes bacterium GMDsbC7 |
| Bacteroidetes bacterium BAL63 | Bacteroidetes bacterium GMDsbM5 |
| Bacteroidetes bacterium BAL64 | Bacteroidetes bacterium GS |
| Bacteroidetes bacterium BAL65 | Bacteroidetes bacterium GWS-BW-H4M |
| Bacteroidetes bacterium BAL81 | Bacteroidetes bacterium GWS-BW-H70M |
| Bacteroidetes bacterium BAL84 | Bacteroidetes bacterium H30 |
| Bacteroidetes bacterium BAL87 | Bacteroidetes bacterium HH42 |
| Bacteroidetes bacterium BAL93 | Bacteroidetes bacterium HNR18 |
| Bacteroidetes bacterium BAL97 | Bacteroidetes bacterium HPC1 |
| Bacteroidetes bacterium BC2_TSA1F2 | Bacteroidetes bacterium HY2 |
| Bacteroidetes bacterium beta1a-PCAi-E3-2 | Bacteroidetes bacterium HY3 |
| Bacteroidetes bacterium beta2a-PCAi-E3-2 | Bacteroidetes bacterium I-116-1 |
| Bacteroidetes bacterium C-1 | Bacteroidetes bacterium II-116-5 |
| Bacteroidetes bacterium C-12 | Bacteroidetes bacterium J2012s |

TABLE 1-continued

| | |
|---|---|
| Bacteroidetes bacterium C-19 | Bacteroidetes bacterium J2051s |
| Bacteroidetes bacterium C-3 | Bacteroidetes bacterium J2117m |
| Bacteroidetes bacterium C-7 | Bacteroidetes bacterium J879 |
| Bacteroidetes bacterium CH1i | Bacteroidetes bacterium Jbg17 |
| Bacteroidetes bacterium CH6i | Bacteroidetes bacterium Jbg18 |
| Bacteroidetes bacterium CHC10 | Bacteroidetes bacterium Jbg19 |
| Bacteroidetes bacterium CHC2 | Bacteroidetes bacterium Jbg20 |
| Bacteroidetes bacterium CHNCT12 | Bacteroidetes bacterium Jbg21 |
| Bacteroidetes bacterium CK32 5.3 | Bacteroidetes bacterium Jbg22 |
| Bacteroidetes bacterium CN19M_LM14 | Bacteroidetes bacterium JC-3 |
| Bacteroidetes bacterium CN3G2-10 | Bacteroidetes bacterium JGI 0000113-A17 |
| Bacteroidetes bacterium CN9_LM99 | Bacteroidetes bacterium JGI 0000113-N05 |
| Bacteroidetes bacterium CNC19 | Bacteroidetes bacterium JGI 0001001-A08 |
| Bacteroidetes bacterium CNU-914 | Bacteroidetes bacterium JGI 0002002-N21 |
| Bacteroidetes bacterium CNX-216 | Bacteroidetes bacterium JGI 0002003-008 |
| Bacteroidetes bacterium CSC16 | Bacteroidetes bacterium JGI 0002005-G08 |
| Bacteroidetes bacterium D295 | Bacteroidetes bacterium JGI 0002005-I10 |
| Bacteroidetes bacterium E42 | Bacteroidetes bacterium JGI 0002005-J14 |
| Bacteroidetes bacterium EC2 | Bacteroidetes bacterium JGI 0002005-K22 |
| Bacteroidetes bacterium ectosymbiont of Rimicaris exoculata | Bacteroidetes bacterium JS5 |
| Bacteroidetes bacterium Eg28 | Bacteroidetes bacterium K2 |
| Bacteroidetes bacterium EK-I72 | Bacteroidetes bacterium K3 |
| Bacteroidetes bacterium endosymbiont of Bemisia tabaci | Bacteroidetes bacterium K383 |
| Bacteroidetes bacterium endosymbiont of Sogatella furcifera | Bacteroidetes bacterium K4 |
| Bacteroidetes bacterium FH4 | Bacteroidetes bacterium K5 |
| Bacteroidetes bacterium FH5 | Bacteroidetes bacterium K6-27 |
| Bacteroidetes bacterium G13a-B | Bacteroidetes bacterium KILT1 |
| Bacteroidetes bacterium G22 | Bacteroidetes bacterium KJY |
| Bacteroidetes bacterium G33 | Bacteroidetes bacterium Ko310 |
| Bacteroidetes bacterium Ko510 | Bacteroidetes bacterium oral taxon 281 |
| Bacteroidetes bacterium Ko706 | Bacteroidetes bacterium oral taxon 318 |
| Bacteroidetes bacterium Ko710 | Bacteroidetes bacterium oral taxon 320 |
| Bacteroidetes bacterium KUAC3043 cb 68 | Bacteroidetes bacterium oral taxon 321 |
| Bacteroidetes bacterium L2-109 | Bacteroidetes bacterium oral taxon 365 |
| Bacteroidetes bacterium LaBonte_alg11 | Bacteroidetes bacterium oral taxon 436 |
| Bacteroidetes bacterium LC9 | Bacteroidetes bacterium oral taxon 503 |
| Bacteroidetes bacterium LD83 | Bacteroidetes bacterium oral taxon 505 |
| Bacteroidetes bacterium LD84 | Bacteroidetes bacterium oral taxon 507 |
| Bacteroidetes bacterium LJ | Bacteroidetes bacterium oral taxon 509 |
| Bacteroidetes bacterium LYH | Bacteroidetes bacterium oral taxon 511 |
| Bacteroidetes bacterium M-phe-1 | Bacteroidetes bacterium oral taxon 516 |
| Bacteroidetes bacterium M2 | Bacteroidetes bacterium oral taxon B68 |
| Bacteroidetes bacterium M3 | Bacteroidetes bacterium oral taxon D27 |
| Bacteroidetes bacterium M4 | Bacteroidetes bacterium oral taxon E48 |
| Bacteroidetes bacterium M5 | Bacteroidetes bacterium oral taxon F31 |
| Bacteroidetes bacterium M5H2 | Bacteroidetes bacterium oral taxon F44 |
| Bacteroidetes bacterium M6 | Bacteroidetes bacterium oral taxon F60 |
| Bacteroidetes bacterium M7 | Bacteroidetes bacterium oral taxon F69 |
| Bacteroidetes bacterium M775 | Bacteroidetes bacterium oral taxon F70 |
| Bacteroidetes bacterium MA051 | Bacteroidetes bacterium oral taxon G44 |
| Bacteroidetes bacterium MA052 | Bacteroidetes bacterium oral taxon G83 |
| Bacteroidetes bacterium Mo-0.2plat-K3 | Bacteroidetes bacterium ORNL_1UT_ORNL_28 |
| Bacteroidetes bacterium Mo-0.2plat-K5 | Bacteroidetes bacterium OS-21A |
| Bacteroidetes bacterium MO17 | Bacteroidetes bacterium OS-26C |
| Bacteroidetes bacterium MO18 | Bacteroidetes bacterium P073B |
| Bacteroidetes bacterium MO48 | Bacteroidetes bacterium P2 |
| Bacteroidetes bacterium MO49 | Bacteroidetes bacterium P3 |
| Bacteroidetes bacterium MO54 | Bacteroidetes bacterium P3(2010) |
| Bacteroidetes bacterium MOLA 103 | Bacteroidetes bacterium P373 |
| Bacteroidetes bacterium MOLA 411 | Bacteroidetes bacterium P4 |
| Bacteroidetes bacterium MOLA 450 | Bacteroidetes bacterium P4(2013) |
| Bacteroidetes bacterium MU1 | Bacteroidetes bacterium PD4-MRL |
| Bacteroidetes bacterium MU2 | Bacteroidetes bacterium PM13 |
| Bacteroidetes bacterium MWH-CFBk5 | Bacteroidetes bacterium PM24 |
| Bacteroidetes bacterium Mwo1 | Bacteroidetes bacterium PM25 |
| Bacteroidetes bacterium N03AW1 | Bacteroidetes bacterium PM29 |
| Bacteroidetes bacterium N04ML10 | Bacteroidetes bacterium PMR-D |
| Bacteroidetes bacterium N04ML7 | Bacteroidetes bacterium PP2 |
| Bacteroidetes bacterium N04ML8 | Bacteroidetes bacterium PPf50E2 |
| Bacteroidetes bacterium N114 | Bacteroidetes bacterium PPM04 |
| Bacteroidetes bacterium N1mML10c | Bacteroidetes bacterium PS-KroK1 |
| Bacteroidetes bacterium N1mML12 | Bacteroidetes bacterium PS-T12W |
| Bacteroidetes bacterium N1mML3 | Bacteroidetes bacterium R-38326 |
| Bacteroidetes bacterium N1mML4 | Bacteroidetes bacterium R-38398 |
| Bacteroidetes bacterium N2 | Bacteroidetes bacterium R-39049 |
| Bacteroidetes bacterium N2yML1 | Bacteroidetes bacterium R0L5 |
| Bacteroidetes bacterium N3mIS1 | Bacteroidetes bacterium R2-Dec-MIB-3 |
| Bacteroidetes bacterium N3mIS10 | Bacteroidetes bacterium R2A10 |
| Bacteroidetes bacterium N3mML1 | Bacteroidetes bacterium R2A103 |
| Bacteroidetes bacterium N3mML6 | Bacteroidetes bacterium R2A132 |

TABLE 1-continued

Bacteroidetes bacterium N83
Bacteroidetes bacterium N90
Bacteroidetes bacterium N9mIS13
Bacteroidetes bacterium NAB18
Bacteroidetes bacterium NeomS2D4
Bacteroidetes bacterium NP-X
Bacteroidetes bacterium O-014
Bacteroidetes bacterium O32B__LM98
Bacteroidetes bacterium ONB11
Bacteroidetes bacterium ONB13
Bacteroidetes bacterium ONC1
Bacteroidetes bacterium ONC2
Bacteroidetes bacterium OR-1
Bacteroidetes bacterium OR-219
Bacteroidetes bacterium OR-43
Bacteroidetes bacterium OR-53
Bacteroidetes bacterium oral taxon 272
Bacteroidetes bacterium oral taxon 274
Bacteroidetes bacterium oral taxon 280
Bacteroidetes bacterium RNC6
Bacteroidetes bacterium RP28
Bacteroidetes bacterium RX233
Bacteroidetes bacterium S1
Bacteroidetes bacterium S10/1
Bacteroidetes bacterium S10/2
Bacteroidetes bacterium S110(26)-1
Bacteroidetes bacterium S15-4
Bacteroidetes bacterium S22-33
Bacteroidetes bacterium S22-34
Bacteroidetes bacterium S22-35
Bacteroidetes bacterium S3
Bacteroidetes bacterium S7
Bacteroidetes bacterium S923
Bacteroidetes bacterium SAC2
Bacteroidetes bacterium SB27
Bacteroidetes bacterium SC-1
Bacteroidetes bacterium SCGC AAA008-C03
Bacteroidetes bacterium SCGC AAA015-O21
Bacteroidetes bacterium SCGC AAA023-B19
Bacteroidetes bacterium SCGC AAA023-E22
Bacteroidetes bacterium SCGC AAA023-J07
Bacteroidetes bacterium SCGC AAA023-K17
Bacteroidetes bacterium SCGC AAA023-M10
Bacteroidetes bacterium SCGC AAA023-N17
Bacteroidetes bacterium SCGC AAA024-A13
Bacteroidetes bacterium SCGC AAA024-B16
Bacteroidetes bacterium SCGC AAA024-E18
Bacteroidetes bacterium SCGC AAA024-I08
Bacteroidetes bacterium SCGC AAA024-M07
Bacteroidetes bacterium SCGC AAA024-N18
Bacteroidetes bacterium SCGC AAA024-O02
Bacteroidetes bacterium SCGC AAA024-O05
Bacteroidetes bacterium SCGC AAA024-P05
Bacteroidetes bacterium SCGC AAA024-P11
Bacteroidetes bacterium SCGC AAA027-A23
Bacteroidetes bacterium SCGC AAA027-C18
Bacteroidetes bacterium SCGC AAA027-D09
Bacteroidetes bacterium SCGC AAA027-D11
Bacteroidetes bacterium SCGC AAA027-D14
Bacteroidetes bacterium SCGC AAA027-D22
Bacteroidetes bacterium SCGC AAA027-E17
Bacteroidetes bacterium SCGC AAA027-F10
Bacteroidetes bacterium SCGC AAA027-F20
Bacteroidetes bacterium SCGC AAA027-G08
Bacteroidetes bacterium SCGC AAA027-G09
Bacteroidetes bacterium SCGC AAA027-J08
Bacteroidetes bacterium SCGC AAA027-J16
Bacteroidetes bacterium SCGC AAA027-K06
Bacteroidetes bacterium SCGC AAA027-L16
Bacteroidetes bacterium SCGC AAA027-L18
Bacteroidetes bacterium SCGC AAA027-M16
Bacteroidetes bacterium SCGC AAA027-M20
Bacteroidetes bacterium SCGC AAA027-N15
Bacteroidetes bacterium SCGC AAA027-N20
Bacteroidetes bacterium SCGC AAA027-N21
Bacteroidetes bacterium SCGC AAA027-O02
Bacteroidetes bacterium SCGC AAA027-O08
Bacteroidetes bacterium SCGC AAA027-P03
Bacteroidetes bacterium SCGC AAA027-P14
Bacteroidetes bacterium SCGC AAA028-D13
Bacteroidetes bacterium R2A5
Bacteroidetes bacterium R43
Bacteroidetes bacterium R634
Bacteroidetes bacterium R8-Ret-T12-11d
Bacteroidetes bacterium R8-Ret-T53-23g
Bacteroidetes bacterium RAS63
Bacteroidetes bacterium RBE2CD-132
Bacteroidetes bacterium RBE2CD-50
Bacteroidetes bacterium RBE2CD-54
Bacteroidetes bacterium RD4.3
Bacteroidetes bacterium RG1-1
Bacteroidetes bacterium RI121
Bacteroidetes bacterium RI269
Bacteroidetes bacterium RL-C
Bacteroidetes bacterium RM22
Bacteroidetes bacterium RM23
Bacteroidetes bacterium RM69
Bacteroidetes bacterium RNC11
Bacteroidetes bacterium RNC12
Bacteroidetes bacterium SCGC AAA043-M05
Bacteroidetes bacterium SCGC AAA043-N02
Bacteroidetes bacterium SCGC AAA043-O14
Bacteroidetes bacterium SCGC AAA043-P05
Bacteroidetes bacterium SCGC AAA076-B23
Bacteroidetes bacterium SCGC AAA158-A05
Bacteroidetes bacterium SCGC AAA158-J09
Bacteroidetes bacterium SCGC AAA160-A02
Bacteroidetes bacterium SCGC AAA160-A08
Bacteroidetes bacterium SCGC AAA160-A14
Bacteroidetes bacterium SCGC AAA160-A21
Bacteroidetes bacterium SCGC AAA160-B09
Bacteroidetes bacterium SCGC AAA160-C05
Bacteroidetes bacterium SCGC AAA160-D03
Bacteroidetes bacterium SCGC AAA160-E07
Bacteroidetes bacterium SCGC AAA160-E08
Bacteroidetes bacterium SCGC AAA160-E20
Bacteroidetes bacterium SCGC AAA160-F07
Bacteroidetes bacterium SCGC AAA160-F08
Bacteroidetes bacterium SCGC AAA160-F18
Bacteroidetes bacterium SCGC AAA160-G10
Bacteroidetes bacterium SCGC AAA160-G14
Bacteroidetes bacterium SCGC AAA160-I16
Bacteroidetes bacterium SCGC AAA160-L03
Bacteroidetes bacterium SCGC AAA160-L04
Bacteroidetes bacterium SCGC AAA160-L09
Bacteroidetes bacterium SCGC AAA160-L15
Bacteroidetes bacterium SCGC AAA160-L18
Bacteroidetes bacterium SCGC AAA160-L19
Bacteroidetes bacterium SCGC AAA160-N02
Bacteroidetes bacterium SCGC AAA160-N18
Bacteroidetes bacterium SCGC AAA160-N19
Bacteroidetes bacterium SCGC AAA160-O17
Bacteroidetes bacterium SCGC AAA160-P02
Bacteroidetes bacterium SCGC AAA160-P09
Bacteroidetes bacterium SCGC AAA163-F15
Bacteroidetes bacterium SCGC AAA164-L19
Bacteroidetes bacterium SCGC AAA166-B07
Bacteroidetes bacterium SCGC AAA166-B16
Bacteroidetes bacterium SCGC AAA166-C08
Bacteroidetes bacterium SCGC AAA166-G16
Bacteroidetes bacterium SCGC AAA166-I10
Bacteroidetes bacterium SCGC AAA166-J04
Bacteroidetes bacterium SCGC AAA166-O05
Bacteroidetes bacterium SCGC AAA166-P21
Bacteroidetes bacterium SCGC AAA168-G15
Bacteroidetes bacterium SCGC AAA204-D06
Bacteroidetes bacterium SCGC AAA204-N13
Bacteroidetes bacterium SCGC AAA206-C09
Bacteroidetes bacterium SCGC AAA206-D16
Bacteroidetes bacterium SCGC AAA206-E07
Bacteroidetes bacterium SCGC AAA206-I05
Bacteroidetes bacterium SCGC AAA206-J13
Bacteroidetes bacterium SCGC AAA206-P04
Bacteroidetes bacterium SCGC AAA240-A06
Bacteroidetes bacterium SCGC AAA240-K15
Bacteroidetes bacterium SCGC AAA278-L16
Bacteroidetes bacterium SCGC AAA280-A07
Bacteroidetes bacterium SCGC AAA288-M09
Bacteroidetes bacterium SCGC AAA300-E18
Bacteroidetes bacterium SCGC AAA487-A10

TABLE 1-continued

| | |
|---|---|
| Bacteroidetes bacterium SCGC AAA028-G19 | Bacteroidetes bacterium SCGC AAA487-A14 |
| Bacteroidetes bacterium SCGC AAA028-N16 | Bacteroidetes bacterium SCGC AAA487-E10 |
| Bacteroidetes bacterium SCGC AAA041-C10 | Bacteroidetes bacterium SCGC AAA487-F20 |
| Bacteroidetes bacterium SCGC AAA041-L03 | Bacteroidetes bacterium SCGC AAA487-G14 |
| Bacteroidetes bacterium SCGC AAA041-P16 | Bacteroidetes bacterium SCGC AAA487-G22 |
| Bacteroidetes bacterium SCGC AAA041-P17 | Bacteroidetes bacterium SCGC AAA487-I22 |
| Bacteroidetes bacterium SCGC AAA043-A05 | Bacteroidetes bacterium SCGC AAA487-J05 |
| Bacteroidetes bacterium SCGC AAA043-A17 | Bacteroidetes bacterium SCGC AAA487-N10 |
| Bacteroidetes bacterium SCGC AAA043-I08 | Bacteroidetes bacterium SCGC AAA487-O06 |
| Bacteroidetes bacterium SCGC AAA487-O21 | Bacteroidetes bacterium WD584 |
| Bacteroidetes bacterium Schreyahn_Kolonie_Aster_14 | Bacteroidetes bacterium WD59 |
| Bacteroidetes bacterium SDX12 | Bacteroidetes bacterium WD65 |
| Bacteroidetes bacterium SED4 | Bacteroidetes bacterium WD7 |
| Bacteroidetes bacterium SF1 | Bacteroidetes bacterium WD96 |
| Bacteroidetes bacterium SF11 | Bacteroidetes bacterium WF73 |
| Bacteroidetes bacterium SF12 | Bacteroidetes bacterium WH009150s |
| Bacteroidetes bacterium SF2 | Bacteroidetes bacterium wo21 |
| Bacteroidetes bacterium SF47 | Bacteroidetes bacterium wo31 |
| Bacteroidetes bacterium SM21 | Bacteroidetes bacterium X3-d |
| Bacteroidetes bacterium SM23 | Bacteroidetes bacterium ZHC17 |
| Bacteroidetes bacterium SM26 | Bacteroidetes bacterium ZHC20 |
| Bacteroidetes bacterium SM32 | Bacteroidetes bacterium zj02 |
| Bacteroidetes bacterium SM35 | Bacteroidetes bacterium zj05 |
| Bacteroidetes bacterium SM46 | Bacteroidetes bacterium ZNB16 |
| Bacteroidetes bacterium SM55 | Bacteroidetes bacterium zo30 |
| Bacteroidetes bacterium SM57 | Bacteroidetes bacterium zo31 |
| Bacteroidetes bacterium Smarlab 3301186 | Bacteroidetes bacterium zo34 |
| Bacteroidetes bacterium so23 | Bacteroidetes bacterium zo35 |
| Bacteroidetes bacterium so40 | Bacteroidetes CH12 |
| Bacteroidetes bacterium so46 | Bacteroidetes endosymbiont of *Aspidiotus destructor* |
| Bacteroidetes bacterium SOMOC25 | Bacteroidetes endosymbiont of *Metaseiulus occidentalis* |
| Bacteroidetes bacterium SOVto10 | Bacteroidetes oral taxon 274 |
| Bacteroidetes bacterium SS1 | Bacteroidetes symbiont of *Icerya purchasi* |
| Bacteroidetes bacterium SS12 | CFB group bacterium 22(2010) |
| Bacteroidetes bacterium SS14.29 | CFB group bacterium A0653 |
| Bacteroidetes bacterium SS14.30 | CFB group bacterium A1002 |
| Bacteroidetes bacterium SS14.31 | CFB group bacterium GOBB3-210 |
| Bacteroidetes bacterium SS4 | CFB group bacterium GOBB3-308 |
| Bacteroidetes bacterium SS9.12 | CFB group bacterium GOBB3-CL142 |
| Bacteroidetes bacterium SS9.38 | CFB group bacterium ikaite c9 |
| Bacteroidetes bacterium SSL04 | CFB group bacterium kba13f |
| Bacteroidetes bacterium SW15 | CFB group bacterium kba28f |
| Bacteroidetes bacterium SW4 | CFB group bacterium kbc05f |
| Bacteroidetes bacterium T213BY3 | CFB group bacterium kbc13 |
| Bacteroidetes bacterium T4-KAD-str1 | CFB group bacterium KbC5-B2 |
| Bacteroidetes bacterium TDB-023 | CFB group bacterium KbC5-B3 |
| Bacteroidetes bacterium TDB-148 | CFB group bacterium KbN1-B1 |
| Bacteroidetes bacterium TDB-212 | CFB group bacterium OI-1-1 |
| Bacteroidetes bacterium Tf 235 | CFB group bacterium OI-1-2 |
| Bacteroidetes bacterium TH-G48 | CFB group bacterium OI-1-4 |
| Bacteroidetes bacterium TH-G49 | CFB group bacterium OI-14-4 |
| Bacteroidetes bacterium THS | CFB group bacterium OI-15-2 |
| Bacteroidetes bacterium TRS1-A1 | CFB group bacterium OI-20-1 |
| Bacteroidetes bacterium TSW03CA1B | CFB group bacterium OI-9-1 |
| Bacteroidetes bacterium U-3 | CFB group bacterium SFLA10 |
| Bacteroidetes bacterium U-5 | CFB group bacterium SI-9-3 |
| Bacteroidetes bacterium U-9 | CFB-group bacterium QA93A |
| Bacteroidetes bacterium UBF2 | cilia-associated respiratory bacterium |
| Bacteroidetes bacterium UBF3 | cilia-associated respiratory bacterium 243-54 |
| Bacteroidetes bacterium UBF5 | cilia-associated respiratory bacterium 246-57 |
| Bacteroidetes bacterium UBF7 | cilia-associated respiratory bacterium 95-15405 |
| Bacteroidetes bacterium UBF9 | cilia-associated respiratory bacterium 96-1590 |
| Bacteroidetes bacterium UL2 | cilia-associated respiratory bacterium 96-4763 |
| Bacteroidetes bacterium UVps | cilia-associated respiratory bacterium M1 |
| Bacteroidetes bacterium VAS35 | cilia-associated respiratory bacterium R1 |
| Bacteroidetes bacterium VAS36 | cilia-associated respiratory bacterium R2 |
| Bacteroidetes bacterium W-2003a | cilia-associated respiratory bacterium R3 |
| Bacteroidetes bacterium W21 | cilia-associated respiratory bacterium R4 |
| Bacteroidetes bacterium WD195 | *Coleomegilla maculata* male-killing endosymbiont |
| Bacteroidetes bacterium WD250 | Cytophagales str. AND6 |
| Bacteroidetes bacterium WD300 | Cytophagales str. B6 |
| Bacteroidetes bacterium WD309 | Cytophagales str. KAT4 |
| Bacteroidetes bacterium WD317 | Cytophagales str. KAT5 |
| Bacteroidetes bacterium WD385 | Cytophagales str. KAT7 |
| Bacteroidetes bacterium WD411 | Cytophagales str. MBIC4147 |
| Bacteroidetes bacterium WD501 | Cytophagales str. MED10 |
| Bacteroidetes bacterium WD509 | Cytophagales str. MED11 |
| Bacteroidetes bacterium WD537 | Cytophagales str. MED21 |
| Bacteroidetes bacterium WD538 | Cytophagales str. MED25 |
| Cytophagales str. MED9 | marine CFB-group bacterium MBIC04466 |

TABLE 1-continued

| | |
|---|---|
| Cytophagales str. QSSC5-1 | marine CFB-group bacterium MBIC04467 |
| Elbe River snow isolate Iso8 | marine CFB-group bacterium MBIC04468 |
| *Encarsia berlesei* endosymbiont | marine CFB-group bacterium MBIC04469 |
| *Encarsia citrina* endosymbiont | marine CFB-group bacterium MBIC04470 |
| *Encarsia hispida* endosymbiont | marine CFB-group bacterium MBIC04471 |
| *Encarsia pergandiella* asexual line endosymbiont | marine CFB-group bacterium MBIC04472 |
| *Encarsia pergandiella* sexual line endosymbiont | marine CFB-group bacterium MBIC04473 |
| endosymbiont of *Aphytis lingnanensis* | marine CFB-group bacterium MBIC04474 |
| endosymbiont of *Aspidiotus nerii* | marine CFB-group bacterium MBIC04475 |
| endosymbiont of *Bemisia tabaci* (biotype A) | marine CFB-group bacterium MBIC04476 |
| endosymbiont of *Brevipalpus californicus* | marine CFB-group bacterium MBIC04477 |
| endosymbiont of *Brevipalpus lewisi* | marine CFB-group bacterium MBIC04478 |
| endosymbiont of *Brevipalpus obovatus* | marine CFB-group bacterium MBIC04487 |
| endosymbiont of *Brevipalpus phoenicis* | marine CFB-group bacterium MBIC05204 |
| endosymbiont of *Diaspis echinocacti* | marine CFB-group bacterium MBIC05558 |
| endosymbiont of *Dicranotropis hamata* | marine CFB-group bacterium N43 |
| endosymbiont of *Encarsia lutea* | marine CFB-group bacterium S3 |
| endosymbiont of *Encarsiella noyesi* | marine CFB-group bacterium SB12 |
| endosymbiont of *Metaseiulus occidentalis* | marine CFB-group bacterium SB15 |
| endosymbiont of *Oppiella nova* | marine CFB-group bacterium SB17 |
| endosymbiont of *Petrobia harti* | marine CFB-group bacterium SB9 |
| endosymbiont of *Zigia versicolor* | marine CFB-group bacterium SY009 |
| enrichment culture LET-13 | marine CFB-group bacterium SY010 |
| *Eubostrichus dianae epibacterium* 1_60 | marine CFB-group bacterium SY011 |
| filamentous bacterium Plant1 Iso10B | marine CFB-group bacterium SY013 |
| filamentous bacterium Plant1 Iso8 | marine CFB-group bacterium SY022 |
| freshwater obligate oligotroph IO-95 | marine CFB-group bacterium SY023 |
| gut bacterium S2 of *Coptotermes formosanus* | marine CFB-group bacterium SY024 |
| marine bacterium 13731 | marine CFB-group bacterium SY038 |
| marine bacterium GY9 | marine CFB-group bacterium SY040 |
| marine bacterium MC8 | marine CFB-group bacterium SY049 |
| marine bacterium NBF6 | marine CFB-group bacterium SY088 |
| marine bacterium SIMO-IS106 | marine CFB-group bacterium SY121 |
| marine bacterium SIMO-IS107 | marine CFB-group bacterium SY156 |
| marine bacterium SIMO-IS108 | marine CFB-group bacterium SY186 |
| marine bacterium SIMO-IS109 | marine CFB-group bacterium SY204 |
| marine bacterium SIMO-IS110 | marine CFB-group bacterium SY221 |
| marine bacterium SIMO-IS111 | marine CFB-group bacterium SY224 |
| marine bacterium SIMO-IS112 | marine CFB-group bacterium SY226 |
| marine bacterium SIMO-IS113 | marine CFB-group bacterium SY227 |
| marine bacterium SIMO-IS114 | marine CFB-group bacterium SY229 |
| marine bacterium SIMO-IS115 | marine CFB-group bacterium SY231 |
| marine bacterium SIMO-IS117 | marine CFB-group bacterium SY244 |
| marine bacterium SIMO-IS118 | marine psychrophile ACAM210 |
| marine bacterium SIMO-IS122 | marine psychrophile IC054 |
| marine bacterium SIMO-IS129 | marine psychrophile IC076 |
| marine bacterium SIMO-IS130 | marine psychrophile IC148 |
| marine bacterium SIMO-IS132 | marine psychrophile IC157 |
| marine bacterium SIMO-IS190 | marine psychrophile IC159 |
| marine Bacteroidetes bacterium RS.Sph.009 | marine psychrophile IC164 |
| marine CFB-group bacterium MBIC01539 | marine psychrophile SW17 |
| marine CFB-group bacterium MBIC01599 | monochloroacetic-acid-degrading bacterium 'Band E' |
| marine CFB-group bacterium MBIC04441 | monochloroacetic-acid-degrading bacterium 'Band F' |
| marine CFB-group bacterium MBIC04442 | obligately oligotrophic bacteria POC-121 |
| marine CFB-group bacterium MBIC04443 | obligately oligotrophic bacteria POC-122 |
| marine CFB-group bacterium MBIC04444 | obligately oligotrophic bacteria POC-8 |
| marine CFB-group bacterium MBIC04445 | obligately oligotrophic bacteria POCPN-73 |
| marine CFB-group bacterium MBIC04446 | obligately oligotrophic bacteria POCPN-74 |
| marine CFB-group bacterium MBIC04447 | saltmarsh sediment bacterium NRL-CB18 |
| marine CFB-group bacterium MBIC04449 | saltmarsh sediment bacterium NRL-CB19 |
| marine CFB-group bacterium MBIC04450 | saltmarsh sediment bacterium NRL-SS36 |
| marine CFB-group bacterium MBIC04451 | saltmarsh sediment bacterium NRL-TS20 |
| marine CFB-group bacterium MBIC04452 | Bacteroidetes sp. BG31 |
| marine CFB-group bacterium MBIC04453 | Bacteroidetes sp. MG12 |
| marine CFB-group bacterium MBIC04454 | Bacteroidetes sp. MG21 |
| marine CFB-group bacterium MBIC04455 | Bacteroidetes sp. OL02 |
| marine CFB-group bacterium MBIC04456 | Bacteroidetes sp. OM02 |
| marine CFB-group bacterium MBIC04458 | Bacteroidetes sp. OM05 |
| marine CFB-group bacterium MBIC04465 | Bacteroidetes symbiont of *Osedax* sp. |
| endosymbiont of *Acanthamoeba* sp. KA/E21 | Bacteroidetes bacterium enrichment culture clone HB_77 |
| endosymbiont of *Aphytis* sp. 3 | Bacteroidetes bacterium enrichment culture clone HB_86 |
| endosymbiont of *Aphytis* sp. 4 | Bacteroidetes bacterium enrichment culture clone HB_97 |
| endosymbiont of *Balaustium* sp. | Bacteroidetes bacterium enrichment culture clone L1 |
| endosymbiont of *Encarsia* sp. 2 | Bacteroidetes bacterium enrichment culture clone L11_2_53 |
| endosymbiont of *Encarsia* sp. 3 | Bacteroidetes bacterium enrichment culture clone L35B_118 |
| *Robbea* sp. associated bacterium 4 | Bacteroidetes bacterium enrichment culture clone L35B_121 |
| *Stilbonema* sp. associated bacterium 2 | Bacteroidetes bacterium enrichment culture clone L35B_13 |
| *Stilbonema* sp. associated bacterium 3 | Bacteroidetes bacterium enrichment culture clone L35B_144 |
| *Stilbonema* sp. associated bacterium 4 | Bacteroidetes bacterium enrichment culture clone L35B_21 |
| *Stilbonema* sp. associated bacterium 5 | Bacteroidetes bacterium enrichment culture clone L35B_50 |

TABLE 1-continued

*Stilbonema* sp. associated bacterium 6
*Stilbonema* sp. associated bacterium 7
unidentified bacterium WP13
Bacteroidetes Order II. Incertae sedis
Rhodothermaceae
*Rhodothermus*
*Rubricoccus*
*Salinibacter*
*Salisaeta*
unclassified Rhodothermaceae
environmental samples
Bacteroidetes Order III. Incertae sedis
*Thermonema*
*Thermonema lapsum*
*Thermonema rossianum*
environmental samples
environmental samples
Bacteriodetes bacterium enrichment culture clone AP-FeEnrich3
Bacteriodetes bacterium enrichment culture clone AP-FeEnrich4
Bacteriodetes bacterium enrichment culture clone AP-FeEnrich5
Bacteriodetes bacterium enrichment culture clone AP-FeEnrich6
Bacteriodetes bacterium enrichment culture C4_1
Bacteroidetes bacterium enrichment culture clone 06-1235251-117
Bacteroidetes bacterium enrichment culture clone 12
Bacteroidetes bacterium enrichment culture clone 293MTBE
Bacteroidetes bacterium enrichment culture clone 4.17a Bac band 1
Bacteroidetes bacterium enrichment culture clone 4.17b Bac band 6
Bacteroidetes bacterium enrichment culture clone 4.17b Bac band 7
Bacteroidetes bacterium enrichment culture clone 4.17c Bac band 1
Bacteroidetes bacterium enrichment culture clone AQ1-2
Bacteroidetes bacterium enrichment culture clone AVCTGRB7A
Bacteroidetes bacterium enrichment culture clone AVCTGRB9A
Bacteroidetes bacterium enrichment culture clone AVCTGRB9B
Bacteroidetes bacterium enrichment culture clone B1-B-73
Bacteroidetes bacterium enrichment culture clone B2
Bacteroidetes bacterium enrichment culture clone B20
Bacteroidetes bacterium enrichment culture clone 820(2010)
Bacteroidetes bacterium enrichment culture clone CTBE CDB1001B01
Bacteroidetes bacterium enrichment culture clone D2CL_Bac_16S_Clone21
Bacteroidetes bacterium enrichment culture clone D2CL_Bac_16S_Clone22
Bacteroidetes bacterium enrichment culture clone D2CL_Bac_16S_Clone23
Bacteroidetes bacterium enrichment culture clone DT-1962
Bacteroidetes bacterium enrichment culture clone EAMFC7
Bacteroidetes bacterium enrichment culture clone EE2-III
Bacteroidetes bacterium enrichment culture clone EE2-IV
Bacteroidetes bacterium enrichment culture clone EE2-V
Bacteroidetes bacterium enrichment culture clone EE2-VII
Bacteroidetes bacterium enrichment culture clone H12_2_55
Bacteroidetes bacterium enrichment culture clone HB_102
Bacteroidetes bacterium enrichment culture clone HB_110
Bacteroidetes bacterium enrichment culture clone HB_120
Bacteroidetes bacterium enrichment culture clone HB_53
Bacteroidetes bacterium enrichment culture clone HB_61
Bacteroidetes bacterium enrichment culture clone HB_63
Bacteroidetes bacterium enrichment culture clone HB_71
*Flexibacter maritimus*-like bacterium S3C20
marine *eubacterium* 'DDGE band 3'
metal-contaminated soil clone K20-37
metal-contaminated soil clone K20-51
metal-contaminated soil clone K20-54
metal-contaminated soil clone K20-69
Bacteroidetes sp. oral clone FX069
uncultured bacterium #0319-2D9
uncultured bacterium #0319-6J10
uncultured bacterium #0319-7J6
uncultured bacterium #0319-7K9
uncultured bacterium #0319-8P19
uncultured bacterium B6
uncultured bacterium BA11
uncultured bacterium BA12
uncultured bacterium BA13
uncultured bacterium BA2
uncultured bacterium BA5
uncultured bacterium BA6
uncultured bacterium BA7
uncultured bacterium BA8
Bacteroidetes bacterium enrichment culture clone L35B_72
Bacteroidetes bacterium enrichment culture clone L35B_83
Bacteroidetes bacterium enrichment culture clone L35B_95
Bacteroidetes bacterium enrichment culture clone L4
Bacteroidetes bacterium enrichment culture clone L55B-11
Bacteroidetes bacterium enrichment culture clone L55B-120
Bacteroidetes bacterium enrichment culture clone L55B-124
Bacteroidetes bacterium enrichment culture clone L55B-131
Bacteroidetes bacterium enrichment culture clone L55B-36
Bacteroidetes bacterium enrichment culture clone L55B-60
Bacteroidetes bacterium enrichment culture clone L55B-63
Bacteroidetes bacterium enrichment culture clone L55B-81
Bacteroidetes bacterium enrichment culture clone LiUU-12-16
Bacteroidetes bacterium enrichment culture clone LiUU-12-52
Bacteroidetes bacterium enrichment culture clone LiUU-12-67
Bacteroidetes bacterium enrichment culture clone LiUU-12-81
Bacteroidetes bacterium enrichment culture clone LiUU-15-341
Bacteroidetes bacterium enrichment culture clone LiUU-15-745
Bacteroidetes bacterium enrichment culture clone LiUU-15-762
Bacteroidetes bacterium enrichment culture clone LiUU-15-773
Bacteroidetes bacterium enrichment culture clone LiUU-15-794
Bacteroidetes bacterium enrichment culture clone LiUU-16-310
Bacteroidetes bacterium enrichment culture clone LiUU-16-703
Bacteroidetes bacterium enrichment culture clone LiUU-16-715
Bacteroidetes bacterium enrichment culture clone LiUU-16-729
Bacteroidetes bacterium enrichment culture clone LiUU-16-748
Bacteroidetes bacterium enrichment culture clone LiUU-16-756
Bacteroidetes bacterium enrichment culture clone LiUU-16-769
Bacteroidetes bacterium enrichment culture clone LiUU-16-794
Bacteroidetes bacterium enrichment culture clone LiUU-17-320
Bacteroidetes bacterium enrichment culture clone LiUU-17-363
Bacteroidetes bacterium enrichment culture clone LiUU-17-386
Bacteroidetes bacterium enrichment culture clone LiUU-17-389
Bacteroidetes bacterium enrichment culture clone LiUU-17-737
Bacteroidetes bacterium enrichment culture clone LiUU-17-770
Bacteroidetes bacterium enrichment culture clone LiUU-17-793
Bacteroidetes bacterium enrichment culture clone LiUU-17-795
Bacteroidetes bacterium enrichment culture clone LiUU-18-303
Bacteroidetes bacterium enrichment culture clone LiUU-18-376
Bacteroidetes bacterium enrichment culture clone LiUU-18-385
Bacteroidetes bacterium enrichment culture clone LiUU-18-392
Bacteroidetes bacterium enrichment culture clone LiUU-18-713
Bacteroidetes bacterium enrichment culture clone LiUU-18-728
Bacteroidetes bacterium enrichment culture clone LiUU-18-740
Bacteroidetes bacterium enrichment culture clone LiUU-18-765
Bacteroidetes bacterium enrichment culture clone LiUU-18-791
Bacteroidetes bacterium enrichment culture clone NKiF2Sl
Bacteroidetes bacterium enrichment culture clone phylotype P11
Bacteroidetes bacterium enrichment culture clone S1
Bacteroidetes bacterium enrichment culture clone SGLB4-2
Bacteroidetes bacterium enrichment culture clone SGLB4-22
Bacteroidetes bacterium enrichment culture clone VNC3B008
Bacteroidetes bacterium enrichment culture clone WIP20m1H
Bacteroidetes bacterium enrichment culture clone YFZ3
Bacteroidetes bacterium enrichment culture clone YFZ5
Bacteroidetes bacterium enrichment culture clone YYS7
Bacteroidetes bacterium enrichment culture DGGE band 39
*Flexibacter maritimus*-like bacterium S3C18
*Flexibacter maritimus*-like bacterium S3C19
uncultured bacterium IAFESB3
uncultured bacterium KC303
uncultured bacterium KC305
uncultured bacterium KC307
uncultured bacterium KC309
uncultured bacterium KC310
uncultured bacterium KC312
uncultured bacterium KC318
uncultured bacterium KC319
uncultured bacterium KC320
uncultured bacterium KC328
uncultured bacterium KC429
uncultured bacterium KC430
uncultured bacterium MK01
uncultured bacterium MK02
uncultured bacterium MK03
uncultured bacterium MK04
uncultured bacterium MK05
uncultured bacterium MK06
uncultured bacterium MK07
uncultured bacterium MK08

TABLE 1-continued

| | |
|---|---|
| uncultured bacterium BA9 | uncultured bacterium MK09 |
| uncultured bacterium BAx1 | uncultured bacterium MK10 |
| uncultured bacterium BAx3 | uncultured bacterium MK11 |
| uncultured bacterium BAx4 | uncultured bacterium MK12 |
| uncultured bacterium BAx5 | uncultured bacterium MK13 |
| uncultured bacterium BS1 | uncultured bacterium MK14 |
| uncultured bacterium BS2 | uncultured bacterium MK15 |
| uncultured bacterium BS3 | uncultured bacterium MK16 |
| uncultured bacterium BS4 | uncultured bacterium MK17 |
| uncultured bacterium BS5 | uncultured bacterium MK18 |
| uncultured bacterium BS7 | uncultured bacterium MK19 |
| uncultured bacterium BURTON-43 | uncultured bacterium MK21 |
| uncultured bacterium BURTON-6 | uncultured bacterium MK22 |
| uncultured bacterium FukuN104 | uncultured bacterium MK23 |
| uncultured bacterium FukuN21 | uncultured bacterium MK24 |
| uncultured bacterium FukuN23 | uncultured bacterium mle1-2 |
| uncultured bacterium FukuN24 | uncultured bacterium O11D1 |
| uncultured bacterium FukuN3 | uncultured bacterium PHOS-HC26 |
| uncultured bacterium FukuN36 | uncultured bacterium PHOS-HC44 |
| uncultured bacterium FukuN47 | uncultured bacterium PHOS-HC48 |
| uncultured bacterium FukuN50 | uncultured bacterium PHOS-HD32 |
| uncultured bacterium FukuN54 | uncultured bacterium PHOS-HE19 |
| uncultured bacterium FukuN63 | uncultured bacterium PHOS-HE25 |
| uncultured bacterium FukuS140 | uncultured bacterium PHOS-HE28 |
| uncultured bacterium FukuS188 | uncultured bacterium PHOS-HE31 |
| uncultured bacterium FukuS20 | uncultured bacterium PHOS-HE35 |
| uncultured bacterium FukuS59 | uncultured bacterium PHOS-HE45 |
| uncultured bacterium GKS2-106 | uncultured bacterium PHOS-HE51 |
| uncultured bacterium GKS2-111 | uncultured bacterium PHOS-HE61 |
| uncultured bacterium GKS2-112 | uncultured bacterium PHOS-HE62 |
| uncultured bacterium GKS2-120 | uncultured bacterium PHOS-HE67 |
| uncultured bacterium GKS2-121 | uncultured bacterium PHOS-HE77 |
| uncultured bacterium GKS2-142 | uncultured bacterium PHOS-HE79 |
| uncultured bacterium GKS2-15 | uncultured bacterium PHOS-HE99 |
| uncultured bacterium GKS2-155 | uncultured bacterium PL1 |
| uncultured bacterium GKS2-164 | uncultured bacterium Pn9 |
| uncultured bacterium GKS2-19 | uncultured bacterium TAYNAYA-17 |
| uncultured bacterium GKS2-205 | uncultured bacterium TAYNAYA-27 |
| uncultured bacterium GKS2-207 | uncultured bacterium TX2 |
| uncultured bacterium GKS2-208 | uncultured bacterium TX3 |
| uncultured bacterium GKS2-217 | uncultured bacterium UASB_TL54 |
| uncultured bacterium GKS2-232 | uncultured Bacteroidetes bacterium |
| uncultured bacterium GKS2-33 | uncultured Bacteroidetes bacterium 'SBI2-18 P41A3' |
| uncultured bacterium GKS2-63 | uncultured Bay of Fundy bacterium BA10-1C |
| uncultured bacterium GKS2-7 | uncultured Bay of Fundy bacterium BA10-1D |
| uncultured bacterium GKS2-70 | uncultured Bay of Fundy bacterium BA10-1E |
| uncultured bacterium GKS2-88 | uncultured CFB group bacterium B2M39 |
| uncultured bacterium GR-WP33-44 | uncultured CFB group bacterium B2M41 |
| uncultured bacterium IAFESA5 | uncultured CFB group bacterium B2M45 |
| uncultured CFB group bacterium CtaxAus-22 | uncultured Lake Michigan sediment bacterium LMBA1 |
| uncultured CFB group bacterium CtaxAus-4 | uncultured Lake Michigan sediment bacterium LMBA22 |
| uncultured CFB group bacterium CtaxAus-7 | uncultured Lake Michigan sediment bacterium LMBA29 |
| uncultured CFB group bacterium CtaxMed-1 | uncultured Lake Michigan sediment bacterium LMBA40 |
| uncultured CFB group bacterium CtaxMed-15 | uncultured Lake Michigan sediment bacterium LMBGA6-26 |
| uncultured CFB group bacterium CtaxMed-18 | uncultured marine bacterium AY-32 |
| uncultured CFB group bacterium CtaxMed-37 | uncultured marine bacterium AY-33 |
| uncultured CFB group bacterium CtaxMed-46 | uncultured marine bacterium AY-37 |
| uncultured CFB group bacterium CtaxMed-5 | uncultured marine bacterium AY-38 |
| uncultured CFB group bacterium CtaxPhil-13 | uncultured marine bacterium AY-56 |
| uncultured CFB group bacterium CtaxTah-24 | uncultured marine bacterium BY-19 |
| uncultured CFB group bacterium EBAC322 | uncultured marine bacterium BY-64 |
| uncultured CFB group bacterium EBAC34 | uncultured marine bacterium BY-65 |
| uncultured CFB group bacterium EBAC391 | uncultured marine bacterium BY-66 |
| uncultured CFB group bacterium EBAC40 | uncultured marine bacterium BY-7 |
| uncultured CFB group bacterium EBAC43 | uncultured marine bacterium BY-71 |
| uncultured CFB group bacterium kpa13rc | uncultured marine bacterium pC2-105 |
| uncultured CFB group bacterium kpc103f | uncultured marine bacterium pM-36 |
| uncultured CFB group bacterium kpc113rc | uncultured marine bacterium ZD0203 |
| uncultured CFB group bacterium kpc116rc | uncultured marine bacterium ZD0255 |
| uncultured CFB group bacterium kpc26 | uncultured marine bacterium ZD0403 |
| uncultured CFB group bacterium kpc29 | uncultured marine *cytophaga* DHB-3 |
| uncultured CFB group bacterium kpj11rc | uncultured marine *Cytophaga* MBE2 |
| uncultured CFB group bacterium kpj167rc | uncultured marine *Cytophaga* MBE7 |
| uncultured CFB group bacterium kpj254f | uncultured marine *eubacterium* OTU_A |
| uncultured CFB group bacterium kpj431f | uncultured marine *eubacterium* OTU_B |
| uncultured CFB group bacterium kpj56rc | uncultured marine *eubacterium* OTU_C |
| uncultured CFB group bacterium kpj57rc | uncultured marine *eubacterium* OTU_D |
| uncultured CFB group bacterium kpj59rc | uncultured rumen bacterium 109pARRO |
| uncultured CFB group bacterium kpj60f | uncultured rumen bacterium 119pARRO |
| uncultured CFBgroupbacterium NAC60-3 | uncultured rumen bacterium 120pARRO |

TABLE 1-continued

| | |
|---|---|
| uncultured CFB-group bacterium 107ev | uncultured rumen bacterium 122pARRO |
| uncultured CFB-group bacterium 122ev | uncultured rumen bacterium 125cARRO |
| uncultured CFB-group bacterium 168ev | uncultured rumen bacterium 194pARRO |
| uncultured CFB-group bacterium 204ev | uncultured rumen bacterium 231cARRO |
| uncultured CFB-group bacterium 22ev | uncultured rumen bacterium 242pARRO |
| uncultured CFB-group bacterium 240ev | uncultured rumen bacterium 243pARRO |
| uncultured CFB-group bacterium 279ev | uncultured rumen bacterium 262pARRO |
| uncultured CFB-group bacterium 338ev | uncultured rumen bacterium 268pARRO |
| uncultured CFB-group bacterium 36ev | uncultured rumen bacterium 343pARRO |
| uncultured CFB-group bacterium 416ev | uncultured rumen bacterium 351pARRO |
| uncultured CFB-group bacterium 421ev | uncultured rumen bacterium 353pARRO |
| uncultured CFB-group bacterium 429ev | uncultured rumen bacterium 362cARRO |
| uncultured CFB-group bacterium 42ev | uncultured rumen bacterium 445pARRO |
| uncultured CFB-group bacterium 439ev | uncultured rumen bacterium 509cARRO |
| uncultured CFB-group bacterium 61ev | uncultured rumen bacterium 509pARRO |
| uncultured CFB-group bacterium 65ev | uncultured rumen bacterium 523cARRO |
| uncultured CFB-group bacterium 87ev | uncultured rumen bacterium 588cARRO |
| uncultured CFB-group bacterium 93ev | uncultured rumen bacterium 5cARRO |
| uncultured coastal Alaskan Arctic bacterium AWS98-11d | uncultured rumen bacterium 626pARRO |
| uncultured coastal Alaskan Arctic bacterium AWS98-19d | uncultured rumen bacterium 62pARRO |
| uncultured coastal Alaskan Arctic bacterium AWS98-7d | uncultured rumen bacterium 635cARRO |
| uncultured cytophaga DCM-FREE-10 | uncultured rumen bacterium 636cARRO |
| uncultured cytophaga DCM-FREE-35 | uncultured rumen bacterium 637cARRO |
| uncultured *eubacterium* DgEPI2 | uncultured rumen bacterium 648pARRO |
| uncultured *eubacterium* DgEPK | uncultured rumen bacterium 68pARRO |
| uncultured *eubacterium* WCHA1-01 | uncultured rumen bacterium 90cARRO |
| uncultured *eubacterium* WCHA1-14 | uncultured rumen bacterium j1RRI |
| uncultured *eubacterium* WCHA2-47 | uncultured rumen bacterium j2RRI |
| uncultured *eubacterium* WCHB1-29 | uncultured rumen bacterium j3RRI |
| uncultured *eubacterium* WCHB1-32 | uncultured rumen bacterium j4RRI |
| uncultured *eubacterium* WCHB1-53 | uncultured rumen bacterium jw11RRI |
| uncultured *eubacterium* WsCH39 | uncultured rumen bacterium jw12RRI |
| uncultured fecal bacterium TB101 | uncultured rumen bacterium jw13RRI |
| uncultured fecal bacterium TB106 | uncultured rumen bacterium jw14RRI |
| uncultured fecal bacterium TB13 | uncultured rumen bacterium jw15RRI |
| uncultured fecal bacterium TB135 | uncultured rumen bacterium jw181RRI |
| uncultured fecal bacterium TB141 | uncultured rumen bacterium jw2-7RRI |
| uncultured fecal bacterium TB146 | uncultured rumen bacterium jw20RRI |
| uncultured fecal bacterium TB147 | uncultured rumen bacterium jw22RRI |
| uncultured rumen bacterium jw25RRI | unidentified Cytophagales OPB73 |
| uncultured rumen bacterium jw26RRI | unidentified Cytophagales OPB88 |
| uncultured rumen bacterium jw27RRI | unidentified Cytophagales OPS1 |
| uncultured rumen bacterium jw29RRI | unidentified *eubacterium* clone ESH167E |
| uncultured rumen bacterium jw30RRI | unidentified *eubacterium* clone ESH30-3 |
| uncultured rumen bacterium jw5RRI | unidentified *eubacterium* clone LGA#1 |
| uncultured rumen bacterium jw6RRI | unidentified *eubacterium* clone LGB#27 |
| uncultured rumen bacterium jw7RRI | unidentified *eubacterium* clone PS#8 |
| uncultured rumen bacterium jw81RRI | unidentified *eubacterium* SCB37 |
| uncultured rumen bacterium jw9RRI | unidentified *eubacterium* SCB38 |
| uncultured sludge bacterium A12b | unidentified *eubacterium* SCB40 |
| unidentified cytophagales groupA | unidentified *eubacterium* SCB41 |
| unidentified cytophagales groupB | unidentified *eubacterium* SCB45 |
| unidentified cytophagales groupG | unidentified *eubacterium* SCB49 |

Genus: *Lactobacillus*

| | |
|---|---|
| *Lactobacillus acetotolerans* | *Lactobacillus coleohominis* |
| *Lactobacillus acetotolerans* JCM 3825 | *Lactobacillus coleohominis* 101-4-CHN |
| *Lactobacillus acidifarinae* | *Lactobacillus coleohominis* DSM 14060 |
| *Lactobacillus acidipiscis* | *Lactobacillus collinoides* |
| *Lactobacillus acidipiscis* KCTC 13900 | *Lactobacillus composti* |
| *Lactobacillus acidophilus* | *Lactobacillus concavus* |
| *Lactobacillus acidophilus* 30SC | *Lactobacillus coryniformis* |
| *Lactobacillus acidophilus* ATCC 4796 | *Lactobacillus coryniformis* subsp. *coryniformis* |
| *Lactobacillus acidophilus* CIP 76.13 | *Lactobacillus coryniformis* subsp. *coryniformis* CECT 5711 |
| *Lactobacillus acidophilus* CIRM-BIA 442 | *Lactobacillus coryniformis* subsp. *coryniformis* KCTC 3167 |
| *Lactobacillus acidophilus* CIRM-BIA 445 | *Lactobacillus coryniformis* subsp. *torquens* |
| *Lactobacillus acidophilus* CRBIP 24179 | *Lactobacillus coryniformis* subsp. *torquens* KCTC 3535 |
| *Lactobacillus acidophilus* DSM 20242 | *Lactobacillus crispatus* |
| *Lactobacillus acidophilus* DSM 9126 | *Lactobacillus crispatus* 125-2-CHN |
| *Lactobacillus acidophilus* JV3179 | *Lactobacillus crispatus* 2029 |
| *Lactobacillus acidophilus* La-14 | *Lactobacillus crispatus* 214-1 |
| *Lactobacillus acidophilus* NCFM | *Lactobacillus crispatus* CTV-05 |
| *Lactobacillus agilis* | *Lactobacillus crispatus* EX533959VC01 |
| *Lactobacillus algidus* | *Lactobacillus crispatus* EX533959VC03 |
| *Lactobacillus alimentarius* | *Lactobacillus crispatus* EX533959VC04 |
| *Lactobacillus alvei* | *Lactobacillus crispatus* EX533959VC05 |
| *Lactobacillus alvi* | *Lactobacillus crispatus* EX533959VC06 |
| *Lactobacillus amylolyticus* | *Lactobacillus crispatus* EX533959VC07 |
| *Lactobacillus amylolyticus* DSM 11664 | *Lactobacillus crispatus* EX533959VC13 |
| *Lactobacillus amylophilus* | *Lactobacillus crispatus* EX849587VC01 |

TABLE 1-continued

| | |
|---|---|
| Lactobacillus amylophilus JCM 1125 | Lactobacillus crispatus EX849587VC02 |
| Lactobacillus amylotrophicus | Lactobacillus crispatus EX849587VC04 |
| Lactobacillus amylovorus | Lactobacillus crispatus EX849587VC07 |
| Lactobacillus amylovorus DSM 16698 | Lactobacillus crispatus EX849587VC08 |
| Lactobacillus amylovorus GRL 1112 | Lactobacillus crispatus FB049-03 |
| Lactobacillus amylovorus GRL 1115 | Lactobacillus crispatus FB077-07 |
| Lactobacillus amylovorus GRL1118 | Lactobacillus crispatus JCM 1185 |
| Lactobacillus animalis | Lactobacillus crispatus JV-V01 |
| Lactobacillus animalis KCTC 3501 | Lactobacillus crispatus MV-1A-US |
| Lactobacillus animata | Lactobacillus crispatus MV-3A-US |
| Lactobacillus antri | Lactobacillus crispatus SJ-3C-US |
| Lactobacillus antri DSM 16041 | Lactobacillus crispatus ST1 |
| Lactobacillus apis | Lactobacillus crustorum |
| Lactobacillus apodemi | Lactobacillus crustorum FH4 |
| Lactobacillus aquaticus | Lactobacillus curvatus |
| Lactobacillus aviarius | Lactobacillus curvatus CRL 705 |
| Lactobacillus aviarius subsp. araffmosus | Lactobacillus curvatus F16_9 |
| Lactobacillus aviarius subsp. aviarius | Lactobacillus curvatus JCM 1096 |
| Lactobacillus backi | Lactobacillus curvatus WSU1 |
| Lactobacillus bifermentans | Lactobacillus brevisimilis |
| Lactobacillus brantae | Lactobacillus buchneri |
| Lactobacillus brevis | Lactobacillus buchneri ATCC 11577 |
| Lactobacillus brevis AG48 | Lactobacillus buchneri CD034 |
| Lactobacillus brevis ATCC 14869 | Lactobacillus buchneri NRRL B-30929 |
| Lactobacillus brevis ATCC 367 | Lactobacillus cacaonum |
| Lactobacillus brevis KB290 | Lactobacillus camelliae |
| Lactobacillus brevis subsp. gravesensis | Lactobacillus capillatus |
| Lactobacillus brevis subsp. gravesensis ATCC 27305 | Lactobacillus casei group |
| Lactobacillus casei | Lactobacillus delbrueckii subsp. bulgaricus 2038 |
| Lactobacillus casei 12A | Lactobacillus delbrueckii subsp. bulgaricus ATCC 11842 |
| Lactobacillus casei 21/1 | Lactobacillus delbrueckii subsp. bulgaricus ATCC BAA-365 |
| Lactobacillus casei 32G | Lactobacillus delbrueckii subsp. bulgaricus CNCM I-1519 |
| Lactobacillus casei A2-362 | Lactobacillus delbrueckii subsp. bulgaricus CNCM I-1632 |
| Lactobacillus casei ATCC 334 | Lactobacillus delbrueckii subsp. bulgaricus ND02 |
| Lactobacillus casei BD-II | Lactobacillus delbrueckii subsp. bulgaricus PB2003/044-T3-4 |
| Lactobacillus casei BL23 | Lactobacillus delbrueckii subsp. delbrueckii |
| Lactobacillus casei CRF28 | Lactobacillus delbrueckii subsp. indicus |
| Lactobacillus casei DN-114001 | Lactobacillus delbrueckii subsp. lactis |
| Lactobacillus casei Lc-10 | Lactobacillus delbrueckii subsp. lactis CRL581 |
| Lactobacillus casei LC2W | Lactobacillus delbrueckii subsp. lactis DSM 20072 |
| Lactobacillus casei LcA | Lactobacillus delbrueckii subsp. sunkii |
| Lactobacillus casei LcY | Lactobacillus delbrueckii ZN7a-9 |
| Lactobacillus casei LOCK919 | Lactobacillus dextrinicus |
| Lactobacillus casei Lpc-37 | Lactobacillus diolivorans |
| Lactobacillus casei M36 | Lactobacillus equi |
| Lactobacillus casei str. Zhang | Lactobacillus equicursoris |
| Lactobacillus casei subsp. casei ATCC 393 | Lactobacillus equicursoris CIP 110162 |
| Lactobacillus casei T71499 | Lactobacillus equigenerosi |
| Lactobacillus casei UCD174 | Lactobacillus fabifermentans |
| Lactobacillus casei UW1 | Lactobacillus faeni |
| Lactobacillus casei UW4 | Lactobacillus farciminis |
| Lactobacillus casei W56 | Lactobacillus farciminis KCTC 3681 |
| Lactobacillus paracasei | Lactobacillus farraginis |
| Lactobacillus paracasei COM0101 | Lactobacillus fermentum |
| Lactobacillus paracasei subsp. paracasei | Lactobacillus fermentum 28-3-CHN |
| Lactobacillus paracasei subsp. tolerans | Lactobacillus fermentum 3872 |
| Lactobacillus paracasei TXW | Lactobacillus fermentum ATCC 14931 |
| Lactobacillus zeae | Lactobacillus fermentum CECT 5716 |
| Lactobacillus zeae KCTC 3804 | Lactobacillus fermentum F-6 |
| Lactobacillus sp. LA601 | Lactobacillus fermentum FTDC8312 |
| Lactobacillus sp. Od.76 | Lactobacillus fermentum IFO 3956 |
| Lactobacillus catenofornis | Lactobacillus fermentum Lf1 |
| Lactobacillus catenofornis DSM 20559 | Lactobacillus fermentum MTCC 8711 |
| Lactobacillus ceti | Lactobacillus floricola |
| Lactobacillus ceti DSM 22408 | Lactobacillus florum |
| Lactobacillus fuchuensis | Lactobacillus florum 2F |
| Lactobacillus futsaii | Lactobacillus florum 8D |
| Lactobacillus gallinarum | Lactobacillus fornicalis |
| Lactobacillus gasseri | Lactobacillus fructivorans |
| Lactobacillus gasseri 2016 | Lactobacillus fructivorans KCTC 3543 |
| Lactobacillus gasseri 202-4 | Lactobacillus frumenti |
| Lactobacillus gasseri 224-1 | Lactobacillus mali |
| Lactobacillus gasseri ADL-351 | Lactobacillus mali KCTC 3596 = DSM 20444 |
| Lactobacillus gasseri ATCC 33323 | Lactobacillus manihotivorans |
| Lactobacillus gasseri CECT 5714 | Lactobacillus mindensis |
| Lactobacillus gasseri EX336960VC01 | Lactobacillus mobilis |
| Lactobacillus gasseri EX336960VC02 | Lactobacillus mucosae |
| Lactobacillus gasseri EX336960VC03 | Lactobacillus mucosae LM1 |
| Lactobacillus gasseri EX336960VC06 | Lactobacillus murinus |
| Lactobacillus gasseri EX336960VC07 | Lactobacillus murinus ASF361 |

TABLE 1-continued

| | |
|---|---|
| Lactobacillus gasseri EX336960VC10 | Lactobacillus guizhouensis |
| Lactobacillus gasseri EX336960VC13 | Lactobacillus halophilus |
| Lactobacillus gasseri EX336960VC15 | Lactobacillus hammesii |
| Lactobacillus gasseri JV-V03 | Lactobacillus hamsteri |
| Lactobacillus gasseri K7 | Lactobacillus harbinensis |
| Lactobacillus gasseri MV-22 | Lactobacillus harbinensis DSM 16991 |
| Lactobacillus gasseri SJ-9E-US | Lactobacillus hayakitensis |
| Lactobacillus gasseri SV-16A-US | Lactobacillus helveticus |
| Lactobacillus gastricus | Lactobacillus helveticus CIRM-BIA 101 |
| Lactobacillus gastricus PS3 | Lactobacillus helveticus CIRM-BIA 103 |
| Lactobacillus genomosp. C1 | Lactobacillus helveticus CIRM-BIA 104 |
| Lactobacillus genomosp. C2 | Lactobacillus helveticus CIRM-BIA 951 |
| Lactobacillus ghanensis | Lactobacillus helveticus CIRM-BIA 953 |
| Lactobacillus gigeriorum | Lactobacillus helveticus CNRZ32 |
| Lactobacillus gigeriorum CRBIP 24.85 | Lactobacillus helveticus DPC 4571 |
| Lactobacillus graminis | Lactobacillus helveticus DSM 20075 |
| Lactobacillus delbrueckii | Lactobacillus helveticus H10 |
| Lactobacillus delbrueckii subsp. bulgaricus | Lactobacillus helveticus H9 |
| Lactobacillus helveticus MTCC 5463 | Lactobacillus kunkeei |
| Lactobacillus helveticus R0052 | Lactobacillus larvae |
| Lactobacillus helveticus subsp. jugurti | Lactobacillus leichmannii |
| Lactobacillus heterohiochii | Lactobacillus letivazi |
| Lactobacillus hilgardii | Lactobacillus lindneri |
| Lactobacillus hilgardii ATCC 8290 | Lactobacillus malefermentans |
| Lactobacillus hokkaidonensis | Lactobacillus malefermentans KCTC 3548 |
| Lactobacillus hominis | Lactobacillus sunkii |
| Lactobacillus hominis CRBIP 24.179 | Lactobacillus taiwanensis |
| Lactobacillus homohiochii | Lactobacillus thailandensis |
| Lactobacillus hordei | Lactobacillus tucceti |
| Lactobacillus iatae | Lactobacillus ultunensis |
| Lactobacillus iners | Lactobacillus ultunensis DSM 16047 |
| Lactobacillus iners AB-1 | Lactobacillus uvarum |
| Lactobacillus iners ACS-070-V-Col3 | Lactobacillus vaccinostercus |
| Lactobacillus iners ATCC 55195 | Lactobacillus vaginalis |
| Lactobacillus iners DSM 13335 | Lactobacillus vaginalis ATCC 49540 |
| Lactobacillus iners LactinV 01V1-a | Lactobacillus vaginalis EX336960VC05 |
| Lactobacillus iners LactinV 03V1-b | Lactobacillus vaginalis EX336960VC11 |
| Lactobacillus iners LactinV 09V1-c | Lactobacillus vaginalis EX336960VC12 |
| Lactobacillus iners LactinV 11V1-d | Lactobacillus vermiforme |
| Lactobacillus iners LEAF 2052A-d | Lactobacillus versmoldensis |
| Lactobacillus iners LEAF 2053A-b | Lactobacillus versmoldensis KCTC 3814 |
| Lactobacillus iners LEAF 2062A-h1 | Lactobacillus vini |
| Lactobacillus iners LEAF 3008A-a | Lactobacillus vini DSM 20605 |
| Lactobacillus iners SPIN 1401G | Lactobacillus vini JP7.8.9 |
| Lactobacillus iners SPIN 2503V10-D | Lactobacillus zymae |
| Lactobacillus iners UPII 143-D | Lactobacillus sp. |
| Lactobacillus iners UPII 60-B | Lactobacillus sp. 0-C-2 |
| Lactobacillus ingluviei | Lactobacillus sp. 1-3-3 |
| Lactobacillus ingluviei str. Autruche 4 | Lactobacillus sp. 1.1424 |
| Lactobacillus insectis | Lactobacillus nagelii |
| Lactobacillus intermedius | Lactobacillus namurensis |
| Lactobacillus intestinalis | Lactobacillus nantensis |
| Lactobacillus japonicus | Lactobacillus nasuensis |
| Lactobacillus jensenii | Lactobacillus nodensis |
| Lactobacillus jensenii 115-3-CHN | Lactobacillus nodensis NBRC 107160 |
| Lactobacillus jensenii 1153 | Lactobacillus odoratitofui |
| Lactobacillus jensenii 208-1 | Lactobacillus oeni |
| Lactobacillus jensenii 269-3 | Lactobacillus oligofermentans |
| Lactobacillus jensenii 27-2-CHN | Lactobacillus oligofermentans LMG 22743 |
| Lactobacillus jensenii EX533959VC02 | Lactobacillus oris |
| Lactobacillus jensenii EX849587VC03 | Lactobacillus oris F0423 |
| Lactobacillus jensenii EX849587VC05 | Lactobacillus oris PB013-T2-3 |
| Lactobacillus jensenii EX849587VC06 | Lactobacillus oryzae |
| Lactobacillus jensenii JV-V16 | Lactobacillus otakiensis |
| Lactobacillus jensenii MD IIE-70(2) | Lactobacillus otakiensis JCM 15040 |
| Lactobacillus jensenii SJ-7A-US | Lactobacillus ozensis |
| Lactobacillus johnsonii | Lactobacillus panis |
| Lactobacillus johnsonii 135-1-CHN | Lactobacillus pantheris |
| Lactobacillus johnsonii 16 | Lactobacillus parabrevis |
| Lactobacillus johnsonii ATCC 33200 | Lactobacillus parabrevis ATCC 53295 |
| Lactobacillus johnsonii DPC 6026 | Lactobacillus parabuchneri |
| Lactobacillus johnsonii FI9785 | Lactobacillus paracollinoides |
| Lactobacillus johnsonii NCC 533 | Lactobacillus parafarraginis |
| Lactobacillus johnsonii pf01 | Lactobacillus parafarraginis F0439 |
| Lactobacillus kalixensis | Lactobacillus parakefiri |
| Lactobacillus kefiranofaciens | Lactobacillus paralimentarius |
| Lactobacillus kefiranofaciens subsp. kefiranofaciens | Lactobacillus paraplantarum |
| Lactobacillus kefiranofaciens subsp. kefirgranum | Lactobacillus pasteurii |
| Lactobacillus kefiranofaciens ZW3 | Lactobacillus pasteurii CRBIP 24.76 |
| Lactobacillus kefiri | Lactobacillus pentosus |

TABLE 1-continued

| | |
|---|---|
| *Lactobacillus kefiri* JCM 5818 | *Lactobacillus pentosus* IG1 |
| *Lactobacillus kimchicus* | *Lactobacillus pentosus* KCA1 |
| *Lactobacillus kimchicus* JCM 15530 | *Lactobacillus pentosus* MP-10 |
| *Lactobacillus kimchiensis* | *Lactobacillus perolens* |
| *Lactobacillus kimchii* | *Lactobacillus plantarum* |
| *Lactobacillus kisonensis* | *Lactobacillus plantarum* 16 |
| *Lactobacillus kisonensis* F0435 | *Lactobacillus plantarum* 2025 |
| *Lactobacillus kitasatonis* | *Lactobacillus plantarum* 2165 |
| *Lactobacillus plantarum* 4_3 | *Lactobacillus ruminis* |
| *Lactobacillus plantarum* AY01 | *Lactobacillus ruminis* ATCC 25644 |
| *Lactobacillus plantarum* CMPG5300 | *Lactobacillus ruminis* ATCC 27782 |
| *Lactobacillus plantarum* DOMLa | *Lactobacillus ruminis* SPM0211 |
| *Lactobacillus plantarum* EGD-AQ4 | *Lactobacillus saerimneri* |
| *Lactobacillus plantarum* IPLA88 | *Lactobacillus saerimneri* 30a |
| *Lactobacillus plantarum* JDM1 | *Lactobacillus saerimneri* DSM 16049 |
| *Lactobacillus plantarum* subsp. *argentoratensis* | *Lactobacillus sakei* |
| *Lactobacillus plantarum* subsp. *plantarum* | *Lactobacillus sakei* dgh6 |
| *Lactobacillus plantarum* subsp. *plantarum* ATCC 14917 | *Lactobacillus sakei* L45 |
| *Lactobacillus plantarum* subsp. *plantarum* KCA-1 | *Lactobacillus sakei* subsp. *carnosus* |
| *Lactobacillus plantarum* subsp. *plantarum* NC8 | *Lactobacillus sakei* subsp. *carnosus* DSM 15831 |
| *Lactobacillus plantarum* subsp. *plantarum* P-8 | *Lactobacillus sakei* subsp. *sakei* |
| *Lactobacillus plantarum* subsp. *plantarum* R0403 | *Lactobacillus sakei* subsp. *sakei* 23K |
| *Lactobacillus plantarum* subsp. *plantarum* ST-III | *Lactobacillus sakei* subsp. *sakei* LS25 |
| *Lactobacillus plantarum* UCMA 3037 | *Lactobacillus salivarius* |
| *Lactobacillus plantarum* WCFS1 | *Lactobacillus salivarius* ACS-116-V-Col5a |
| *Lactobacillus plantarum* ZJ316 | *Lactobacillus salivarius* ATCC 11741 |
| *Lactobacillus pobuzihii* | *Lactobacillus salivarius* B-30514 |
| *Lactobacillus pobuzihii* E100301 | *Lactobacillus salivarius* CECT 5713 |
| *Lactobacillus pontis* | *Lactobacillus salivarius* CELA2 |
| *Lactobacillus psittaci* | *Lactobacillus salivarius* cp400 |
| *Lactobacillus psittaci* DSM 15354 | *Lactobacillus salivarius* DPC 6502 |
| *Lactobacillus rapi* | *Lactobacillus salivarius* GJ-24 |
| *Lactobacillus rennini* | *Lactobacillus salivarius* NIAS840 |
| *Lactobacillus reuteri* | *Lactobacillus salivarius* SMXD51 |
| *Lactobacillus reuteri* 100-23 | *Lactobacillus salivarius* str. *Ren* |
| *Lactobacillus reuteri* 1063 | *Lactobacillus salivarius* UCC118 |
| *Lactobacillus reuteri* ATCC 53608 | *Lactobacillus sanfranciscensis* |
| *Lactobacillus reuteri* CF48-3A | *Lactobacillus sanfranciscensis* TMW 1.1304 |
| *Lactobacillus reuteri* DSM 20016 | *Lactobacillus saniviri* |
| *Lactobacillus reuteri* F275 | *Lactobacillus satsumensis* |
| *Lactobacillus reuteri* I5007 | *Lactobacillus secaliphilus* |
| *Lactobacillus reuteri* JCM 1112 | *Lactobacillus senioris* |
| *Lactobacillus reuteri* lpuph | *Lactobacillus senmaizukei* |
| *Lactobacillus reuteri* mlc3 | *Lactobacillus senmaizukei* NBRC 103853 |
| *Lactobacillus reuteri* MM2-2 | *Lactobacillus sharpeae* |
| *Lactobacillus reuteri* MM2-3 | *Lactobacillus sharpeae* JCM 1186 |
| *Lactobacillus reuteri* MM4-1A | *Lactobacillus shenzhenensis* |
| *Lactobacillus reuteri* SD2112 | *Lactobacillus shenzhenensis* LY-73 |
| *Lactobacillus reuteri* TD1 | *Lactobacillus silagei* |
| *Lactobacillus rhamnosus* | *Lactobacillus siliginis* |
| *Lactobacillus rhamnosus* 2166 | *Lactobacillus similis* |
| *Lactobacillus rhamnosus* ATCC 21052 | *Lactobacillus similis* JCM 2765 |
| *Lactobacillus rhamnosus* ATCC 8530 | *Lactobacillus spicheri* |
| *Lactobacillus rhamnosus* CASL | *Lactobacillus sucicola* |
| *Lactobacillus rhamnosus* CRL1505 | *Lactobacillus suebicus* |
| *Lactobacillus rhamnosus* DSM 14870 | *Lactobacillus suebicus* KCTC 3549 |
| *Lactobacillus rhamnosus* GG | *Lactobacillus* sp. 14.2.14 |
| *Lactobacillus rhamnosus* LMG 25859 | *Lactobacillus* sp. 14.2.15 |
| *Lactobacillus rhamnosus* LMG 27229 | *Lactobacillus* sp. 14.2.18 |
| *Lactobacillus rhamnosus* HN001 | *Lactobacillus* sp. 14.2.20 |
| *Lactobacillus rhamnosus* K32 | *Lactobacillus* sp. 14.2.30 |
| *Lactobacillus rhamnosus* L31 | *Lactobacillus* sp. 14.2.31 |
| *Lactobacillus rhamnosus* L33 | *Lactobacillus* sp. 14.2.33 |
| *Lactobacillus rhamnosus* L34 | *Lactobacillus* sp. 14.2.37 |
| *Lactobacillus rhamnosus* L35 | *Lactobacillus* sp. 14.2.39 |
| *Lactobacillus rhamnosus* Lc 705 | *Lactobacillus* sp. 14.2.4 |
| *Lactobacillus rhamnosus* LMS2-1 | *Lactobacillus* sp. 14.2.41 |
| *Lactobacillus rhamnosus* LOCK900 | *Lactobacillus* sp. 14.2.46 |
| *Lactobacillus rhamnosus* LOCK908 | *Lactobacillus* sp. 14.2.48 |
| *Lactobacillus rhamnosus* LRHMDP2 | *Lactobacillus* sp. 14.2.9 |
| *Lactobacillus rhamnosus* LRHMDP3 | *Lactobacillus* sp. 14.8.15 |
| *Lactobacillus rhamnosus* MSUIS1 | *Lactobacillus* sp. 14.8.19 |
| *Lactobacillus rhamnosus* MTCC 5462 | *Lactobacillus* sp. 14.8.23 |
| *Lactobacillus rhamnosus* NBRC 3425 | *Lactobacillus* sp. 14.8.24 |
| *Lactobacillus rhamnosus* R0011 | *Lactobacillus* sp. 14.8.36 |
| *Lactobacillus rogosae* | *Lactobacillus* sp. 14.8.40 |
| *Lactobacillus rossiae* | *Lactobacillus* sp. 14.8.43 |
| *Lactobacillus rossiae* DSM 15814 | *Lactobacillus* sp. 14.8.44 |
| *Lactobacillus* sp. 14.8.6 | *Lactobacillus* sp. 7.8.26 |
| *Lactobacillus* sp. 14.8.7 | *Lactobacillus* sp. 7.8.27 |

TABLE 1-continued

*Lactobacillus* sp. 14B10
*Lactobacillus* sp. 166
*Lactobacillus* sp. 16DCCH01MX
*Lactobacillus* sp. 18BSM
*Lactobacillus* sp. 19-2
*Lactobacillus* sp. 19DCCH01MX
*Lactobacillus* sp. 1L
*Lactobacillus* sp. 20(2010)
*Lactobacillus* sp. 2011_Ileo_VSA_C1
*Lactobacillus* sp. 2011_Ileo_VSA_C5
*Lactobacillus* sp. 2011_Ileo_VSA_D2
*Lactobacillus* sp. 2011_Ileo_VSA_E2
*Lactobacillus* sp. 2011_Oral_VSA_C7
*Lactobacillus* sp. 20326H4L1
*Lactobacillus* sp. 24DCCH01MX
*Lactobacillus* sp. 3-6
*Lactobacillus* sp. 3.1.1
*Lactobacillus* sp. 3.2.22
*Lactobacillus* sp. 3.2.35
*Lactobacillus* sp. 3.8.18
*Lactobacillus* sp. 3.8.40
*Lactobacillus* sp. 3.8.42
*Lactobacillus* sp. 3.8.8
*Lactobacillus* sp. 30.2.8
*Lactobacillus* sp. 30A
*Lactobacillus* sp. 30BPM
*Lactobacillus* sp. 326
*Lactobacillus* sp. 34-10B
*Lactobacillus* sp. 39D2CCL02MX
*Lactobacillus* sp. 39DCCL02MX
*Lactobacillus* sp. 3AB9
*Lactobacillus* sp. 3b
*Lactobacillus* sp. 3d
*Lactobacillus* sp. 3F11
*Lactobacillus* sp. 41DCCL02MX
*Lactobacillus* sp. 43D2CCL02MX
*Lactobacillus* sp. 43DCCL02MX
*Lactobacillus* sp. 45
*Lactobacillus* sp. 459
*Lactobacillus* sp. 46-211
*Lactobacillus* sp. 47DCCL02MX
*Lactobacillus* sp. 49DCCL02MX
*Lactobacillus* sp. 4B13
*Lactobacillus* sp. 4B31
*Lactobacillus* sp. 5-1-2
*Lactobacillus* sp. 52A
*Lactobacillus* sp. 54DCEP01MX
*Lactobacillus* sp. 59DCEP01MX
*Lactobacillus* sp. 5D32
*Lactobacillus* sp. 6225121
*Lactobacillus* sp. 6225335
*Lactobacillus* sp. 6225616
*Lactobacillus* sp. 62DACEP01MX
*Lactobacillus* sp. 66c
*Lactobacillus* sp. 6D3
*Lactobacillus* sp. 7-19
*Lactobacillus* sp. 7.2.21
*Lactobacillus* sp. 7.2.29
*Lactobacillus* sp. 7.2.33
*Lactobacillus* sp. 7.2.35
*Lactobacillus* sp. 7.2.36
*Lactobacillus* sp. 7.2.40
*Lactobacillus* sp. 7.2.46
*Lactobacillus* sp. 7.2.48
*Lactobacillus* sp. 7.2.49
*Lactobacillus* sp. 7.2.50
*Lactobacillus* sp. 7.8.15
*Lactobacillus* sp. 7.8.17
*Lactobacillus* sp. B9
*Lactobacillus* sp. BB9
*Lactobacillus* sp. BBDP73
*Lactobacillus* sp. BCRC16000
*Lactobacillus* sp. BH0900
*Lactobacillus* sp. 713
*Lactobacillus* sp. 74(2011)
*Lactobacillus* sp. 7_1_47FAA
*Lactobacillus* sp. 7b
*Lactobacillus* sp. 8525126
*Lactobacillus* sp. 88
*Lactobacillus* sp. 8BAM
*Lactobacillus* sp. 7.8.33
*Lactobacillus* sp. 7.8.6
*Lactobacillus* sp. 70811
*Lactobacillus* sp. 70819
*Lactobacillus* sp. 71
*Lactobacillus* sp. 711
*Lactobacillus* sp. 100-23
*Lactobacillus* sp. 100-5
*Lactobacillus* sp. 11050
*Lactobacillus* sp. 11102
*Lactobacillus* sp. 120-6-20
*Lactobacillus* sp. 121B
*Lactobacillus* sp. 123B
*Lactobacillus* sp. 14-3-19
*Lactobacillus* sp. 14.2.12
*Lactobacillus* sp. 14.2.13
*Lactobacillus* sp. Anhor4
*Lactobacillus* sp. Anhoto7
*Lactobacillus* sp. Anhoto8
*Lactobacillus* sp. Anuhmto13
*Lactobacillus* sp. Anuhmto23
*Lactobacillus* sp. ARB2
*Lactobacillus* sp. Arif Mardan-1
*Lactobacillus* sp. ASS
*Lactobacillus* sp. ASF360
*Lactobacillus* sp. ATCC 8291
*Lactobacillus* sp. Atm5
*Lactobacillus* sp. Autruche 4
*Lactobacillus* sp. Autruche 5
*Lactobacillus* sp. B 225
*Lactobacillus* sp. B 226
*Lactobacillus* sp. B 227
*Lactobacillus* sp. B 228
*Lactobacillus* sp. B 229
*Lactobacillus* sp. B 230
*Lactobacillus* sp. B 236
*Lactobacillus* sp. B 237
*Lactobacillus* sp. B 238
*Lactobacillus* sp. B 239
*Lactobacillus* sp. B 245
*Lactobacillus* sp. B 246
*Lactobacillus* sp. B 247
*Lactobacillus* sp. B 248
*Lactobacillus* sp. B 249
*Lactobacillus* sp. B 250
*Lactobacillus* sp. B 251
*Lactobacillus* sp. B 252
*Lactobacillus* sp. B 253
*Lactobacillus* sp. B 254
*Lactobacillus* sp. B 255
*Lactobacillus* sp. B10
*Lactobacillus* sp. B13
*Lactobacillus* sp. B16
*Lactobacillus* sp. B164
*Lactobacillus* sp. B18
*Lactobacillus* sp. B2
*Lactobacillus* sp. B21
*Lactobacillus* sp. B22
*Lactobacillus* sp. B3
*Lactobacillus* sp. B3(2009)
*Lactobacillus* sp. B4
*Lactobacillus* sp. B5
*Lactobacillus* sp. B5406
*Lactobacillus* sp. B5407
*Lactobacillus* sp. B6
*Lactobacillus* sp. B6(2012)
*Lactobacillus* sp. B7
*Lactobacillus* sp. B8
*Lactobacillus* sp. Adhmto1
*Lactobacillus* sp. Adhmto15
*Lactobacillus* sp. Adhmto19
*Lactobacillus* sp. Adhmto21
*Lactobacillus* sp. Adporo6
*Lactobacillus* sp. AF20(2010)
*Lactobacillus* sp. AF26(2010)
*Lactobacillus* sp. Afhot1
*Lactobacillus* sp. AFL13-2
*Lactobacillus* sp. AFL17-5
*Lactobacillus* sp. AFL18-2
*Lactobacillus* sp. AFL18-5

TABLE 1-continued

| | |
|---|---|
| *Lactobacillus* sp. 9C4 | *Lactobacillus* sp. AFL19-3 |
| *Lactobacillus* sp. 9C6 | *Lactobacillus* sp. Afpor8 |
| *Lactobacillus* sp. 9D10 | *Lactobacillus* sp. Afpoto13 |
| *Lactobacillus* sp. 9D6 | *Lactobacillus* sp. Afpoto14 |
| *Lactobacillus* sp. 9D8 | *Lactobacillus* sp. Afpoto7 |
| *Lactobacillus* sp. AA | *Lactobacillus* sp. AI197 |
| *Lactobacillus* sp. Aabbto16 | *Lactobacillus* sp. AI460 |
| *Lactobacillus* sp. Aabbto7 | *Lactobacillus* sp. AI461 |
| *Lactobacillus* sp. Aahmro15 | *Lactobacillus* sp. AK113 |
| *Lactobacillus* sp. Aahmto12 | *Lactobacillus* sp. AK21 |
| *Lactobacillus* sp. Aahonto7 | *Lactobacillus* sp. Akhmbto4 |
| *Lactobacillus* sp. AB015 | *Lactobacillus* sp. Akhmr6 |
| *Lactobacillus* sp. AB032 | *Lactobacillus* sp. Akhmro1 |
| *Lactobacillus* sp. AB05 | *Lactobacillus* sp. Akhmto18 |
| *Lactobacillus* sp. AB05-1 | *Lactobacillus* sp. Akhmto2 |
| *Lactobacillus* sp. AB06 | *Lactobacillus* sp. Akpobro1 |
| *Lactobacillus* sp. ab2 | *Lactobacillus* sp. Akporo7 |
| *Lactobacillus* sp. ab3-w1 | *Lactobacillus* sp. AL2 |
| *Lactobacillus* sp. AB511 | *Lactobacillus* sp. AL5 |
| *Lactobacillus* sp. AB511-2 | *Lactobacillus* sp. Alhm1to4 |
| *Lactobacillus* sp. AB5115-9 | *Lactobacillus* sp. Alhm2to11 |
| *Lactobacillus* sp. AB5216-2 | *Lactobacillus* sp. Alhonto3 |
| *Lactobacillus* sp. AB523-1 | *Lactobacillus* sp. Alhonto4 |
| *Lactobacillus* sp. AB5252 | *Lactobacillus* sp. Am 09 |
| *Lactobacillus* sp. AB5261-2 | *Lactobacillus* sp. AMC1 |
| *Lactobacillus* sp. AB5262 | *Lactobacillus* sp. AMC2 |
| *Lactobacillus* sp. AB5281 | *Lactobacillus* sp. AmmhmR15 |
| *Lactobacillus* sp. AB5282 | *Lactobacillus* sp. AmmhmR3 |
| *Lactobacillus* sp. ab6 | *Lactobacillus* sp. AmmhmR5 |
| *Lactobacillus* sp. ABRIINW-GOL4 | *Lactobacillus* sp. AmmhmT7 |
| *Lactobacillus* sp. ABRIINW.F58 | *Lactobacillus* sp. Ammohmr1 |
| *Lactobacillus* sp. ABT L1 | *Lactobacillus* sp. Ammohmr22 |
| *Lactobacillus* sp. ABT L2 | *Lactobacillus* sp. Ammohmt5 |
| *Lactobacillus* sp. AbxANB3 | *Lactobacillus* sp. Ammopor13 |
| *Lactobacillus* sp. AbxANB4 | *Lactobacillus* sp. Ammopor2 |
| *Lactobacillus* sp. ACD7 | *Lactobacillus* sp. AmmpolR3 |
| *Lactobacillus* sp. Achmto16 | *Lactobacillus* sp. AmmpolR6 |
| *Lactobacillus* sp. Achmto2 | *Lactobacillus* sp. Amsbbr17 |
| *Lactobacillus* sp. AcjLac1 | *Lactobacillus* sp. Amsbbr19 |
| *Lactobacillus* sp. AcjLac10 | *Lactobacillus* sp. Amsbbr2 |
| *Lactobacillus* sp. AcjLac11 | *Lactobacillus* sp. Amsbbr24 |
| *Lactobacillus* sp. AcjLac12 | *Lactobacillus* sp. Amsbbr6 |
| *Lactobacillus* sp. AcjLac13 | *Lactobacillus* sp. Amsbbt11 |
| *Lactobacillus* sp. AcjLac14 | *Lactobacillus* sp. DSM 15502 |
| *Lactobacillus* sp. AcjLac15 | *Lactobacillus* sp. DSM 20197 |
| *Lactobacillus* sp. AcjLac16 | *Lactobacillus* sp. DumLac1 |
| *Lactobacillus* sp. AcjLac17 | *Lactobacillus* sp. DumLac10 |
| *Lactobacillus* sp. AcjLac18 | *Lactobacillus* sp. DumLac11 |
| *Lactobacillus* sp. AcjLac3 | *Lactobacillus* sp. DumLac12 |
| *Lactobacillus* sp. AcjLac4 | *Lactobacillus* sp. DumLac13 |
| *Lactobacillus* sp. AcjLac5 | *Lactobacillus* sp. DumLac14 |
| *Lactobacillus* sp. AcjLac6 | *Lactobacillus* sp. DumLac15 |
| *Lactobacillus* sp. AcjLac7 | *Lactobacillus* sp. DumLac17 |
| *Lactobacillus* sp. AcjLac8 | *Lactobacillus* sp. DumLac18 |
| *Lactobacillus* sp. AcjLac9 | *Lactobacillus* sp. DumLac19 |
| *Lactobacillus* sp. Acpor9 | *Lactobacillus* sp. DumLac2 |
| *Lactobacillus* sp. Adhmro12 | *Lactobacillus* sp. DumLac20 |
| *Lactobacillus* sp. Adhmro7 | *Lactobacillus* sp. DumLac21 |
| *Lactobacillus* sp. DumLac22 | *Lactobacillus* sp. GL1 |
| *Lactobacillus* sp. DumLac23 | *Lactobacillus* sp. GL2 |
| *Lactobacillus* sp. DumLac24 | *Lactobacillus* sp. GM01 |
| *Lactobacillus* sp. DumLac25 | *Lactobacillus* sp. GS21 |
| *Lactobacillus* sp. DumLac26 | *Lactobacillus* sp. GTH1 |
| *Lactobacillus* sp. DumLac27 | *Lactobacillus* sp. GTH10 |
| *Lactobacillus* sp. DumLac28 | *Lactobacillus* sp. GTH13 |
| *Lactobacillus* sp. DumLac29 | *Lactobacillus* sp. GTH15 |
| *Lactobacillus* sp. DumLac3 | *Lactobacillus* sp. GTH17 |
| *Lactobacillus* sp. DumLac30 | *Lactobacillus* sp. GTH18 |
| *Lactobacillus* sp. DumLac31 | *Lactobacillus* sp. GTH2 |
| *Lactobacillus* sp. DumLac32 | *Lactobacillus* sp. GTH20 |
| *Lactobacillus* sp. DumLac33 | *Lactobacillus* sp. GTH22 |
| *Lactobacillus* sp. DumLac34 | *Lactobacillus* sp. GTH24 |
| *Lactobacillus* sp. DumLac35 | *Lactobacillus* sp. GTH26 |
| *Lactobacillus* sp. DumLac36 | *Lactobacillus* sp. GTH28 |
| *Lactobacillus* sp. DumLac37 | *Lactobacillus* sp. GTH29 |
| *Lactobacillus* sp. DumLac38 | *Lactobacillus* sp. GTH30 |
| *Lactobacillus* sp. DumLac39 | *Lactobacillus* sp. GTH32 |
| *Lactobacillus* sp. DumLac4 | *Lactobacillus* sp. GTH33 |
| *Lactobacillus* sp. DumLac40 | *Lactobacillus* sp. GTH5 |
| *Lactobacillus* sp. DumLac41 | *Lactobacillus* sp. GTH6 |

TABLE 1-continued

| | |
|---|---|
| *Lactobacillus* sp. DumLac42 | *Lactobacillus* sp. GTH7 |
| *Lactobacillus* sp. DumLac43 | *Lactobacillus* sp. GTH8 |
| *Lactobacillus* sp. DumLac44 | *Lactobacillus* sp. GTP1 |
| *Lactobacillus* sp. DumLac45 | *Lactobacillus* sp. GTP2 |
| *Lactobacillus* sp. DumLac46 | *Lactobacillus* sp. GTP3 |
| *Lactobacillus* sp. DumLac47 | *Lactobacillus* sp. GTP4 |
| *Lactobacillus* sp. DumLac48 | *Lactobacillus* sp. GTP5 |
| *Lactobacillus* sp. DumLac49 | *Lactobacillus* sp. GTP6 |
| *Lactobacillus* sp. DumLac5 | *Lactobacillus* sp. GTR1 |
| *Lactobacillus* sp. DumLac50 | *Lactobacillus* sp. GTR2 |
| *Lactobacillus* sp. DumLac51 | *Lactobacillus* sp. GTS2 |
| *Lactobacillus* sp. DumLac52 | *Lactobacillus* sp. GV6 |
| *Lactobacillus* sp. DumLac53 | *Lactobacillus* sp. H1HS25N |
| *Lactobacillus* sp. DumLac54 | *Lactobacillus* sp. H1HS38N |
| *Lactobacillus* sp. DumLac6 | *Lactobacillus* sp. H4 |
| *Lactobacillus* sp. DumLac8 | *Lactobacillus* sp. H4bb18N |
| *Lactobacillus* sp. DumLac9 | *Lactobacillus* sp. H4BP4N |
| *Lactobacillus* sp. E12 | *Lactobacillus* sp. H6HS1N |
| *Lactobacillus* sp. EG12 | *Lactobacillus* sp. H6HS21N |
| *Lactobacillus* sp. EL3 | *Lactobacillus* sp. H6HS25N |
| *Lactobacillus* sp. EL6 | *Lactobacillus* sp. H6HS28N |
| *Lactobacillus* sp. EL7 | *Lactobacillus* sp. Hadi Naser-1 |
| *Lactobacillus* sp. EMML 3041 | *Lactobacillus* sp. Hadi Tajabadi-1 |
| *Lactobacillus* sp. F-2 | *Lactobacillus* sp. HG209 |
| *Lactobacillus* sp. F1 | *Lactobacillus* sp. HJ1 |
| *Lactobacillus* sp. F11 | *Lactobacillus* sp. HJ2 |
| *Lactobacillus* sp. F16 | *Lactobacillus* sp. HL7 |
| *Lactobacillus* sp. F2 | *Lactobacillus* sp. Hma11N |
| *Lactobacillus* sp. F2(2009) | *Lactobacillus* sp. Hma2 |
| *Lactobacillus* sp. F31 | *Lactobacillus* sp. Hma2N |
| *Lactobacillus* sp. F52 | *Lactobacillus* sp. Hma8 |
| *Lactobacillus* sp. F7 | *Lactobacillus* sp. Hma8N |
| *Lactobacillus* sp. Faegheh Dilah-1 | *Lactobacillus* sp. Hon2 |
| *Lactobacillus* sp. Faegheh Hadi-1 | *Lactobacillus* sp. Hon2N |
| *Lactobacillus* sp. FAM-02 | *Lactobacillus* sp. HRPRS2 |
| *Lactobacillus* sp. FAM-04 | *Lactobacillus* sp. HRPRTE3 |
| *Lactobacillus* sp. fhon13 | *Lactobacillus* sp. HRROT1 |
| *Lactobacillus* sp. Fhon13N | *Lactobacillus* sp. HRROT3 |
| *Lactobacillus* sp. Fhon2N | *Lactobacillus* sp. HRROTE4 |
| *Lactobacillus* sp. FKU23 | *Lactobacillus* sp. HumaH4 |
| *Lactobacillus* sp. FL1 | *Lactobacillus* sp. HumL3 |
| *Lactobacillus* sp. FL2 | *Lactobacillus* sp. ID9203 |
| *Lactobacillus* sp. FL4 | *Lactobacillus* sp. IDLAc |
| *Lactobacillus* sp. FS1111 | *Lactobacillus* sp. IDSAc |
| *Lactobacillus* sp. FT | *Lactobacillus* sp. IJ-K2 |
| *Lactobacillus* sp. G1 | *Lactobacillus* sp. IL3 |
| *Lactobacillus* sp. G24 | *Lactobacillus* sp. IV-132 |
| *Lactobacillus* sp. GB001 | *Lactobacillus* sp. BH1398 |
| *Lactobacillus* sp. BH1480 | *Lactobacillus* sp. CL6 |
| *Lactobacillus* sp. Bin4 | *Lactobacillus* sp. CL8 |
| *Lactobacillus* sp. Bin4N | *Lactobacillus* sp. CL9 |
| *Lactobacillus* sp. Biut2 | *Lactobacillus* sp. CLE-4 |
| *Lactobacillus* sp. Biut2N | *Lactobacillus* sp. Com4 |
| *Lactobacillus* sp. BJ H8-4 | *Lactobacillus* sp. CPP1 |
| *Lactobacillus* sp. BJ32B3 | *Lactobacillus* sp. CR-609S |
| *Lactobacillus* sp. BJ32B4D | *Lactobacillus* sp. CR-6AS |
| *Lactobacillus* sp. BJ32B4S | *Lactobacillus* sp. CR-7AS |
| *Lactobacillus* sp. BJ4-6B | *Lactobacillus* sp. CRA21 |
| *Lactobacillus* sp. BL263 | *Lactobacillus* sp. CS10 |
| *Lactobacillus* sp. BL301 | *Lactobacillus* sp. CS24.2 |
| *Lactobacillus* sp. BL302 | *Lactobacillus* sp. CWBI/B-659/(E912) |
| *Lactobacillus* sp. BL303 | *Lactobacillus* sp. CY1 |
| *Lactobacillus* sp. BL304 | *Lactobacillus* sp. D2-2-1 |
| *Lactobacillus* sp. BLB1a | *Lactobacillus* sp. D5-2 |
| *Lactobacillus* sp. BLB1b | *Lactobacillus* sp. D6-4 |
| *Lactobacillus* sp. BLB1c | *Lactobacillus koreensis* |
| *Lactobacillus* sp. BLB2 | *Lactobacillus* sp. DCY65 |
| *Lactobacillus* sp. BLB3 | *Lactobacillus* sp. DCY75 |
| *Lactobacillus* sp. Bma5 | *Lactobacillus* sp. DF1 |
| *Lactobacillus* sp. Bma5N | *Lactobacillus* sp. DI71 |
| *Lactobacillus* sp. BS-05 | *Lactobacillus* sp. DI83 |
| *Lactobacillus* sp. BS-09 | *Lactobacillus* sp. Dilah Makhdzir-1 |
| *Lactobacillus* sp. BS-10 | *Lactobacillus* sp. DJF_B156 |
| *Lactobacillus* sp. BS-11 | *Lactobacillus* sp. DJF_CR11 |
| *Lactobacillus* sp. BS-15 | *Lactobacillus* sp. DJF_RP24 |
| *Lactobacillus* sp. BS-19 | *Lactobacillus* sp. DJF_SLA41 |
| *Lactobacillus* sp. BS-22 | *Lactobacillus* sp. DJF_WC57 |
| *Lactobacillus* sp. BS-27 | *Lactobacillus* sp. DL-DW |
| *Lactobacillus* sp. BS-29 | *Lactobacillus* sp. DL3 |
| *Lactobacillus* sp. BS-32 | *Lactobacillus* sp. DL6 |

TABLE 1-continued

| | |
|---|---|
| *Lactobacillus* sp. BS-33 | *Lactobacillus* sp. *Dorsata* |
| *Lactobacillus* sp. BS-36 | *Lactobacillus* sp. DSA-8Z |
| *Lactobacillus* sp. BS1 | *Lactobacillus* sp. L24 |
| *Lactobacillus* sp. BT6 | *Lactobacillus* sp. L25 |
| *Lactobacillus* sp. BTLCH M1/2 | *Lactobacillus* sp. L26 |
| *Lactobacillus* sp. C30An22 | *Lactobacillus* sp. L27 |
| *Lactobacillus* sp. C30An7 | *Lactobacillus* sp. L28 |
| *Lactobacillus* sp. C30An8 | *Lactobacillus* sp. L29 |
| *Lactobacillus* sp. C33LV5 | *Lactobacillus* sp. L3 |
| *Lactobacillus* sp. C56 | *Lactobacillus* sp. L30 |
| *Lactobacillus* sp. C9 | *Lactobacillus* sp. L31 |
| *Lactobacillus* sp. CCC 96S9L | *Lactobacillus* sp. L32 |
| *Lactobacillus* sp. CCTCC 'M 2011381' | *Lactobacillus* sp. L33 |
| *Lactobacillus* sp. CD6 | *Lactobacillus* sp. L34 |
| *Lactobacillus* sp. cemb29 | *Lactobacillus* sp. L35 |
| *Lactobacillus* sp. CF38 | *Lactobacillus* sp. L37 |
| *Lactobacillus* sp. CHU-R | *Lactobacillus* sp. L376 |
| *Lactobacillus* sp. CIA-04 | *Lactobacillus* sp. L38 |
| *Lactobacillus* sp. CIA-40BC | *Lactobacillus* sp. L39 |
| *Lactobacillus* sp. CIDCA 83110 | *Lactobacillus* sp. L4 |
| *Lactobacillus* sp. CIDCA 83111 | *Lactobacillus* sp. L40 |
| *Lactobacillus* sp. CIDCA 83116 | *Lactobacillus* sp. L41 |
| *Lactobacillus* sp. CIDCA 8314 | *Lactobacillus* sp. L42 |
| *Lactobacillus* sp. CIDCA 8315 | *Lactobacillus* sp. L43 |
| *Lactobacillus* sp. CIDCA 8317 | *Lactobacillus* sp. L44 |
| *Lactobacillus* sp. CIDCA 8321 | *Lactobacillus* sp. L45 |
| *Lactobacillus* sp. CIDCA 8325 | *Lactobacillus* sp. L5gt |
| *Lactobacillus* sp. CIDCA 8326 | *Lactobacillus* sp. L5km |
| *Lactobacillus* sp. CIDCA 8332 | *Lactobacillus* sp. L6 |
| *Lactobacillus* sp. CIDCA 8337 | *Lactobacillus* sp. L6 N139 |
| *Lactobacillus* sp. CIDCA 8343 | *Lactobacillus* sp. L6 N18 |
| *Lactobacillus* sp. CIDCA 8345 | *Lactobacillus* sp. L6 N23 |
| *Lactobacillus* sp. CIDCA 8347 | *Lactobacillus* sp. L6 N6 |
| *Lactobacillus* sp. CIDCA 8348 | *Lactobacillus* sp. L6 N68 |
| *Lactobacillus* sp. CL | *Lactobacillus* sp. L63(2011) |
| *Lactobacillus* sp. CL11 | *Lactobacillus* sp. L67 |
| *Lactobacillus* sp. CL3 | *Lactobacillus* sp. L7 |
| *Lactobacillus* sp. CL5 | *Lactobacillus* sp. L8 |
| *Lactobacillus* sp. L8(2006) | *Lactobacillus* sp. MA |
| *Lactobacillus* sp. L9 | *Lactobacillus* sp. Makhdzir Dilah-1 |
| *Lactobacillus* sp. L9(2006) | *Lactobacillus* sp. Makhdzir Mardan-1 |
| *Lactobacillus* sp. L9(2008) | *Lactobacillus* sp. Makhdzir Naser-1 |
| *Lactobacillus* sp. LA-6 | *Lactobacillus* sp. Mardan Mustafa- 1 |
| *Lactobacillus* sp. LAB-1 | *Lactobacillus* sp. Mardan Naser-1 |
| *Lactobacillus* sp. LAB-3 | *Lactobacillus* sp. Mardan Yazid-1 |
| *Lactobacillus* sp. LAB10 | *Lactobacillus* sp. *Mardanium* |
| *Lactobacillus* sp. lab11 | *Lactobacillus* sp. mashak 26 |
| *Lactobacillus* sp. lab13 | *Lactobacillus* sp. MB1A |
| *Lactobacillus* sp. lab2 | *Lactobacillus* sp. MB1C |
| *Lactobacillus* sp. Lac 1 | *Lactobacillus* sp. MB1D |
| *Lactobacillus* sp. Lac 2 | *Lactobacillus* sp. MbBbr1 |
| *Lactobacillus* sp. Lac 3 | *Lactobacillus* sp. MbBipro17 |
| *Lactobacillus* sp. Lac 4 | *Lactobacillus* sp. MbBipro19 |
| *Lactobacillus* sp. Lac 5 | *Lactobacillus* sp. MbBipro7 |
| *Lactobacillus* sp. Lac 6 | *Lactobacillus* sp. MbBipto3 |
| *Lactobacillus* sp. Lact01 | *Lactobacillus* sp. MbHmro1 |
| *Lactobacillus* sp. Lact02 | *Lactobacillus* sp. MbHmro5 |
| *Lactobacillus* sp. Lact03 | *Lactobacillus* sp. Mbhoto3 |
| *Lactobacillus* sp. Lact04 | *Lactobacillus* sp. Mbhsr5 |
| *Lactobacillus* sp. Lact05 | *Lactobacillus* sp. Mbobb2r6 |
| *Lactobacillus* sp. Lact06 | *Lactobacillus* sp. Mbohmt7 |
| *Lactobacillus* sp. Lact08 | *Lactobacillus* sp. Mboho2r2 |
| *Lactobacillus* sp. Lact09 | *Lactobacillus* sp. Mbohs2r12 |
| *Lactobacillus* sp. Lact11 | *Lactobacillus* sp. Mbohs2t2 |
| *Lactobacillus* sp. Lact12 | *Lactobacillus* sp. Mbohs2t7 |
| *Lactobacillus* sp. Lact13 | *Lactobacillus* sp. Mbopo2r2 |
| *Lactobacillus* sp. Lact14 | *Lactobacillus* sp. Mbopo2t4 |
| *Lactobacillus* sp. Lact15 | *Lactobacillus* sp. Mbopo2t6 |
| *Lactobacillus* sp. lb01 | *Lactobacillus* sp. MBUL75 |
| *Lactobacillus* sp. LB1 | *Lactobacillus* sp. MD-1 |
| *Lactobacillus* sp. LB6 | *Lactobacillus* sp. MEB1 |
| *Lactobacillus* sp. LBS-27 | *Lactobacillus* sp. MF-07 |
| *Lactobacillus* sp. ljubL1r | *Lactobacillus* sp. MF1 |
| *Lactobacillus* sp. ljubL4to | *Lactobacillus* sp. MF19(2010) |
| *Lactobacillus* sp. LM-17 | *Lactobacillus* sp. MF213 |
| *Lactobacillus* sp. LMG 17676 | *Lactobacillus* sp. MF41(2010) |
| *Lactobacillus* sp. LOOC279 | *Lactobacillus* sp. MF44(2010) |
| *Lactobacillus* sp. LQC 1642 | *Lactobacillus* sp. MIB1 |
| *Lactobacillus* sp. LQC 1677 | *Lactobacillus* sp. MMP239 |
| *Lactobacillus* sp. LQC 1693 | *Lactobacillus* sp. MMP241 |

TABLE 1-continued

| | |
|---|---|
| *Lactobacillus* sp. LQC 1930 | *Lactobacillus* sp. MMP242 |
| *Lactobacillus* sp. LQC 1937 | *Lactobacillus* sp. MNFS-3 |
| *Lactobacillus* sp. LQC 1938 | *Lactobacillus* sp. MONT4 |
| *Lactobacillus* sp. LQC 1942 | *Lactobacillus* sp. MR-1 |
| *Lactobacillus* sp. LQC 1951 | *Lactobacillus* sp. MR-2 |
| *Lactobacillus* sp. LQC 1954 | *Lactobacillus* sp. MRS-II22 |
| *Lactobacillus* sp. LQC 1958 | *Lactobacillus* sp. MRS-III06 |
| *Lactobacillus* sp. LQC 1959 | *Lactobacillus* sp. MRSB |
| *Lactobacillus* sp. LS1 | *Lactobacillus* sp. MSUGMIR-3 |
| *Lactobacillus* sp. LS3 | *Lactobacillus* sp. MWBPC 1-3-1 |
| *Lactobacillus* sp. LS7 | *Lactobacillus* sp. MYMRS/TEN2 |
| *Lactobacillus* sp. ls79 | *Lactobacillus* sp. MYMRS/TLU1 |
| *Lactobacillus* sp. LS8 | *Lactobacillus* sp. MYMRS/TLU1-T |
| *Lactobacillus* sp. Lu3 | *Lactobacillus* sp. MYTPY/TEN3 |
| *Lactobacillus* sp. Lu5 | *Lactobacillus* sp. N1-5-2 |
| *Lactobacillus* sp. Lu7 | *Lactobacillus* sp. N19 |
| *Lactobacillus* sp. M.D.L2 | *Lactobacillus* sp. N2-7-1 |
| *Lactobacillus* sp. M1 | *Lactobacillus* sp. N20 |
| *Lactobacillus* sp. M1T3B2 | *Lactobacillus* sp. N27 |
| *Lactobacillus* sp. M1T4B2 | *Lactobacillus* sp. N3-1-1 |
| *Lactobacillus* sp. M20 | *Lactobacillus* sp. N3-10-1 |
| *Lactobacillus* sp. M23 | *Lactobacillus* sp. N3-6 |
| *Lactobacillus* sp. M2T2B4 | *Lactobacillus* sp. N4-4 |
| *Lactobacillus* sp. M3T1B1 | *Lactobacillus* sp. N4-6 |
| *Lactobacillus* sp. M3T1B2 | *Lactobacillus* sp. N4-9 |
| *Lactobacillus* sp. M3T1B5 | *Lactobacillus* sp. N54 |
| *Lactobacillus* sp. M8 | *Lactobacillus* sp. Naser Makhdzir-1 |
| *Lactobacillus* sp. M9-1 | *Lactobacillus* sp. Naser Tajabadi-1 |
| *Lactobacillus* sp. NBRC 101665 | *Lactobacillus* sp. NBRC 107254 |
| *Lactobacillus* sp. NBRC 101976 | *Lactobacillus* sp. NBRC 107255 |
| *Lactobacillus* sp. NBRC 106011 | *Lactobacillus* sp. NBRC 107257 |
| *Lactobacillus* sp. NBRC 106019 | *Lactobacillus* sp. NBRC 107258 |
| *Lactobacillus* sp. NBRC 106020 | *Lactobacillus* sp. NBRC 107259 |
| *Lactobacillus* sp. NBRC 106022 | *Lactobacillus* sp. NBRC 107261 |
| *Lactobacillus* sp. NBRC 106024 | *Lactobacillus* sp. NBRC 107262 |
| *Lactobacillus* sp. NBRC 106029 | *Lactobacillus* sp. NBRC 107263 |
| *Lactobacillus* sp. NBRC 106038 | *Lactobacillus* sp. NBRC 107265 |
| *Lactobacillus* sp. NBRC 106039 | *Lactobacillus* sp. NBRC 107266 |
| *Lactobacillus* sp. NBRC 106040 | *Lactobacillus* sp. NBRC 107267 |
| *Lactobacillus* sp. NBRC 106041 | *Lactobacillus* sp. NBRC 107268 |
| *Lactobacillus* sp. NBRC 106042 | *Lactobacillus* sp. NBRC 107270 |
| *Lactobacillus* sp. NBRC 106044 | *Lactobacillus* sp. NBRC 107273 |
| *Lactobacillus* sp. NBRC 106045 | *Lactobacillus* sp. NBRC 107274 |
| *Lactobacillus* sp. NBRC 106046 | *Lactobacillus* sp. NBRC 107275 |
| *Lactobacillus* sp. NBRC 106047 | *Lactobacillus* sp. NBRC 107276 |
| *Lactobacillus* sp. NBRC 107174 | *Lactobacillus* sp. NBRC 107279 |
| *Lactobacillus* sp. NBRC 107175 | *Lactobacillus* sp. NBRC 107282 |
| *Lactobacillus* sp. NBRC 107177 | *Lactobacillus* sp. NBRC 107283 |
| *Lactobacillus* sp. NBRC 107179 | *Lactobacillus* sp. NBRC 107284 |
| *Lactobacillus* sp. NBRC 107180 | *Lactobacillus* sp. NBRC 107285 |
| *Lactobacillus* sp. NBRC 107181 | *Lactobacillus* sp. NBRC 107286 |
| *Lactobacillus* sp. NBRC 107182 | *Lactobacillus* sp. NBRC 107288 |
| *Lactobacillus* sp. NBRC 107183 | *Lactobacillus* sp. NBRC 107289 |
| *Lactobacillus* sp. NBRC 107184 | *Lactobacillus* sp. NBRC 107290 |
| *Lactobacillus* sp. NBRC 107185 | *Lactobacillus* sp. NBRC 107292 |
| *Lactobacillus* sp. NBRC 107187 | *Lactobacillus* sp. NBRC 107293 |
| *Lactobacillus* sp. NBRC 107188 | *Lactobacillus* sp. NBRC 107294 |
| *Lactobacillus* sp. NBRC 107191 | *Lactobacillus* sp. NBRC 107295 |
| *Lactobacillus* sp. NBRC 107192 | *Lactobacillus* sp. NBRC 107297 |
| *Lactobacillus* sp. NBRC 107194 | *Lactobacillus* sp. NBRC 107298 |
| *Lactobacillus* sp. NBRC 107195 | *Lactobacillus* sp. NBRC 107300 |
| *Lactobacillus* sp. NBRC 107196 | *Lactobacillus* sp. NBRC 107301 |
| *Lactobacillus* sp. NBRC 107197 | *Lactobacillus* sp. NBRC 107302 |
| *Lactobacillus* sp. NBRC 107198 | *Lactobacillus* sp. NBRC 107304 |
| *Lactobacillus* sp. NBRC 107199 | *Lactobacillus* sp. NBRC 107305 |
| *Lactobacillus* sp. NBRC 107200 | *Lactobacillus* sp. NBRC 107307 |
| *Lactobacillus* sp. NBRC 107201 | *Lactobacillus* sp. NBRC 107308 |
| *Lactobacillus* sp. NBRC 107202 | *Lactobacillus* sp. NBRC 107311 |
| *Lactobacillus* sp. NBRC 107203 | *Lactobacillus* sp. NBRC 107312 |
| *Lactobacillus* sp. NBRC 107205 | *Lactobacillus* sp. NBRC 107313 |
| *Lactobacillus* sp. NBRC 107207 | *Lactobacillus* sp. NBRC 107315 |
| *Lactobacillus* sp. NBRC 107208 | *Lactobacillus* sp. NBRC 107316 |
| *Lactobacillus* sp. NBRC 107210 | *Lactobacillus* sp. NBRC 107318 |
| *Lactobacillus* sp. NBRC 107211 | *Lactobacillus* sp. NBRC 107320 |
| *Lactobacillus* sp. NBRC 107212 | *Lactobacillus* sp. NBRC 107321 |
| *Lactobacillus* sp. NBRC 107214 | *Lactobacillus* sp. NBRC 107323 |
| *Lactobacillus* sp. NBRC 107215 | *Lactobacillus* sp. NBRC 107324 |
| *Lactobacillus* sp. NBRC 107216 | *Lactobacillus* sp. NBRC 107325 |
| *Lactobacillus* sp. NBRC 107220 | *Lactobacillus* sp. NBRC 107326 |
| *Lactobacillus* sp. NBRC 107223 | *Lactobacillus* sp. NBRC 107327 |

TABLE 1-continued

| | |
|---|---|
| *Lactobacillus* sp. NBRC 107224 | *Lactobacillus* sp. NBRC 107328 |
| *Lactobacillus* sp. NBRC 107226 | *Lactobacillus* sp. NBRC 107329 |
| *Lactobacillus* sp. NBRC 107227 | *Lactobacillus* sp. NBRC 107330 |
| *Lactobacillus* sp. NBRC 107228 | *Lactobacillus* sp. NBRC 107332 |
| *Lactobacillus* sp. NBRC 107229 | *Lactobacillus* sp. NBRC 107334 |
| *Lactobacillus* sp. NBRC 107232 | *Lactobacillus* sp. NBRC 107336 |
| *Lactobacillus* sp. NBRC 107233 | *Lactobacillus* sp. NBRC 107337 |
| *Lactobacillus* sp. NBRC 107234 | *Lactobacillus* sp. NBRC 107338 |
| *Lactobacillus* sp. NBRC 107236 | *Lactobacillus* sp. NBRC 107339 |
| *Lactobacillus* sp. NBRC 107237 | *Lactobacillus* sp. NBRC 107340 |
| *Lactobacillus* sp. NBRC 107238 | *Lactobacillus* sp. NBRC 107341 |
| *Lactobacillus* sp. NBRC 107239 | *Lactobacillus* sp. NBRC 107342 |
| *Lactobacillus* sp. NBRC 107240 | *Lactobacillus* sp. NBRC 107347 |
| *Lactobacillus* sp. NBRC 107242 | *Lactobacillus* sp. NBRC 107348 |
| *Lactobacillus* sp. NBRC 107246 | *Lactobacillus* sp. NBRC 107349 |
| *Lactobacillus* sp. NBRC 107249 | *Lactobacillus* sp. NBRC 107351 |
| *Lactobacillus* sp. NBRC 107252 | *Lactobacillus* sp. NBRC 107352 |
| *Lactobacillus* sp. NBRC 107253 | *Lactobacillus* sp. NBRC 14511 |
| *Lactobacillus* sp. NBRC 14512 | *Lactobacillus* sp. JCM 8637 |
| *Lactobacillus* sp. NBRC 14513 | *Lactobacillus* sp. JCM 8652 |
| *Lactobacillus* sp. NBRC 3229 | *Lactobacillus* sp. JCM 8653 |
| *Lactobacillus* sp. NBRC 3231 | *Lactobacillus* sp. JCM 9717 |
| *Lactobacillus* sp. NBRC 3914 | *Lactobacillus* sp. JCM 9721 |
| *Lactobacillus* sp. NBRC 3954 | *Lactobacillus* sp. JN05 |
| *Lactobacillus* sp. NEQAS6172 | *Lactobacillus* sp. JN1 |
| *Lactobacillus* sp. NGRI 0001 | *Lactobacillus* sp. JN10 |
| *Lactobacillus* sp. NGRI 0130 | *Lactobacillus* sp. JN2 |
| *Lactobacillus* sp. NGRI 0130Q | *Lactobacillus* sp. JN3 |
| *Lactobacillus* sp. NGRI 0304 | *Lactobacillus* sp. JN4 |
| *Lactobacillus* sp. NGRI 0305 | *Lactobacillus* sp. JN5 |
| *Lactobacillus* sp. NIR2 | *Lactobacillus* sp. JN6 |
| *Lactobacillus* sp. NIR20 | *Lactobacillus* sp. JN7 |
| *Lactobacillus* sp. NIR24 | *Lactobacillus* sp. JN8 |
| *Lactobacillus* sp. NIR4 | *Lactobacillus* sp. JN9 |
| *Lactobacillus* sp. NIR5 | *Lactobacillus* sp. JSB1 |
| *Lactobacillus* sp. NIR6 | *Lactobacillus* sp. JV-2006 |
| *Lactobacillus* sp. NIR7 | *Lactobacillus* sp. JW04 |
| *Lactobacillus* sp. NIR8 | *Lactobacillus* sp. KC19 |
| *Lactobacillus* sp. NIRD-P2 | *Lactobacillus* sp. KC35b |
| *Lactobacillus* sp. NM120-1 | *Lactobacillus* sp. KC36a |
| *Lactobacillus* sp. NM191-2 | *Lactobacillus* sp. KC36b |
| *Lactobacillus* sp. NM191-3 | *Lactobacillus* sp. KC38 |
| *Lactobacillus* sp. NM48-2 | *Lactobacillus* sp. KC45a |
| *Lactobacillus* sp. IV-136 | *Lactobacillus* sp. KC45b |
| *Lactobacillus* sp. IV-145 | *Lactobacillus* sp. KLB46 |
| *Lactobacillus* sp. IWT246 | *Lactobacillus* sp. KLB58 |
| *Lactobacillus* sp. IWT248 | *Lactobacillus* sp. KLB79 |
| *Lactobacillus* sp. j0227 | *Lactobacillus* sp. KLDS 1.0701 |
| *Lactobacillus* sp. j0228 | *Lactobacillus* sp. KLDS 1.0702 |
| *Lactobacillus* sp. j0230 | *Lactobacillus* sp. KLDS 1.0703 |
| *Lactobacillus* sp. j0238 | *Lactobacillus* sp. KLDS 1.0704 |
| *Lactobacillus* sp. j0383 | *Lactobacillus* sp. KLDS 1.0705 |
| *Lactobacillus* sp. JC-11 | *Lactobacillus* sp. KLDS 1.0706 |
| *Lactobacillus* sp. JCM 1013 | *Lactobacillus* sp. KLDS 1.0707 |
| *Lactobacillus* sp. JCM 1033 | *Lactobacillus* sp. KLDS 1.0708 |
| *Lactobacillus* sp. JCM 1034 | *Lactobacillus* sp. KLDS 1.0709 |
| *Lactobacillus* sp. JCM 1035 | *Lactobacillus* sp. KLDS 1.0710 |
| *Lactobacillus* sp. JCM 1088 | *Lactobacillus* sp. KLDS 1.0711 |
| *Lactobacillus* sp. JCM 1102 | *Lactobacillus* sp. KLDS 1.0712 |
| *Lactobacillus* sp. JCM 11039 | *Lactobacillus* sp. KLDS 1.0713 |
| *Lactobacillus* sp. JCM 1177 | *Lactobacillus* sp. KLDS 1.0714 |
| *Lactobacillus* sp. JCM 1179 | *Lactobacillus* sp. KLDS 1.0715 |
| *Lactobacillus* sp. JCM 1183 | *Lactobacillus* sp. KLDS 1.0716 |
| *Lactobacillus* sp. JCM 1552 | *Lactobacillus* sp. KLDS 1.0717 |
| *Lactobacillus* sp. JCM 1555 | *Lactobacillus* sp. KLDS 1.0718 |
| *Lactobacillus* sp. JCM 20043 | *Lactobacillus* sp. KLDS 1.0719 |
| *Lactobacillus* sp. JCM 20061 | *Lactobacillus* sp. kvahm3N |
| *Lactobacillus* sp. JCM 2010 | *Lactobacillus* sp. L-YJ |
| *Lactobacillus* sp. JCM 20147 | *Lactobacillus* sp. L01 |
| *Lactobacillus* sp. JCM 2048 | *Lactobacillus* sp. L02 |
| *Lactobacillus* sp. JCM 2049 | *Lactobacillus* sp. L03 |
| *Lactobacillus* sp. JCM 2761 | *Lactobacillus* sp. L1 |
| *Lactobacillus* sp. JCM 2762 | *Lactobacillus* sp. L10 |
| *Lactobacillus* sp. JCM 2763 | *Lactobacillus* sp. L11 |
| *Lactobacillus* sp. JCM 2764 | *Lactobacillus* sp. L12 |
| *Lactobacillus* sp. JCM 2768 | *Lactobacillus* sp. L13 |
| *Lactobacillus* sp. JCM 2770 | *Lactobacillus* sp. L13(2006) |
| *Lactobacillus* sp. JCM 2774 | *Lactobacillus* sp. L14 |
| *Lactobacillus* sp. JCM 5867 | *Lactobacillus* sp. L15 |
| *Lactobacillus* sp. JCM 5868 | *Lactobacillus* sp. L17 |

TABLE 1-continued

| | |
|---|---|
| *Lactobacillus* sp. JCM 5869 | *Lactobacillus* sp. L18 |
| *Lactobacillus* sp. JCM 7524 | *Lactobacillus* sp. L19 |
| *Lactobacillus* sp. JCM 7525 | *Lactobacillus* sp. L2 |
| *Lactobacillus* sp. JCM 7527 | *Lactobacillus* sp. L20 |
| *Lactobacillus* sp. JCM 8601 | *Lactobacillus* sp. L21 |
| *Lactobacillus* sp. JCM 8609 | *Lactobacillus* sp. L215 |
| *Lactobacillus* sp. JCM 8616 | *Lactobacillus* sp. L22 |
| *Lactobacillus* sp. JCM 8633 | *Lactobacillus* sp. L23 |
| *Lactobacillus* sp. SR2 | *Lactobacillus* sp. TBZ3 |
| *Lactobacillus* sp. SW201 | *Lactobacillus* sp. TFC 4301 |
| *Lactobacillus* sp. SWM_Isolation_3 | *Lactobacillus* sp. THK-O24 |
| *Lactobacillus* sp. SXVIII10(2011) | *Lactobacillus* sp. THK-V2 |
| *Lactobacillus* sp. SXVIII11(2011) | *Lactobacillus* sp. THK-V8 |
| *Lactobacillus* sp. SXVIII9(2011) | *Lactobacillus* sp. THK-W28 |
| *Lactobacillus* sp. T057 | *Lactobacillus* sp. THK-W4 |
| *Lactobacillus* sp. T059 | *Lactobacillus* sp. Thmro15 |
| *Lactobacillus* sp. T11g2 | *Lactobacillus* sp. Thmro2 |
| *Lactobacillus* sp. T13/5 | *Lactobacillus* sp. Thmro6 |
| *Lactobacillus* sp. T17/4D | *Lactobacillus* sp. Thoto2 |
| *Lactobacillus* sp. T17/4F | *Lactobacillus* sp. TL33a |
| *Lactobacillus* sp. T1R1C12 | *Lactobacillus* sp. TL35 |
| *Lactobacillus* sp. T1R2C3 | *Lactobacillus* sp. TLMP1 |
| *Lactobacillus* sp. T1R3C2 | *Lactobacillus* sp. TLMP2 |
| *Lactobacillus* sp. T23/3 | *Lactobacillus* sp. TLMP3 |
| *Lactobacillus* sp. T2R1C4 | *Lactobacillus* sp. TLMP4 |
| *Lactobacillus* sp. T2R2C12 | *Lactobacillus* sp. TLMP5 |
| *Lactobacillus* sp. T2R4C3 | *Lactobacillus* sp. TMW 1.1309 |
| *Lactobacillus* sp. T3R1C1 | *Lactobacillus* sp. TN615 |
| *Lactobacillus* sp. T3R2C12 | *Lactobacillus* sp. TN627 |
| *Lactobacillus* sp. T3R2C13 | *Lactobacillus* sp. TN644 |
| *Lactobacillus* sp. T4R2C14 | *Lactobacillus* sp. Tporo2 |
| *Lactobacillus* sp. T4R3C18 | *Lactobacillus* sp. TR7.2.20 |
| *Lactobacillus* sp. T5R1C10 | *Lactobacillus* sp. TR7.3.17 |
| *Lactobacillus* sp. T5R3C15 | *Lactobacillus* sp. TR7.4.12 |
| *Lactobacillus* sp. T5R3C19 | *Lactobacillus* sp. TRC1 |
| *Lactobacillus* sp. T5R3C24 | *Lactobacillus* sp. TRC7 |
| *Lactobacillus* sp. T5R4C21 | *Lactobacillus* sp. TRF5 |
| *Lactobacillus* sp. TAB-01 | *Lactobacillus* sp. TRF7 |
| *Lactobacillus* sp. TAB-02 | *Lactobacillus* sp. TRF8 |
| *Lactobacillus* sp. TAB-03 | *Lactobacillus* sp. TS1 |
| *Lactobacillus* sp. TAB-04 | *Lactobacillus* sp. TS2 |
| *Lactobacillus* sp. TAB-05 | *Lactobacillus* sp. TS3 |
| *Lactobacillus* sp. TAB-06 | *Lactobacillus* sp. TS4 |
| *Lactobacillus* sp. TAB-07 | *Lactobacillus* sp. TSK G32-2 |
| *Lactobacillus* sp. TAB-08 | *Lactobacillus* sp. TTp12 |
| *Lactobacillus* sp. TAB-09 | *Lactobacillus* sp. TTp13 |
| *Lactobacillus* sp. TAB-10 | *Lactobacillus* sp. TTp14 |
| *Lactobacillus* sp. TAB-11 | *Lactobacillus* sp. TTp4 |
| *Lactobacillus* sp. TAB-13 | *Lactobacillus* sp. TTp6 |
| *Lactobacillus* sp. TAB-15 | *Lactobacillus* sp. V2 |
| *Lactobacillus* sp. TAB-16 | *Lactobacillus* sp. VITPRS49 |
| *Lactobacillus* sp. TAB-19 | *Lactobacillus* sp. VM9 |
| *Lactobacillus* sp. TAB-20 | *Lactobacillus* sp. W2 |
| *Lactobacillus* sp. TAB-21 | *Lactobacillus* sp. W20 |
| *Lactobacillus* sp. TAB-22 | *Lactobacillus* sp. W56 |
| *Lactobacillus* sp. TAB-23 | *Lactobacillus* sp. WC2 |
| *Lactobacillus* sp. TAB-24 | *Lactobacillus* sp. WDC04 |
| *Lactobacillus* sp. TAB-25 | *Lactobacillus* sp. WK2S-6B |
| *Lactobacillus* sp. TAB-26 | *Lactobacillus* sp. WX131 |
| *Lactobacillus* sp. TAB-29 | *Lactobacillus* sp. WX212 |
| *Lactobacillus* sp. TAB-30 | *Lactobacillus* sp. WX213 |
| *Lactobacillus* sp. TAB-31 | *Lactobacillus* sp. X1 |
| *Lactobacillus* sp. TAB-33 | *Lactobacillus* sp. Y10 |
| *Lactobacillus* sp. Taj Amir-1 | *Lactobacillus* sp. Yazid Arash-1 |
| *Lactobacillus* sp. Taj Mahdi | *Lactobacillus* sp. Yazid Taj-1 |
| *Lactobacillus* sp. Taj Mar-1 | *Lactobacillus* sp. YE06 |
| *Lactobacillus* sp. Taj Mustafa-1 | *Lactobacillus* sp. YE07 |
| *Lactobacillus* sp. Taj Naser-1 | *Lactobacillus* sp. YE08 |
| *Lactobacillus* sp. Taj Yazid-1 | *Lactobacillus* sp. YE10 |
| *Lactobacillus* sp. Taj-KH107 | *Lactobacillus* sp. YFPB2BMX |
| *Lactobacillus* sp. Taj-KH109 | *Lactobacillus* sp. YW |
| *Lactobacillus* sp. Taj-KH123 | *Lactobacillus* sp. YYS |
| *Lactobacillus* sp. Taj-KS164 | *Lactobacillus* sp. ZL7 |
| *Lactobacillus* sp. Taj-KS82 | *Lactobacillus* sp. ZYM7 |
| *Lactobacillus* sp. Tajabadi-1 | *Lactobacillus* sp. A A18 |
| *Lactobacillus* sp. Tbbto15 | *Lactobacillus* sp. A A21 |
| *Lactobacillus* sp. TBZ | *Lactobacillus* sp. A A25 |
| *Lactobacillus* sp. TBZ2 | *Lactobacillus* sp. A A29 |
| *Lactobacillus* sp. A A35 | *Lactobacillus* sp. r2 |
| *Lactobacillus* sp. A A44 | *Lactobacillus* sp. R4B |

TABLE 1-continued

| | |
|---|---|
| *Lactobacillus* sp. A A45 | *Lactobacillus* sp. R4C |
| *Lactobacillus* sp. A A48 | *Lactobacillus* sp. r5-w10 |
| *Lactobacillus* sp. A A49 | *Lactobacillus* sp. r7 |
| *Lactobacillus* sp. A A85 | *Lactobacillus* sp. r8 |
| *Lactobacillus* sp. A A96 | *Lactobacillus* sp. RA2053 |
| *Lactobacillus* sp. B A100 | *Lactobacillus* sp. RA2062 |
| *Lactobacillus* sp. B A101 | *Lactobacillus* sp. RA2066 |
| *Lactobacillus* sp. B A102 | *Lactobacillus* sp. RA2113 |
| *Lactobacillus* sp. B A103 | *Lactobacillus* sp. RA2120 |
| *Lactobacillus* sp. B A12 | *Lactobacillus* sp. rennanqilfy10 |
| *Lactobacillus* sp. B A13 | *Lactobacillus* sp. rennanqilfy11 |
| *Lactobacillus* sp. B A14 | *Lactobacillus* sp. rennanqilfy14 |
| *Lactobacillus* sp. B A16 | *Lactobacillus* sp. rennanqilfy15 |
| *Lactobacillus* sp. B A19 | *Lactobacillus* sp. rennanqilfy16 |
| *Lactobacillus* sp. B A20 | *Lactobacillus* sp. rennanqilfy17 |
| *Lactobacillus* sp. B A23 | *Lactobacillus* sp. rennanqilfy19 |
| *Lactobacillus* sp. B A31 | *Lactobacillus* sp. rennanqilfy2 |
| *Lactobacillus* sp. B A33 | *Lactobacillus* sp. rennanqilfy20 |
| *Lactobacillus* sp. NM59-6 | *Lactobacillus* sp. rennanqilfy32 |
| *Lactobacillus* sp. NR1006 | *Lactobacillus* sp. rennanqilfy34 |
| *Lactobacillus* sp. NRCT-KU 1 | *Lactobacillus* sp. rennanqilfy61 |
| *Lactobacillus* sp. NS111 | *Lactobacillus* sp. rennanqilyf13 |
| *Lactobacillus* sp. NS123 | *Lactobacillus* sp. rennanqilyf4 |
| *Lactobacillus* sp. NS133 | *Lactobacillus* sp. rennanqilyf5 |
| *Lactobacillus* sp. Oh-3 | *Lactobacillus* sp. rennanqilyf7 |
| *Lactobacillus* sp. Oh-4 | *Lactobacillus* sp. rennanqilyf8 |
| *Lactobacillus* sp. OR 11 | *Lactobacillus* sp. rennanqilyf9 |
| *Lactobacillus* sp. OR 9 | *Lactobacillus* sp. RIC11-BK004 |
| *Lactobacillus* sp. OR1 | *Lactobacillus* sp. RIC11-BK008 |
| *Lactobacillus* sp. OR6 | *Lactobacillus* sp. RIC11-BK009 |
| *Lactobacillus* sp. oral taxon 052 | *Lactobacillus* sp. RIC11-MK006 |
| *Lactobacillus* sp. oral taxon 418 | *Lactobacillus* sp. RIC11-MK010 |
| *Lactobacillus* sp. oral taxon 424 | *Lactobacillus* sp. RIC12-Oh002 |
| *Lactobacillus* sp. oral taxon 461 | *Lactobacillus* sp. RIC12-Oh004 |
| *Lactobacillus* sp. oral taxon A89 | *Lactobacillus* sp. RKY2 |
| *Lactobacillus* sp. oral taxon B73 | *Lactobacillus* sp. RMS3-1 |
| *Lactobacillus* sp. oral taxon B80 | *Lactobacillus* sp. Rnm4 |
| *Lactobacillus* sp. oral taxon D06 | *Lactobacillus* sp. Rrv5 |
| *Lactobacillus* sp. oral taxon G15 | *Lactobacillus* sp. RU1 |
| *Lactobacillus* sp. oral taxon G16 | *Lactobacillus* sp. S1 |
| *Lactobacillus* sp. oral taxon G18 | *Lactobacillus* sp. S14 |
| *Lactobacillus* sp. oral taxon G19 | *Lactobacillus* sp. S15 |
| *Lactobacillus* sp. oral taxon G98 | *Lactobacillus* sp. S16 |
| *Lactobacillus* sp. oral taxon H08 | *Lactobacillus* sp. S19 |
| *Lactobacillus* sp. oral taxon H12 | *Lactobacillus* sp. S4-3 |
| *Lactobacillus* sp. oral taxon H14 | *Lactobacillus* sp. S4B |
| *Lactobacillus* sp. oral taxon H25 | *Lactobacillus* sp. S4C |
| *Lactobacillus* sp. OS10 | *Lactobacillus* sp. Sal8 |
| *Lactobacillus* sp. OS72 | *Lactobacillus* sp. SCA34 |
| *Lactobacillus* sp. P22 | *Lactobacillus* sp. SCA39 |
| *Lactobacillus* sp. P23 | *Lactobacillus* sp. SCA52 |
| *Lactobacillus* sp. P8 | *Lactobacillus* sp. SCA7 |
| *Lactobacillus* sp. PC-3 | *Lactobacillus* sp. SD2 |
| *Lactobacillus* sp. PC121B | *Lactobacillus* sp. SDR1 |
| *Lactobacillus* sp. pep8 | *Lactobacillus* sp. SH.Z4 |
| *Lactobacillus* sp. Probio-24 | *Lactobacillus* sp. sh.zh1 |
| *Lactobacillus* sp. Probio-27 | *Lactobacillus* sp. sh.zh2 |
| *Lactobacillus* sp. QOX-01BC | *Lactobacillus* sp. sh.zh3 |
| *Lactobacillus* sp. QOX-02BC | *Lactobacillus* sp. Shuhaimi Arash-1 |
| *Lactobacillus* sp. QOX-06BC | *Lactobacillus* sp. Shuhaimi Mardan-1 |
| *Lactobacillus* sp. QOX-10BC | *Lactobacillus* sp. Shuhaimi naser-1 |
| *Lactobacillus* sp. QOX-20G | *Lactobacillus* sp. Shuhaimi Taj-1 |
| *Lactobacillus* sp. R-17510 | *Lactobacillus* sp. Shuhaimi Yazid-1 |
| *Lactobacillus* sp. R-17516 | *Lactobacillus* sp. SK007 |
| *Lactobacillus* sp. R-17818 | *Lactobacillus* sp. SL |
| *Lactobacillus* sp. R-21386 | *Lactobacillus* sp. SR1 |
| *Lactobacillus* sp. R-42633 | *Lactobacillus* sp. B AB1 |
| *Lactobacillus* sp. r1w3 | *Lactobacillus* sp. B CG1 |
| *Lactobacillus* sp. B CG3 | *Lactobacillus* sp. B A98 |
| *Lactobacillus* sp. B CG53 | *Lactobacillus* sp. B CG71 |
| *Lactobacillus* sp. B CG63 | *Lactobacillus* sp. B CG76 |
| *Lactobacillus* sp. B A34 | environmental samples |
| *Lactobacillus* sp. B A36 | *Lactobacillus amylovorus* CAG:719 |
| *Lactobacillus* sp. B A37 | *Lactobacillus ruminis* CAG:367 |
| *Lactobacillus* sp. B A41 | *Lactobacillus* sp. DGGE band 26 |
| *Lactobacillus* sp. B A42 | *Lactobacillus* sp. DGGE band 29 |
| *Lactobacillus* sp. B A52 | *Lactobacillus* sp. enrichment culture clone 1 |
| *Lactobacillus* sp. B A53 | *Lactobacillus* sp. enrichment culture clone 58 |
| *Lactobacillus* sp. B A64 | *Lactobacillus* sp. enrichment culture clone PSR03 |
| *Lactobacillus* sp. B A65 | *Lactobacillus* sp. enrichment culture clone PSR2 |

TABLE 1-continued

| | |
|---|---|
| *Lactobacillus* sp. B A76 | *Lactobacillus* sp. enrichment culture clone PTmrs6 |
| *Lactobacillus* sp. B A78 | *Lactobacillus* sp. enrichment culture DGGE gel band 10 |
| *Lactobacillus* sp. B A81 | *Lactobacillus* sp. enrichment culture DGGE gel band 12 |
| *Lactobacillus* sp. B A86 | *Lactobacillus* sp. enrichment culture DGGE gel band 4 |
| *Lactobacillus* sp. B A87 | *Lactobacillus* sp. enrichment culture DGGE gel band 8 |
| *Lactobacillus* sp. B A89 | *Lactobacillus* sp. enrichment culture DGGE gel band 9 |
| *Lactobacillus* sp. B A90 | *Lactobacillus* sp. oral clone CX036 |
| *Lactobacillus* sp. B A91 | *Lactobacillus* sp. oral clone HT002 |
| *Lactobacillus* sp. B A95 | *Lactobacillus* sp. oral clone HT070 |
| *Lactobacillus* sp. B A97 | uncultured *Lactobacillus* sp. |

Genus: *Bifidobacterium*

| | |
|---|---|
| *Bifidobacterium adolescentis* | *Bifidobacterium breve* EX336960VC18 |
| *Bifidobacterium adolescentis* ATCC 15703 | *Bifidobacterium breve* EX336960VC19 |
| *Bifidobacterium adolescentis* L2-32 | *Bifidobacterium breve* EX336960VC21 |
| *Bifidobacterium angulatum* | *Bifidobacterium breve* EX533959VC21 |
| *Bifidobacterium angulatum* DSM 20098 = JCM 7096 | *Bifidobacterium breve* HPH0326 |
| *Bifidobacterium angulatum* F16_22 | *Bifidobacterium breve* JCP7499 |
| *Bifidobacterium animalis* | *Bifidobacterium breve* S27 |
| *Bifidobacterium animalis* subsp. *animalis* | *Bifidobacterium breve* UCC2003 |
| *Bifidobacterium animalis* subsp. *animalis* ATCC 25527 | *Bifidobacterium callitrichos* |
| *Bifidobacterium animalis* subsp. *lactis* | *Bifidobacterium catenulatum* |
| *Bifidobacterium animalis* subsp. *lactis* AD011 | *Bifidobacterium catenulatum* DSM 16992 = JCM 1194 |
| *Bifidobacterium animalis* subsp. *lactis* ATCC 27673 | *Bifidobacterium choerinum* |
| *Bifidobacterium animalis* subsp. *lactis* B420 | *Bifidobacterium choerinum* DSM 20434 |
| *Bifidobacterium animalis* subsp. *lactis* BB-12 | *Bifidobacterium coryneforme* |
| *Bifidobacterium animalis* subsp. *lactis* Bi-07 | *Bifidobacterium crudilactis* |
| *Bifidobacterium animalis* subsp. *lactis* Bl-04 | *Bifidobacterium cuniculi* |
| *Bifidobacterium animalis* subsp. *lactis* B112 | *Bifidobacterium dentium* |
| *Bifidobacterium animalis* subsp. *lactis* BLC1 | *Bifidobacterium dentium* ATCC 27678 |
| *Bifidobacterium animalis* subsp. *lactis* BS 01 | *Bifidobacterium dentium* ATCC 27679 |
| *Bifidobacterium animalis* subsp. *lactis* CNCM I-2494 | *Bifidobacterium dentium* Bd1 |
| *Bifidobacterium animalis* subsp. *lactis* DSM 10140 | *Bifidobacterium dentium* JCM 1195 |
| *Bifidobacterium animalis* subsp. *lactis* HN019 | *Bifidobacterium dentium* JCVIHMP022 |
| *Bifidobacterium animalis* subsp. *lactis* V9 | *Bifidobacterium gallicum* |
| *Bifidobacterium asteroides* | *Bifidobacterium gallicum* DSM 20093 |
| *Bifidobacterium asteroides* PRL2011 | *Bifidobacterium gallinarum* |
| *Bifidobacterium biavatii* | *Bifidobacterium indicum* |
| *Bifidobacterium bifidum* | |
| *Bifidobacterium bifidum* ATCC 29521 = JCM 1255 | *Bifidobacterium indicum* LMG 11587 |
| *Bifidobacterium bifidum* BGN4 | *Bifidobacterium kashiwanohense* |
| *Bifidobacterium bifidum* CECT 7366 | *Bifidobacterium kashiwanohense* JCM 15439 |
| *Bifidobacterium bifidum* DSM 20215 | *Bifidobacterium longum* |
| *Bifidobacterium bifidum* IPLA 20015 | *Bifidobacterium longum* 3_1_37DFAAB |
| *Bifidobacterium bifidum* JCM 1254 | *Bifidobacterium longum* AGR2137 |
| *Bifidobacterium bifidum* LMG 13195 | *Bifidobacterium longum* BORI |
| *Bifidobacterium bifidum* NCIMB 41171 | *Bifidobacterium longum* D2957 |
| *Bifidobacterium bifidum* PRL2010 | *Bifidobacterium longum* DJO10A |
| *Bifidobacterium bifidum* S17 | *Bifidobacterium longum* E18 |
| Bifidobacterium bombi | *Bifidobacterium longum* NCC2705 |
| Bifidobacterium bombi DSM 19703 | *Bifidobacterium longum* subsp. *infantis* |
| Bifidobacterium bourn | *Bifidobacterium longum* subsp. *infantis* 157F |
| *Bifidobacterium breve* | *Bifidobacterium longum* subsp. *infantis* ATCC 15697 = JCM 1222 |
| *Bifidobacterium breve* ACS-071-V-Sch8b | *Bifidobacterium longum* subsp. *infantis* CCUG 52486 |
| *Bifidobacterium breve* CECT 7263 | *Bifidobacterium longum* subsp. *longum* |
| *Bifidobacterium breve* DPC 6330 | *Bifidobacterium longum* subsp. *longum* 1-5B |
| *Bifidobacterium breve* DSM 20213 = JCM 1192 | *Bifidobacterium longum* subsp. *longum* 1-6B |
| *Bifidobacterium longum* subsp. *longum* 17-1B | *Bifidobacterium* sp. 234 |
| *Bifidobacterium longum* subsp. *longum* 2-2B | *Bifidobacterium* sp. 265 |
| *Bifidobacterium longum* subsp. *longum* 35B | *Bifidobacterium* sp. 266 |
| *Bifidobacterium longum* subsp. *longum* 44B | *Bifidobacterium* sp. 27 |
| *Bifidobacterium longum* subsp. *longum* 7-1B | *Bifidobacterium* sp. 272 |
| *Bifidobacterium longum* subsp. *longum* ATCC 55813 | *Bifidobacterium* sp. 283 |
| *Bifidobacterium longum* subsp. *longum* BBMN68 | *Bifidobacterium* sp. 286 |
| *Bifidobacterium longum* subsp. *longum* CECT 7347 | *Bifidobacterium* sp. 316 |
| *Bifidobacterium longum* subsp. *longum* CMCC P0001 | *Bifidobacterium* sp. 320 |
| *Bifidobacterium longum* subsp. *longum* F8 | *Bifidobacterium* sp. 323 |
| *Bifidobacterium longum* subsp. *longum* GT15 | *Bifidobacterium* sp. 33 |
| *Bifidobacterium longum* subsp. *longum* JCM 1217 | *Bifidobacterium* sp. 343 |
| *Bifidobacterium longum* subsp. *longum* JDM301 | *Bifidobacterium* sp. 344 |
| *Bifidobacterium longum* subsp. *longum* KACC 91563 | *Bifidobacterium* sp. 360 |
| *Bifidobacterium longum* subsp. *suis* | *Bifidobacterium* sp. 397 |
| *Bifidobacterium magnum* | *Bifidobacterium* sp. 401 |
| *Bifidobacterium magnum* DSM 20222 | *Bifidobacterium* sp. 434 |
| *Bifidobacterium merycicum* | *Bifidobacterium* sp. 445 |
| *Bifidobacterium minimum* | *Bifidobacterium* sp. 470 |
| *Bifidobacterium minimum* DSM 20102 | *Bifidobacterium* sp. 471 |
| *Bifidobacterium mongoliense* | *Bifidobacterium* sp. 65947 |
| *Bifidobacterium pseudocatenulatum* | *Bifidobacterium* sp. 69 |
| *Bifidobacterium pseudocatenulatum* D2CA | *Bifidobacterium* sp. 7101 |

TABLE 1-continued

| | |
|---|---|
| *Bifidobacterium pseudocatenulatum* DSM 20438 = JCM 1200 | *Bifidobacterium* sp. 77 |
| *Bifidobacterium pseudolongum* | *Bifidobacterium* sp. 84 |
| *Bifidobacterium pseudolongum* AGR2145 | *Bifidobacterium* sp. 98 |
| *Bifidobacterium pseudolongum* subsp. *globosum* | *Bifidobacterium* sp. A1 |
| *Bifidobacterium pseudolongum* subsp. *pseudolongum* | *Bifidobacterium* sp. A11 |
| *Bifidobacterium psychraerophilum* | *Bifidobacterium* sp. A15 |
| *Bifidobacterium pullorum* | *Bifidobacterium* sp. A24 |
| *Bifidobacterium pullorum* ATCC 49618 | *Bifidobacterium* sp. A30 |
| *Bifidobacterium reuteri* | *Bifidobacterium* sp. Aabbto19 |
| *Bifidobacterium ruminantium* | *Bifidobacterium* sp. Aahmro6 |
| *Bifidobacterium saeculare* | *Bifidobacterium* sp. Aahmto9 |
| *Bifidobacterium saguini* | *Bifidobacterium* sp. Acbbto5 |
| *Bifidobacterium scardovii* | *Bifidobacterium* sp. Achmro11 |
| *Bifidobacterium scardovii* JCM 12489 | *Bifidobacterium* sp. AcjBF1 |
| *Bifidobacterium simiae* | *Bifidobacterium* sp. AcjBF10 |
| *Bifidobacterium stellenboschense* | *Bifidobacterium* sp. AcjBF11 |
| *Bifidobacterium stercoris* | *Bifidobacterium* sp. AcjBF2 |
| *Bifidobacterium subtile* | *Bifidobacterium* sp. AcjBF3 |
| *Bifidobacterium subtile* DSM 20096 | *Bifidobacterium* sp. AcjBF4 |
| *Bifidobacterium thermacidophilum* | *Bifidobacterium* sp. AcjBF5 |
| *Bifidobacterium thermacidophilum* subsp. *porcinum* | *Bifidobacterium* sp. AcjBF6 |
| *Bifidobacterium thermacidophilum* subsp. *thermacidophilum* | *Bifidobacterium* sp. AcjBF7 |
| *Bifidobacterium thermacidophilum* subsp. *thermacidophilum* DSM 15837 | *Bifidobacterium* sp. AcjBF8 |
| | *Bifidobacterium* sp. AcjBF9 |
| *Bifidobacterium thermophilum* | *Bifidobacterium* sp. Adhmto10 |
| *Bifidobacterium thermophilum* RBL67 | *Bifidobacterium* sp. AFB22-4 |
| *Bifidobacterium tsurumiense* | *Bifidobacterium* sp. Afpor11 |
| *Bifidobacterium tsurumiense* DSM 17777 | *Bifidobacterium* sp. Afpor3 |
| *Bifidobacterium* sp. | *Bifidobacterium* sp. Afpoto19 |
| *Bifidobacterium* sp. 103 | *Bifidobacterium* sp. AGR2158 |
| *Bifidobacterium* sp. 108 | *Bifidobacterium* sp. Alhonro1 |
| *Bifidobacterium* sp. 11-5-G | *Bifidobacterium* sp. Ammopor6 |
| *Bifidobacterium* sp. 113 | *Bifidobacterium* sp. AmmpolR4 |
| *Bifidobacterium* sp. 120 | *Bifidobacterium* sp. Amsbbr10 |
| *Bifidobacterium* sp. 126 | *Bifidobacterium* sp. Amsbbt12 |
| *Bifidobacterium* sp. 129 | *Bifidobacterium* sp. Amshmr9 |
| *Bifidobacterium* sp. 12_1_47BFAA | *Bifidobacterium* sp. Amshor11 |
| *Bifidobacterium* sp. 138 | *Bifidobacterium* sp. Anbbr2 |
| *Bifidobacterium* sp. 150 | *Bifidobacterium* sp. Anuhmto12 |
| *Bifidobacterium* sp. 17 | *Bifidobacterium* sp. B4 |
| *Bifidobacterium* sp. 172 | *Bifidobacterium* sp. BBDP69 |
| *Bifidobacterium* sp. 176 | *Bifidobacterium* sp. BcRW10 |
| *Bifidobacterium* sp. 182 | *Bifidobacterium* sp. Bin2 |
| *Bifidobacterium* sp. 197 | *Bifidobacterium* sp. Bin7 |
| *Bifidobacterium* sp. 202 | *Bifidobacterium* sp. Bisn6 |
| *Bifidobacterium* sp. 215 | *Bifidobacterium* sp. Bma6 |
| *Bifidobacterium* sp. 216 | *Bifidobacterium* sp. CB38 |
| *Bifidobacterium* sp. CB8 | *Bifidobacterium* sp. M45 |
| *Bifidobacterium* sp. CFAR 172 | *Bifidobacterium* sp. M7 |
| *Bifidobacterium* sp. CJ59 | *Bifidobacterium* sp. Mbobb2r3 |
| *Bifidobacterium* sp. CJ75 | *Bifidobacterium* sp. Mbobb2t2 |
| *Bifidobacterium* sp. CS16 | *Bifidobacterium* sp. Mbpor2 |
| *Bifidobacterium* sp. CS2 | *Bifidobacterium* sp. MSTE12 |
| *Bifidobacterium* sp. CS30 | *Bifidobacterium* sp. MSX5B |
| *Bifidobacterium* sp. CWCAST32 | *Bifidobacterium* sp. MW-222 |
| *Bifidobacterium* sp. CWCAST40 | *Bifidobacterium* sp. MW-613 |
| *Bifidobacterium* sp. CWSAB40 | *Bifidobacterium* sp. MW-623 |
| *Bifidobacterium* sp. CWSAB6 | *Bifidobacterium* sp. MW-81 |
| *Bifidobacterium* sp. DJF_RP64k1 | *Bifidobacterium* sp. N33 |
| *Bifidobacterium* sp. DJF_WC44 | *Bifidobacterium* sp. oral strain A32ED |
| *Bifidobacterium* sp. DPTE6 | *Bifidobacterium* sp. oral strain H6-M4 |
| *Bifidobacterium* sp. DPVI-TET3 | *Bifidobacterium* sp. PB24 |
| *Bifidobacterium* sp. DPVI-TET6 | *Bifidobacterium* sp. PEB0163 |
| *Bifidobacterium* sp. F-10 | *Bifidobacterium* sp. PFGE 14 |
| *Bifidobacterium* sp. F-11 | *Bifidobacterium* sp. PFGE 18 |
| *Bifidobacterium* sp. F2 | *Bifidobacterium* sp. PFGE 8 |
| *Bifidobacterium* sp. F8 | *Bifidobacterium* sp. PFGE 9a |
| *Bifidobacterium* sp. G29 | *Bifidobacterium* sp. PG10 |
| *Bifidobacterium* sp. GC61 | *Bifidobacterium* sp. PG12A |
| *Bifidobacterium* sp. group I-3 | *Bifidobacterium* sp. PG12B |
| *Bifidobacterium* sp. group II-3 | *Bifidobacterium* sp. PG13 |
| *Bifidobacterium* sp. group III-3 | *Bifidobacterium* sp. PG15 |
| *Bifidobacterium* sp. h12 | *Bifidobacterium* sp. PG18 |
| *Bifidobacterium* sp. HGAT1 | *Bifidobacterium* sp. PG19 |
| *Bifidobacterium* sp. HGAT10 | *Bifidobacterium* sp. PG2 |
| *Bifidobacterium* sp. HGAT2 | *Bifidobacterium* sp. PG22 |
| *Bifidobacterium* sp. HGAT3 | *Bifidobacterium* sp. PG30 |
| *Bifidobacterium* sp. HGAT4 | *Bifidobacterium* sp. PG9 |
| *Bifidobacterium* sp. HGAT5 | *Bifidobacterium* sp. PL1 |
| *Bifidobacterium* sp. HGAT6 | *Bifidobacterium* sp. S-10 |

TABLE 1-continued

| | |
|---|---|
| *Bifidobacterium* sp. HGAT7 | *Bifidobacterium* sp. S13-05 |
| *Bifidobacterium* sp. HGAT8 | *Bifidobacterium* sp. S18-11 |
| *Bifidobacterium* sp. HGAT9 | *Bifidobacterium* sp. SLPYG-1 |
| *Bifidobacterium* sp. Hma3 | *Bifidobacterium* sp. SMst02 |
| *Bifidobacterium* sp. HMLN1 | *Bifidobacterium* sp. SRW-001 |
| *Bifidobacterium* sp. HMLN12 | *Bifidobacterium* sp. SRW-002 |
| *Bifidobacterium* sp. HMLN13 | *Bifidobacterium* sp. SRW-003 |
| *Bifidobacterium* sp. HMLN14 | *Bifidobacterium* sp. SRW-004 |
| *Bifidobacterium* sp. HMLN5 | *Bifidobacterium* sp. Tbbto10 |
| *Bifidobacterium* sp. HMLN8 | *Bifidobacterium* sp. Thsr10 |
| *Bifidobacterium* sp. HMSH1 | *Bifidobacterium* sp. Thsr18 |
| *Bifidobacterium* sp. HMSH2 | *Bifidobacterium* sp. Thsr2 |
| *Bifidobacterium* sp. HMSH5 | *Bifidobacterium* sp. TM-7 |
| *Bifidobacterium* sp. IR007-108 | *Bifidobacterium* sp. Trm9 |
| *Bifidobacterium* sp. IR007-113 | environmental samples |
| *Bifidobacterium* sp. IR007-15 | *Bifidobacterium adolescentis* CAG:119 |
| *Bifidobacterium* sp. IR007-57 | *Bifidobacterium bifidum* CAG:234 |
| *Bifidobacterium* sp. IR007-93 | *Bifidobacterium longum* CAG:69 |
| *Bifidobacterium* sp. IR007-94 | *Bifidobacterium pseudocatenulatum* CAG:263 |
| *Bifidobacterium* sp. ISO3519 | *Bifidobacterium* sp. enrichment culture DGGE gel band 6 |
| *Bifidobacterium* sp. JCM 6439 | *Bifidobacterium* sp. enrichment culture DGGE gel band 7 |
| *Bifidobacterium* sp. JCM 7013 | *Bifidobacterium* sp. oral clone 5RH-30 |
| *Bifidobacterium* sp. JCM 7022 | *Bifidobacterium* sp. oral clone CX010 |
| *Bifidobacterium* sp. JCM 7023 | uncultured *Bifidobacterium* sp. |
| *Bifidobacterium* sp. JCM 7027 | uncultured *Bifidobacterium* sp. 1-2A |
| *Bifidobacterium* sp. JCM 7028 | uncultured *Bifidobacterium* sp. 1-2B |
| *Bifidobacterium* sp. JCM 7042 | uncultured *Bifidobacterium* sp. 1-5A |
| *Bifidobacterium* sp. JEMLUCVII-1 | uncultured *Bifidobacterium* sp. 13D |
| *Bifidobacterium* sp. JEMLUCVIII-4 | uncultured *Bifidobacterium* sp. 15A |
| *Bifidobacterium* sp. LISLUCII-P2 | uncultured *Bifidobacterium* sp. 15B |
| *Bifidobacterium* sp. LISLUCIII-2 | uncultured *Bifidobacterium* sp. 15D |
| *Bifidobacterium* sp. LISLUCIII-P2 | uncultured *Bifidobacterium* sp. 16B |
| *Bifidobacterium* sp. LISPASI-P3 | uncultured *Bifidobacterium* sp. 16C |
| *Bifidobacterium* sp. LLS001 | uncultured *Bifidobacterium* sp. 16F |
| *Bifidobacterium* sp. LUCL-P3 | uncultured *Bifidobacterium* sp. 2-3A |
| *Bifidobacterium* sp. LUCL-W4 | uncultured *Bifidobacterium* sp. 3-3A |
| *Bifidobacterium* sp. M24 | uncultured *Bifidobacterium* sp. 3-4A |
| uncultured *Bifidobacterium* sp. 3-4B | uncultured *Bifidobacterium* sp. 9A |
| uncultured *Bifidobacterium* sp. 7B | uncultured *Bifidobacterium* sp. 9B |
| uncultured *Bifidobacterium* sp. 7G | uncultured *Bifidobacterium* sp. 9C |

Genus: *Acidopholus*

*Lactobacillus acidophilus*

---

The invention claimed is:

1. A composition comprising at least one non-pathogenic bacterial cell, wherein the non-pathogenic bacterial cell comprises at least a first, a second, and a third nucleic acid sequence, the first and second nucleic acid sequences each comprising a lux gene operably linked to the third nucleic acid sequence, the third nucleic acid encoding at least one therapeutic agent comprising a cellular toxin with at least 85% sequence identity to the amino acid sequence encoded by SEQ ID NO:6, wherein each lux gene is an exogenous inducible promoter responsive to at least one stimuli and the at least one stimuli comprises the presence of a certain density or a certain number of bacterial cells comprising the first and second nucleic acid sequences.

2. The composition of claim 1, wherein at least one non-pathogenic bacterial cell is chosen from one or a combination of bacterial cells of the genera chosen from: *Salmonella, Escherichia, Firmicutes, Bacteroidetes, Lactobacillus,* or *Bifidobacteria.*

3. The composition of claim 1, wherein the bacterial cell further comprises a fourth exogenous nucleic acid sequence, wherein the fourth exogenous nucleic acid sequence encodes an amino acid sequence that directs targeting of the at least one therapeutic to a cancer cell or a cell associated with a hyperproliferative disorder.

4. The composition of claim 1, wherein the exogenous lux genes are responsive to the presence of AHL.

5. The composition of claim 1, wherein the at least one stimuli comprises the presence of a biofilm of bacteria.

6. The composition of claim 1, wherein the therapeutic agent is a fusion protein encoded by the third nucleic acid sequence, the fusion protein comprising at least a first and second moiety, wherein the first moiety comprises an amino acid sequence with at least 90% sequence identity to the amino acid sequence encoded by SEQ ID NO:6 and the second moiety is a targeting sequence.

7. The composition of claim 1, wherein the at least one bacterial cell comprises a plasmid with at least 95% sequence identity to SEQ ID NO:1.

8. The composition of claim 1, wherein the at least one bacterial cell comprises a plasmid consisting of SEQ ID NO:1.

9. The composition of claim 1, wherein the at least one bacterial cell comprises at least two lux genes operably linked to one or more cellular toxin comprising at least 95% sequence identity to the amino acid sequence encoded by SEQ ID NO:6;

wherein the at least one bacterial strain is an attenuated bacterial cell from the genus chosen from: *Salmonella, Escherichia* or *Lactobacillus*; and wherein the at least one bacterial cell is capable of colonizing tumor cells or cancer cells, or cell associated with a hyperproliferative disorder.

10. A pharmaceutical composition comprising:
 (a) the composition of claim 1, and
 (b) a pharmaceutically acceptable carrier or a pharmaceutically acceptable salt thereof;
wherein the composition comprises a therapeutically effective dose of the at least one bacterial cell.

11. The pharmaceutical composition of claim 10, further comprising:
 (c) a chemotherapeutic compound.

12. The pharmaceutical composition of claim 10, wherein the pharmaceutical composition comprises one more radioactive isotopes.

13. A kit comprising the pharmaceutical composition of claim 10.

14. The composition of claim 3, wherein the fourth exogenous nucleic acid sequence encodes an amino acid sequence with at least 85% sequence identity to the amino acid sequence encoded by SEQ ID NO: 5.

* * * * *

UNITED STATES PATENT AND TRADEMARK OFFICE
CERTIFICATE OF CORRECTION

PATENT NO. : 9,994,809 B2
APPLICATION NO. : 14/428341
DATED : June 12, 2018
INVENTOR(S) : Bhatia et al.

Page 1 of 1

It is certified that error appears in the above-identified patent and that said Letters Patent is hereby corrected as shown below:

In the Claims

At Column 169, Line 6, in Claim 1, change "comprising a lux gene operably linked to the third nucleic" to -- comprising a *lux* gene operably linked to the third nucleic --.

At Column 169, Line 10, in Claim 1, change "by SEQ ID NO:6, wherein each lux gene is an exogenous" to -- by SEQ ID NO:6, wherein each *lux* gene is an exogenous --.

At Column 169, Line 26, in Claim 4, change "4. The composition of claim 1, wherein the exogenous lux" to -- 4. The composition of claim 1, wherein the exogenous *lux* --.

At Column 170, Line 8, in Claim 9, change "bacterial cell comprises at least two lux genes operably" to -- bacterial cell comprises at least two *lux* genes operably --.

Signed and Sealed this
Thirteenth Day of August, 2019

Andrei Iancu
*Director of the United States Patent and Trademark Office*